(12) United States Patent  
Lindsey

(10) Patent No.: US 6,420,648 B1  
(45) Date of Patent: Jul. 16, 2002

(54) LIGHT HARVESTING ARRAYS

(75) Inventor: Jonathan S. Lindsey, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 09/621,797

(22) Filed: Jul. 21, 2000

(51) Int. Cl.⁷ ..................... H01L 31/0248; H01L 31/04

(52) U.S. Cl. ................. 136/263; 136/252; 136/256; 257/40; 257/431; 429/111; 429/306; 429/310; 429/314; 429/317

(58) Field of Search .................. 136/252, 256, 136/263; 257/40, 431; 429/111, 306, 310, 314, 317

(56) References Cited

U.S. PATENT DOCUMENTS

| | | | | |
|---|---|---|---|---|
| 4,618,509 A | * | 10/1986 | Bulkowski | 427/74 |
| 5,280,183 A | * | 1/1994 | Batzel et al. | 257/40 |
| 5,424,974 A | | 6/1995 | Liu et al. | 365/112 |
| 5,441,827 A | | 8/1995 | Gratzel et al. | 429/111 |
| 5,525,811 A | * | 6/1996 | Sakurai et al. | 257/40 |
| 6,208,553 B1 | * | 3/2001 | Gryko et al. | 365/151 |
| 6,212,093 B1 | * | 4/2001 | Lindsey | 365/151 |
| 6,232,547 B1 | * | 5/2001 | Meissner et al. | 136/263 |
| 6,272,038 B1 | * | 8/2001 | Clausen et al. | 365/151 |
| 6,281,430 B1 | * | 8/2001 | Lupo et al. | 136/263 |

FOREIGN PATENT DOCUMENTS

| | | |
|---|---|---|
| WO | WO 98/50393 | 11/1998 |
| WO | WO 00/11725 | 3/2000 |

OTHER PUBLICATIONS

Fungo et al, "Synthesis of porphyrin dyads with potential use in solar energy conversion", J. Matter. Chem., 10: pp. 645–650, (2000).*

International Search Report, International Application Ser. No. PCT/US01/23010 dated Oct. 19, 2001.

Strachan et al.; Rational Synthesis of Meso–Substituted Chlorin Building Blocks, J. of Org. Chem., 65(10):3160–3172 (2000).

Wagner et al.; Soluble Synthetic Multiporphyrin Arrays. 1. Modular Design and Synthesis, J. Am. Chem. Soc., 118(45):11166–11180 (1996).

Kuciauskas et al.; An Artificial Photosynthetic Antenna–Reaction Center Complex, J. Am. Chem. Soc., 121(37):8604–8614 (1999).

Li et al.; Efficient Synthesis of Light–Harvesting Arrays Composed of Eight Porphyrins and One Phthalocyanine, J. of Org. Chem., 64(25):9101–9108 (1999).

Wagner et al.; A Molecular Photonic Wire, J. Am. Chem. Soc., 116:9759–9760 (1994).

(List continued on next page.)

Primary Examiner—Alan Diamond  
(74) Attorney, Agent, or Firm—Myers Bigel Sibley & Sajovec

(57) ABSTRACT

A light harvesting array useful for the manufacture of devices such as solar cells comprises: (a) a first substrate comprising a first electrode; and (b) a layer of light harvesting rods electrically coupled to the first electrode, each of the light harvesting rods comprising a polymer of Formula I:

$$X^1\text{-}(X^{m+1})_m \qquad (I)$$

wherein m is at least 1, and may be from two, three or four to 20 or more; $X^1$ is a charge separation group (and preferably a porphyrinic macrocycle, which may be one ligand of a double-decker sandwich compound) having an excited-state of energy equal to or lower than that of $X^2$, and $X^2$ through $X^{m+1}$ are chromophores (and again are preferably porphyrinic macrocycles).

125 Claims, 57 Drawing Sheets

OTHER PUBLICATIONS

Fungo et al.; Synthesis of Porphyrin Dyads with Potential Use in Solar, *J. Mater. Chem.*, 10:645–650 (2000).

Parkinson et al.; Recent Advances In High Quantum Yield Dye Sensitization of Semiconductor Electrodes, *Electrochimica Acta.*, 37(5):943–948 (1992).

Schon et al.; Efficient Organic Photovoltaic Diodes Based on Doped Pentacene, *Nature*, 403:408–410 (Jan. 27, 2000).

Moss et al.; Sensitization of Nanocrystalline $TiO_2$ by Electropolymerized Thin Films, *Chem. Mater.*, 10(7):1748–1750 (1998).

O'Regan et al.; A Low–Cost, High Efficiency Solar Cell Based on Dye–Sensitized Colloidal $TiO_2$ Films, *Nature*, 353:737–739 (Oct. 1991).

Bach et al.; Solid–State Dye–Sensitized Mesoporous $TiO_2$ Solar Cells with High Photon–to–Electron Conversion Efficiencies, *Nature*, 395:583–585 (Oct. 1998).

W. John Albery; Development of Photogalvanic Cells for Solar Energy Conversion, *Acc. Chem. Res.*, 15:142–148 (1982).

* cited by examiner

◇ PIGMENT

L = LINKER

☐ CSU

Y = ATTACHMENT GROUP FOR ELECTRODE

Z = CAPPING GROUP OR ATTACHMENT GROUP FOR ELECTRODE

1. LIGHT ABSORPTION BY ONE OF THE
PIGMENTS (SHOWN HERE FOR THE DISTAL
PIGMENT) IN THE LH ARRAY

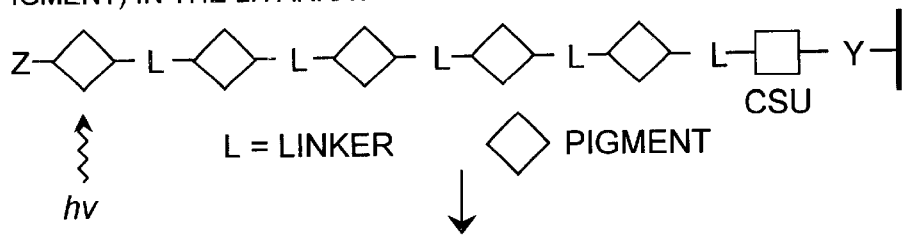

L = LINKER   ◇ PIGMENT

2. ENERGY MIGRATION FROM THE SITE OF ABSORPTION
AMONG PIGMENTS IN THE LH ARRAY TO THE CSU.

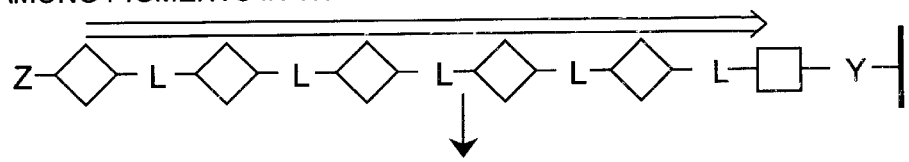

3. THE EXCITED-STATE CSU IS FORMED.

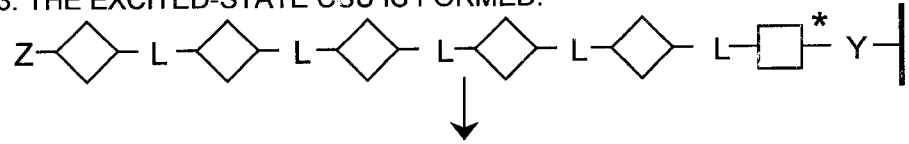

4. CHARGE SEPARATION IN THE CSU RESULTS IN
ELECTRON INJECTION INTO THE CONDUCTION BAND.

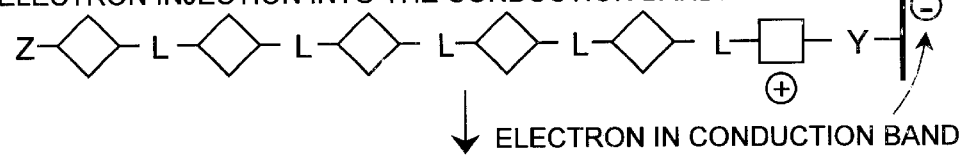

ELECTRON IN CONDUCTION BAND

5. THE HOLE REACTS WITH A MOBILE CHARGE CARRIER.

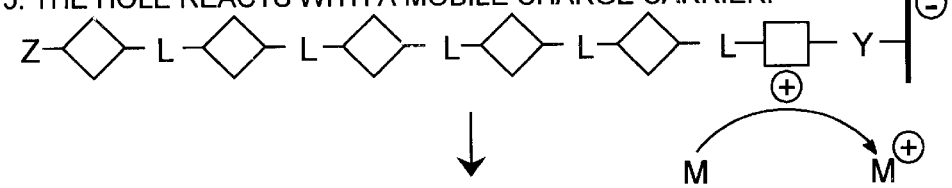

6. THE CSU IS REGENERATED AND THE MOBILE CHARGE
CARRIER TRANSPORTS CHARGE TO THE OTHER ELECTRODE.

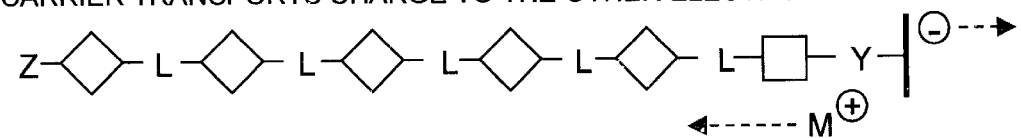

DESIGN I

*FIG. 3*

1. LIGHT ABSORPTION BY ONE OF THE
PIGMENTS (SHOWN HERE FOR THE DISTAL     ELECTRODE
PIGMENT) IN THE LH ARRAY.

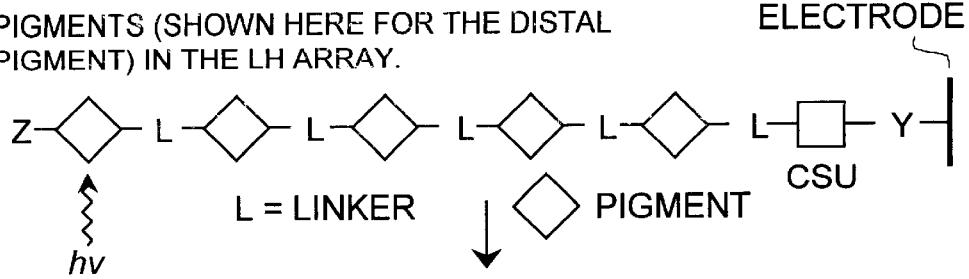

L = LINKER   ◇ PIGMENT

2. ENERGY MIGRATION FROM THE SITE OF ABSORPTION
AMONG PIGMENTS IN THE LH ARRAY TO THE CSU.

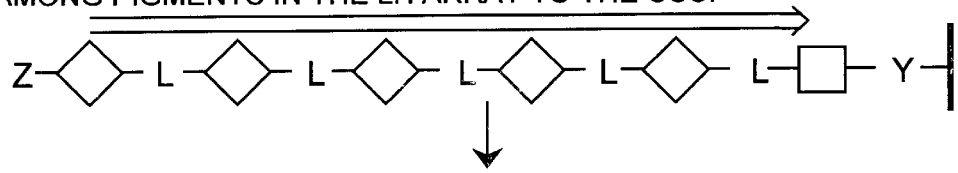

3. THE EXCITED-STATE CSU IS FORMED.

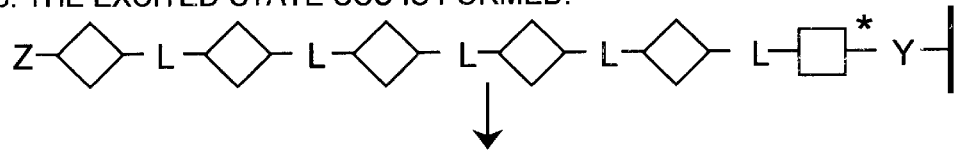

4. CHARGE SEPARATION IN THE CSU RESULTS IN
ELECTRON INJECTION INTO THE CONDUCTION BAND.

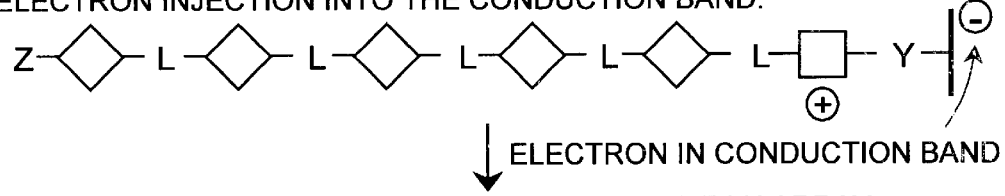

ELECTRON IN CONDUCTION BAND

5. THE HOLE MIGRATES AMONG PIGMENTS IN THE LH ARRAY,
REGENERATING THE CSU.

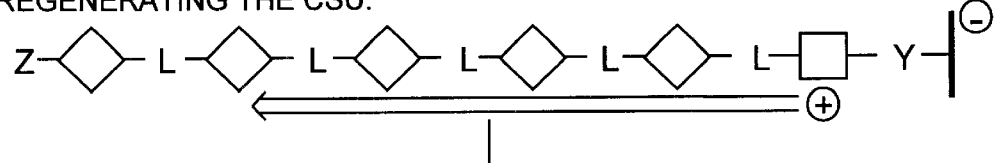

6. THE HOLE REACTS WITH A MOBILE CHARGE CARRIER.

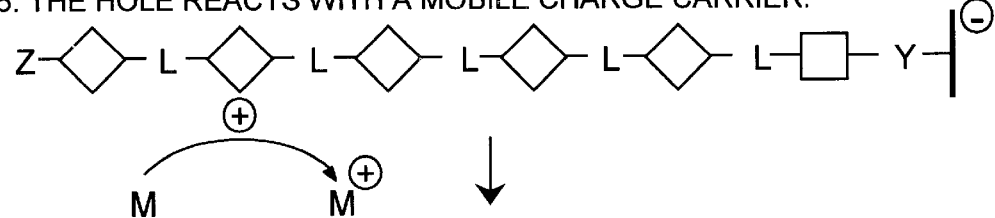

7. THE MOBILE CHARGE CARRIER TRANSPORTS CHARGE TO THE OTHER
ELECTRODE.

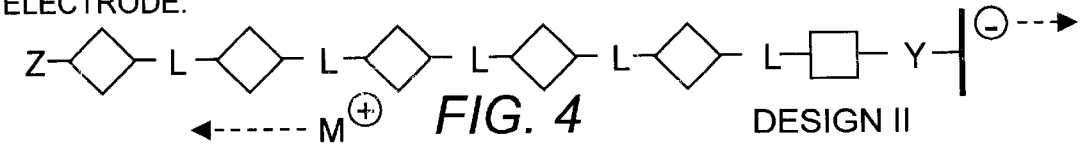

*FIG. 4*          DESIGN II

1. LIGHT ABSORPTION BY ONE OF THE
PIGMENTS (SHOWN HERE FOR THE DISTAL
PIGMENT) IN THE LH ARRAY.

ELECTRODE

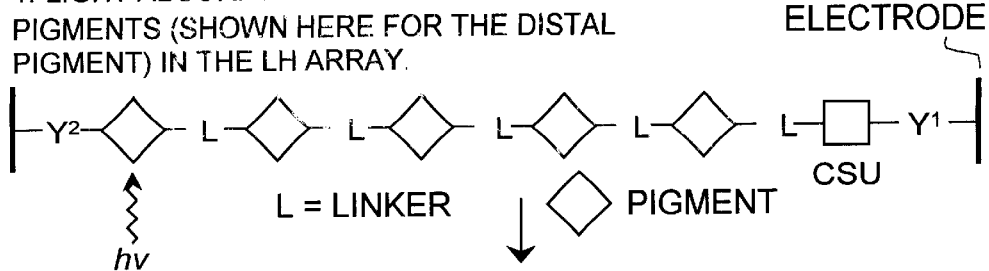

L = LINKER   ◇ PIGMENT   CSU

2. ENERGY MIGRATION FROM THE SITE OF ABSORPTION
AMONG PIGMENTS IN THE LH ARRAY TO THE CSU.

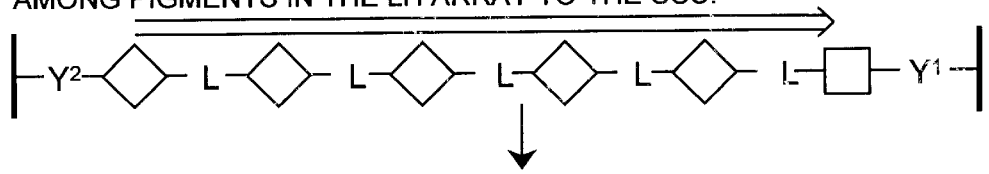

3. THE EXCITED-STATE CSU IS FORMED.

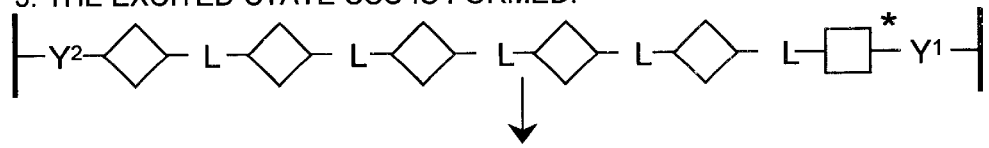

4. CHARGE SEPARATION IN THE CSU RESULTS IN
ELECTRON INJECTION INTO THE CONDUCTION BAND.

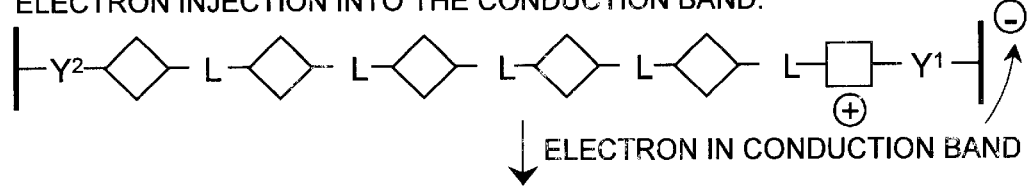

ELECTRON IN CONDUCTION BAND

5. THE HOLE MIGRATES AMONG PIGMENTS IN THE LH ARRAY,
REACHING THE OTHER ELECTRODE, AND REGENERATING THE CSU.

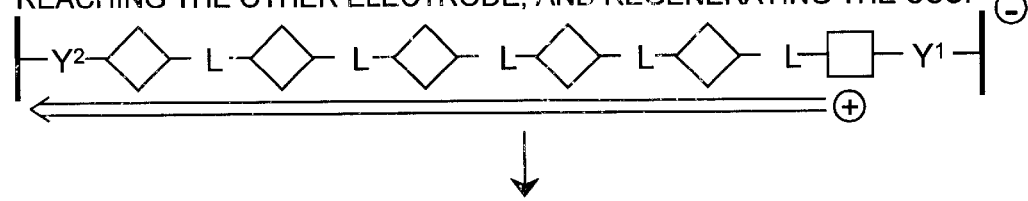

6. THE HOLE AND ELECTRON REACH THEIR RESPECTIVE ELECTRODES
WITHOUT ANY MOBILE (I.E., DIFFUSIVE) CHARGE CARRIERS.

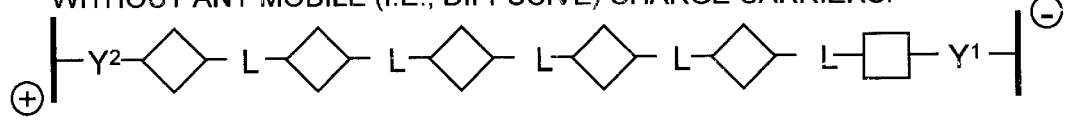

DESIGN III

*FIG. 5*

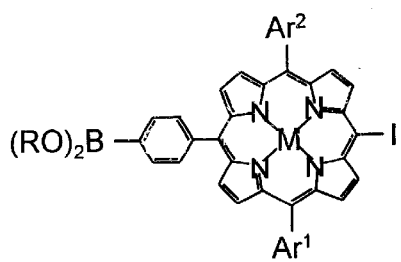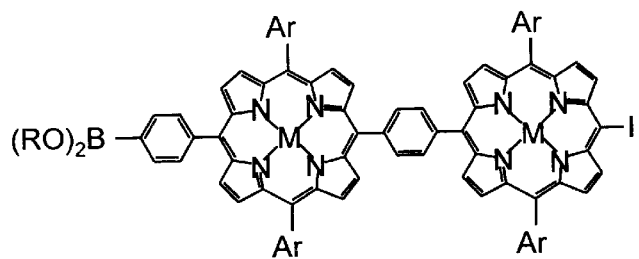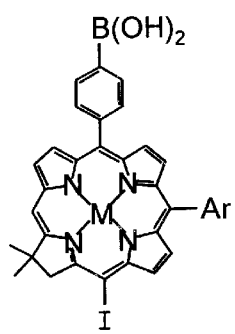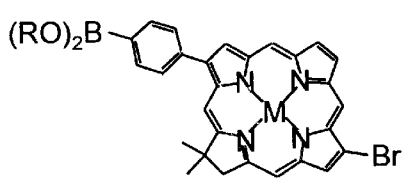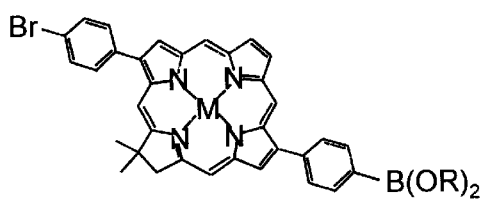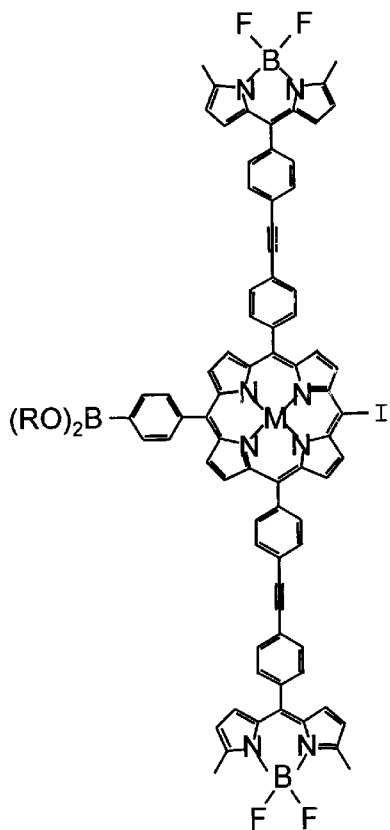
FIG. 15

ETHYNE-SUBSTITUTED OLIGOMER READY FOR SUBSEQUENT COUPLINGS

| M | Ar¹ | Ar² |
|---|---|---|
| H, H | Ms | p-TOLYL |
| Zn | Ms | p-TOLYL |
| Cu | Ms | p-TOLYL |
| H, H | $C_6F_5$ | $C_6F_5$ |
| Zn | $C_6F_5$ | $C_6F_5$ |
| H, H | 4-IODOPHENYL | p-TOLYL |
| Zn | 4-IODOPHENYL | p-TOLYL |
| H, H | 4-(TMS-CC)PHENYL | p-TOLYL |
| Zn | 4-(TMS-CC)PHENYL | p-TOLYL |

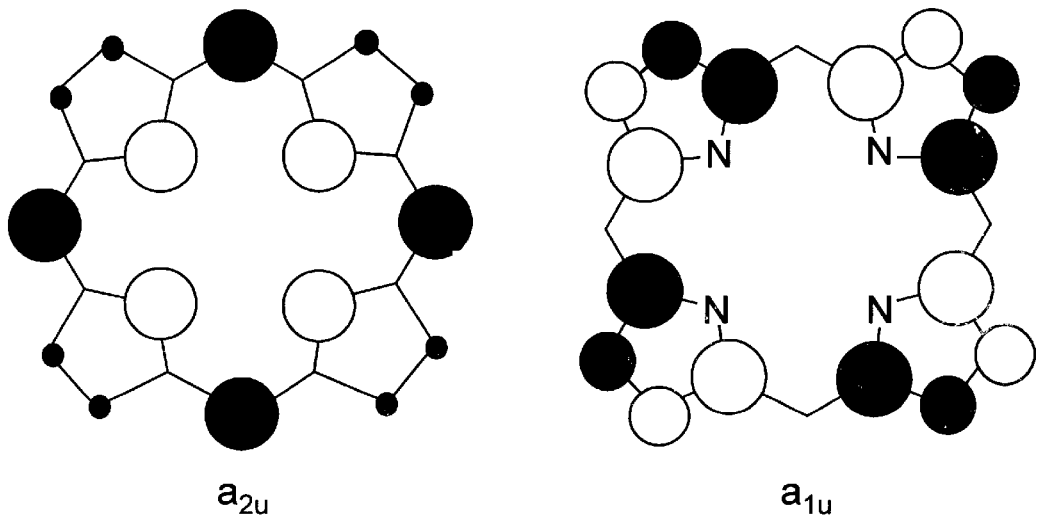
HIGHEST OCCUPIED
MOLECULAR ORBITALS
(THE ELECTRON DENSITY AT THE β POSITIONS
IN THE $a_{2u}$ ORBITAL IS EXAGGERATED FOR CLARITY)
*TERMINOLOGY:*
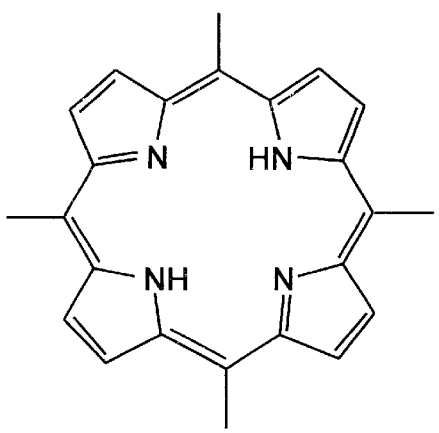
A *MESO*-SUBSTITUTED
PORPHYRIN
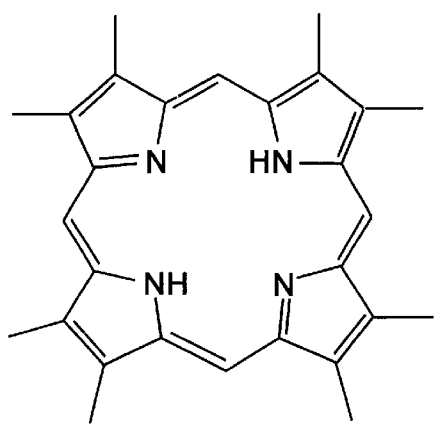
A β-SUBSTITUTED
PORPHYRIN
*FIG. 28*

TRANS-CHLORINS WITH TWO β SUBSTITUENTS
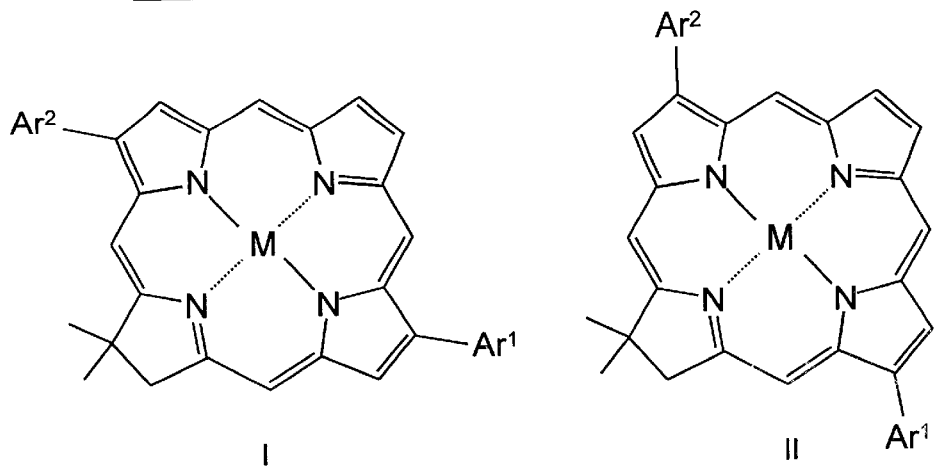
I  II
TRANS-CHLORINS WITH TWO MESO SUBSTITUENTS
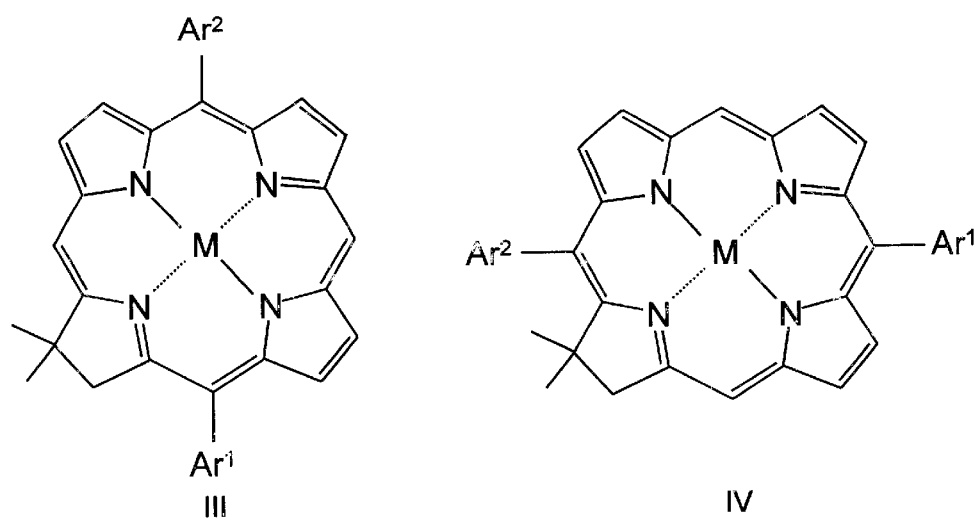
III  IV
CHLORIN NOMENCLATURE SHOWING IUPAC-IUB RING LABELS A-D
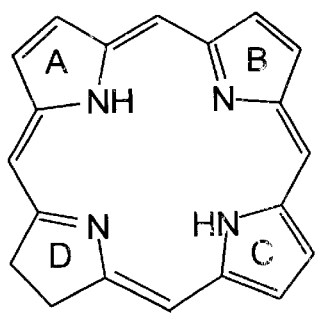
FIG. 29

ORIENTATION OF THE TRANSITION DIPOLE
MOMENT OF THE LONG-WAVELENGTH
ABSORPTION BAND

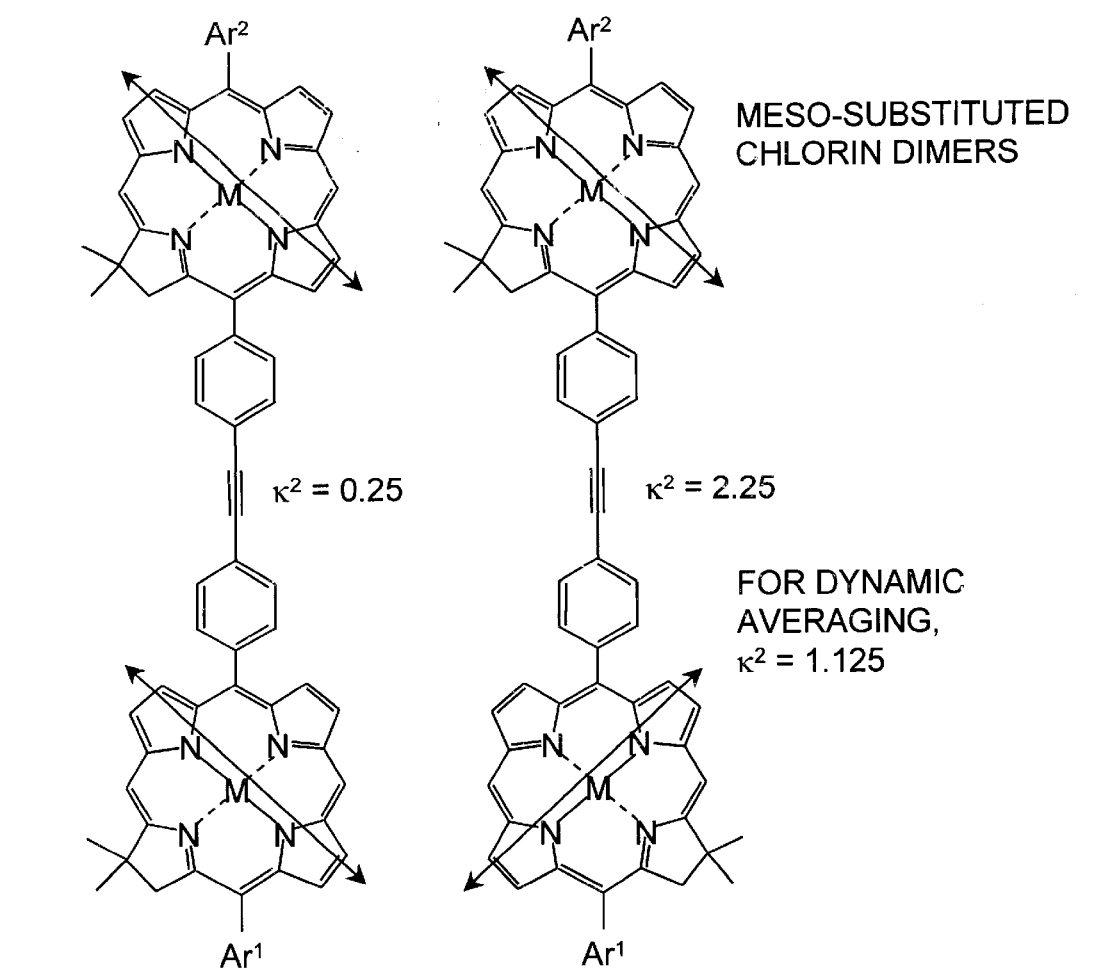
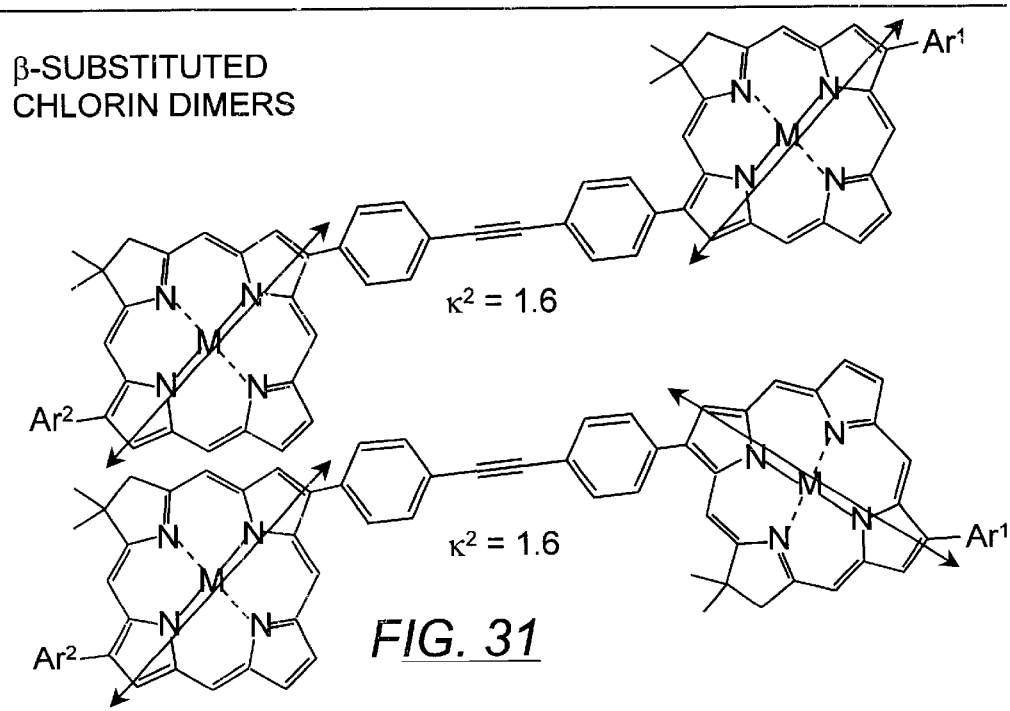
FIG. 31

CHLORIN HOMO

$a_2$ MO

TRANS-CHLORIN BUILDING BLOCK WITH TWO β SUBSTITUENTS (M = A DIVALENT METAL OR TWO PROTONS)

TRANS-CHLORIN BUILDING BLOCKS WITH TWO β SUBSTITUENTS
(M = A DIVALENT METAL OR TWO PROTONS)

1. LIGHT ABSORPTION BY ONE OF THE PIGMENTS (SHOWN HERE FOR THE DISTAL PIGMENT) IN THE LH ARRAY.

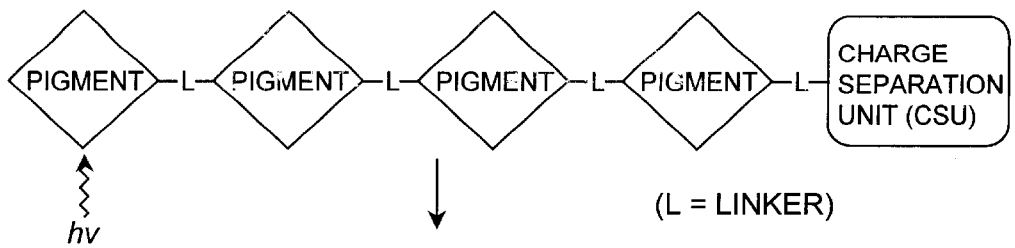

(L = LINKER)

2. ENERGY MIGRATION FROM THE SITE OF ABSORPTION AMONG PIGMENTS IN THE LH ARRAY TO THE CSU.

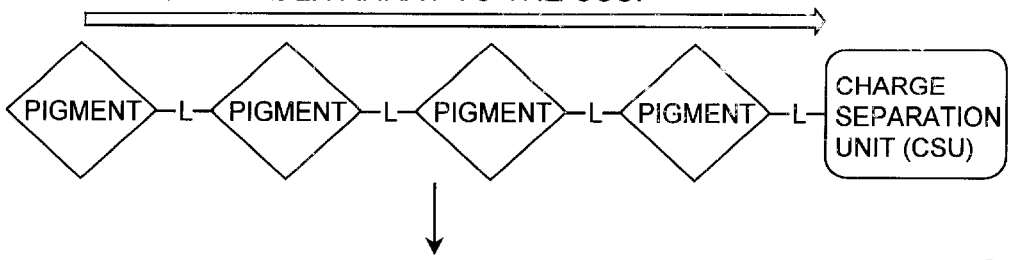

3. CHARGE SEPARATION IN THE CSU.

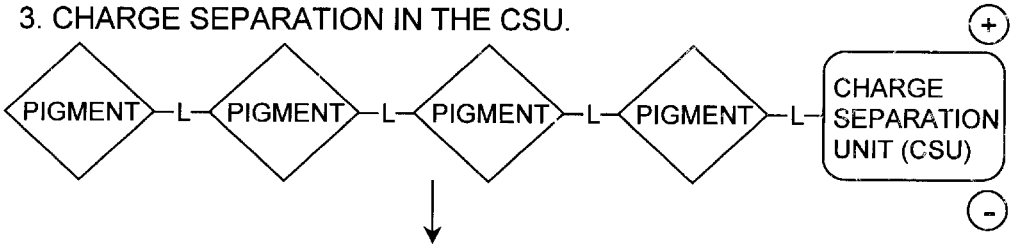

4. HOLE MIGRATION FROM THE CSU TO THE DISTAL END OF THE LH ARRAY.

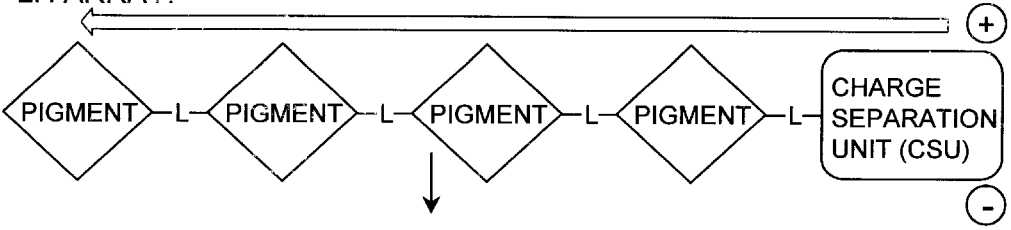

5. FINAL CHARGE-SEPARATED STATE. THE ELECTRON CAN ALSO TRANSFER FROM THE CSU TO ANOTHER ACCEPTOR (NOT SHOWN).

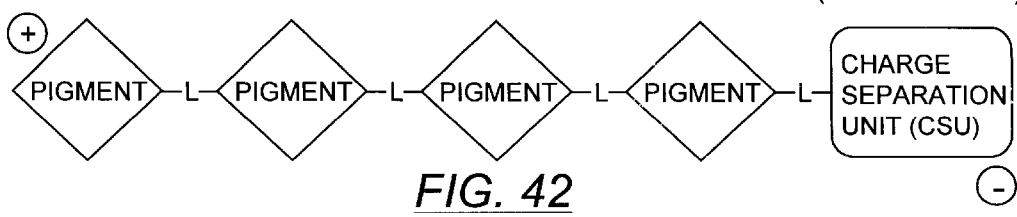

| $J^2$ | $J^3$ | REACTION TYPE |
|---|---|---|
| -B(OH)$_2$ | -Cl, -Br, I | SUZUKI |
| ≡—H | -Cl, -Br, I | SONOGASHIRA |
| ≡—H | ≡—H | GLASER |
| ≡—H | ≡—X | CADIOT-CHODKIEWICZ |
| -CHO | -Br, I | WITTIG |
| —HC=CH$_2$ | -Br, I | HECK |

*FIG. 51*

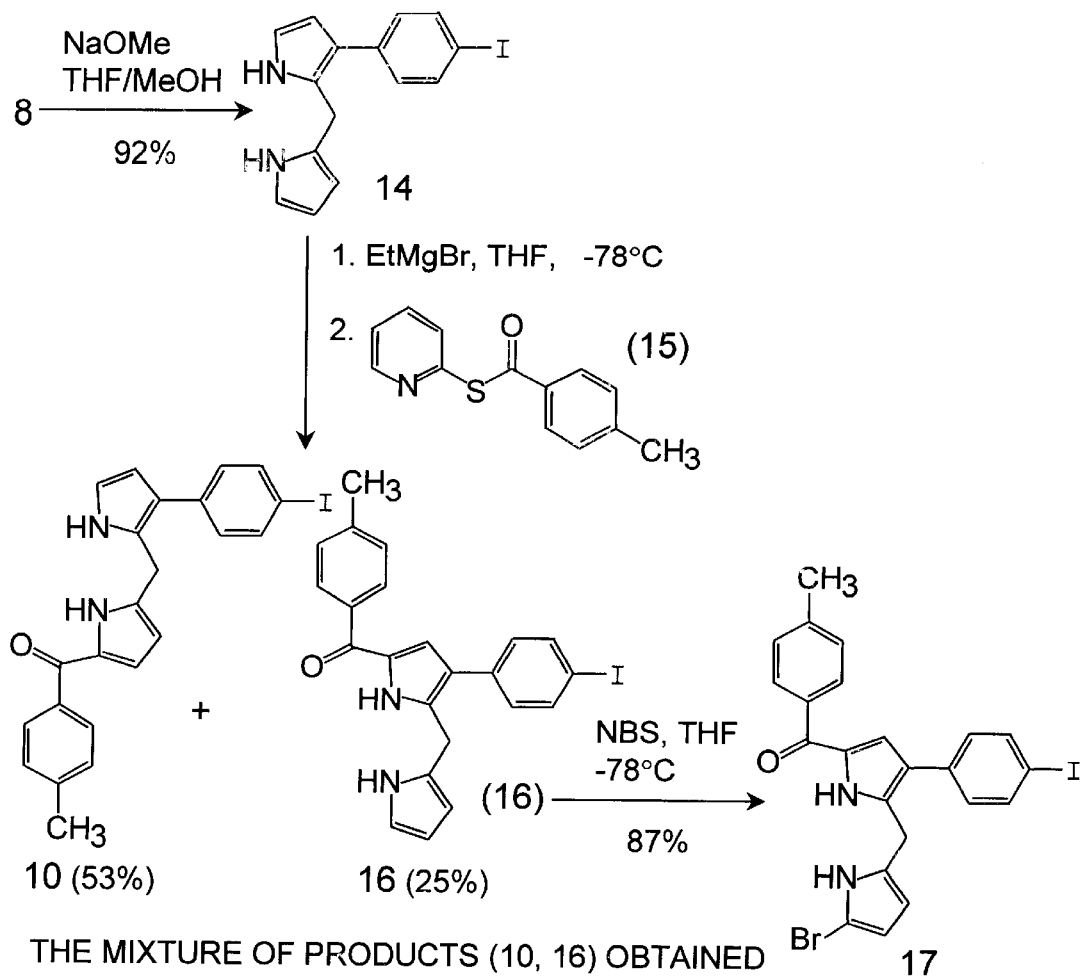
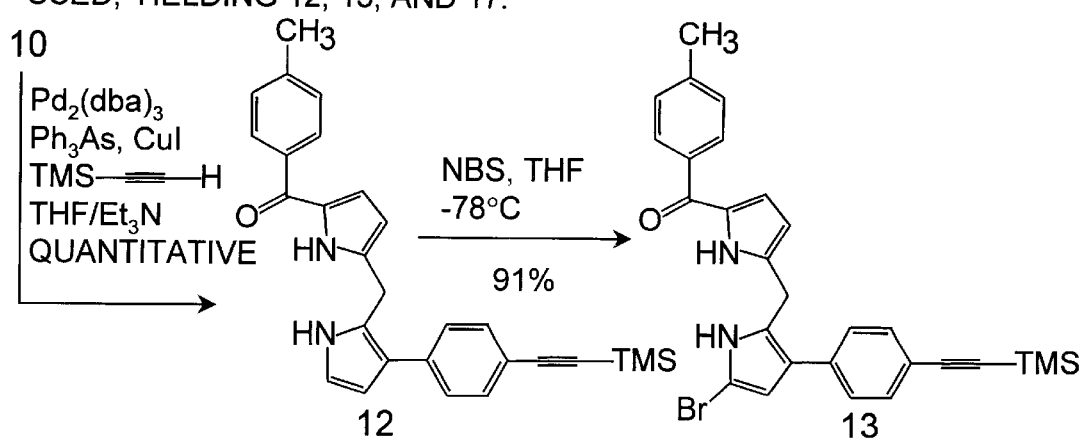
THE MIXTURE OF PRODUCTS (10, 16) OBTAINED WAS PURIFIED. BOTH PURIFIED PRODUCTS WERE USED, YIELDING 12, 13, AND 17.
FIG. 55

FIG. 56  β-SUBSTITUTED WESTERN HALF

LIGHT HARVESTING ARRAYS

This invention was made with Government support under Grant No. DE-FG02-96ER14632 from the Department of Energy and Grant No. GM36238 from the National Institutes of Health. The Government has certain rights to this invention.

FIELD OF THE INVENTION

The present invention concerns solar cells, particularly regenerative solar cells, and light harvesting arrays useful in such solar cells.

BACKGROUND OF THE INVENTION

Molecular approaches for converting sunlight to electrical energy have a rich history with measurable "photoeffects" reported as early as 1887 in Vienna (Moser, J. *Montash. Chem.* 1887, 8, 373.). The most promising designs were explored in considerable detail in the 1970's (Gerischer, H. *Photochem. Photobiol.* 1972, 16, 243; Gerischer, H. *Pure Appl. Chem.* 1980, 52, 2649; Gerischer, H.; Willig, F. *Top. Curr. Chem.* 1976, 61, 31). Two common approaches are shown in FIG. 1, both of which incorporate molecules that selectively absorb sunlight, termed photosensitizers or simply sensitizers (S), covalently bound to conductive electrodes. Light absorption by the sensitizer creates an excited state, S*, that injects an electron into the electrode and then oxidizes a species in solution. The right hand side depicts a simplified photoelectrosynthetic cell. This cell produces both electrical power and chemical products. Many of the molecular approaches over the past few decades were designed to operate in the manner shown with the goal of splitting water into hydrogen and oxygen. Shown on the left hand side is a regenerative cell that converts light into electricity with no net chemistry. In the regenerative solar cell shown, the oxidation reactions that take place at the photoanode are reversed at the dark cathode.

The principal difficulty with these solar cell designs is that a monolayer of a molecular sensitizer on a flat surface does not absorb a significant fraction of incident visible light. As a consequence, even if the quantum yields of electron transfer are high on an absorbed photon basis, the solar conversion efficiency will be impractically low because so little light is absorbed. Early researchers recognized this problem and tried to circumvent it by utilizing thick films of sensitizers. This strategy of employing thick absorbing layers was unsuccessful as intermolecular excited-state quenching in the thick sensitizer film decreased the yield of electron injection into the electrode.

One class of thick film sensitizers is provided by the so-called organic solar cells (Tang, C. W. and Albrecht, A. C. *J. Chem. Phys.* 1975, 63, 953–961). Here a 0.01 to 5 $\mu$m thick film, typically comprised of phthalocyanines, perylenes, chlorophylls, porphyrins, or mixtures thereof, is deposited onto an electrode surface and is employed in wet solar cells like those shown, or as solid-state devices where a second metal is deposited on top of the organic film. The organic layer is considered to be a small bandgap semiconductor with either n- or p-type photoconductivity and the proposed light-to-electrical energy conversion mechanisms incorporate excitonic energy transfer among the pigments in the film toward the electrode surface where interfacial electron transfer takes place. However, the importance of these proposed mechanistic steps is not clear. Increased efficiencies that result from vectorial energy transfer among the pigments have not been convincingly demonstrated. Furthermore, the reported excitonic diffusion lengths are short relative to the penetration depth of the light. Accordingly, most of the light is absorbed in a region where the energy cannot be translated to the semiconductor surface. The excitons are also readily quenched by impurities or incorporated solvent, leading to significant challenges in reproducibility and fabrication. The state-of-the-art organic solar cells are multilayer organic "heterojunction" films or doped organic layers that yield ~2% efficiencies under low irradiance, but the efficiency drops markedly as the irradiance approaches that of one sun (Forrest, S. R. et al., *J. Appl. Phys.* 1989, 183, 307; Schon, J. H. et al., *Nature* 2000, 403, 408).

Another class of molecular-based solar cells are the so-called photogalvanic cells that were the hallmark molecular level solar energy conversion devices of the 1940's–1950's (Albery, W. J. *Acc. Chem. Res.* 1982, 15, 142). These cells are distinguished from those discussed above in that the excited sensitizer does not undergo interfacial electron transfer. The cells often contain sensitizers embedded in a membrane that allows ion transfer and charge transfer; the membrane physically separates two dark metal electrodes and photogenerated redox equivalents. The geometric arrangement precludes direct excited-state electron transfer from a chromophore to or from the electrodes. Rather, intermolecular charge separation occurs and the reducing and oxidizing equivalents diffuse to electrodes where thermal interfacial electron transfer takes place. A transmembrane Nernst potential can be generated by photodriven electron transfer occurring in the membrane. In photoelectrosynthetic galvanic cells, chemical fuels may be formed as well. This general strategy for dye sensitization of electrodes has been employed in many guises over the years, but the absolute efficiencies remain very low. Albery concluded that an efficiency of ~13% theoretically could be achieved in an aqueous regenerative photogalvanic cell. However, efficiencies realized to date are typically less than 2%.

In 1991, a breakthrough was reported by Grätzel and O'Regan (O'Regan, B. et al., *J. Phys. Chem.* 1990, 94, 8720; O'Regan, B. and Gratzel, M. *Nature* 1991, 353, 737). By replacing the planar electrodes with a thick porous colloidal semiconductor film, the surface area for sensitizer binding increased by over 1000-fold. Gratzel and O'Regan demonstrated that a monolayer of sensitizer coating the semiconductor particles resulted in absorption of essentially all of the incident light, and incident photon-to-electron energy conversion efficiencies were unity at individual wavelengths of light in regenerative solar cells. Furthermore, a global efficiency of 5% was realized under air-mass 1.5 illumination conditions; this efficiency has risen to a confirmed 10.69% today (Gratzel, M. in "Future Generation Photovoltaic Technologies" McConnell, R. D.; AIP Conference Proceedings 404, 1997, page 119). These "Gratzel" solar cells have already found niche markets and are commercially available in Europe.

These high surface area colloidal semiconductor films (Gratzel cells) achieve a high level of absorption but also have the following significant drawbacks. (1) A liquid junction is required for high efficiency (because the highly irregular surface structure makes deposition of a solid-state conductive layer essentially impossible). (2) The colloidal semiconductor films require high temperature annealing steps to reduce internal resistances. Such high temperatures impose severe limitations on the types of conductive substrates that can be used. For example, polymeric substrates that melt below the required annealing temperatures cannot be used. (3) Significant losses are associated with transporting charge through the thick semiconductor films. These losses do not appreciably decrease the photocurrent, but have a large effect on the voltage output and thus the power is decreased significantly (Hagfeldt, A.; Grätzel, M. *Chem. Rev.* 1995, 95, 49). Accordingly, there remains a need for new molecular approaches to the construction of solar cells.

SUMMARY OF THE INVENTION

Accordingly, the present invention provides, among other things, a light harvesting array useful for the manufacture of solar cells. The light harvesting array comprises:

(a) a first substrate comprising a first electrode; and (b) a layer of light harvesting rods electrically coupled to the first electrode, each of the light harvesting rods comprising a polymer of Formula I:

wherein:
  m is at least 1, and may be from two, three or four to 20 or more;
  $X^1$ is a charge separation group having an excited-state of energy equal to or lower than that of $X^2$; and
  $X^2$ through $X^{m+1}$ are chromophores.

In light harvesting rods of Formula I herein, $X^1$ preferably comprises a porphyrinic macrocycle, which may be in the form of a double-decker sandwich compound. Further, $X^2$ through $X^{m+1}$ also preferably comprise porphyrinic macrocycles.

In one preferred embodiment of the light harvesting rods of Formula I herein, at least one of (e.g., two, three, a plurality of, the majority of or all of) $X^1$ through $X^{m+1}$ is/are selected from the group consisting of chlorins, bacteriochlorins, and isobacteriochlorins.

A particular embodiment of a light harvesting array as described above provides for the movement of holes in the opposite direction of excited-state energy along some or all of the length of the light harvesting rods, and comprises:

(a) a first substrate comprising a first electrode; and (b) a layer of light harvesting rods electrically coupled to the first electrode, each of the light harvesting rods comprising a polymer of Formula I:

wherein:
  m is at least 1 (typically two, three or four to twenty or more);
  $X^1$ is a charge separation group having an excited-state of energy equal to or lower than that of $X^2$;
  $X^2$ through $X^{m+1}$ are chromophores; and
  $X^1$ through $X^{m+1}$ are selected so that, upon injection of either an electron or hole from $X^1$ into the first electrode, the corresponding hole or electron from $X^1$ is transferred to at least $X^2$, and optionally to $X^3$, $X^4$, and all the way through $X^{m+1}$. In a currently preferred embodiment, $X^1$ through $X^{m+1}$ are selected so that, upon injection of an electron from $X^1$ into the first electrode, the corresponding hole from $X^1$ is transferred to at least $X^2$, and optionally through $X^{m+1}$.

Light-harvesting arrays provide intense absorption of light and deliver the resulting excited state to a designated location within the molecular array. There are a variety of applications of light-harvesting arrays. Light-harvesting arrays can be used as components of low-level light detection systems, especially where control is desired over the wavelength of light that is collected. Light-harvesting arrays can be used as input elements in optoelectronic devices, and as an input unit and energy relay system in molecular-based signaling systems. One application of the latter includes use in molecular-based fluorescence sensors. The molecular-based sensor employs a set of probe groups (which bind an analyte) attached to a molecular backbone that undergoes excited-state energy transfer. The binding of a single analyte to any one of the probe groups yields a complex that can quench the excited state that freely migrates along the backbone (i.e., exciton). The quenching phenomenon results in diminished fluorescence from the molecular backbone. Because only one bound analyte can cause the quenching phenomenon, the sensitivity is much higher than if there was a 1:1 ratio of probe groups and fluorescence groups. Previously, such molecular-based fluorescence sensors have employed UV or near-UV absorbing chromophores in the molecular backbone. The light-harvesting arrays described herein are ideally suited as components for a new class of molecular-based fluorescence sensors that absorb (and fluoresce) strongly in the visible and near-infrared region.

A particular application of the light-harvesting arrays described herein is in solar cells. A solar cell as described herein typically comprises:

(a) a first substrate comprising a first electrode;

(b) a second substrate comprising a second electrode, with the first and second substrate being positioned to form a space therebetween, and with at least one of (i) the first substrate and the first electrode and (ii) the second substrate and the second electrode being transparent;

(c) a layer of light harvesting rods electrically coupled to the first electrode, each of the light harvesting rods comprising a polymer of Formula I:

wherein:
  m is at least 1 (and typically two, three or four to twenty or more);
  $X^1$ is a charge separation group having an excited-state of energy equal to or lower than that of $X^2$;
  $X^2$ through $X^{m+1}$ are chromophores; and
  $X^1$ is electrically coupled to the first electrode; the solar cell further comprising (d) an electrolyte in the space between the first and second substrates. A mobile charge carrier can optionally be included in the electrolyte.

In a particular embodiment of the foregoing (sometimes referred to as "design II" herein), the solar cell comprises:

(a) a first substrate comprising a first electrode;

(b) a second substrate comprising a second electrode, with the first and second substrate being positioned to form a space therebetween, and with at least one of (i) the first substrate and the first electrode and (ii) the second substrate and the second electrode being transparent;

(c) a layer of light harvesting rods electrically coupled to the first electrode, each of the light harvesting rods comprising a polymer of Formula I:

wherein:
  m is at least 1 (and typically two, three or four to twenty or more);

$X^1$ is a charge separation group having an excited-state of energy equal to or lower than that of $X^2$;

$X^2$ through $X^{m+1}$ are chromophores;

$X^1$ is electrically coupled to the first electrode; and $X^1$ through $X^{m+1}$ are selected so that, upon injection of either an electron or hole from $X^1$ into the first electrode, the corresponding hole or electron from $X^1$ is transferred to $X^2$ (and optionally to $X^3$, $X^4$, and in some cases all the way to $X^{m+1}$); the solar cell further comprising (d) an electrolyte in the space between the first and second substrates; and (e) optionally, but preferably, a mobile charge carrier in the electrolyte. In a currently preferred embodiment, $X^1$ through $X^{m+1}$ are selected so that, upon injection of an electron from $X^1$ into the first electrode, the corresponding hole from $X^1$ is transferred to $X^2$ through $X^{m+1}$.

Another particular embodiment (sometimes referred to as "design III" herein) of a solar cell as described above comprises:

(a) a first substrate comprising a first electrode;

(b) a second substrate comprising a second electrode, with the first and second substrate being positioned to form a space therebetween, and with at least one of (i) the first substrate and the first electrode and (ii) the second substrate and the second electrode being transparent;

(c) a layer of light harvesting rods electrically coupled to the first electrode, each of the light harvesting rods comprising a polymer of Formula I:

$$X^1-(X^{m+1})_m \qquad (I)$$

wherein:

m is at least 1 (and typically two, three or four to twenty or more);

$X^1$ is a charge separation group having an excited-state of energy equal to or lower than that of $X^2$;

$X^2$ through $X^{m+1}$ are chromophores;

$X^1$ is electrically coupled to the first electrode; and $X^{m+1}$ is electrically coupled to the second electrode; the solar cell further comprising (d) an electrolyte in the space between the first and second substrates. Again, $X^1$ through $X^{m+1}$ may be selected so that, upon injection of an electron or hole (preferably an electron) from $X^1$ into the first electrode, the corresponding hole or electron from $X^1$ is transferred to $X^2$, or optionally to $X^3$ or $X^4$ or all the way through $X^{m+1}$.

A variety of different electrical devices comprised of a solar cell as described above having circuits (typically resistive loads) electrically coupled thereto can be produced with the solar cells of the invention, as discussed in greater detail below.

The present invention is explained in greater detail in the drawings herein and the specification set forth below.

BRIEF DESCRIPTION OF THE DRAWINGS

FIG. 3. Energy migration along the light harvesting rod and use of a mobile charge carrier to regenerate the charge separation unit following electron injection (Design I).

FIG. 4. Energy migration and hole hopping in opposite directions (Design II).

FIG. 5. Energy migration and hole hopping in opposite directions with the light harvesting rod sandwiched between the two electrodes (Design III).

FIG. 15. Bifunctional building blocks for use in Suzuki polymerizations.

FIG. 28. In a porphyrin having an $a_{2u}$ HOMO (which has electron density predominantly at the meso positions and little at the β positions), faster rates (2.5–10-fold) are observed with linkers at the meso rather than β positions.

FIG. 29. Four different chlorin building blocks, and chlorin nomenclature showing IUPAC-IUB ring labels A–D.

FIG. 31. Pairwise interaction of chlorin building blocks upon incorporation in covalently linked arrays.

FIG. 42. Here a novel means of moving the oxidizing equivalent away from the charge-separation unit is designed. Energy flows along the light-harvesting array to the charge-separation unit, while the oxidizing equivalent (hole) flows in the reverse direction from the CSU to a site in the antenna where subsequent electron-transfer reactions can take place.

FIG. 51 illustrates reactions suitable for preparing light-harvesting rod oligomers.

FIG. 55 further illustrates the synthesis of β-substituted chlorin eastern half precursors.

DETAILED DESCRIPTION OF THE PREFERRED EMBODIMENTS

Figure 1:
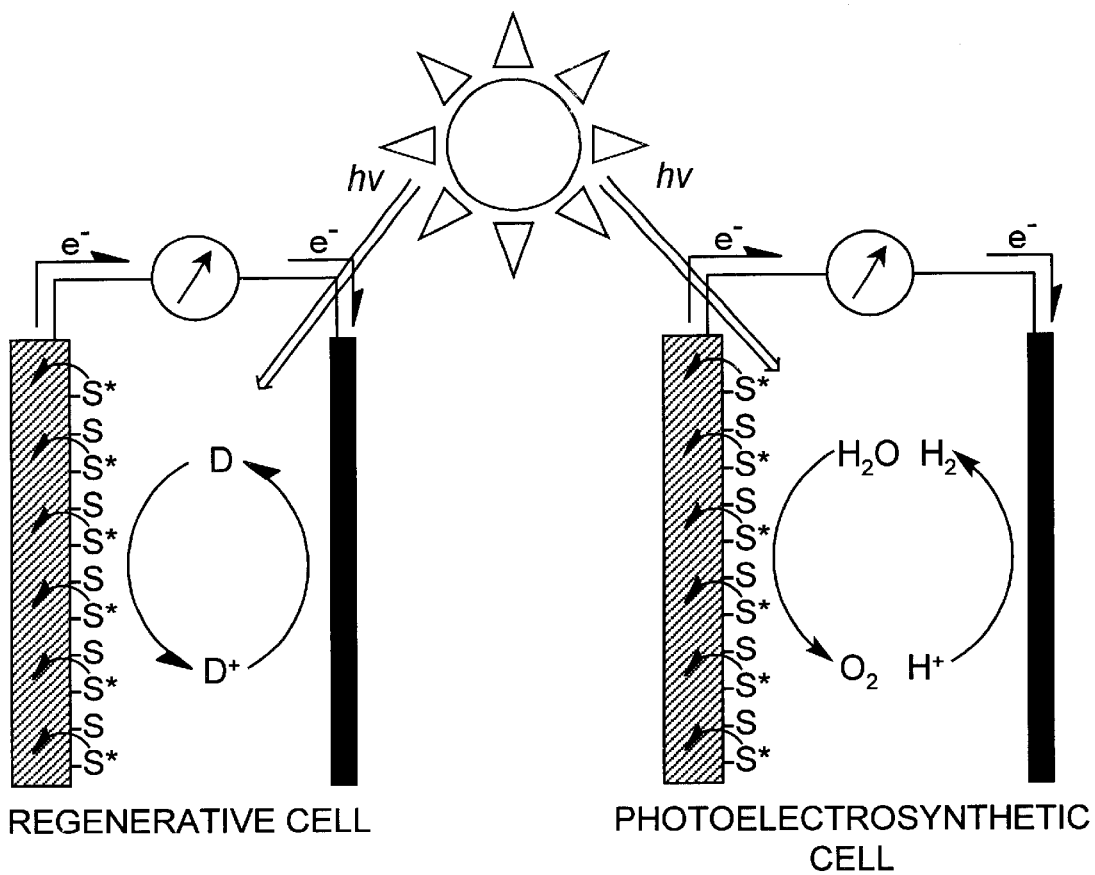
FIG. 1. Diagrams of the two common molecular approaches for light to electrical energy conversion.

The solar cells described herein entail the use of linear chromophore arrays (light harvesting rods) that provide strong absorption of light. In addition, and when desired, the solar cells described herein provide for energy migration and charge migration in opposite directions. Thus the chromophore arrays absorb light and may exhibit an intrinsic molecular level rectification in the flow of excited-state energy and ground-state holes.

Without wishing to be limiting of the invention, it is noted that some potential advantages of the solar cells described herein include the following: thin (e.g, rods not greater than 500 or even 200 nanometers in length), lightweight, portable, flexible, good efficiency, solid-state (in one embodiment), ease of fabrication, and rational molecular design. Indeed, it is contemplated that the invention described herein will permit, where desired, quantitative conversion of incident photons to electrons at individual wavelengths of light and global efficiencies >5% under solar illumination.

I. Definitions

The following terms and phrases are used herein: A substrate as used herein is preferably a solid material (which may be flexible or rigid) suitable for the attachment of one or more molecules. Substrates can be formed of materials including, but not limited to glass, organic polymers, plastic, silicon, minerals (e.g. quartz), semiconducting materials, ceramics, metals, etc. The substrate may be in any suitable shape, including flat, planar, curved, rod-shaped, etc. The substrate may be inherently conductive and serve itself as an electrode, or an electrode may be formed on or connected to the substrate by any suitable means (e.g., deposition of a gold layer or a conductive oxide layer). Either or both of the substrates in the solar cells may be transparent (that is, wavelengths of light that excite the chromophores can pass through the substrate and corresponding electrode, even if they are visually opaque). In light-harvesting arrays, the substrate and electrode may be of any suitable type. One of the substrates may be opaque with respect to the wavelengths of light that excite the chromophores. One of the substrates may be reflective or provided with a reflective coating so that light that passes through the arrays or rods is reflected back to the arrays or rods.

The term "electrode" refers to any medium capable of transporting charge (e.g. electrons) to and/or from a light harvesting rod. Preferred electrodes are metals (e.g., gold, aluminum), non-metals (e.g., conductive oxides, carbides, sulfide, selinides, tellurides, phosphides, and arsenides such as cadmium sulfide, cadmium telluride, tungsten diselinide, gallium arsenide, gallium phosphide, etc.), and conductive organic molecules. The electrodes can be manufactured to virtually any 2-dimensional or 3-dimensional shape.

The term "conductive oxide" as used herein refers to any suitable conductive oxide including binary metal oxides such as tin oxide, indium oxide, titanium oxide, copper oxide, and zinc oxide, or ternary metal oxides such as strontium titanate and barium titanate. Other examples of suitable conductive oxides include but are not limited to indium tin oxide, titanium dioxide, tin oxide, gallium indium oxide, zinc oxide, and zinc indium oxide. The metal oxide semiconductors may be intrinsic or doped, with trace amounts of materials, to control conductivity.

The term "heterocyclic ligand" as used herein generally refers to any heterocyclic molecule consisting of carbon atoms containing at least one, and preferably a plurality of, hetero atoms (e.g., N, O, S, Se, Te), which hetero atoms may be the same or different, and which molecule is capable of forming a sandwich coordination compound with another heterocyclic ligand (which may be the same or different) and a metal. Such heterocyclic ligands are typically macrocycles, particularly tetrapyrrole derivatives such as the phthalocyanines, porphyrins, and porphyrazines.

The term "porphyrinic macrocycle" refers to a porphyrin or porphyrin derivative. Such derivatives include porphyrins with extra rings ortho-fused, or ortho-perifused, to the porphyrin nucleus, porphyrins having a replacement of one or more carbon atoms of the porphyrin ring by an atom of another element (skeletal replacement), derivatives having a replacement of a nitrogen atom of the porphyrin ring by an atom of another element (skeletal replacement of nitrogen), derivatives having substituents other than hydrogen located at the peripheral (meso-, β-) or core atoms of the porphyrin, derivatives with saturation of one or more bonds of the porphyrin (hydroporphyrins, e.g., chlorins, bacteriochlorins, isobacteriochlorins, decahydroporphyrins, corphins, pyrrocorphins, etc.), derivatives obtained by coordination of one or more metals to one or more porphyrin atoms (metalloporphyrins), derivatives having one or more atoms, including pyrrolic and pyrromethenyl units, inserted in the porphyrin ring (expanded porphyrins), derivatives having one or more groups removed from the porphyrin ring (contracted porphyrins, e.g., corrin, corrole) and combinations of the foregoing derivatives (e.g. phthalocyanines, porphyrazines, naphthalocyanines, subphthalocyanines, and porphyrin isomers). Preferred porphyrinic macrocycles comprise at least one 5-membered ring.

The term porphyrin refers to a cyclic structure typically composed of four pyrrole rings together with four nitrogen atoms and two replaceable hydrogens for which various metal atoms can readily be substituted. A typical porphyrin is hemin.

A "chlorin" is essentially the same as a porphyrin, but differs from a porphyrin in having one partially saturated pyrrole ring. The basic chromophore of chlorophyll, the green pigment of plant photosynthesis, is a chlorin.

A "bacteriochlorin" is essentially the same as a porphyrin, but differs from a porphyrin in having two partially saturated non-adjacent (i.e., trans) pyrrole rings.

An "isobacteriochlorin" is essentially the same as a porphyrin, but differs from a porphyrin in having two partially saturated adjacent (i.e., cis) pyrrole rings.

The terms "sandwich coordination compound" or "sandwich coordination complex" refer to a compound of the formula $L_n M_{n-1}$, where each L is a heterocyclic ligand such as a porphyrinic macrocycle, each M is a metal, n is 2 or more, most preferably 2 or 3, and each metal is positioned between a pair of ligands and bonded to one or more hetero atom (and typically a plurality of hetero atoms, e.g., 2, 3, 4, 5) in each ligand (depending upon the oxidation state of the metal). Thus sandwich coordination compounds are not organometallic compounds such as ferrocene, in which the metal is bonded to carbon atoms. The ligands in the sandwich coordination compound are generally arranged in a stacked orientation (i.e., are generally cofacially oriented and axially aligned with one another, although they may or may not be rotated about that axis with respect to one another). See, e.g., D. Ng and J. Jiang, *Chem. Soc. Rev.* 26, 433–442 (1997). Sandwich coordination compounds may be "homoleptic" (wherein all of the ligands L are the same) or "heteroleptic" (wherein at least one ligand L is different from the other ligands therein).

The term "double-decker sandwich coordination compound" refers to a sandwich coordination compound as described above where n is 2, thus having the formula $L^1 — M^1 — L^2$, wherein each of $L^1$ and $L^2$ may be the same or different. See, e.g., J. Jiang et al., *J. Porphyrins Phthalocyanines* 3, 322–328 (1999).

The term "multiporphyrin array" refers to a discrete number of two or more covalently-linked porphyrinic macrocycles. The multiporphyrin arrays can be linear, cyclic, or branched, but are preferably linear herein. Light harvesting rods herein are preferably multiporphyrin arrays. The light harvesting rods or multiporphyrin arrays may be linear (that is, all porphyrinic macrocycles may be linked in trans) or may contain one or more bends or "kinks" (for example, by including one or more non-linear linkers in a light-harvesting rod, or by including one or more cis-substituted porphyrinic macrocycles in the light harvesting rod) Some of the porphyrinic macrocycles may further include additional ligands, particularly porphyrinic macrocycles, to form sandwich coordination compounds as described further below. The rods optionally but preferably are oriented substantially perpendicularly to either, and most preferably both, of the first and second electrodes.

"Chromophore" means a light-absorbing unit which can be a unit within a molecule or can comprise the entire molecule. Typically a chromophore is a conjugated system (alternating double and single bonds which can include non-bonded electrons but is not restricted to alternating double and single bonds since triple and single bonds, since mixtures of alternating triple/double and single bonds also constitute chromophores. A double or triple bond alone constitutes a chromophore. Heteroatoms can be included in a chromophore.). Examples of chromophores include the cyclic 18 pi-electron conjugated system that imparts color to porphyrinic pigments, the linear system of alternating double and single bonds in the visual pigment retinal, or the carbonyl group in acetone.

"Charge separation group" and "charge separation unit" refer to molecular entities that upon excitation (by direct absorption or energy transfer from another absorber) displace an electron to another part of the same molecule, or transfer an electron to a different molecule, semiconductor, or metal. The "charge separation group" and "charge separation unit" results in storage of some fraction of the excited state energy upon displacement or transfer of an electron. Typically the "charge separation group" and "charge separation unit" is located at the terminus of a light-harvesting array or rod, from which excited-state energy is received. The "charge separation group" and "charge separation unit" facilitates or causes conversion of the excited-state energy into a separate electron and hole or an electron-hole pair. The electron can be injected into the semiconductor by the "charge separation group" or "charge separation unit". It is feasible that the "charge separation group" and "charge separation unit" could extract an electron from a different molecule or semiconductor, thereby creating a negative charge on the "charge separation group" and "charge separation unit" and a hole in the other molecule or semiconductor. The reaction center of bacterial photosynthesis is a premier example of a "charge separation group" or "charge separation unit". Synthetic porphyrin-quinone or porphyrin-buckyball molecules also function to absorb light and utilize the resulting energy to separate charge.

The term "substituent" as used in the formulas herein, particularly designated by S or $S^n$ where n is an integer, in a preferred embodiment refer to electron-rich or electron-deficient groups (subunits) that can be used to adjust the redox potential(s) of the subject compound. Preferred substituents include, but are not limited to, H, aryl, phenyl, cycloalkyl, alkyl, halogen, alkoxy, alkylthio, perfluoroalkyl, perfluoroaryl, pyridyl, cyano, thiocyanato, nitro, amino, alkylamino, acyl, sulfoxyl, sulfonyl, amido, and carbamoyl. In preferred embodiments, a substituted aryl group is attached to a porphyrin or a porphyrinic macrocycle, and the substituents on the aryl group are selected from the group consisting of aryl, phenyl, cycloalkyl, alkyl, halogen, alkoxy, alkylthio, perfluoroalkyl, perfluoroaryl, pyridyl, cyano, thiocyanato, nitro, amino, alkylamino, acyl, sulfoxyl, sulfonyl, amido, and carbamoyl. Additional substituents include, but are not limited to, 4-chlorophenyl, 4-trifluoromethylphenyl, and 4-methoxyphenyl. Preferred substituents provide a redox potential range of less than about 5 volts, preferably less than about 2 volts, more preferably less than about 1 volt.

The term "aryl" refers to a compound whose molecules have the ring structure characteristic of benzene, naphthalene, phenanthrene, anthracene, etc. (i.e., either the 6-carbon ring of benzene or the condensed 6-carbon rings of the other aromatic derivatives). For example, an aryl group may be phenyl ($C_6H_5$) or naphthyl ($C_{10}H_7$). It is recognized that the aryl group, while acting as substituent can itself have additional substituents (e.g. the substituents provided for $S^n$ in the various formulas herein).

The term "alkyl" refers to a paraffinic hydrocarbon group which may be derived from an alkane by dropping one hydrogen from the formula. Examples are methyl ($CH_3$—), ethyl ($C_2H_5$—), propyl ($CH_3CH_2CH_2$—), isopropyl (($CH_3$)$_2CH$—).

The term "halogen" refers to one of the electronegative elements of group VIIA of the periodic table (fluorine, chlorine, bromine, iodine, astatine).

The term "perfluoroalkyl" refers to an alkyl group where every hydrogen atom is replaced with a fluorine atom.

The term "perfluoroaryl" refers to an aryl group where every hydrogen atom is replaced with a fluorine atom.

The term "pyridyl" refers to an aryl group where one CR unit is replaced with a nitrogen atom.

The term "sulfoxyl" refers to a group of composition RS(O)— where R is some alkyl, aryl, cycloalkyl, perfluoroalkyl, or perfluoroaryl group. Examples include, but are not limited to methylsulfoxyl, phenylsulfoxyl, etc.

The term "sulfonyl" refers to a group of composition $RSO_2$— where R is some alkyl, aryl, cycloalkyl, perfluoroalkyl, or perfluoroaryl group. Examples include, but are not limited to methylsulfonyl, phenylsulfonyl, p-toluenesulfonyl, etc.

The term "carbamoyl" refers to the group of composition $R^1(R^2)NC(O)$— where $R^1$ and $R^2$ are H or some alkyl, aryl, cycloalkyl, perfluoroalkyl, or perfluoroaryl group. Examples include, but are not limited to N-ethylcarbamoyl, N,N-dimethylcarbamoyl, etc.

The term "amido" refers to the group of composition $R^1CON(R^2)$— where $R^1$ and $R^2$ are H or some alkyl, aryl, cycloalkyl, perfluoroalkyl, or perfluoroaryl group. Examples include, but are not limited to acetamido, N-ethylbenzamido, etc.

The term "acyl" refers to an organic acid group in which the —OH of the carboxyl group is replaced by some other substituent (RCO—). Examples include, but are not limited to acetyl, benzoyl, etc.

In preferred embodiments, when a metal is designated by "M" or "$M^n$", where n is an integer, it is recognized that the metal may be associated with a counterion.

A linker is a molecule used to couple two different molecules, two subunits of a molecule, or a molecule to a substrate. When all are covalently linked, they form units of a single molecule.

The term "electrically coupled" when used with reference to a light harvesting rod and electrode, or to chromophores, charge separation groups and electrodes, refers to an association between that group or molecule and the coupled group or electrode such that electrons move from the storage medium/molecule to the electrode or from the electrode to the molecule and thereby alter the oxidation state of the storage molecule. Electrical coupling can include direct covalent linkage between the storage medium/molecule and the electrode, indirect covalent coupling (e.g. via a linker), direct or indirect ionic bonding between the storage medium/molecule and the electrode, or other bonding (e.g. hydrophobic bonding). In addition, no actual bonding may be required and the light harvesting rod may simply be contacted with the electrode surface. There also need not necessarily be any contact between the electrode and the light harvesting rod where the electrode is sufficiently close to the light harvesting rod to permit electron tunneling between the medium/molecule and the electrode.

"Excited-state energy" refers to the energy stored in the chromophore in a metastable state following absorption of light (or transfer of energy from an absorber). For an excited singlet (triplet) state, the magnitude of the "excited-state energy" is estimated by energy of the shortest wavelength fluorescence (phosphorescence) band. The magnitude of the "excited-state energy" is greater than or equal to the energy of the separated electron and hole following charge separation.

Electrolytes used to carry out the present invention may be aqueous or non-aqueous electrolytes, including polymer electrolytes. The electrolyte may comprise or consist of a solid, in which latter case the solar cell can be produced devoid of liquid in the space between the first and second substrates. The electrolyte consists of or comprises a substance that increases the electrical conductivity of a carrier medium. Most electrolytes are salts or ionic compounds.

Examples include sodium chloride (table salt), lithium iodide, or potassium bromide in water; tetrabutylammonium hexafluorophosphate or tetraethylammonium perchlorate in acetonitrile or dichloromethane; or an ionic polymer in a gel.

"Mobile charge carriers" refers to an ion, molecule, or other species capable of translating charges (electrons or holes) between the two electrodes in a solar cell. Examples include quinones in water, molten salts, and iodide in a polymer gel such as polyacrylonitrile. Examples of mobile charge carriers include, but are not limited to, iodide, bromide, tetramethyl-1,4-phenylenediamine, tetraphenyl-1, 4-phenylenediamine, p-benzoquinone, $C_{60}$, $C_{70}$, pentacene, tetrathiafulvalene, and methyl viologen.

II. Solar Cells Containing Light-harvesting Rods
A. Introduction.

Figure 2:
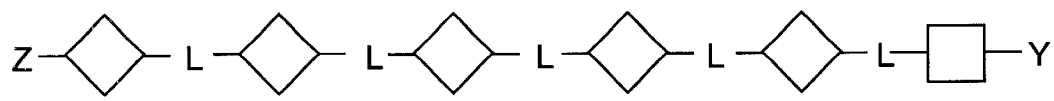
FIG. 2. General diagram of linear chromophore arrays (light harvesting rods).

The objective of developing an ultrathin solar cell with high absorption coefficient is met with the use of linear chromophore arrays that serve as light-harvesting (LH) rods. The generic design of linear chromophore arrays is shown in FIG. 2. The pigments (i.e., chromophore-containing molecules) are joined covalently via linkers to create the linear architecture. At one end of the array is situated the sensitizer or charge-separation unit (CSU). The CSU is also attached to the electrode via a linker and functional group designated by Y. At the distal end of the light-harvesting rod is a capping group designated by Z. The capping group can consist of a simple alkyl or aryl substituent, or can comprise a linker for attachment to a surface or counterelectrode. Upon attachment of the linear LH/CSU molecules to the electrode via attachment group Y, the rods will orient in a more or less vertical fashion. In so doing, the linear rod-like architecture enables a multilayer stack of pigments where each pigment in a rod is held apart from the neighboring pigments in the same rod via linker L. The packing patterns and distances between rods are controlled by substituents integral to the pigments. Generically these are referred to as "chromophore arrays", a term used interchangeably with linear light-harvesting rods (both terms indicate a linear architecture of linked pigments that absorb light efficiently and funnel energy (and holes) in a controlled manner). Note that the terms sensitizer or charge-separation are used unit interchangeably; the latter emphasizes the fact that the photoexcited agent (sensitizer) that injects the electron into the semiconductor can be comprised of multiple units (e.g., porphyrin-chlorin, chlorin-quinone, bacteriochlorin-buckyball).

Three distinct designs are described for the chromophore arrays (vide infia). Implicit in all the design schemes is that fact that the arrays will harvest a large fraction of incident solar irradiation. The strategy of employing a monolayer of molecular sensitizers on a planar electrode surface has historically been flawed because of the small fraction of incident solar light that is absorbed. The described invention conceptualizes a new molecular approach wherein the prefabricated chromophore arrays will be organized on an electrode surface. By assembling the arrays perpendicular to the electrode surface, monolayer coverages will result in significantly increased light absorption. For example, phthalocyanines typically have extinction coefficients of ~250, 000 $M^{-1}cm^{-1}$ in the red part of the visible region (600–700 nm depending on metalation state). A monolayer of such phthalocyanines on a flat surface corresponds to ~$10^{-10}$ mol/cm$^2$ and will absorb about 5.6% of the incident light. An array of 20 phthalocyanines with additive absorption (i.e., no new absorption bands due to aggregation and/or electronic interactions) spatially arranged to occupy the same surface area would absorb 68% of the incident light. If the number of phthalocyanines was increased to 40, or the surface roughness factor of the electrode was two, 90% of the incident light would be absorbed. Many electrode surfaces are inherently rough so that a monolayer of 20-chromophore arrays (i.e., arrays each comprised of 20 chromophores) would result in essentially quantitative light absorption. This projection compares very favorably with the surface roughness factor of ~1000 necessary for efficient light harvesting, as is currently employed in the Gratzel-type cells.

In Design I, the LH/CSU rods are attached to one electrode via attachment group Y (FIG. 3). The cell includes mobile (i.e., diffusive) charge carriers. The linear LH rods, generally comprising 5–20 pigments, absorb light. Excitation energy transfer among pigments in the rod, by through-space and/or through-bond mechanisms, results in energy reaching the CSU (illustrated in step 2, FIG. 3). The excited CSU then injects an electron into the conduction band of the electrode (step 4). The resulting hole resides on the CSU and cannot migrate into the LH rod because the oxidation potential of the CSU is lower than that of the immediately adjacent pigments in the LH rod. Diffusion of a mobile charge carrier in close proximity of the oxidized CSU results in electron/hole transfer, regenerating the CSU and leaving the hole on the mobile charge carrier. The hole then moves by diffusion of the mobile charge carrier and/or subsequent hole-transfer processes among mobile charge carriers until the counterelectrode is reached at the distal end of the LH rod (near Z; not shown).

In Design II, the LH/CSU rods are attached to one electrode via attachment group Y (FIG. 4). The cell includes mobile (i.e., diffusive) charge carriers. All features are the same as in Design I with the exception that the hole formed in the CSU (upon electron injection into the electrode) can migrate into the linear LH rod. This has two consequences. (1) The lifetime of the charge-separated state is increased giving a commensurate decrease in charge recombination processes at the CSU-electrode interface. (2) The mobile charge carriers can access the hole at sites distant from the electrode surface. Sites distant from the surface are anticipated to be more accessible thereby facilitating hole transfer and migration (via diffusion) to the counterelectrode.

In Design III, the LH/CSU rods are attached to one electrode via attachment group Y (FIG. 5). The opposite end of each rod is attached to the counterelectrode. No mobile (i.e., diffusive) charge carriers are present in the cell (though an electrolyte can be present). Absorption of light, energy migration among pigments, and electron transfer at the CSU occur identically with those processes in Designs I and II. However, the hole in the CSU resulting from electron injection into the electrode migrates by hole-hopping among pigments in the LH rod and then transfers to the counterelectrode. There are several ramifications to this design. (1) No diffusive charge carriers are present in the cell. (2) Only two distinct access channels are required at the CSU; one for electron transfer to the electrode, and one provided by the LH rod for transfer in of excitation energy and transfer out of the resulting holes. In contrast, Design I requires three access channels at the CSU, one for inward migration of energy, one for outward transfer of an electron, and one for the mobile charge carrier to gain access to the hole. The absence of mobile charge carriers in Design III results in a solid-state solar cell.

In prior studies of light-harvesting phenomena, star-shaped arrays comprised of porphyrins and phthalocyanines have been created (Li, J.; Lindsey, J. S. *J. Org. Chem.* 1999, 64, 9101–9108; Li, J et al., *J. Org. Chem.* 1999, 64, 9090–9100; Li, F. et al., *J. Mater. Chem.* 1997, 7, 1245–1262), a cluster of boron-dipyrrin dyes surrounding a porphyrin (Li, F. et al *J. Am. Chem. Soc.* 1998, 120, 10001–10017), and a linear array of four porphyrins and one boron-dipyrrin (Wagner, R. W.; Lindsey, J. S. *J Am. Chem. Soc.* 1994, 116, 9759–9760), and cyclic arrays (Li, J. et al., *J. Am. Chem. Soc.* 1999, 121, 8927–8940). The effects of different metals in metalloporphyrins in modulating the rate of energy transfer also has been studied (Hascoat, P. et al., *Inorg. Chem.* 1999, 38, 4849–4853). Also, the effects of different linkers on the rate of energy transfer (Hsiao, J.-S. et al., *J. Am. Chem. Soc.* 1996, 118, 11181–11193; Yang, S. I. et al., *J. Phys. Chem.* 1998, 102, 9426–9436), orbital composition (Strachan, J. P. et al., *J. Am. Chem. Soc.* 1997, 119, 11191–11201), and the position of location of the linker on the porphyrinic pigment (Yang, S. I. et al., *J. Am. Chem. Soc.* 1999, 121, 4008–4018) have been characterized. Simulations of energy migration in linear chromophore arrays also have been performed to evaluate the performance of various molecular architectural designs (Van Patten, P. G. et al., *J. Phys. Chem. B* 1998, 102, 4209–4216). These synthetic light-harvesting molecules absorb strongly in the visible region and undergo highly efficient energy transfer. As part of these studies, examination of the properties of the oxidized complexes revealed rapid hole-hopping among the components (Seth, J. et al., *J. Am. Chem. Soc.* 1994, 116, 10578–10592; Seth, J. et al., *J. Am. Chem. Soc.* 1996, 118, 11194–11207). The features herein proposed to elicit in the design of the linear chromophoric arrays described in this invention are supported, but not at all anticipated, in this body of prior work. The synthetic methods for preparing light-harvesting arrays are sufficient for someone skilled in the art to prepare the molecules described herein. In particular, there are extensive methods for preparing porphyrin building blocks (a) Lindsey, J. S. et al., *Tetrahedron* 1994, 50, 8941–8968. (b) Lindsey, J. S. In *The Porphyrin Handbook*; Kadish, K. M.; Smith, K. M.; Guilard, R., Eds.; Academic Press, San Diego, Calif. 2000, Vol. 1, pp 45–118; Cho, W.-S. et al., *J. Org. Chem.* 1999, 64, 7890–7901; Wagner, R. W. et al., *J. Am. Chem. Soc.* 1996, 118, 11166–11180; Balasubramanian, T.; Lindsey, J. S. *Tetrahedron* 1999, 55, 6771–6784), chlorin building blocks (Strachan, J. P. et al., *J. Org. Chem.* 2000, 65, 3160–3172), phthalocyanines (Yang, S. I. et al., *J. Mater. Chem.* 2000, 10, 283–297; Tomoda, H. et al., *Chem. Lett.* 1980, 1277–1280; Tomoda, H. et al., *Chem. Lett.* 1983, 313–316), and related chromophores (Wagner, R. W.; Lindsey, J. S. *Pure Appl. Chem.* 1996, 68, 1373–1380). Methods for joining the chromophore-containing (i.e., pigment) building blocks into the linear arrays also have been established (Wagner, R. W. et al., *J. Org. Chem.* 1995, 60, 5266–5273; DiMagno, S. G. et al., *J. Org. Chem.* 1993, 58, 5983–5993; Wagner, R. W. et al., *Chem. Mater.* 1999, 11, 2974–2983), which include but are not limited to Pd-mediated coupling methods. More elaborate architectures comprised of light-harvesting arrays and a charge-separation unit have been synthesized that show very high efficiency (Kuciauskas, D. et al., *J. Am. Chem. Soc.* 1999, 121, 8604–8614).

B. Components.

The key requirements for light-harvesting pigments are intense absorption in the visible region, a narrow distribution of energies of the excited state (marked by sharp absorption and fluorescence bands), an excited singlet-state lifetime sufficient for energy transfer (typically a few nanoseconds), and compatibility with the synthetic building block approach giving rise to a linear architecture. The pigments of choice for use in the linear LH rods are drawn from the porphyrinic family (tetrapyrrole macrocycles). Examples include porphyrins, chlorins, bacteriochlorins, tetraazaporphyrins (porphyrazines), phthalocyanines, naphthalocyanines, and derivatives of these compounds. The porphyrinic pigments can be supplemented with accessory pigments such as members of the perylene, lycopene, xanthene, and dipyrromethene families. The absorption spectra of such pigments are well known to those skilled in the art and can be looked up in various reference sources (Du, H. et al., *Photochem. Photobiol.* 1998, 68, 141–142).

The important requirements for the linkers joining the pigments are as follows. (1) Support rapid excited-state energy-transfer processes (through-bond and/or through-space), (2) support ground-state hole-hopping processes in some cases (Designs II and III), and (3) afford compatibility with the synthetic building block approach giving rise to a linear arrangement of pigments. The linkers of choice for joining the pigments in the linear LH rods include 4,4'-diphenylethyne, 4,4'-diphenylbutadiyne, 4,4'-biphenyl, 1,4-phenylene, 4,4'-stilbene, 1,4-bicyclooctane, 4,4'-azobenzene, 4,4'-benzylideneaniline, 4,4"-terphenyl, and no linker (i.e., a direct C—C bond). The p,p'-diphenylethyne and p-phenylene linkers have been shown to support rapid excited-state energy transfer and ground-state hole-hopping processes among porphyrinic molecules.

Figure 6:
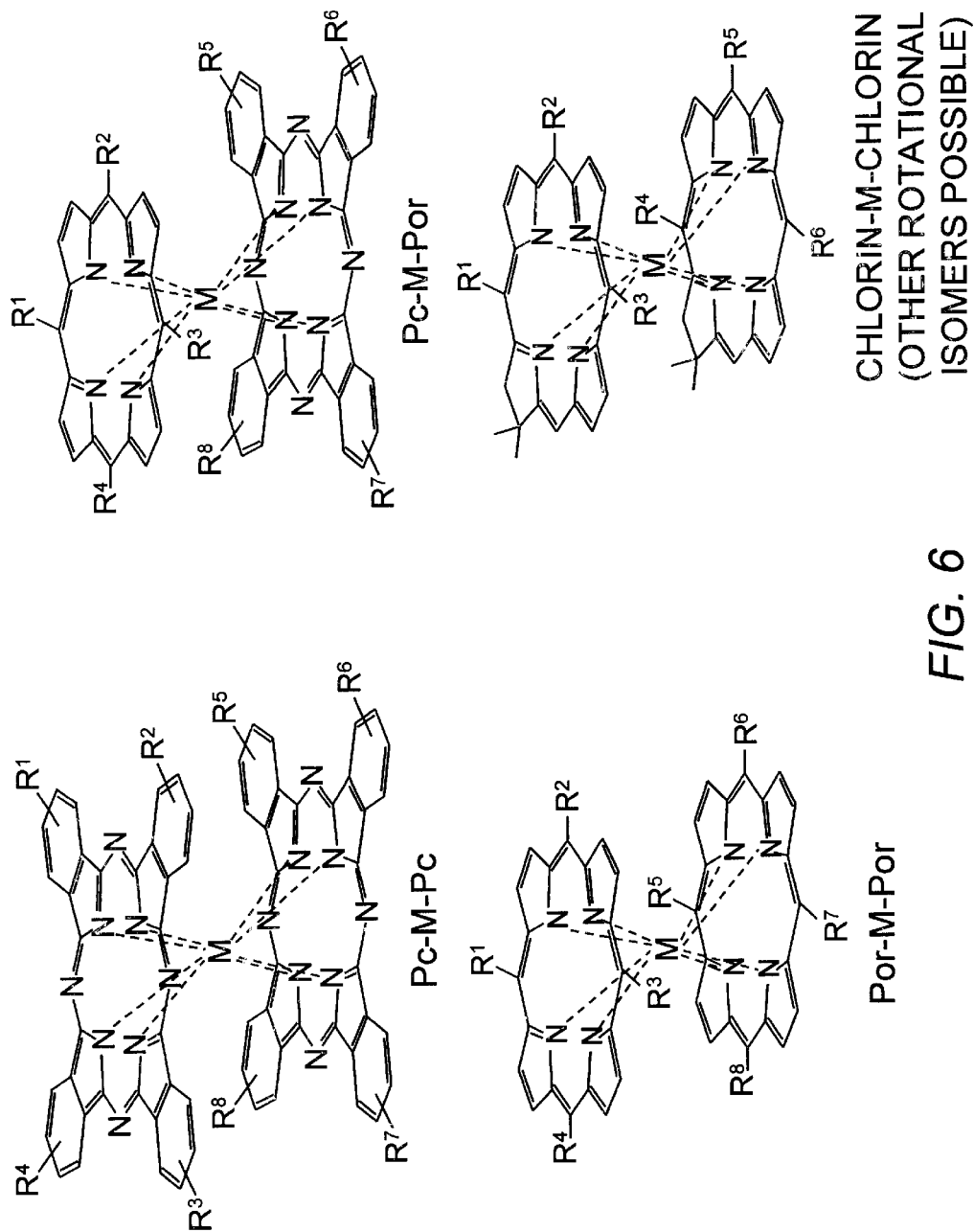
FIG. 6. Double-decker sandwich molecules that may serve as sensitizers.

One important requirement for the charge-separation unit (CSU) is to have an excited-state of energy equal to or lower than that of the adjacent pigments in the LH array (in other words, absorb light at wavelengths equal to or longer than that of the pigments in the LH array). For semiconductor based solar cells the excited-state reduction potential must be greater than the conduction band edge. Additional requirements for the CSU are to undergo rapid excited-state electron transfer, have sufficient energy to inject an electron into the conduction band of the electrode, and afford a stable radical cation. Molecules of choice for the CSU also are drawn from the porphyrinic family, including porphyrins, chlorins, bacteriochlorins, tetraazaporphyrins (porphyrazines), phthalocyanines, naphthalocyanines, and derivatives of these compounds. A particularly attractive group of derivatives is comprised of the double-decker sandwich molecules with a central metal such as zirconium (Kim, K. et al., *Inorg. Chem.* 1991, 30, 2652–2656; Girolami, G. S. et al., *Inorg. Chem.* 1994, 33, 626–627; Girolami, G. S. et al., *Angew. Chem. Int. Ed. Engl.* 1996, 35, 1223–1225; Collman, J. P. et al., *Inorg. Chem.* 1997, 36, 5603–5608). Examples of double-decker sandwich molecules are shown in FIG. 6. Such double deckers can be formed from any of the ligands in the family of tetrapyrrole macrocycles.

In the porphyrinic family the electrochemical potential of a given porphyrin can be tuned over quite a wide range by incorporation of electron-withdrawing or electron-releasing substituents (Yang, S. I. et al., *J. Porphyrins Phthalocyanines* 1999, 3, 117–147). Examples of such substituents include aryl, phenyl, cycloalkyl, alkyl, halogen, alkoxy, alkylthio, perfluoroalkyl, perfluoroaryl, pyridyl, cyano, thiocyanato, nitro, amino, N-alkylamino, acyl, sulfoxyl, sulfonyl, imido, amido, and carbamoyl. With monomeric porphyrins variation in electrochemical potential can also be achieved with different central metals (Fuhrhop, J.-H.; Mauzerall, D. *J. Am. Chem. Soc.* 1969, 91, 4174–4181). A wide variety of metals can be incorporated in porphyrins. Those metals that are photochemically active include Zn, Mg, Al, Sn, Cd, Au, Pd, and Pt. It is understood that some metals carry a counterion. Porphyrins generally form very stable radical cations (Felton, R. H. In *The Porphyrins*; Dolphin, D., Ed.; Academic Press: New York, 1978; Vol. V, pp 53–126).

The linkers joining the CSU to the electrode surface provide a linear architecture, support through-space and/or through-bond electron transfer, and have a functional group suitable for attachment to the electrode. Examples of suitable functional groups include ester, carboxylic acid, boronic acid, thiol, phenol, silane, hydroxy, sulfonic acid, phosphonic acid, alkylthiol, etc. The linkers can consist of 4,4'-diphenylethyne, 4,4'-diphenylbutadiyne, 4,4'-biphenyl, 1,4-phenylene, 4,4'-stilbene, 1,4-bicyclooctane, 4,4'-azobenzene, 4,4'-benzylideneaniline, 4,4"-terphenyl, 1,3-phenyl, 3,4'-diphenylethyne, 3,4'-diphenylbutadiyne, 3,4'-biphenyl, 3,4'-stilbene, 3,4'-azobenzene, 3,4'-benzylideneaniline, 3,4"-terphenyl, etc.

C. Materials.

The innovation of synthesizing chromophoric arrays designed to vectorially translate energy and charge when assembled on electrode surfaces will allow conductive materials to be used as the substrates for solar energy conversion devices. This diversity of materials allows for the development of designer solar cells for specific applications, some of which are described above. Below the materials and solar energy conversion mechanisms (Designs I–III) that are expected to yield improved conversion efficiencies are described.

1. Semiconductor-Chromophoric Array Junctions. Anodic photocurrent generation is the most common and efficient mechanism by which solar energy can be harvested at semiconductors with molecular chromophores (Gerischer, H. *Photochem. Photobiol.* 1972, 16, 243; Gerischer, H. *Pure Appl. Chem.* 1980, 52, 2649; Gerischer, H.; Willig, F. *Top. Curr. Chem.* 1976, 61, 31). Semiconducting materials such as $TiO_2$ (rutile or anatase), ZnO, $SrTiO_3$, $SnO_2$ and $In_2O_3$ are thermodynamically stable and can be processed as thin films, polycrystalline substrates, colloidal particle thin films, or single crystals with high transparency in the visible region. The large band gap (>3 eV) assures that direct excitation of the semiconductor will be minimal for terrestrial applications. Further, materials such as $SnO_2$ are commercially available on flexible polymeric substrates.

Figure 7:
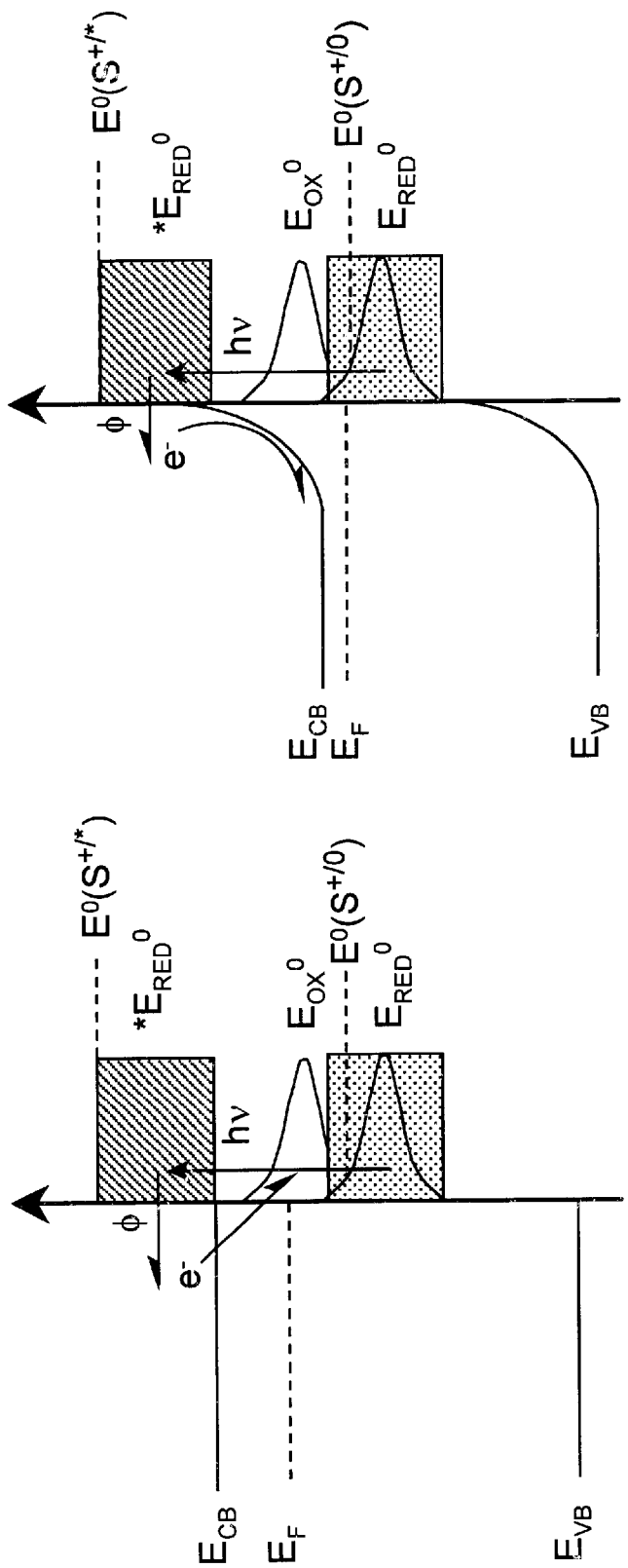
FIG. 7. Sensitization mechanisms for an n-type semiconductor by a sensitizer S. Here $E_{CB}$ and $E_{VB}$ are the semiconductor conduction band and valence band edge, respectively. $E_f$ is the Fermi-level of the semiconductor. $E_o(S^{+/0})$ and $E^o(S^{+/*})$ are the formal reduction potentials of the ground and excited state, respectively. Gerischer's distributions of sensitizer donor and acceptor levels are also shown.

A pictorial representation of a Gerischer-type diagram for the commonly accepted mechanism is given in FIG. 7 for a molecular sensitizer, S. For the case shown the excited-state reduction potential lies above the conduction band edge by an amount greater than the reorganization energy $[E°(S^{+/*})-\lambda > E_{CB}]$. This energetic positioning results in maximum overlap of the sensitizer excited-state donor levels and the semiconductor conduction band continuum, which in turn gives rise to the maximum electron-transfer rate, i.e. activationless interfacial electron transfer. The excess energy of the injected electron is dissipated through lattice vibrations (phonons) as the electron thermalizes to the conduction band edge. Injection of the electron therefore is irreversible, and indeed, repopulation of the excited state has never been observed.

The fate of the injected electron is expected to depend on the bias condition of the semiconductor. If injection occurs when the semiconductor is near the flat band condition (a in FIG. 7), then rapid recombination with the oxidized dye is expected because there is no electric field region to assist the spatial separation of the injected electron and oxidized hole. If the semiconductor is under depletion conditions, then the injected electron is swept toward the bulk by the surface electric field and recombination is inhibited (b in FIG. 7). Therefore, the current onset in photocurrent-voltage measurement can be taken as a crude estimation of the flat band potential. The enhanced lifetime of the charge-separated state at molecular-semiconductor interfaces under depletion conditions allows the sensitizer to be regenerated by an external electron donor for applications in regenerative solar cells.

Figure 8:
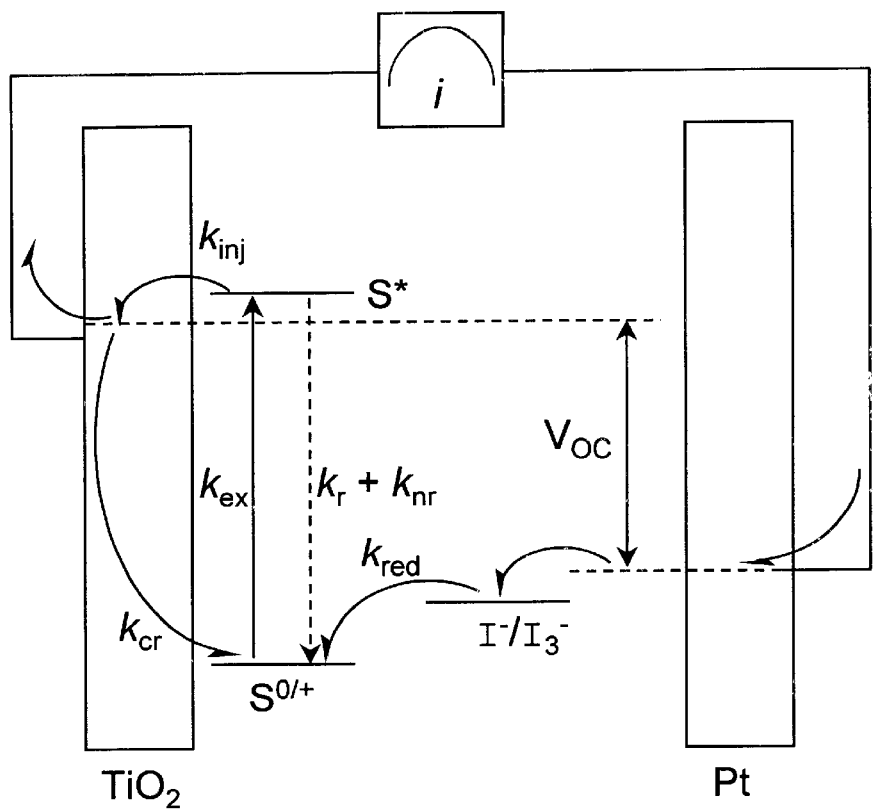
FIG. 8. Simplified representation of the sensitization mechanism of $TiO_2$ by a sensitizer S. Light excitation of the sensitizer forms an excited state S*, which injects an electron injection into the semiconductor with rate constant, $k_{inj}$. The oxidized sensitizer, $S^+$, is then regenerated by an external electron donor (e.g., iodide), with rate constant $k_{red}$. The $V_{oc}$ is the open-circuit photovoltage, which represents the maximum Gibbs free energy that can be abstracted from the cell under conditions of constant illumination. Competing with power production is charge recombination, $k_{cr}$, that can occur (from the semiconductor) to the oxidized sensitizer or the oxidized product of the mobile charge carrier (e.g., triiodide).

A simplified regenerative solar cell based on a molecular sensitizer on an n-type semiconductor is shown schematically in FIG. 8. An excited sensitizer, S*, injects an electron into the semiconductor, with rate constant $k_{inj}$. The oxidized dye molecule accepts an electron from a donor (i.e., mobile charge carrier) present in the electrolyte, $k_{red}$. Iodide is the donor shown in the Figure. The iodide oxidation products are reduced at the dark cathode. The net process allows an electrical current to be generated with light of lower energy than the semiconductor bandgap with no net chemistry. Charge recombination, $k_{cr}$, can occur to the oxidized sensitizer, $S^+$, or an oxidized donor species. The donor shown is iodide, which can be dispersed in water, organic solvent, or polymeric gels. Alternative redox active electrolytes include $Br^-/Br_2$, quinone/hydroquinone, and inorganic coordination compounds.

Figure 9:
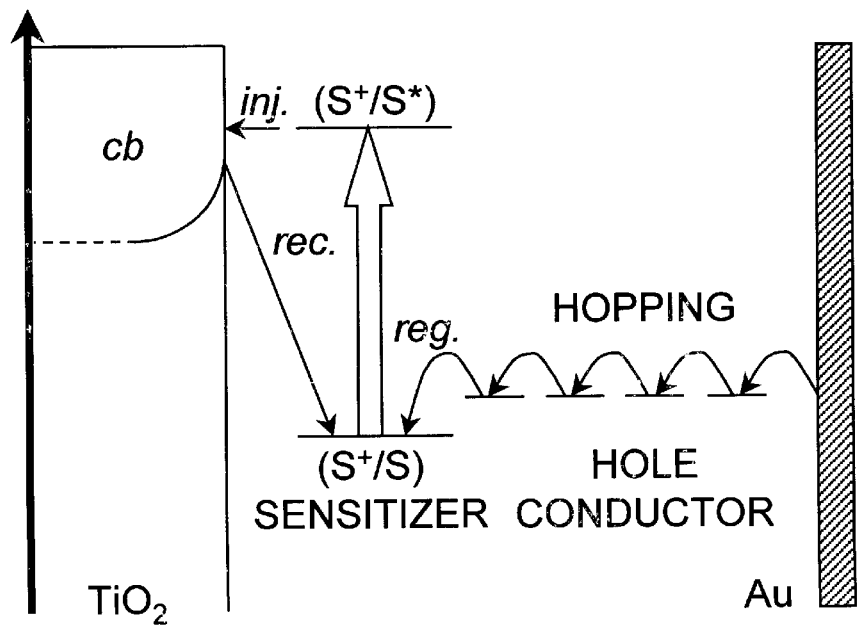
FIG. 9. A regenerative solar cell designed to function like that described for FIG. 8, except that a solid-state hole conductor replaces the iodide/triiodide redox-active electrolyte.

Solid-state cells can be used that would replace the redox active electrolyte by "hole" conductors, p-type semiconductors, or perhaps metals. The first two alternatives have precedence and hole conductors such as TPD (N,N-diphenyl-N',N'-bis(3-methylphenyl)-1,4-phenylenediamine) or OMeTAD [2,2',7,7'-tetrakis(N,N-bis(p-methoxyphenyl) amine]-9,9'-spirobifluorene are known (Salbeck, J. et al., *Synth. Met.* 1997, 91, 209). p-Type semiconductors such as CuNCS have been employed in this regard (O'Regan, B.; Schwartz, D. T. *Chem. Mater.* 1998, 10, 1501). In both cases the materials must be thermodynamically capable of reducing an oxidized component of the chromophore array. An example of how such a cell might work with a hole conductor is shown in FIG. 9.

By employing chromophoric arrays rather then a single monolayer of sensitizer molecules S, considerable improvement in efficiencies will be realized. For example, in Design I the sensitizer S is replaced by the CSU to which a rigid array of chromophores is covalently linked. The entire array extends normal to the electrode surface. The advantage of this approach is that the actual surface area occupied on the electrode surface is comparable to that of a single sensitizer S, but the light harvesting efficiency is significantly larger. In the solar cells described the incident photon-to-current efficiency (IPCE) is the product of three terms, Equation 1.

$$IPCE = LHE \times \Phi_{inj} \times \eta \qquad (1)$$

The term LHE stands for light-harvesting efficiency and is equivalent to the IUPAC term α (absorptance), which is equal to the fraction of light absorbed (i.e., (1–T) where T is the transmittance). The term $\Phi_{inj}$ is the quantum yield of interfacial electron injection into the electrode. The term η is the electron collection efficiency; that is, the fraction of electrons injected that reach the electrical circuit. The chromophore arrays in Design I will increase the LHE without lowering the other terms and a higher solar conversion is therefore expected.

Applying Design II to the sensitized semiconductor electrode is expected to provide increased solar conversion efficiency over Design I, as the 'hole' will be translated toward the terminal chromophore in the array and away from the CSU and the semiconductor electrode. This hole migration will prevent recombination of the electron in the semiconductor with the 'hole' in the chromophoric array. Furthermore, since the regeneration step will occur further from the electrode surface, decreased recombination with the donor oxidation products is expected. Both of these kinetic improvements will increase η, the electron collection efficiency, in Equation 1 and a higher photocurrent is expected. Furthermore, the open circuit photovoltage, $V_{oc}$, is expected to increase. In regenerative solar cells the maximum Gibbs free energy that can be obtained corresponds to the energetic difference between the Fermi level of the semiconductor and the redox potential of the electrolyte, $V_{oc}$. In preventing recombination of the injected electrons the Fermi level is raised and $V_{oc}$ increases. This effect can be very large. For example, in the Gratzel-type cell, recombination losses to the oxidized iodide product only account for the loss of nanoamps of photocurrent while ~200 mV of $V_{oc}$ is sacrificed. Since power is the product of current and voltage. this represents a significant loss.

It might even be possible to avoid redox active electrolytes, hole conductors, or p-type semiconductor junctions and simply use the chromophoric array to shuttle the "hole" directly to a metal counterelectrode as shown in Design III. A related process is envisioned to occur in the "organic semiconductor" films described above and is highly desirable, because mediating hole transport to the counterelectrode always wastes potential energy. Quenching of the excited state of the chromophore arrays by metallic surfaces is an anticipated problem (vide infra). However, since the chromophore array is illuminated through a transparent semiconductor and the array is highly absorbing, very few excited states will be created near the metallic counterelectrode. Accordingly, the availability of linear chromophoric arrays may make it possible to fabricate efficient cells using metallic surfaces.

2. Metal-Chromophoric Arrays. There are two possible excited-state interfacial electron-transfer processes that can occur from a molecular excited state, S*, created at a metal surface: (a) The metal accepts an electron from S* to form S+; or (b) the metal donates an electron to S* to form S−. Neither of these processes has been directly observed. The two processes would be competitive and unless there is some preference, no net charge will cross the interface. In order to obtain a steady-state photoelectrochemical response, interfacial back electron-transfer reactions of S+ (or S−) to yield ground-state products must also be eliminated. Energy transfer from an excited sensitizer to the metal also is thermodynamically favorable and allowed by both Forster and Dexter mechanisms. There exist theoretical predictions and experimental data describing 'energy-transfer' quenching of molecular excited states by metals. However, these studies involve photoluminescence measurements and the actual quenching mechanisms, involving electron or energy transfer, remain speculative. Nevertheless, competitive energy-transfer quenching is often invoked to rationalize the low photocurrent efficiencies measured at sensitized metallic interfaces. However, there are many reasons to predict poor sensitization yields from metal electrodes (Gerischer, H. *Photochem. Photobiol.* 1972, 16, 243; Gerischer, H. Pure *Appl. Chem.* 1980, 52, 2649; Gerischer, H.; Willig, F. *Top. Curr. Chem.* 1976, 61, 31).

The chromophore arrays described herein are designed to shuttle energy toward the photoanode and holes away from the photoanode (Designs II and III). This internal rectification should allow preferential injection of the electron into the illuminated electrode, as well as hole transfer away from the electrode. In this case, the depletion layer assisted charge separation that occurs at semiconductor surfaces may not be necessary, because the relative rates of interfacial charge injection and recombination will give rise to efficient energy conversion. While kinetic control of interfacial electron transfer dynamics has previously been suggested as a practical solar conversion scheme, the efficiencies reported are very low with photocurrents in the nanoamp range (Gregg, B. A.; Fox, M. A.; Bard, A. J. *J. Phys. Chem.* 1990, 94, 1586). If successful, the use of metals would allow any conductive substrate to be used for energy conversion. A wide variety of "transparent metals", i.e. thin metallic films or meshes such as Au, Al, or Pt on transparent substrates are available for this application.

D. Synthetic Approaches.

Two distinct approaches are available for preparing the linear LH/CSU rods. One approach involves a stepwise synthesis and the other approach involves a polymerization process. Both approaches employ pigment building blocks bearing at least one and typically two synthetic handles.

Figure 10:
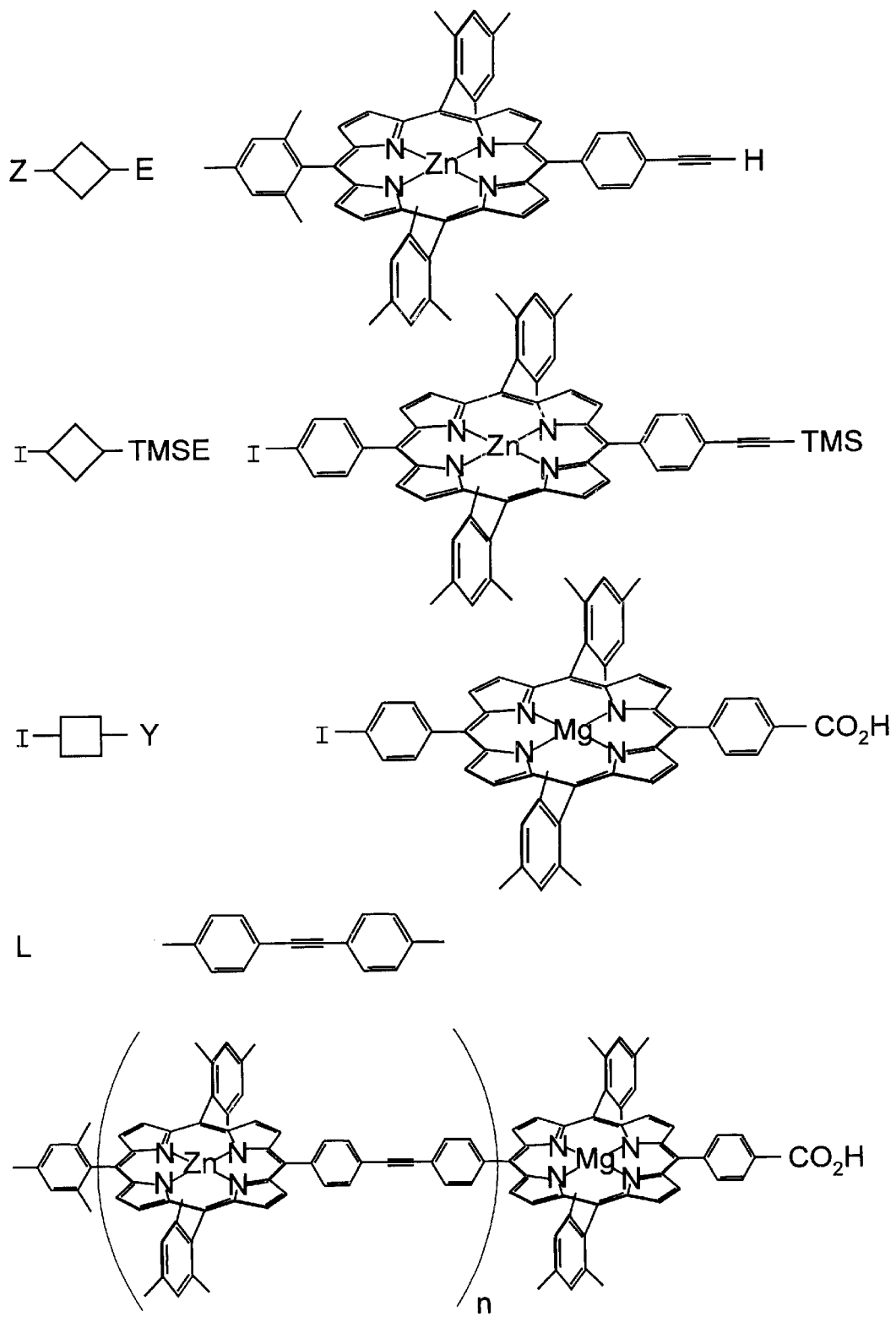
FIG. 10. Examples of building blocks that can be assembled into chromophore arrays.
Figure 11:
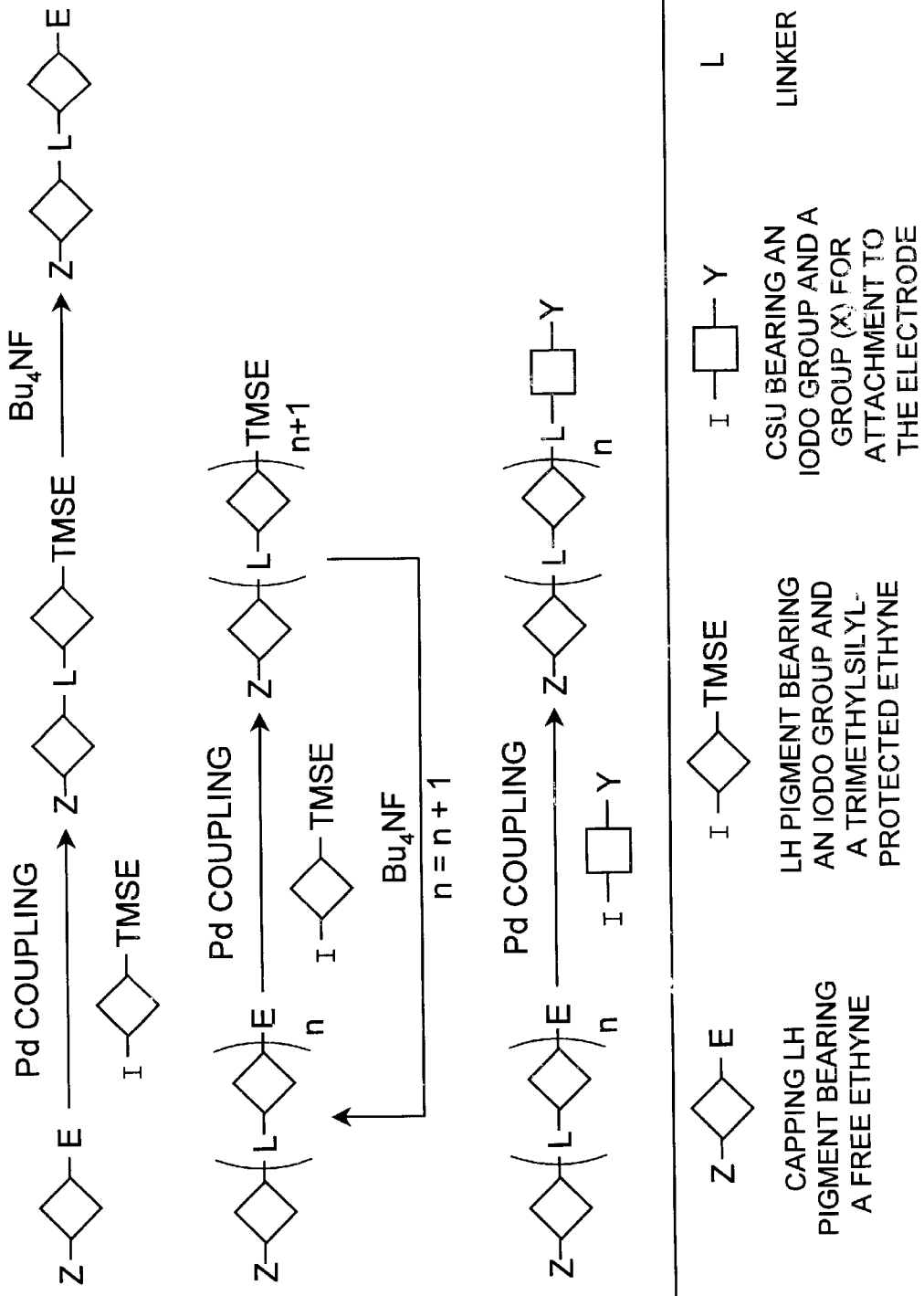
FIG. 11. Synthetic approach for preparing linear chromophore arrays.

One example of the stepwise synthetic approach employs ethyne (E) and iodo-substituted pigment building blocks (FIG. 10). The Pd-mediated coupling of an iodo-substituted pigment and a bifunctional pigment building block bearing an iodo group and a trimethylsilyl-protected ethyne (TMSE) affords the covalently-linked pigment dimer (FIG. 11). Cleavage of the trimethylsilyl-protected ethyne using tetrabutylammonium fluoride makes possible a second Pd-mediated coupling reaction. In this manner the linear architecture is constructed, starting from the distal end and proceeding toward the proximal end. The final reaction involves attachment of the CSU component. The CSU building block bears the attachment group Y required for attachment to the electrode surface. This same method has been employed to prepare ethyne-linked multiporphyrin arrays, as described elsewhere herein.

Figure 12:
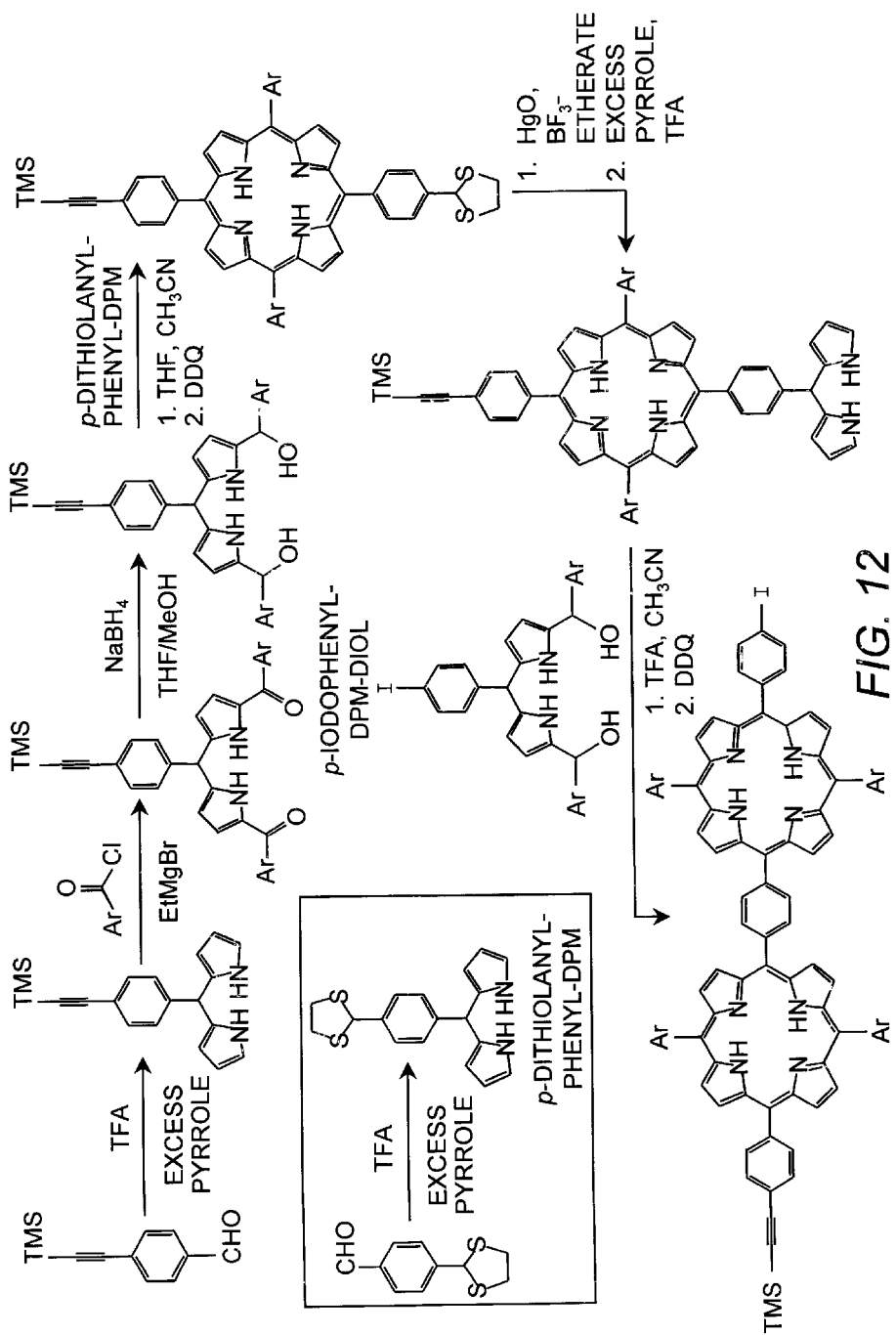
FIG. 12. Rational synthesis of a porphyrin dimeric building block for preparing chromophore arrays.

A wide variety of pigment building blocks can be envisaged, as noted elsewhere herein. In addition, multimeric pigment building blocks can be employed. One example includes a porphyrin dimer bearing a p-iodophenyl group and a p-[2-(trimethylsilyl)ethynyl]phenyl group. The resulting light-harvesting array is composed of p-phenylene-linked porphyrin dimers that are joined by p,p'-diphenylethyne groups. Dimers for this building block approach can be prepared in a rational manner as shown in FIG. 12.

Figure 13:
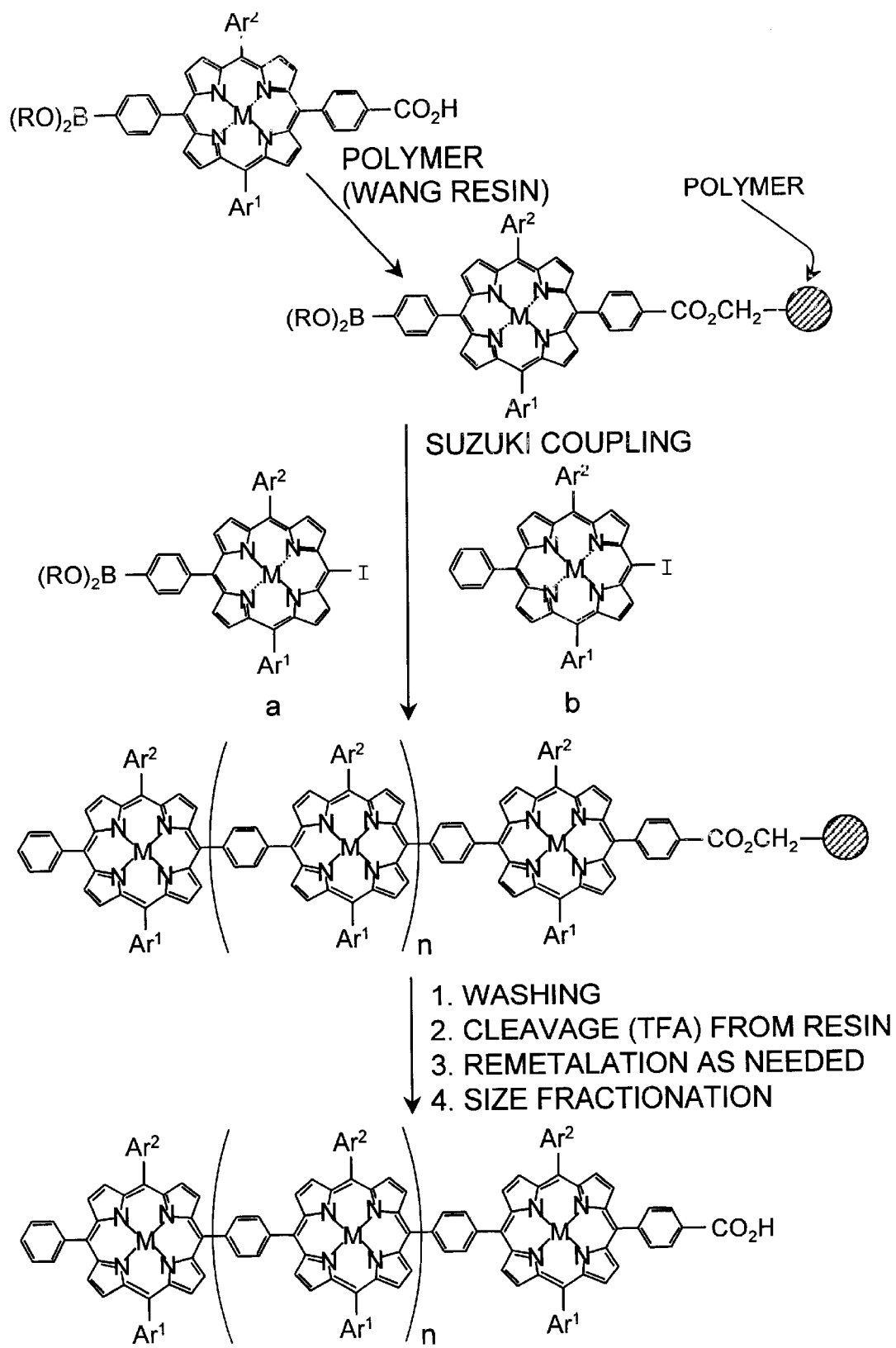
FIG. 13. Solid-phase synthesis using Suzuki coupling to prepare p-phenylene linked porphyrin containing arrays.

The polymerization approach is illustrated in FIG. 13 using the Suzuki coupling method to join pigment building blocks. A pigment building block bearing a carboxy group and a boronic ester group is attached to a solid-phase resin. Many resins are now available; the Wang resin or similar resin is particularly attractive. The Wang resin is a cross-linked polystyrene resin that enables facile attachment of compounds bearing carboxylic acids, and detachment is achieved by treatment with mild acid in organic solvents. The Suzuki coupling is performed using a mixture of a bifunctional pigment building block and a capping unit, and one of the well known sets of conditions employing Pd catalysts and ligands that afford high turnovers and high activity. Here the bifunctional pigment building block bears a boronic ester and an iodo group, while the capping unit bears only an iodo group. The polymerization is performed in the presence of the solid-phase. The average length distribution of the linear rod is controlled by the ratio of the bifunctional pigment building block and the capping unit; in general a ratio of 10:1 or so is employed. Following Suzuki coupling, the solid-phase resin is washed to remove unreacted starting material and coupling byproducts, then the desired product is obtained by cleavage from the resin under standard conditions. With porphyrinic pigments and acidic cleavage conditions, demetalation of the metalloporphyrin is expected and can be redressed by subsequent metalation. The mixture of oligomers is then fractionated by size exclusion chromatography. Note that the synthesis as displayed has proceeded from the CSU unit outward to the distal end, affording the linear LH/CSU rod with attached functional group (carboxy in this case) for attachment to the electrode.

Figure 14:
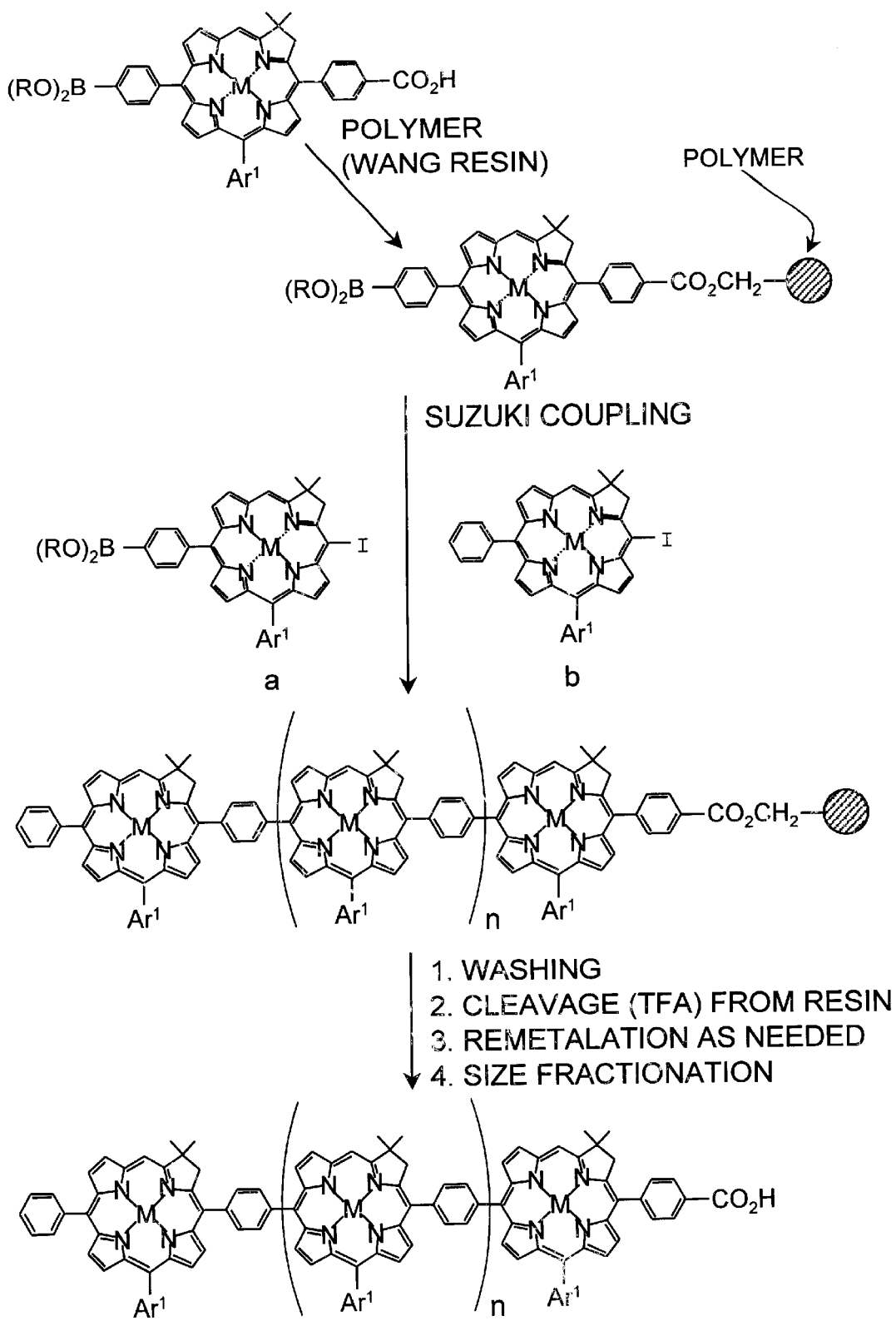
FIG. 14. Solid-phase synthesis using Suzuki coupling to prepare p-phenylene linked chlorin containing arrays.
Figure 16:
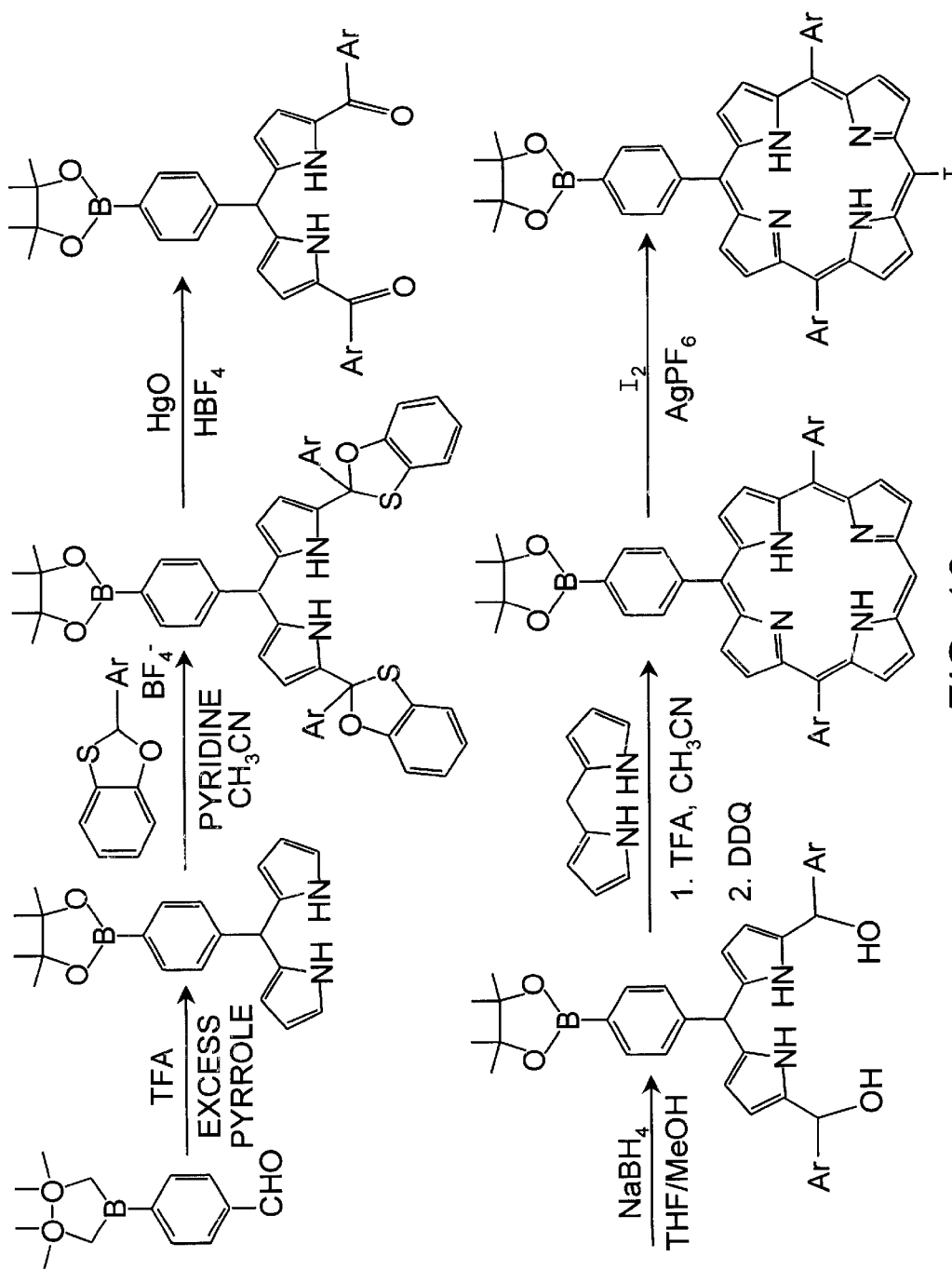
FIG. 16. Rational synthesis of a bifunctional porphyrin building block for use in Suzuki polymerizations.

The same approach can be taken with chlorin building blocks as illustrated in FIG. 14. A broader list illustrating other pigment building blocks suitable for Suzuki coupling is shown in FIG. 15. Two notable examples include a dimeric pigment building block, and a monomeric porphyrin bearing two boron-dipyrromethene dyes. The boron-dipyrromethene dyes absorb strongly in the blue-green region of the solar spectrum, and transmit energy very efficiently to the covalently attached porphyrin. An example of the synthesis of a porphyrin bearing one iodo group and one boronic ester derivative is shown in FIG. 16. This route uses established methods for forming dipyrromethanes, acylating the dipyrromethane selectively at the 1,9 positions, reducing the resulting diketone to the dipyrromethane-dicarbinol, and condensing the dipyrromethane-dicarbinol and a dipyrromethane to form the corresponding porphyrin (Cho, W.-S. et al., *J. Org. Chem.* 1999, 64, 7890–7901). Subsequent iodination at the lone free meso position affords the desired building block suitable for Suzuki coupling.

Figure 17:
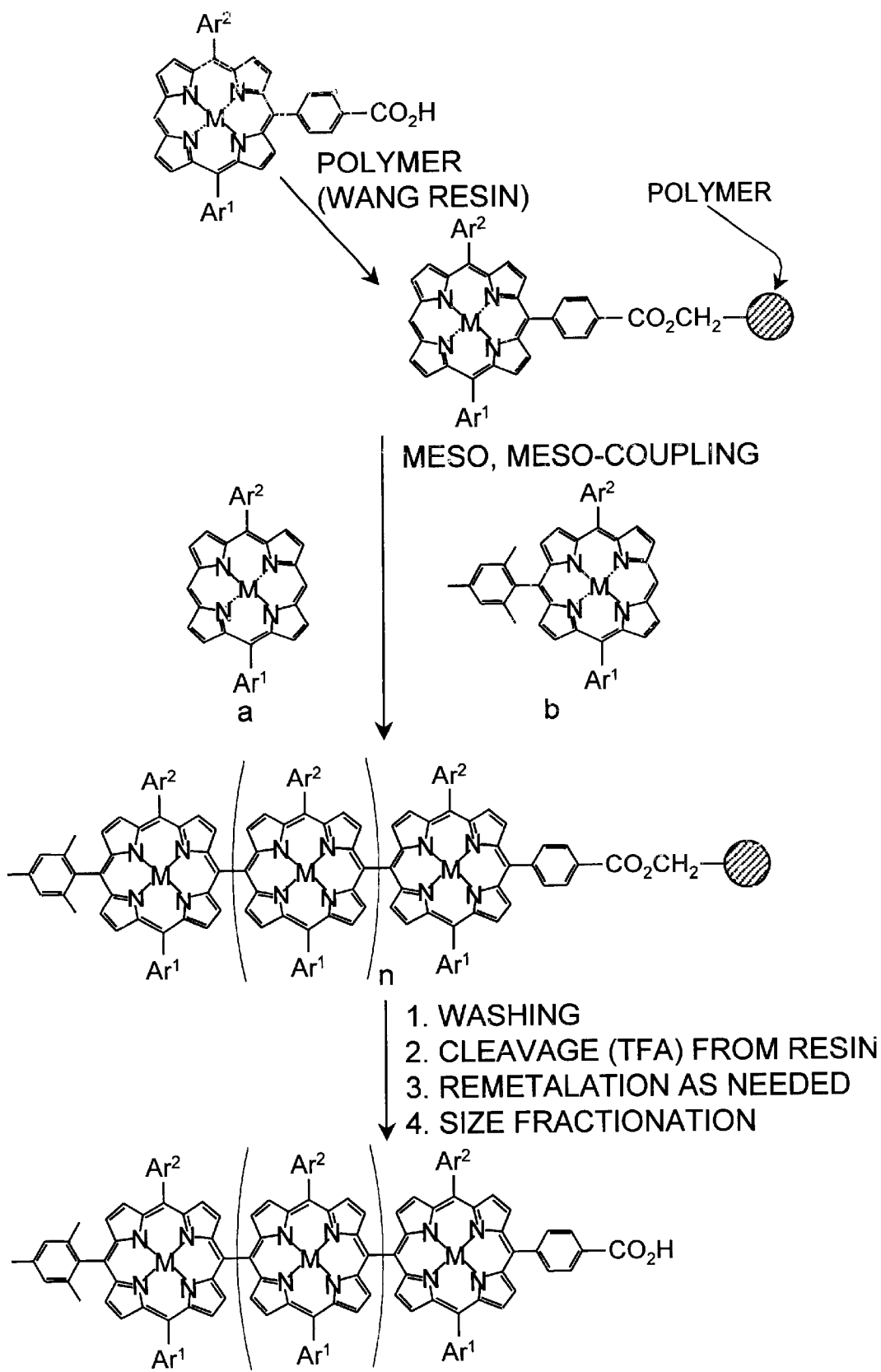
FIG. 17. Solid-phase synthesis of meso,meso-linked porphyrin containing arrays with an attached carboxy handle.

Polymerization is not restricted to Suzuki coupling. An example of meso,meso-coupling is illustrated in FIG. 17. A porphyrin with one free (unsubstituted) meso position is attached to the solid phase, then treated to meso,meso-coupling conditions ($AgPF_6$ or similar oxidant) in the presence of a mixture of porphyrins in order to elaborate the LH rod (Osuka, A.; Shimidzu, H. *Angew. Chem. Int. Ed. Engl.* 1997, 36, 135–137; Yoshida, N. et al., *Chem. Lett.* 1998, 55–56; Nakano, A. et al., *Angew. Chem. Int. Ed.* 1998, 37, 3023–3027; Senge, M. O.; Feng, X. *Tetrahedron Lett.* 1999, 40, 4165–4168). The porphyrin undergoing polymerization has two free meso positions, and the porphyrin that serves as the capping species has only one free meso position. The meso,meso-coupled oligomers have strongly split and broadened Soret bands, an attractive feature for achieving absorption across the solar spectrum.

Figure 18:
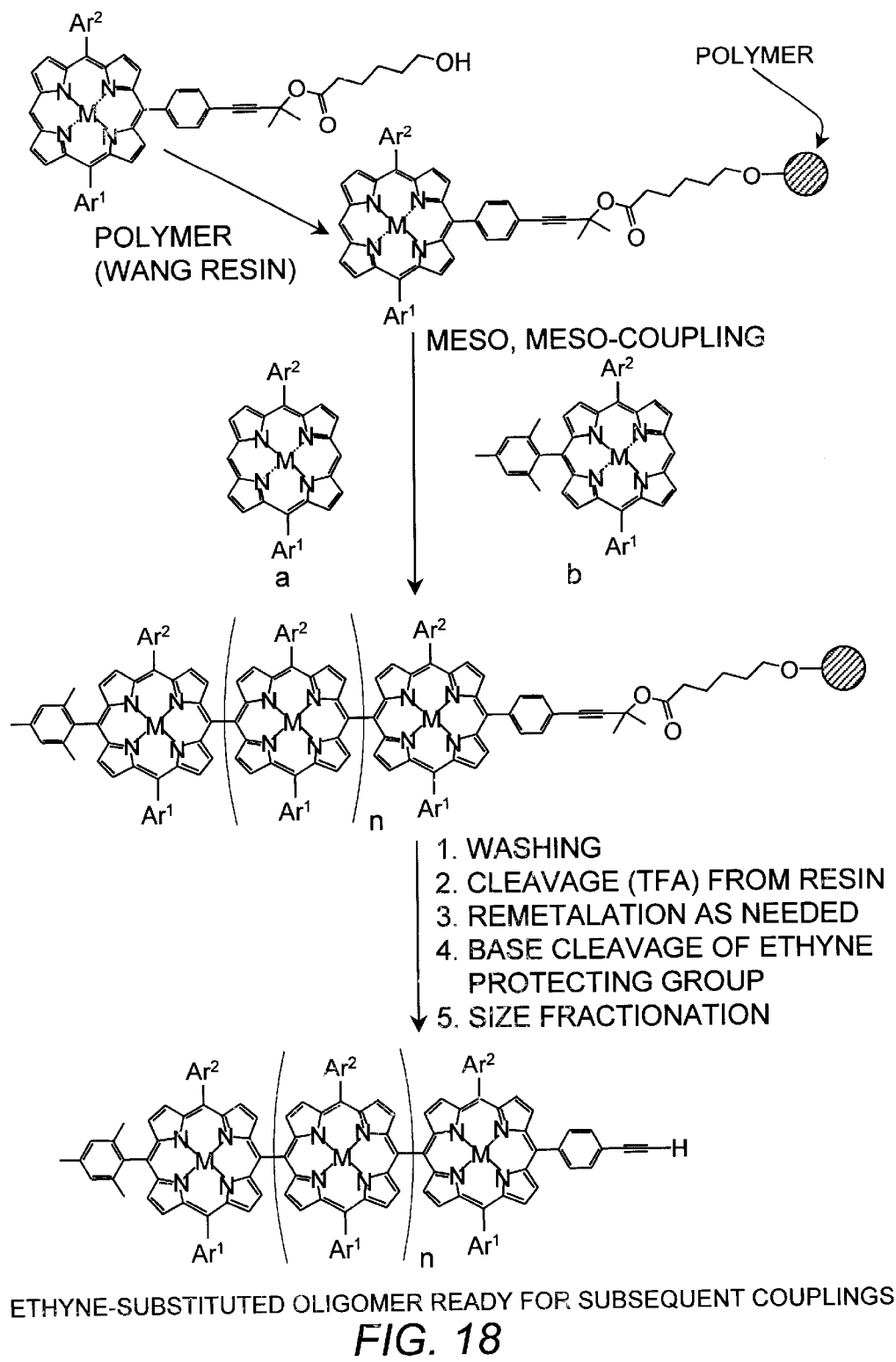
FIG. 18. Solid-phase synthesis of meso,meso-linked porphyrin containing arrays with an attached ethyne handle.
Figure 19:
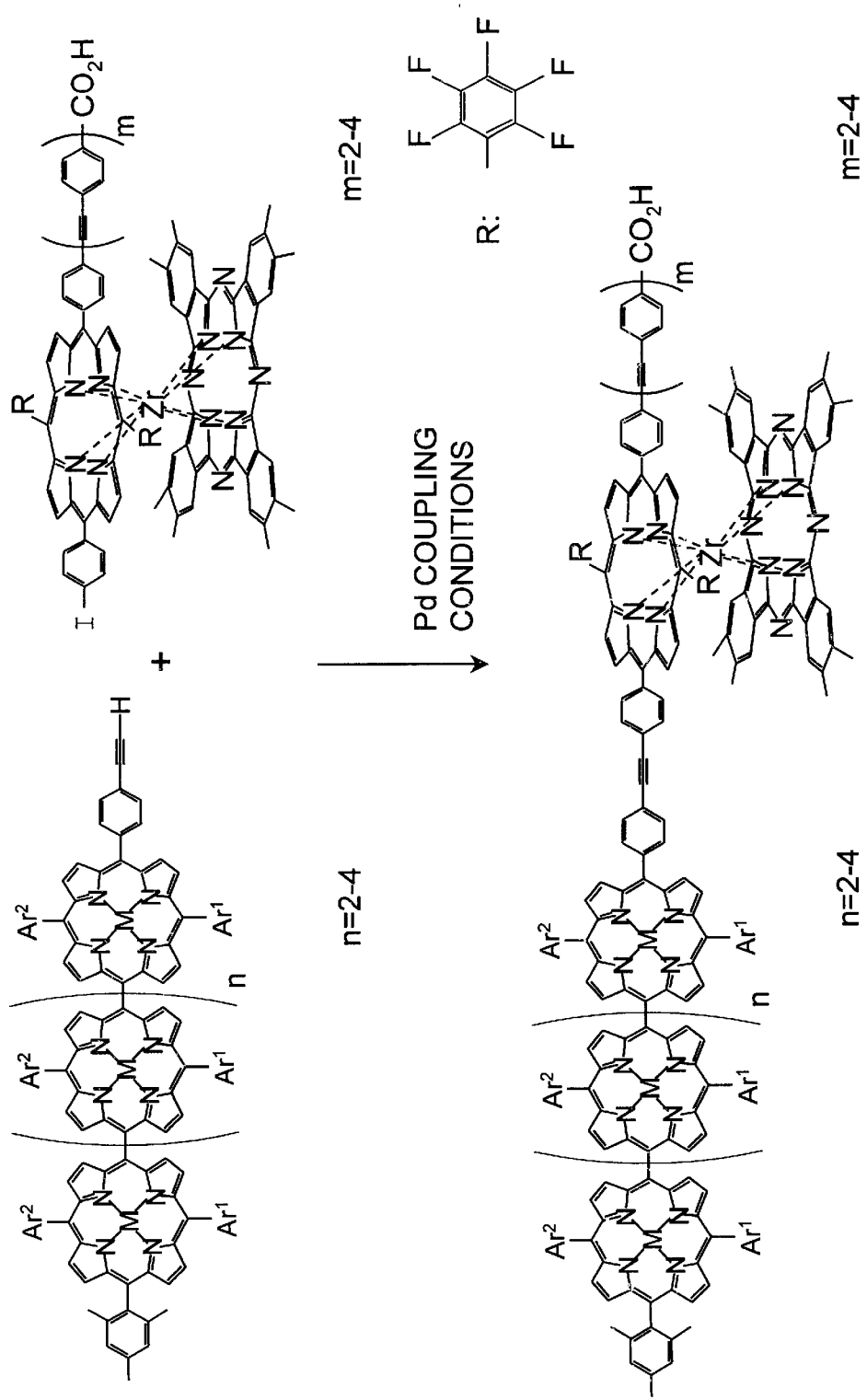
FIG. 19. Attachment of a meso,meso-linked array to a zirconium double decker sandwich molecule.

This same polymerization approach can be carried out to yield a meso,meso-linked oligomer bearing an ethyne at the terminus (FIG. 18). This synthesis is performed using a novel linker to attach the ethynyl-porphyrin to the solid phase. After cleavage the ethyne-substituted meso,meso-linked oligomer can then be subjected to a stepwise coupling procedure in order to attach a CSU. An example illustrating attachment of a zirconium porphyrin-phthalocyanine is shown in FIG. 19. Alternatively, other pigments can be attached via stepwise coupling procedures before joining to a CSU. CSU molecules of choice include chlorins, bacteriochlorins, phthalocyanines, naphthalocyanines, or zirconium double-decker sandwich molecules. This same synthetic approach is particularly attractive for use with chlorin-linked oligomers (vide infra).

Each of the two synthesis approaches has advantages and disadvantages. The stepwise approach affords an oligomeric product of defined length and enables incorporation of different pigments at defined sites. However, the stepwise approach requires substantial synthetic manipulations, including multiple cycles of deprotection and coupling, to obtain the desired product. The polymerization approach rapidly affords linear oligomers of substantial length. However, the oligomers are polydisperse and the synthesis does not afford control over placement of different pigments in an array. These features cause the two approaches to have distinct applications.

For Designs I and II where identical pigments are employed throughout the LH rod, the polymerization approach can be employed. For Design III where the LH/CSU rods need to be of defined and uniform length for placement between electrode and counterelectrode, the stepwise synthesis approach must be employed. The only exception would occur when size fractionation can effect desired length uniformity, as might occur when rather short oligomers are desired, in which case polymerization can be employed. For Designs I, II, and III where different pigments are to be incorporated in the LH rod, the stepwise approach must be employed. Combinations of polymerization and stepwise procedures also can be performed.

Particular examples of porphyrinic macrocycles that may be used as ligands to carry out the present invention include compounds of Formula X, Formula XI, Formula XII, Formula XIII, Formula XIV, Formula XV, Formula XVI, and Formula XVII below (with formulas XII through XVII representing various chlorins, including bacteriochlorins and isobacteriochlorins).

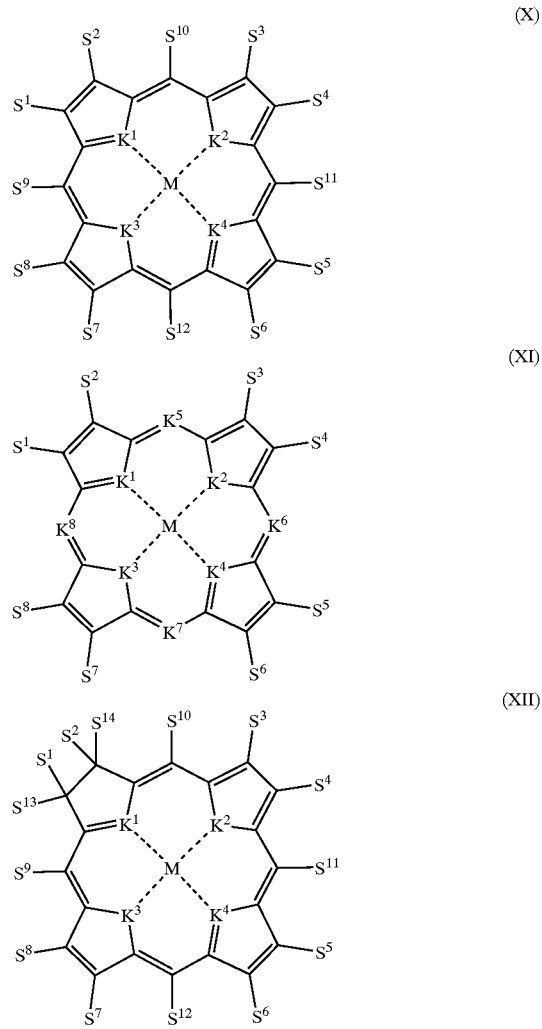

(XIII)

(XIV)

(XV)

(XVI)

(XVII)

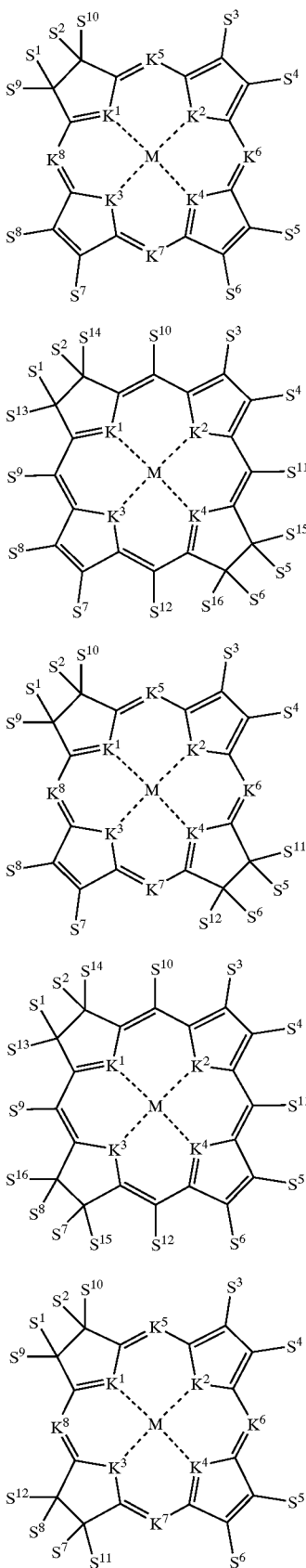

wherein:

M is a metal, such as a metal selected from the group consisting of Zn, Mg, Pt, Pd, Sn and Al, or M is absent (in which case the ring hetero atoms $K^1$ through $K^4$ are substituted with H,H as required to satisfy neutral valency);

$K^1$, $K^2$, $K^3$, $K^4$, $K^5$, $K^6$, $K^7$, and $K^8$ are hetero atoms, such as hetero atoms independently selected from the group consisting of N, O, S, Se, Te, and CH;

$S^1$, $S^2$, $S^3$, $S^4$, $S^5$, $S^6$, $S^7$, $S^8$, $S^9$, $S^{10}$, $S^{11}$, $S^{12}$, $S^{13}$, $S^{14}$, $S^{15}$ and $S^{16}$ are independently selected substituents that preferably provide a redox potential of less than about 5, 2 or even 1 volt. Example substituents $S^1$, $S^2$, $S^3$, $S^4$ include, but are not limited to, H, aryl, phenyl, cycloalkyl, alkyl, halogen, alkoxy, alkylthio, perfluoroalkyl, perfluoroaryl, pyridyl, cyano, thiocyanato, nitro, amino, alkylamino, acyl, sulfoxyl, sulfonyl, imido, amido, and carbamoyl.

In addition, each pair of $S^1$ and $S^2$, $S^3$ and $S^4$, $S^5$ and $S^6$, and $S^7$ and $S^8$, may independently form an annulated arene, such as a benzene, naphthalene, or anthracene, which in turn may be unsubstituted or substituted one or more times with a substituent that preferably provides a redox potential of less than about 5, 2 or even 1 volt, such as H, aryl, phenyl, cycloalkyl, alkyl, halogen, alkoxy, alkylthio, perfluoroalkyl, perfluoroaryl, pyridyl, cyano, thiocyanato, nitro, amino, alkylamino, acyl, sulfoxyl, sulfonyl, imido, amido, and carbamoyl. Examples of such annulated arenes include, but are not limited to:

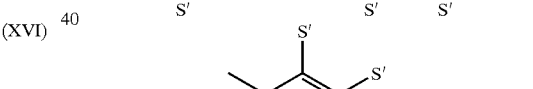

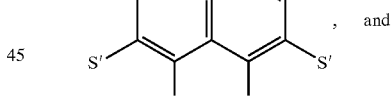

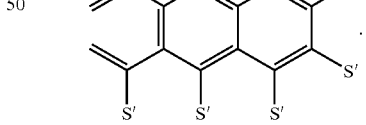

(It being understood that the rings are appropriately conjugated to retain aromaticity of the fused rings); and wherein each substituent S' is independently selected and preferably provides a redox potential of less than about 5, 2 or even 1 volt. Examples of such substituents include, but are not limited to, H, aryl, phenyl, cycloalkyl, alkyl, halogen, alkoxy, alkylthio, perfluoroalkyl, perfluoroaryl, pyridyl, cyano, thiocyanato, nitro, amino, alkylamino, acyl, sulfoxyl, sulfonyl, imido, amido, and carbamoyl. Particular examples of compounds as described above containing annulated arenes are exemplified by Formulas XX–XXIV below.

In addition, $S^1$ through $S^{16}$ may comprise a linking group (—Q—) covalently linked to an adjacent porphyrinic macrocycle of $X^1$ through $X^{m+1}$ or a linking group covalently linked to said first electrode. In one embodiment of the invention, the linking groups of each porphyrinic macrocycle are oriented in trans; in another embodiment of the invention, one or more porphyrinic macrocycles contains linking groups that are oriented in cis to one another so that the the light harvesting rods contain bends or kinks, or the linker itself is non-linear or oblique.

Examples of porphyrinic macrocycles that contain annulated arenes as described above include, but are not limited to, porphyrinic macrocycles of Formula XX, XXI, XXIII and XXIV below:

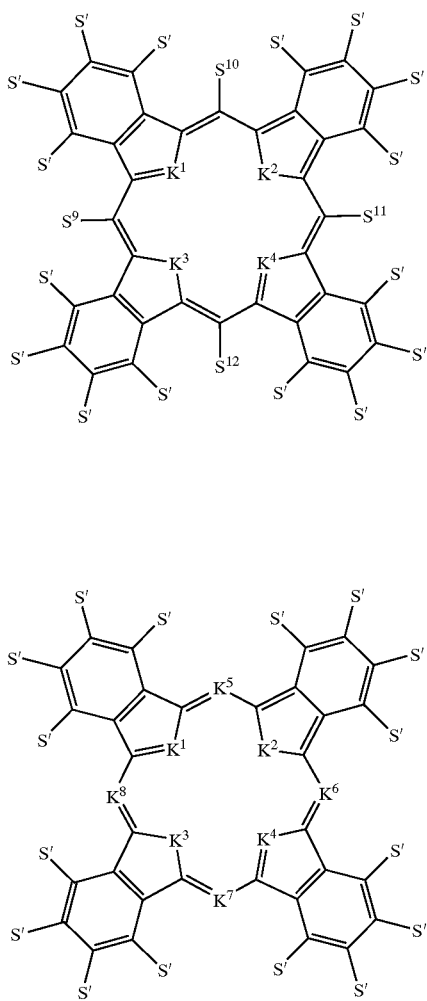

(XX)

(XXI)

(XXIII)

(XXIV)

wherein each substituent S' is independently selected and preferably provides a redox potential of less than about 5, 2 or even 1 volt. Examples of such substituents include, but are not limited to, H, aryl, phenyl, cycloalkyl, alkyl, halogen, alkoxy, alkylthio, perfluoroalkyl, perfluoroaryl, pyridyl, cyano, thiocyanato, nitro, amino, alkylamino, acyl, sulfoxyl, sulfonyl, imido, amido, and carbamoyl. Again, to link the porphyrinic macrocycle to a substrate, or to another compound such as another porphyrinic macrocycle in the manners described above, the porphyrinic macrocycle will have to contain at least one substituent and preferably two substituents S' which is or are a linker, particularly a linker containing a reactive group (where multiple linkers are substituted on the ligand, the linkers may be the same or independently selected). Such linkers are as described above.

Particular examples of sandwich coordination compounds that may be used to carry out the present invention have the Formula XXV (for double-decker sandwich compounds):

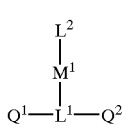

(XXV)

wherein:

M$^1$ is a metal of the lanthanide series, as well as Y, Zr, Hf. and Bi, and in the actinide series Th and U (radioactive elements such as Pm are generally less preferred);

L$^1$ and L$^2$ are independently selected ligands (e.g. porphyrinic macrocycles); and Q$^1$ and Q$^2$ may be present or absent and when present are independently selected linkers as described above (the linker preferably including a protected or unprotected reactive group such as thio, seleno or telluro group). Preferably, at least one of Q$^1$ or Q$^2$ is present.

It will also be appreciated that each ligand L may be substituted with a single linker Q, or may be multiply substituted with linkers Q, as explained in greater detail below. Thus the molecule of Formula XXV may be covalently linked to an electrode or substrate by at least one of Q$^1$ or Q$^2$.

Each ligand L may be further substituted without departing from the scope of the compounds of Formula XI above. For example, and as explained in greater detail below, ligands may be covalently joined to another porphyrinic macrocycle, to a ligand of another sandwich coordination compound, etc.

To link the porphyrinic macrocycle (which may or may not be a component of a sandwich coordination compound) to a substrate, or to another compound such as another porphyrinic macrocycle in the manners described above, at least one ligand in the porphyrinic macrocycle will have to contain at least one and preferably two substituents S$^1$ through S$^n$ or S' which is a linker, particularly a linker containing a reactive group (where multiple linkers are substituted on the ligand, the linkers may be the same or independently selected). Such linkers are designated as Y—Q— herein, where: Q is a linker, and Y is a substrate, a reactive site or group that can covalently couple to a substrate, or a reactive site or group that can jonically couple to a substrate.

Q may be a linear linker or an oblique linker, with linear linkers currently 5 preferred. Examples of oblique linkers include, but are not limited to, 4,3'-diphenylethyne, 4,3'-diphenylbutadiyne, 4,3'-biphenyl, 1,3-phenylene, 4,3'-stilbene, 4,3'-azobenzene, 4,3'-benzylideneaniline, and 4,3''-terphenyl. Examples of linear linkers include, but are not limited to, 4,4'-diphenylethyne, 4,4'-diphenylbutadiyne, 4,4'-biphenyl, 1,4-phenylene, 4,4'-stilbene, 1,4-bicyclooctane, 4,4'-azobenzene, 4,4'-benzylideneaniline, 4,4''-terphenyl, 3-mercaptophenyl, 3-mercaptomethylphenyl, 3-(2-mercaptoethyl)phenyl, 3-(3-mercaptopropyl)phenyl, 3-(2-(4-mercaptophenyl)ethynyl)phenyl, 3-carboxyphenyl, 3-carboxymethylphenyl, etc.

Y may be a protected or unprotected reactive site or group on the linker such as a thio, seleno or telluro group.

Thus, examples of linear linkers for Y—Q— are: 4-[2-mercaptoethyl)phenyl, 4-[3-mercaptopropyl)phenyl, an ω-alkylthiol of form HS(CH$_2$)$_n$— where n=1–20, 4-carboxyphenyl, 4-carboxymethylphenyl, 4-(2-carboxyethyl)phenyl, an ω-alkylcarboxylic acid of form HO$_2$C(CH$_2$)$_n$— where n=1–20, 4-(2-(4-carboxyphenyl)ethynyl)phenyl, 4-(2-(4-carboxymethylphenyl)ethynyl)phenyl, 4-(2-(4-(2-carboxyethyl)phenyl)ethynyl)phenyl, 4-(2-(4-mercaptophenyl)ethynyl)phenyl, 4-mercaptomethylphenyl, 4-hydroselenophenyl, 3-(2-(4-hydroselenophenyl)ethynyl)phenyl, 4-hydrotellurophenyl, and 4-(2-(4-hydrotellurophenyl)ethynyl)phenyl.

Examples of oblique linkers for Y—Q— are: 3-(2-(4-mercaptophenyl)ethynyl)phenyl, 3-mercaptomethylphenyl, 3-hydroselenophenyl, 3-(2-(4-hydroselenopenyl)ethynyl)phenyl, 3-hydrotellurophenyl, and 3-(2-(4-hydrotellurophenyl)ethynyl)phenyl; etc.

Other suitable linkers include, but are not limited to, 2-(4-mercaptophenyl)ethynyl, 2-(4-hydroselenophenyl)ethynyl, and 2-(4-hydrotellurophenyl)ethynyl.

Thus, linkers between adjacent porphyrinic macrocycles within a light harvesting rod, or between a porphyrinic macrocycle and an electrode, are typically those that permit superexchange between the linked chromophores (mediated electronic communication between chromophores which permits or allows excited-state energy transfer and/or exchange of electrons and/or holes). Examples of suitable linkers may be generally represented by the formula —Q—, where Q may be a direct covalent bond or a linking group of the Formula:

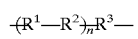

wherein:

n is from 0 or 1 to 5 or 10;

R$^3$ may be present or absent (yielding a direct covalent bond when R$^3$ is absent and n is 0); and R$^1$, R$^2$, and R$^3$ are each independently selected from the group consisting of ethene, ethyne, aryl, and heteroaryl groups (e.g., phenyl, and derivatives of pyridine, thiophene, pyrrole, phenyl, etc., which aryl and heteroaryl groups may be unsubstituted or substituted one or more times with the same substituents listed above with respect to porphyrinic macrocycles).

The geometry of the linkers with respect to the various chromophores and charge separation groups in the light harvesting rods can vary. In one embodiment, at least one of X$^2$ through X$^{m+1}$ comprises a meso-linked porphyrinic macrocycle. In another embodiment, at least one of X$^2$ through X$^{m+1}$ comprises a trans meso-linked porphyrinic macrocycle. In another embodiment, X$^2$ through X$^{m+1}$ consist of meso-linked porphyrinic macrocycles. In another embodiment, X$^2$ through X$^{m+1}$ consist of trans meso-linked porphyrinic macrocycles. In another embodiment, at least one of X$^2$ through X$^{m+1}$ comprises a β-linked porphyrinic macrocycle. In another embodiment, at least one of X$^2$ through X$^{m+1}$ comprises a trans β-linked porphyrinic macrocycle. In still another embodiment, X$^2$ through X$^{m+1}$ consist of β-linked porphyrinic macrocycles. In still another embodiment, X$^2$ through X$^{m+1}$ consist of trans β-linked porphyrinic macrocycles.

E. Design Examples.

Figure 20:
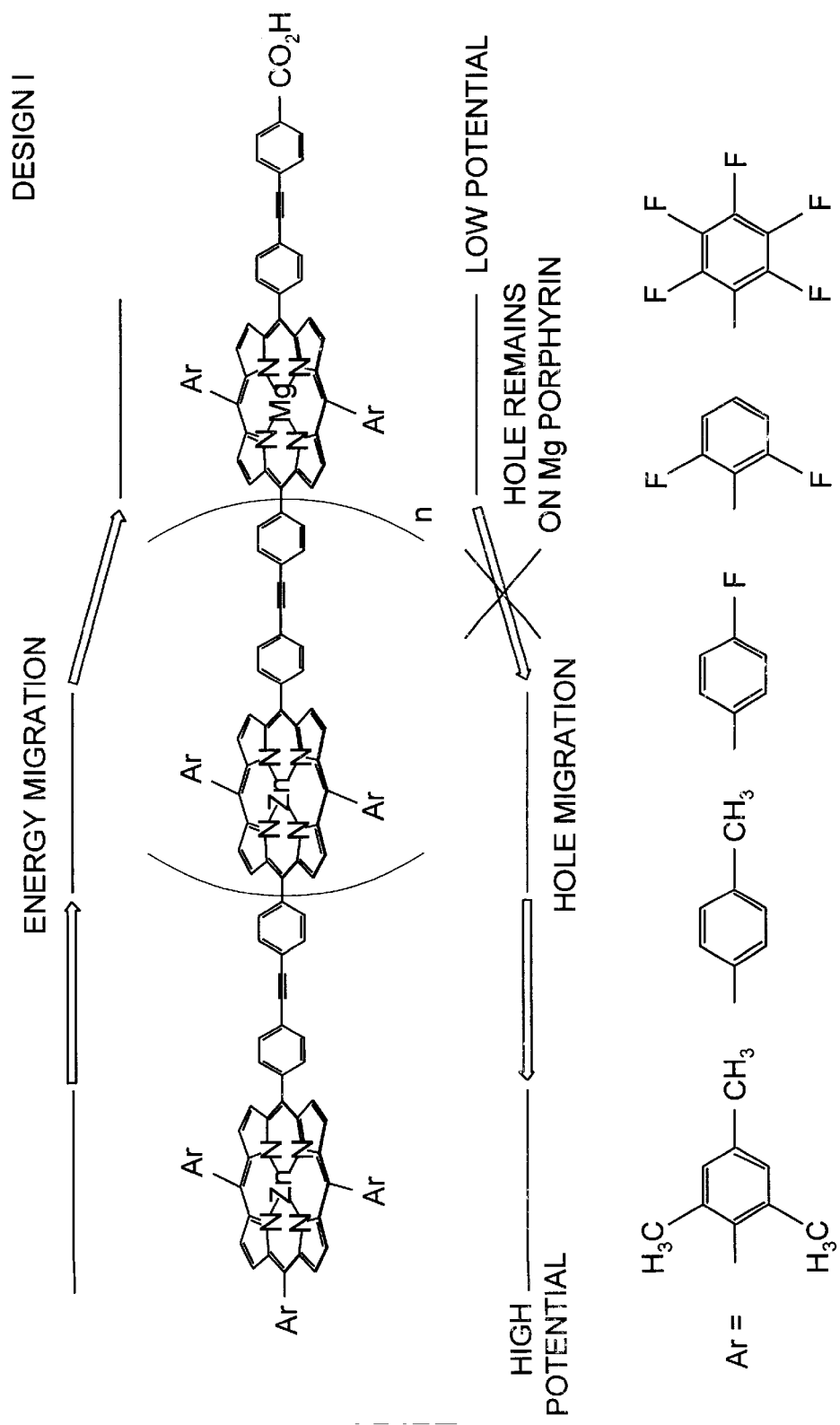
FIG. 20. Example of energy migration but no hole migration in a chromophore array.

Examples of specific molecules that can achieve the various designs are shown in the following schemes. An example of Design I is shown in FIG. 20. The Zn porphyrins constitute the LH rod and the Mg porphyrin comprises the CSU. Energy transfer occurs reversibly among the Zn porphyrins but occurs irreversibly (downhill) to the Mg porphyrin (Hascoat, P. et al., *Inorg. Chem.* 1999, 38, 4849–4853). In this design each of the Zn and Mg porphyrins has identical non-linking meso substituents. Upon charge separation, the hole resides on the Mg porphyrin. The hole cannot transfer to the Zn porphyrins because the Mg porphyrin lies at lower potential than the Zn porphyrins (Wagner, R. W. et al., *J. Am. Chem. Soc.* 1996, 118, 3996–3997). The oxidation potential of the CSU can be tuned through alteration of the inductive effect of the two non-linking meso substituents. By changing the non-linking meso substituents on the Zn porphyrins as well, again the hole is forced to remain on the Mg porphyrin (the CSU).

Figure 21:
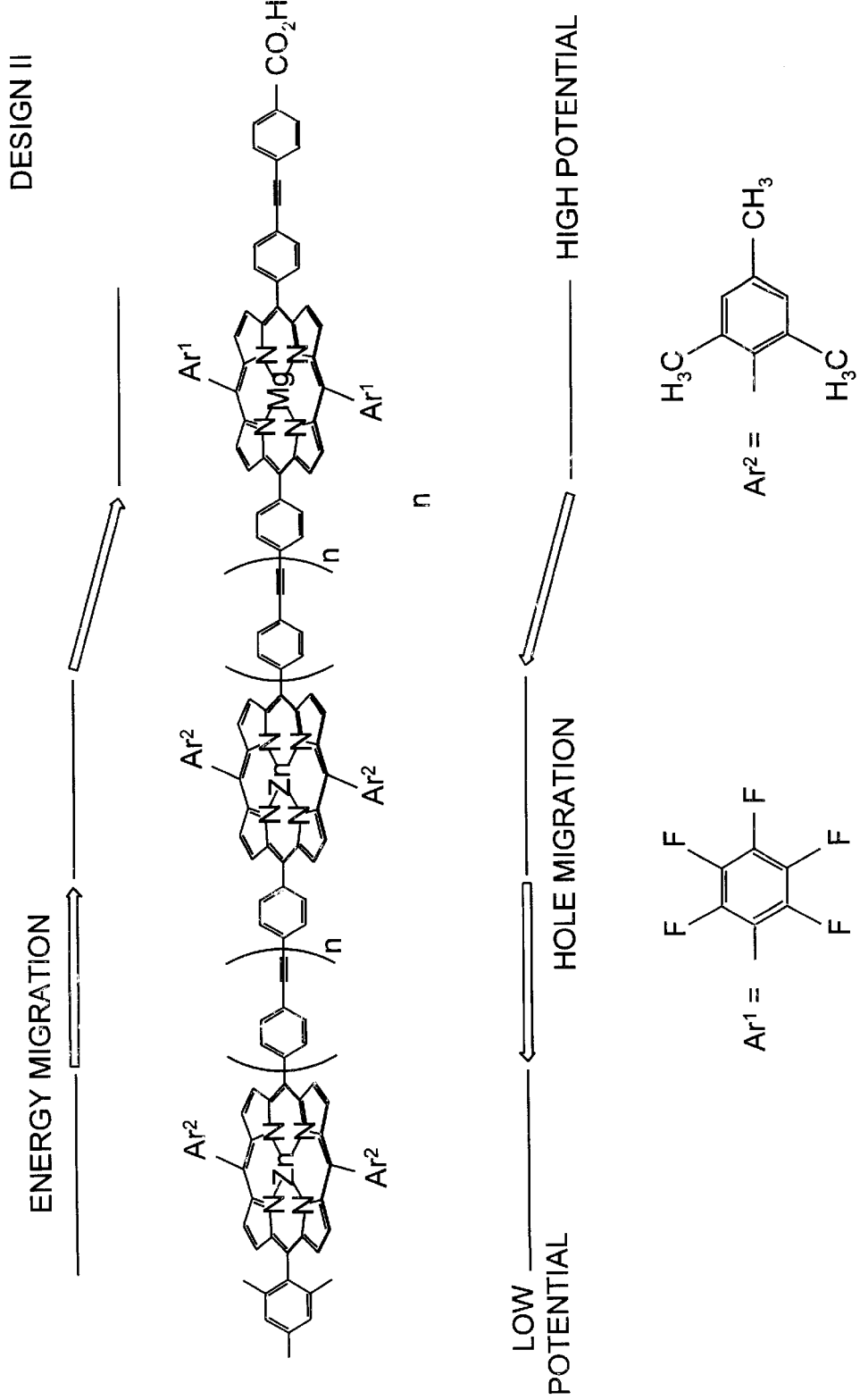
FIG. 21. Example of energy migration and hole migration in opposite directions in a chromophore array.

An example of Design II is shown in FIG. 21. This design is similar to that shown in FIG. 19 but the non-linking meso substituents on the Zn and Mg porphyrins are different. Strongly electron-withdrawing substituents are placed on the Mg porphyrin (CSU) but not on the Zn porphyrins. Consequently, upon injection of an electron into the electrode, the hole on the CSU transfers to the Zn porphyrins in the LH array. Hole transfer is favored because the Zn porphyrins are at lower potential than the Mg porphyrin.

Figure 22:
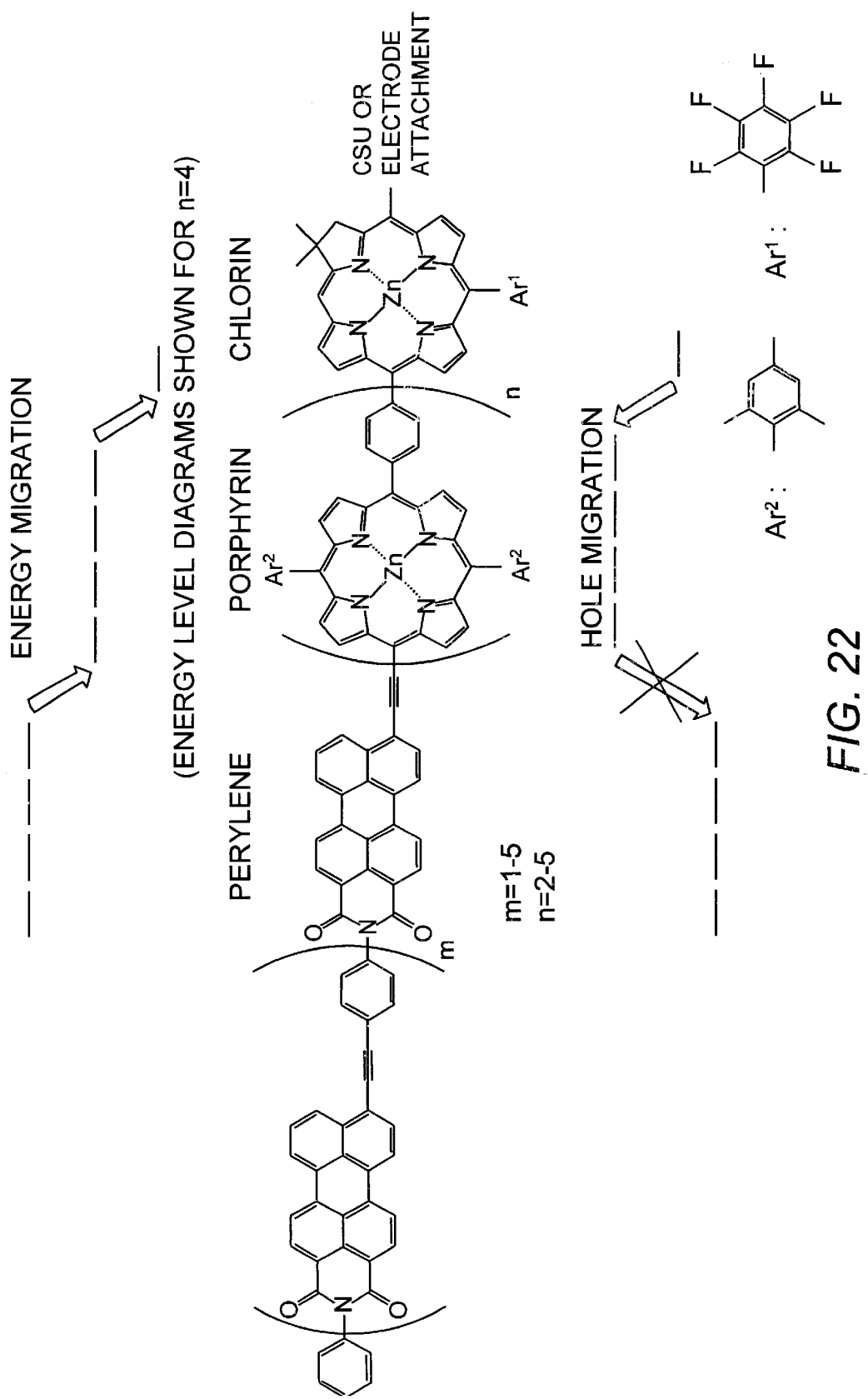
FIG. 22. Example of a cascade of energy migration and hole migration in opposite directions in a chromophore array. Hole migration occurs over a defined region of the array.

A related example of Design II is shown in FIG. 22. Here the linear LH rod is comprised of a series of m perylene components and a series of n Zn porphyrins, and the CSU is comprised of a Zn chlorin. Energy flows irreversibly from the set of perylenes to the Zn porphyrins to the Zn chlorin. The hole created at the CSU upon electron injection into the electrode migrates to the lower potential Zn porphyrins but cannot migrate into the perylene array. This array is synthesized using a perylene building block bearing an ethyne and an iodo group analogous to porphyrin building blocks.

Figure 23:
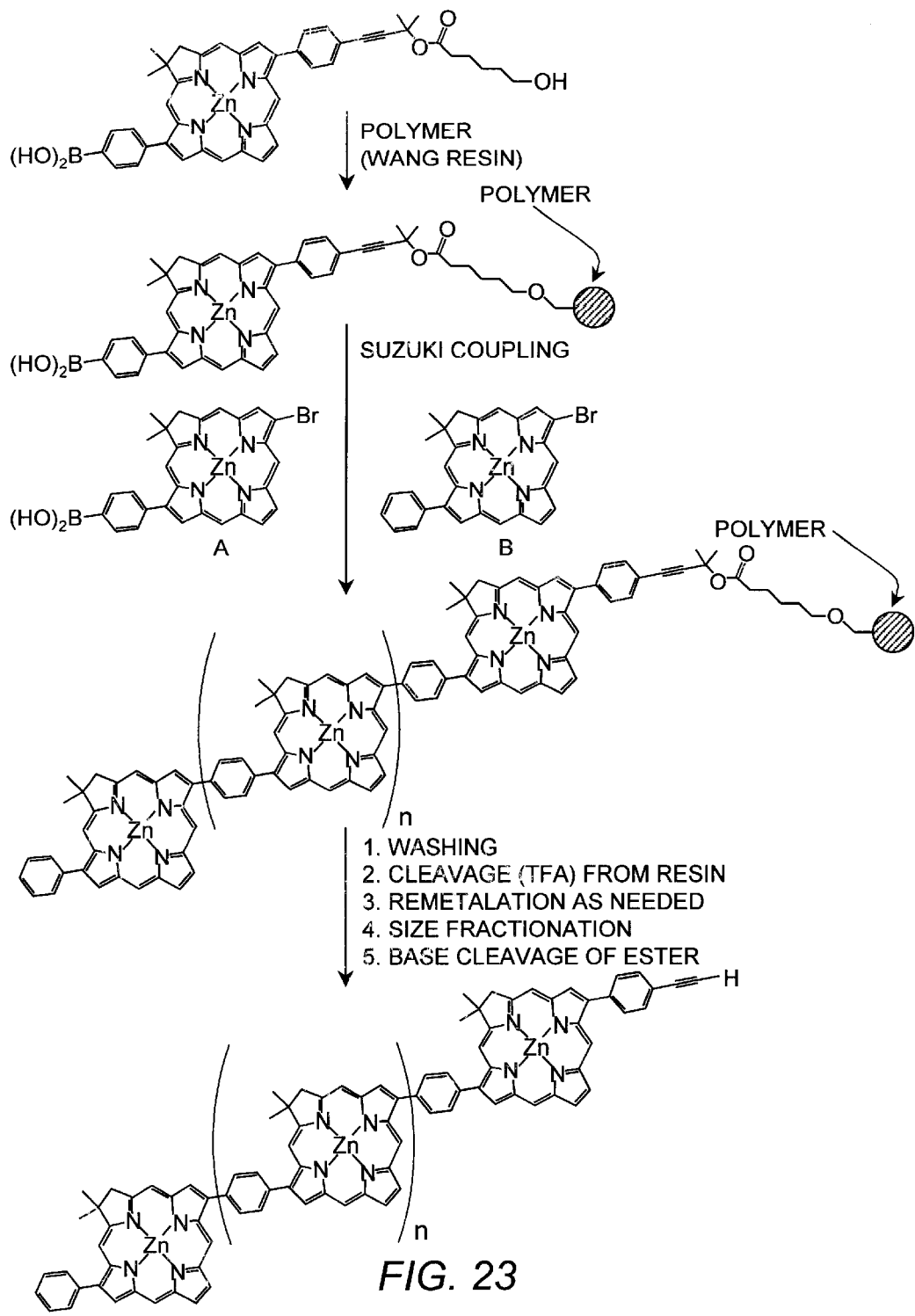
FIG. 23. Another example of solid-phase synthesis using Suzuki coupling to prepare p-phenylene linked chlorin containing arrays with an ethyne handle.
Figure 24:
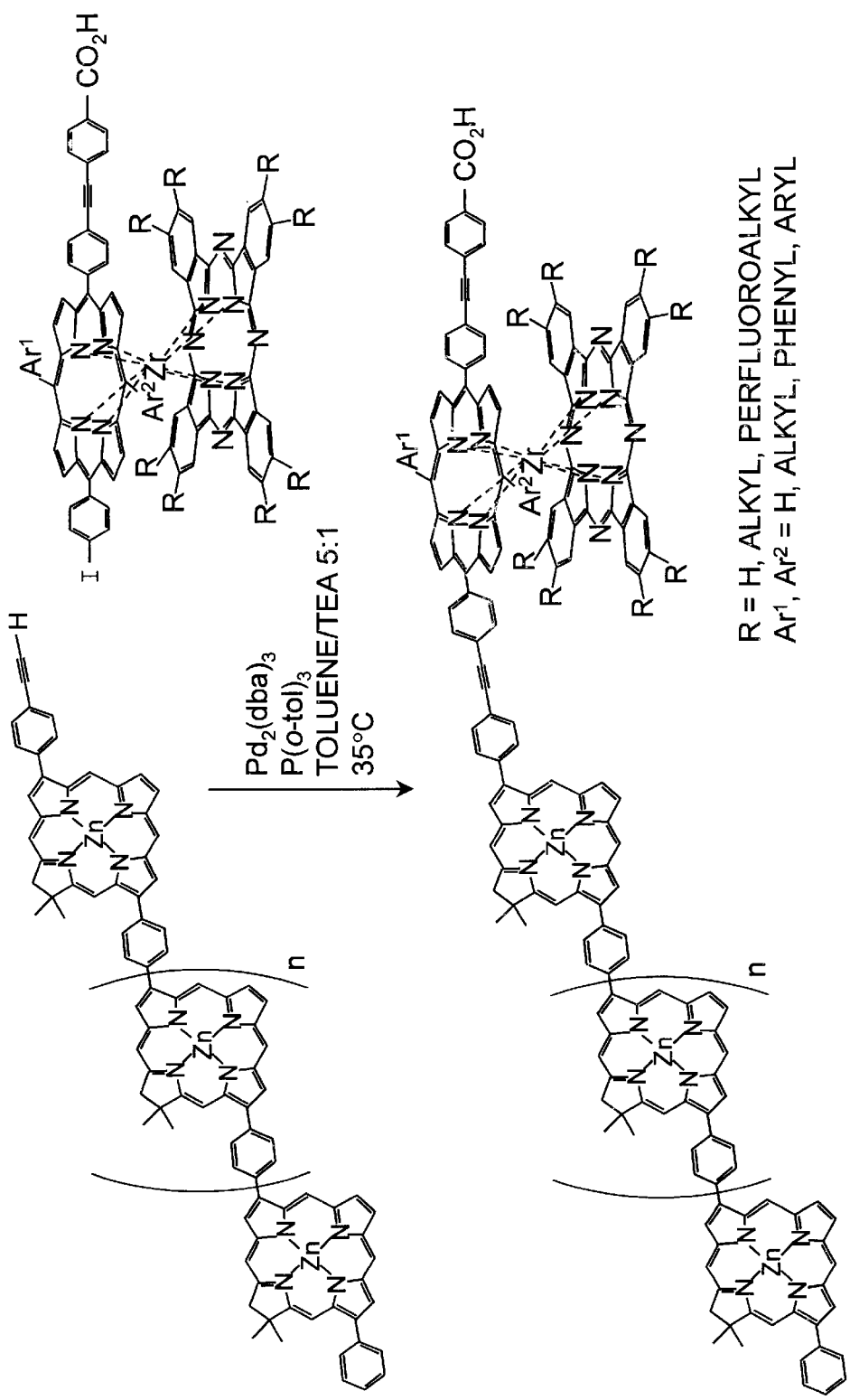
FIG. 24. Attachment of a p-phenylene linked chlorin containing array to a zirconium double decker sandwich molecule.

An additional example illustrating Designs I and II is shown in FIGS. 23 and 24. Here β,β'-substituted chlorins are employed in the LH rod, and a zirconium double-decker porphyrin-phthalocyanine sandwich molecule serves as the CSU. Zirconium double-decker porphyrinic sandwich molecules are known to be photochemically active. The synthesis involves Suzuki coupling to form the p-phenylene linked chlorin LH rod, which employs a linker for attaching an ethyne to the solid phase. Upon cleavage from the solid phase and deprotection, the ethynyl-substituted LH rod can be attached to the zirconium double decker via a Pd-mediated ethynylation reaction. The zirconium double decker can be obtained by known methods employing the desired trans-substituted porphyrin. By choosing the types of substituents in the porphyrin and phthalocyanine components of the double decker, the oxidation potential can be tuned as desired. With no electron-releasing substituents, the oxidation potential is quite low and the hole (formed upon electron injection into the electrode) resides on the CSU (Design I). With electron-withdrawing substituents (e.g., R=F or perfluoroalkyl; $Ar^1=Ar^2=$ perfluoroalkyl or pentafluorophenyl) the oxidation potential is increased and the hole migrates to the Zn chlorins in the LH rod (Design II).

Figure 25:
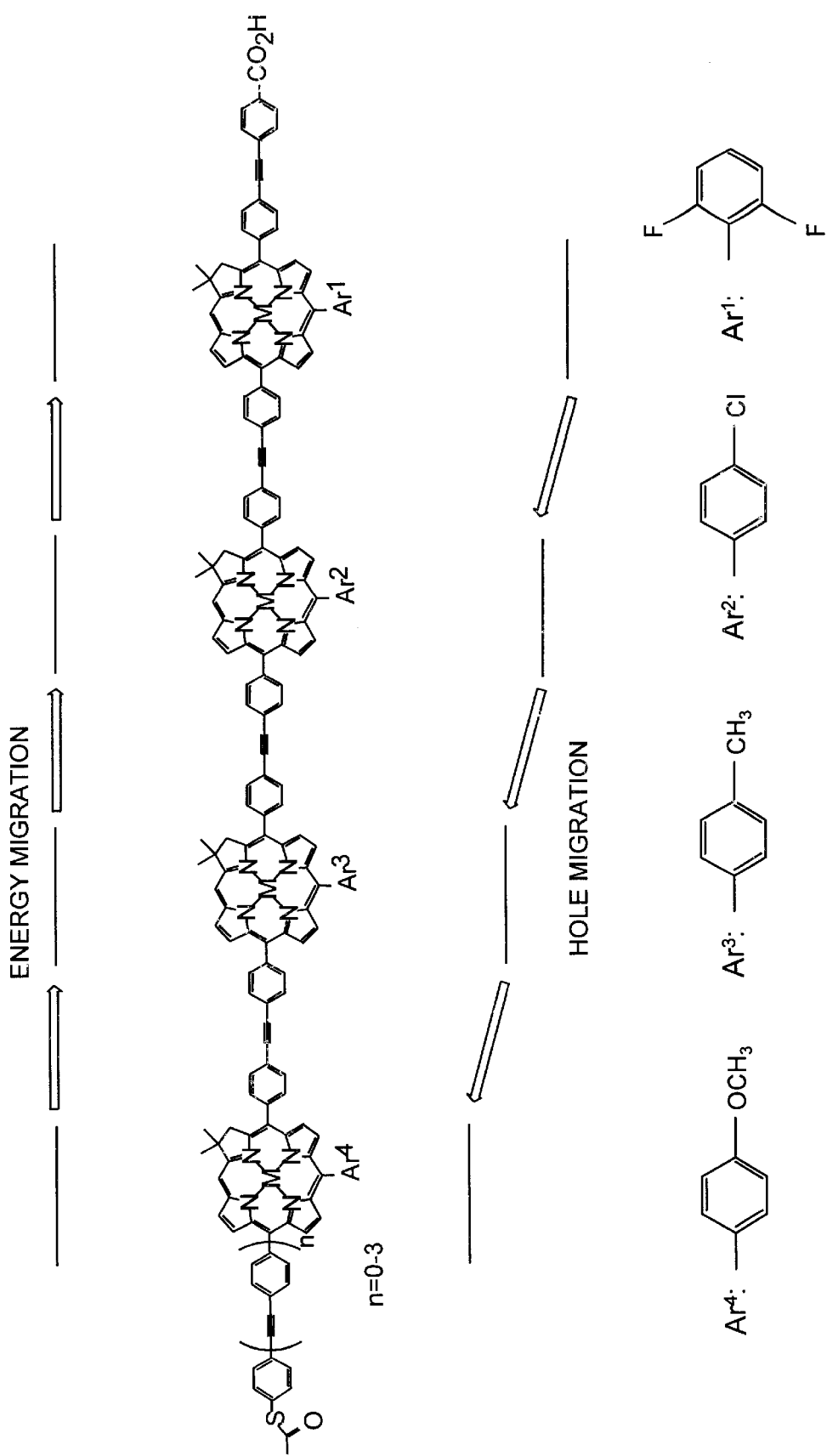
FIG. 25. Example of reversible energy migration and irreversible hole migration in a chromophore array.

An example of Design III is shown in FIG. 25. The LH rod is constituted with a series of metallochlorins. The linker for attachment to the electrode is a benzoic acid derivative, and the linker for attachment to the counterelectrode is a thioacetate. Such S-acetyl protected thiols undergo cleavage upon exposure to strong base or upon contact with electroactive surfaces such as gold (Gryko, D. T. et al., *J. Org. Chem.* 1999, 64, 8635–8647). The LH and CSU components are designed to facilitate hole migration from the CSU to the distal end where the attachment is made to the counterelectrode.

Figure 26:
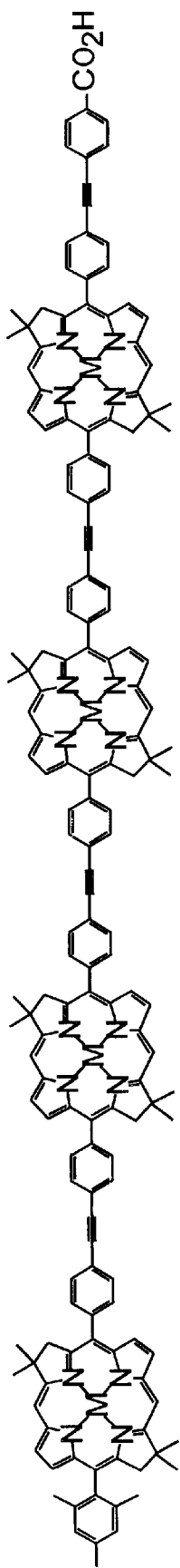
FIG. 26. A diphenylethyne-linked bacteriochlorin containing array.

Another type of pigment that can be used in these designs is a bacteriochlorin. Bacteriochlorins absorb strongly in the blue, like porphyrins, but also absorb strongly in the near-infrared and across the visible region (e.g., tetraphenylbacteriochlorin, $\epsilon_{378\ nm}$=160,000 $M^{-1}cm^{-1}$, $\epsilon_{520\ nm}$=160,000 $M^{-1}cm^{-1}$, $\epsilon_{740\ nm}$=130,000 $M^{-1}cm^{-1}$)(Whitlock, H. W. et al. *J. Am. Chem. Soc.* 1969, 91, 7485). The structure of a linear LH rod comprised of bacteriochlorins is shown in FIG. 26.

F. Comparisons of Architectures and Intrinsic Rectification.

A very attractive feature of Designs II and III is that the sequence of pigments in the light harvesting rod causes energy to flow irreversibly from the site of absorption to the CSU. Simulations show that such energy gradients provide a dramatic increase in the quantum efficiency for excitation energy reaching the trap (in this case, the charge separation unit) (Van Patten, P. G. et al., *J. Phys. Chem. B* 1998, 102, 4209–4216). An added feature of Design III is that the hole (formed at the CSU) flows irreversibly via hole-hopping from the CSU to the counterelectrode. The judicious selection of pigments makes possible the irreversible flow of energy and holes in opposite directions in the LH rod. Linear rods that enable energy and holes to flow in opposite directions are ideally suited for incorporation in the ultrathin solar cells described herein.

The phenomena described above allows these designs to provide intrinsic rectification. Intrinsic rectification can involve (i) the irreversible flow of excited state energy or electrons along some or all of the length of the light harvesting rod, (ii) the irreversible flow of holes along some or all of the length of the light harvesting rod, or (iii) both (i) and (ii) above, with holes and energy or electrons moving in opposite directions.

For irreversible energy migration (intrinsic rectification of energy or electrons), the light harvesting rod should be structured so that $E^*(X^1) < E^*(x^2) < E^*(x^3) \ldots < E^*(X^n)$, where $E^*(X^i)$ is the energy of the excited state of the $i^{th}$ chromophore component X.

For irreversible hole hopping (intrinsic rectification of holes), the light harvesting rod should be structured so that $E_{1/2}(X^1) > E_{1/2}(X^2) > E_{1/2}(X^3) \ldots > E_{1/2}(X^i)$, where $E_{1/2}$ is the electrochemical midpoint oxidation potential of the $i^{th}$ chromophore component X.

While the chromophores of the light harvesting rods could be isoenergetic, the provision of intrinsic rectification as described above is preferred. However, intrinsic rectification need not occur along the entire light harvesting rod, nor even be provided adjacent to the charge separation unit. For example, one or more isoenergetic chromophores could be provided adjacent to the charge separation unit and intrinsic rectification of holes and/or energy provided elsewhere within the light-harvesting rod, such as in an intermediate or distal segment. Thus the term "intrinsic rectification" of excited-state energy, holes, and/or electrons by a light-harvesting rod refers to intrinsic rectification that is carried out along any segment or portion of said light harvesting rod.

G. Fabrication of the Solar Cell.

The deposition of the linear LH/CSU molecules on the electrode is performned by reacting the electrode with a solution of the LH/CSU molecules, followed by washing to remove any unbound species. Homogeneous or heterogeneous depositions can be performed. That is, a homogeneous population of molecules can be deposited, or mixtures of the LH/CSU molecules can be employed. One advantage of the latter procedure is that molecules having different components in the LH array can be used to cover the solar spectrum. The various types of LH arrays include but are not limited to the following: all-chlorin, bacteriochlorin, porphyrin+phthalocyanine, meso,meso-linked porphyrins, perylene+porphyrin arrays. Mixtures of these types of LH arrays can be used in a solar cell to provide effective solar coverage. In this manner, it is not essential that each LH/CSU rod provide complete coverage of the solar spectrurn.

Photogalvanic-like solar cells can be fabricated by positioning a charge separation unit away from the electrode surfaces. The incorporation of a driving force for electron transfer to the anode and a driving force for hole transfer to the cathode will result in efficient energy conversion. A potential advantage of this approach is that light harvesting and intramolecular charge separation will occur distant from the electrode surfaces thereby minimizing deleterious side reactions of the excited states and the electrode, such as excited-state quenching.

III. Chlorin Building Blocks for the Construction of Light-harvesting Arrays A. Introduction.

Chlorins have three advantages compared with porphyrins for use in solar collection and utilization. (1) Chlorins absorb strongly both in the blue region and in the red region of the visible region (hence their green color), effectively covering much of the solar spectrurn, while porphyrins absorb strongly only in the blue region (hence their red color). (2) The transition dipole moment of the long wavelength absorption in a chlorin is linearly polarized along one N—N axis, affording enhanced directionality of through-space energy transfer with neighboring pigments. In contrast, in a metalloporphyrin the transition dipole moment of the long wavelength absorption band lies in the plane of the macrocycle effectively localized along both N—N axes (planar oscillator), and therefore less directionality of energy transfer is observed. (3) Chlorins are more easily oxidized than porphyrins and therefore are better photoreductants.

Figure 27:
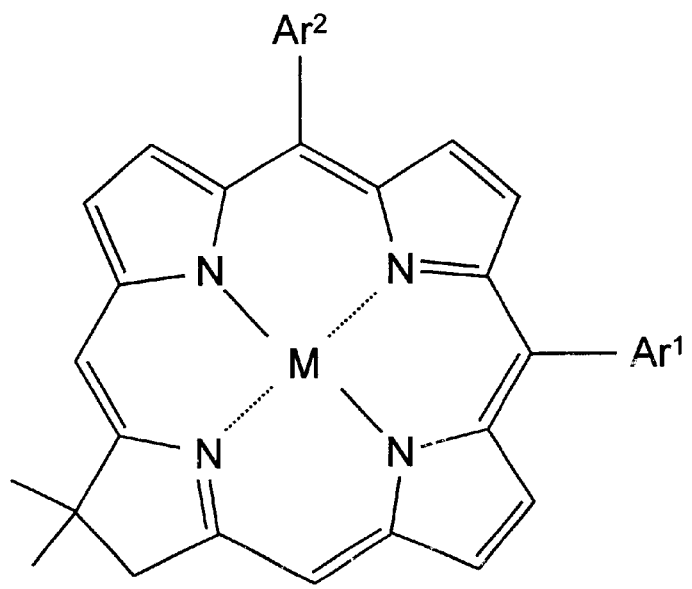
FIG. 27. Chlorin building blocks that have substituents (functional handles) at two of the meso positions, and none at the β positions.

A synthetic route that provides access to a new set of chlorin building blocks has recently been described (Strachan, J. P. et al., *J. Org. Chem.* 2000, 118, 3160–3172). The chlorin building blocks exhibit typical chlorin absorption and fluorescence spectra. The chlorin building blocks have substituents (functional handles) at two of the meso positions, and none at the $\beta$ positions (FIG. 27). In prior studies of energy transfer in multiporphyrin arrays, several findings gerrnane to the design of pigments for incorporation in light-harvesting arrays comprised of covalently-linked pigments were made: (1) The energy transfer process involves both through-space (TS) and through-bond (TB) mechanisms, and the observed rate of energy transfer is the sum of the two processes (Hsiao, J.-S.; et al., *J. Am. Chem. Soc.* 1996, 118, 11181–11193). (2) The rate of TB energy transfer is affected by the nature of the molecular orbitals in the energy donor, energy acceptor, and linker joining the donor and acceptor (Strachan, J. P.et al., *J. Am. Chem. Soc.* 1997, 119, 11191–11201; Yang, S. I. et al.,*J. Am. Chem. Soc.* 1999, 121, 4008–4018). In particular, more extensive electronic communication (and a faster rate of transfer) occurs upon attachment of the linker at sites on the donor and acceptor where the frontier molecular orbitals have high electron density versus sites with low electron density. To be explicit, in a porphyrin having an $a_{2u}$ HOMO (which has electron density predominantly at the meso positions and little at the $\beta$ positions), faster rates (2.5–10-fold) are observed with linkers at the meso rather than $\beta$ positions (FIG. 28). Conversely, in a porphyrin having an $a_{1u}$ HOMO (which has electron density predominantly at the $\beta$ positions and little if any at the meso positions), faster rates are observed with linkers at the $\beta$ rather than meso positions. Such a rate differential is incurred with each pigment-to-pigment energy-transfer step in linear multipigment arrays, which is manifest as a large effect on the overall rate and yield of energy transfer (Van Patten, P. G. et al., *J. Phys. Chem. B* 1998, 102, 4209–4216).

The factors that affect TS energy transfer (Forster mechanism) are well known. Two key determinants are the oscillator strength of the excited-state donor (reflected in the radiative rate for the lowest energy transition) and the oscillator strength of the ground-state acceptor (reflected in the molar absorption coefficient of the lowest energy transition). Chlorins are ideal candidates for TS energy transfer due to their strong oscillator strength of the long-wavelength absorption band, especially compared with porphyrins due to their weak oscillator strength (i.e., weak absorption) in the red. Another key determinant involves the orientation of the respective transition dipole moments of the donor and acceptor. The orientation term ($\kappa^2$) in Forster TS energy transfer takes on values of 0 (orthogonal), 1 (parallel but not collinear), and 4 (collinear) depending on the vector orientation of the transition dipole moments. The most efficient energy transfer occurs with molecular arrangements such that the donor and acceptor transition dipole moments are collinear, and the least efficient occurs with orthogonal orientations (Van Patten, P. G. et al.,*J. Phys. Chem. B* 1998, 102, 4209–4216).

The prediction of the energy-transfer properties of chlorin-containing arrays can be summarized. In diphenylethyne linked multiporphyrin arrays (meso-linked, $a_{2u}$ HOMO), the observed rate of energy transfer from a zinc porphyrin to a free base porphyrin was found to be $(24 \text{ ps})^{-1}$ with contributions of $(720 \text{ ps})^{-1}$ for TS transfer and $(25 \text{ ps})^{-1}$ for TB transfer. For chlorins the radiative rate constant is increased by ~4-fold and the molar absorptivity is increased by $\geq$10-fold vs. porphyrins. Considering the incorporation of chlorins in an ideal geometry for Forster transfer with the same intervening diphenylethyne linker, the orientation term ($\kappa^2$) would be up to ~2 vs. 1.125 for porphyrins. The net result is an expected increase of up to 100-fold in rate of TS energy transfer with chlorins vs. porphyrins.

The TB transfer rate with chlorins is difficult to estimate but should fall into the range observed with the porphyrins, which ranged from $(25 \text{ ps})^{-1}$ to $(360 \text{ ps})^{-1}$ for depending on orbital density at the site of linker connection. The TS transfer for chlorins should be 40–100 fold faster than for porphyrins (i.e., from $(18 \text{ ps})^{-1}$ to $\sim(7 \text{ ps})^{-1}$). Accordingly, the anticipated rate for chlorin-chlorin energy transfer should be in the range of $\sim(10 \text{ ps})^{-1}$ to $\sim(20 \text{ ps})^{-1}$.

In moving from diphenylethyne-linked multiporphyrin arrays to p-phenylene linked arrays the observed energy transfer rate increased from $(24 \text{ ps})^{-1}$ to $(2 \text{ ps})^{-1}$. Upon going to a p-phenylene linker with chlorins, the shorter distance should cause an increase of ~100-fold in the TS contribution to the rate. In this case, the TS mechanism dominates the TB rate. Accordingly, energy-transfer rates from chlorin to chlorin in p-phenylene-linked arrays are anticipated to be in the sub-picosecond regime for both meso- and $\beta$-substituted chlorins.

These rough calculations illustrate that chlorins are anticipated to have a large TS component of the observed energy transfer process in multi-chlorin arrays. The faster rates of energy transfer with chlorins vs. porphyrins, in conjunction with the superior spectral properties (i.e., blue and red absorption) of chlorins vs. porphyrins, provides strong impetus for constructing chlorin-containing light-harvesting arrays. Both meso-substituted chlorin building blocks and β-substituted chlorin building blocks are sought.

B. Molecular Design.

Here chlorin building blocks designed to give efficient energy transfer in chlorin-containing light-harvesting arrays are presented. Objectives are to (1) prepare chlorins with two functional handles such that the chlorins can be readily incorporated into linear arrays, (2) design the chlorin building blocks to have the highest possible value of the orientation term for TS energy transfer, and (3) be connected appropriately to give the most extensive TB energy transfer process. What are the best sites on the chlorin for connection of the linker? Four possible trans-substituted chlorins are displayed in FIG. 29. Two β,β'-substituted chlorins are shown, as are two chlorins each bearing two meso substituents. To evaluate the chlorin building blocks one must consider (1) steric effects of any substituents, (2) the orientation of the transition dipole moment for the long wavelength transition, and (3) the composition of the frontier molecular orbitals.

Examination of the four chlorin building blocks in FIG. 29 reveals steric hindrance in chlorin IV due to the interaction of the meso substituent flanking the geminal methyl groups of ring D. The other three chlorins I–III have no such steric interactions and are superior to IV in this regard.

Figure 30:
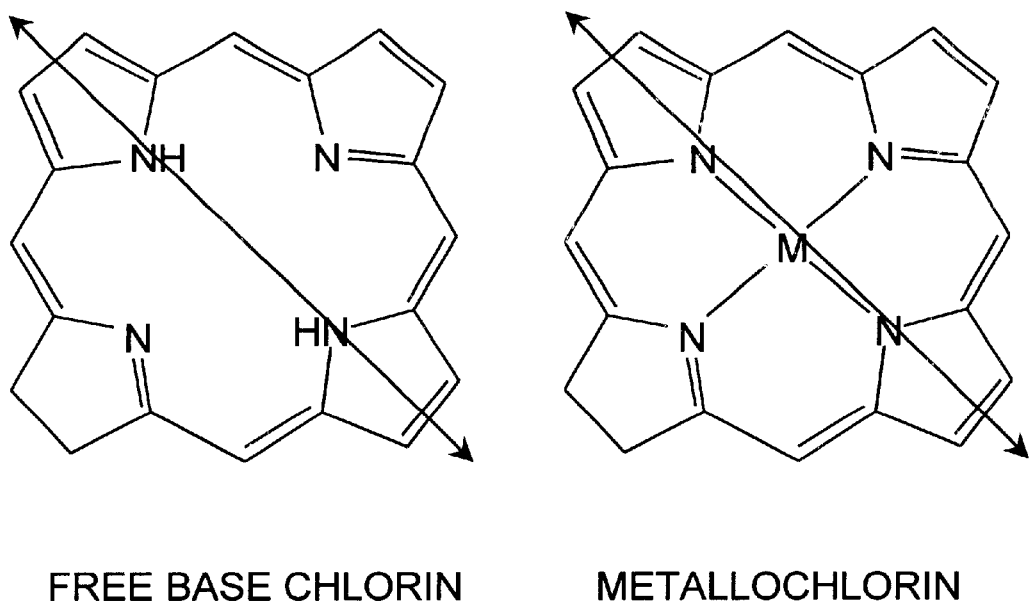
FIG. 30. Orientation of the transition dipole moment of the long-wavelength absorption band in free base chlorin and metallochlorin.

The transition dipole moment for the far-red transition in chlorins is polarized along the N—N axis perpendicular to the reduced ring (ring D), transecting rings A and C not rings B and D (FIG. 30). Evaluation of the four possible trans-chlorins shown in FIG. 29 requires consideration of the geometries obtained upon incorporation in covalently linked arrays. The pairwise interactions are displayed in FIG. 31, where a diphenylethyne linker is employed to join the chlorins (other linkers, including ap-phenylene group could also be employed). For the meso-linked chlorins, $\kappa^2$ takes on limiting values of 0.25 and 2.25 depending on orientation. Assuming free rotation during the lifetime of the excited state (dynamical averaging), the average value of $\kappa^2$ is 1.125. Note that free rotation is expected about the cylindrically symmetric ethyne but the rate of rotation may not be sufficient to cause all molecules to explore all conformations during the few ns lifetime of the excited state. Thus, those molecules in an orientation characterized by a zero or near-zero value of $\kappa^2$ will not give rise to efficient TS energy transfer. The β,β'-substituted chlorins have limiting $\kappa^2$ values of ~1.6 and the value remains >1 regardless of dihedral angle about the ethyne linker. (Note that in this case the center-to-center distance changes slightly upon rotation about the ethyne linker.) Thus, the β,β'-substituted chlorins give slightly better collinearity of the transition dipole moment with the axis of substitution (to be the linear axis of the multi-chlorin array) than is obtained with the meso-substituted chlorins. Taken together, chlorin building blocks I and II are slightly preferred over III and IV for TS energy transfer.

Figure 32:
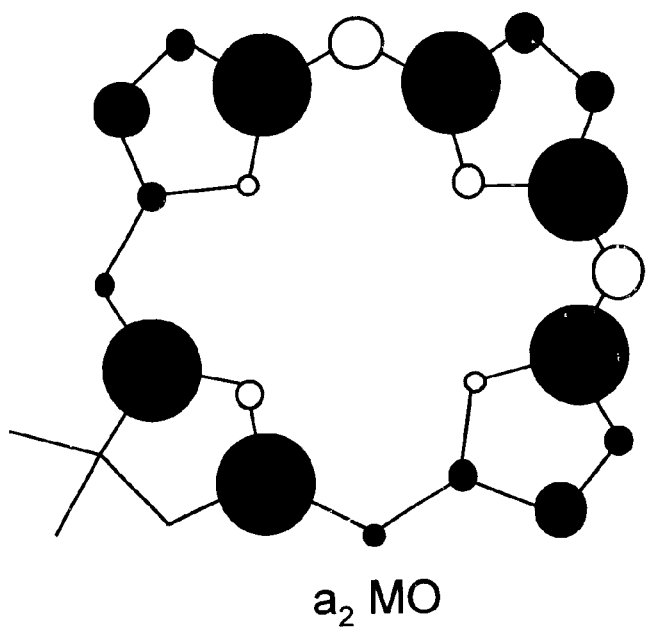
FIG. 32. The highest occupied molecular orbital of a chlorin is an $a_2$ orbital, which places electron density at each of the meso and non-reduced β sites.

The highest occupied molecular orbital of a chlorin is an $a_2$ orbital, which places electron density at each of the meso and β sites (FIG. 32). Accordingly, it is difficult to estimate the relative goodness of meso versus β sites of linker attachment for efficient TB energy transfer. In the absence of this knowledge, the β-substitution chlorins and the meso-substituted chlorins are believed to have comparable utility.

In any event, as the distance of separation of the rings becomes quite short, the TS mechanism will dominate and the TB mechanism will become a relatively minor contributor to the observed rate. The chief disadvantage of the meso-substituted trans chlorins stems from possible ruffling of the macrocycle due to steric congestion with the partially saturated ring. The trans configuration can be achieved with connection to rings A and C. Comparing the four possible trans-chlorins shown in Scheme 4 for TB energy transfer, it is seen that the meso-substituted chlorins (III, IV) are inferior to the β,β'-substituted chlorins (I, II).

In summary, the chlorin building blocks I, II, and III are useful for constructing light-harvesting arrays. From a synthetic standpoint, chlorin building block I is more readily accessible than II. Note that the previous set of chlorin building blocks that were prepared provided typical chlorin absorption properties but were inappropriate for preparing linear arrays having synthetic handles at two adjacent (cis) meso positions rather than two trans meso or β positions (FIG. 27). In contrast, chlorins I and II are ideal components of synthetic light-harvesting arrays and should give fast rates of transfer.

C. Synthesis.

The synthesis of the β-substituted chlorin building blocks (type I) follows the general route previously established for preparing meso-substituted chlorins, as discussed above. In this route, an Eastern half and a Western half undergo condensation followed by oxidative cyclization to give the chlorin. The same approach is used here with a new Eastern half and a new Western half, each bearing one β substituent (FIG. 33).

Figure 34A:
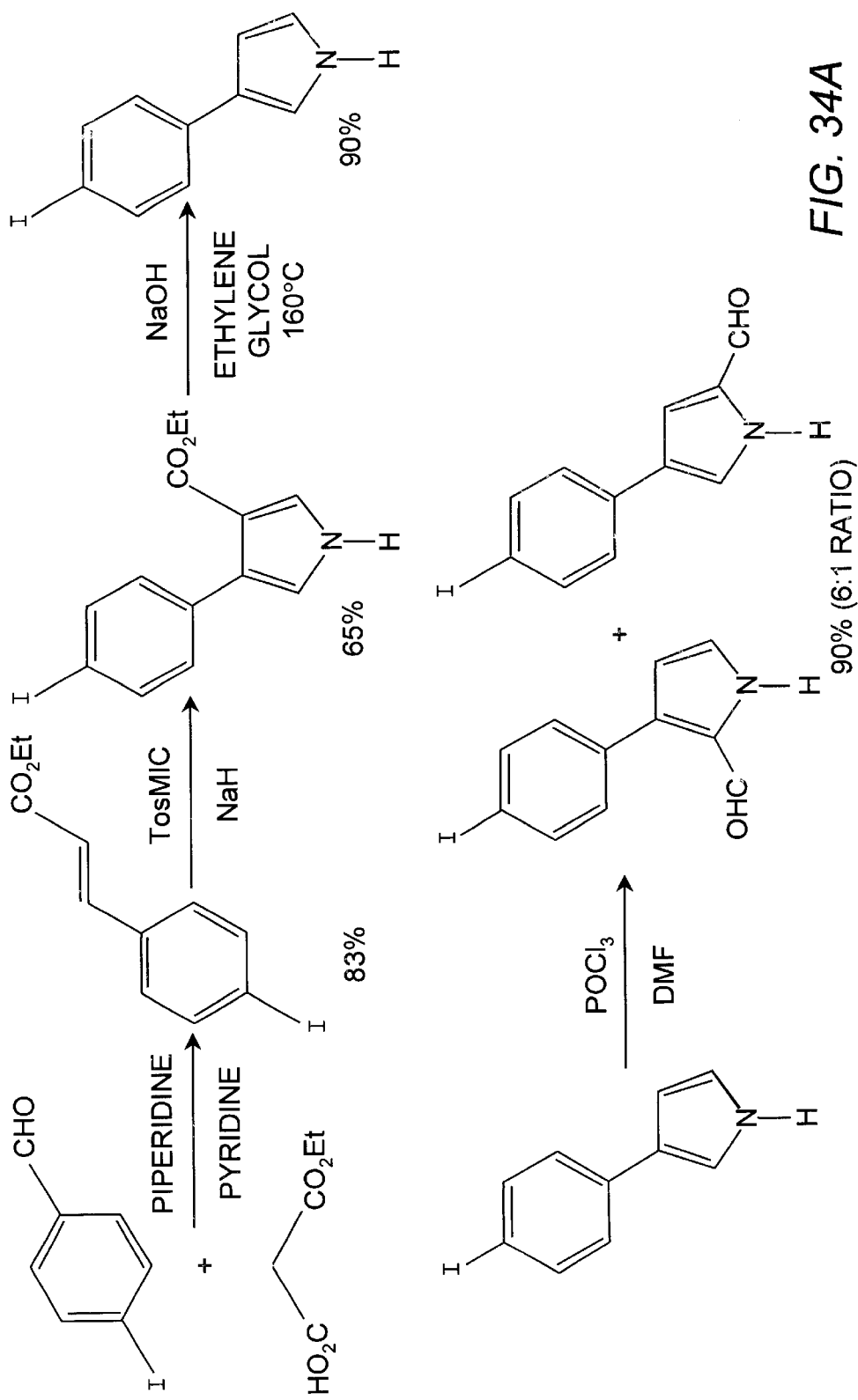
FIG. 34A. The synthesis of the new β-substituted Eastern half for chlorin synthesis.
Figure 34B:
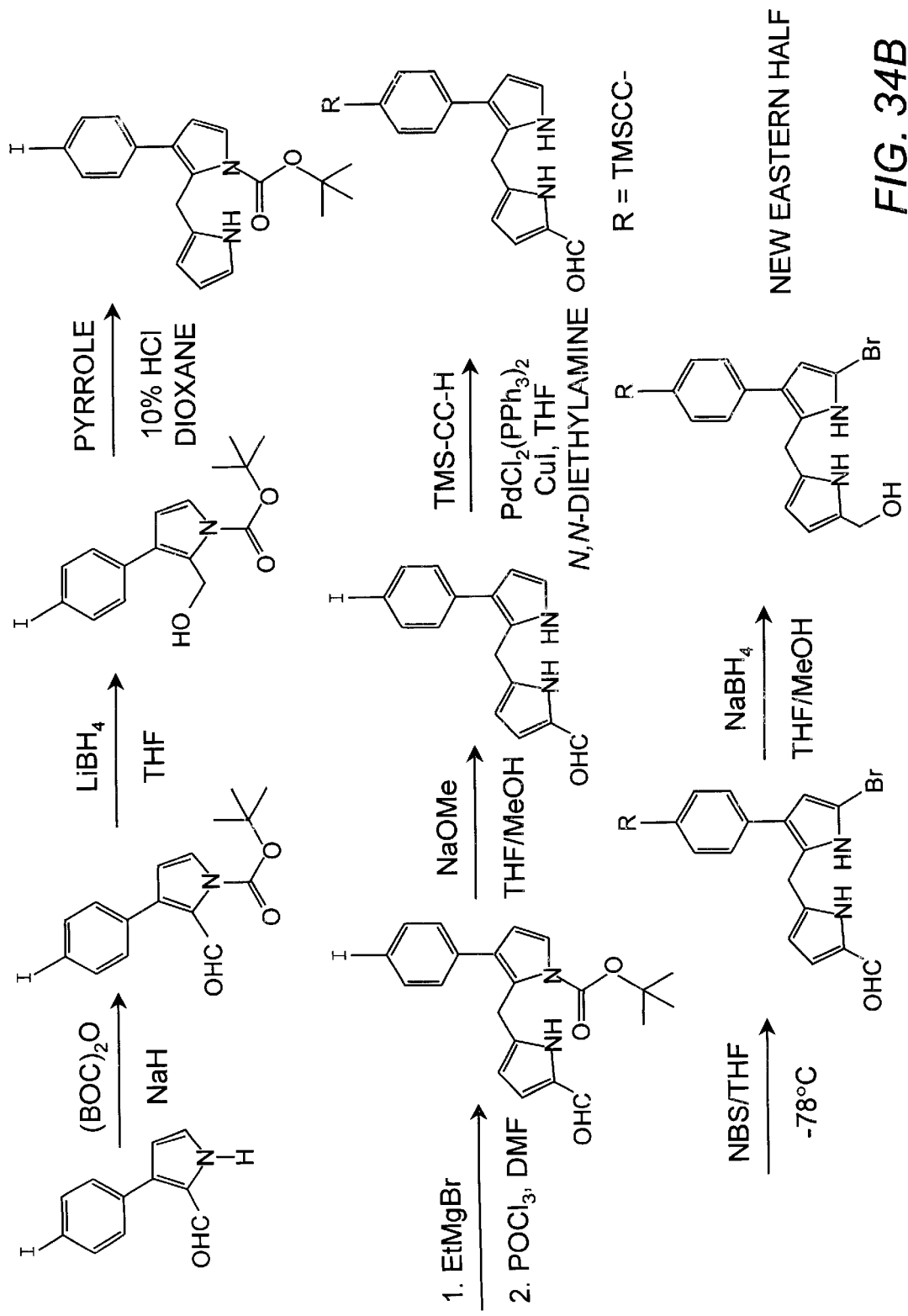
FIG. 34B. The synthesis of the new β-substituted Eastern half for chlorin synthesis, extending the route shown in FIG. 34A.

The synthesis of the new β-substituted Eastern half is shown in FIGS. 34A and 34B. This synthesis, which builds on prior work in developing a route to β-substituted porphyrin building blocks (Balasubramanian, T.; Lindsey, J. S. *Tetrahedron* 1999, 55, 6771–6784), is described in Example 1 below.

Figure 35:
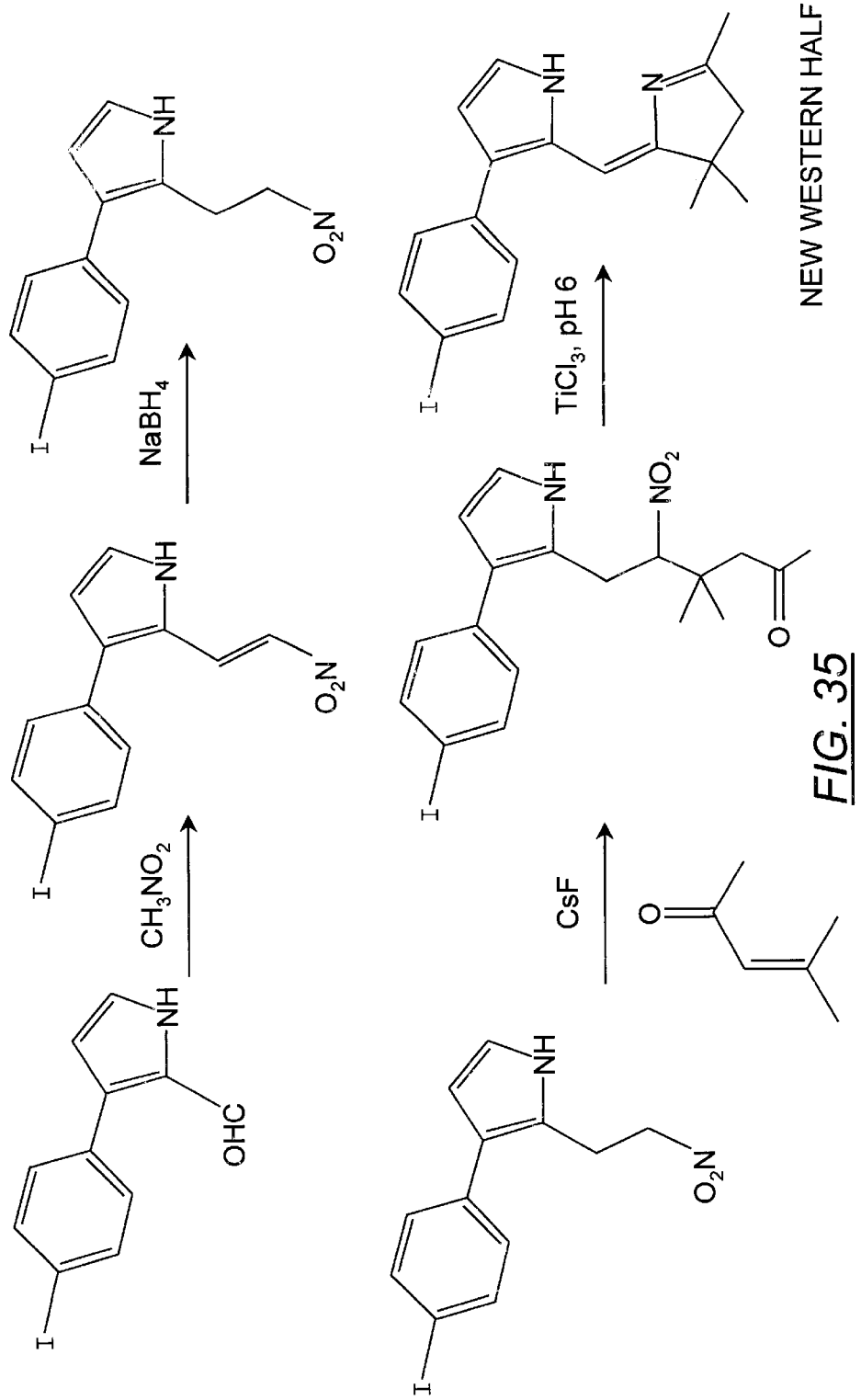
FIG. 35 illustrates the synthesis of the new β-substituted Western half for a chlorin building block.

The synthesis of the new β-substituted Western half is shown in FIG. 35. This route begins with the same critical intermediate as used in the Eastern half, a 2-formyl-3-arylpyrrole (FIG. 34A). The Western half is then prepared following the same sequence of reactions employed for the unsubstituted Western half. This latter route is under examination.

Figure 33:
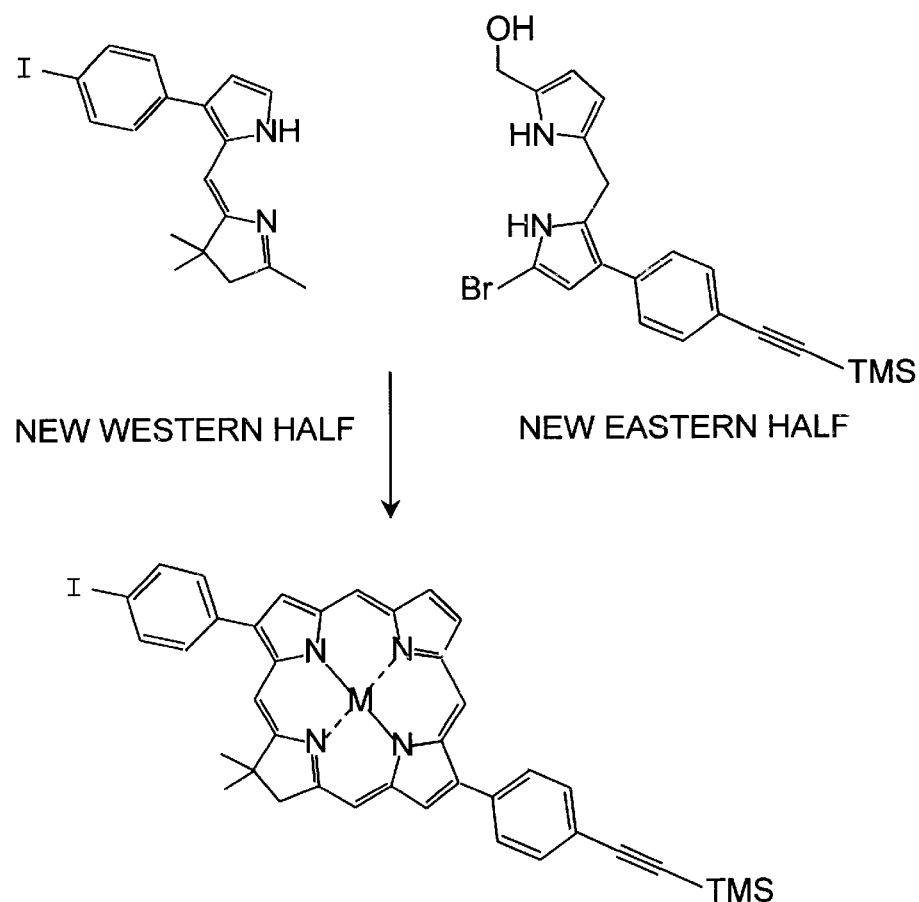
FIG. 33 illustrates the synthesis of a trans-chlorin building block with two β substituents.
Figure 36:
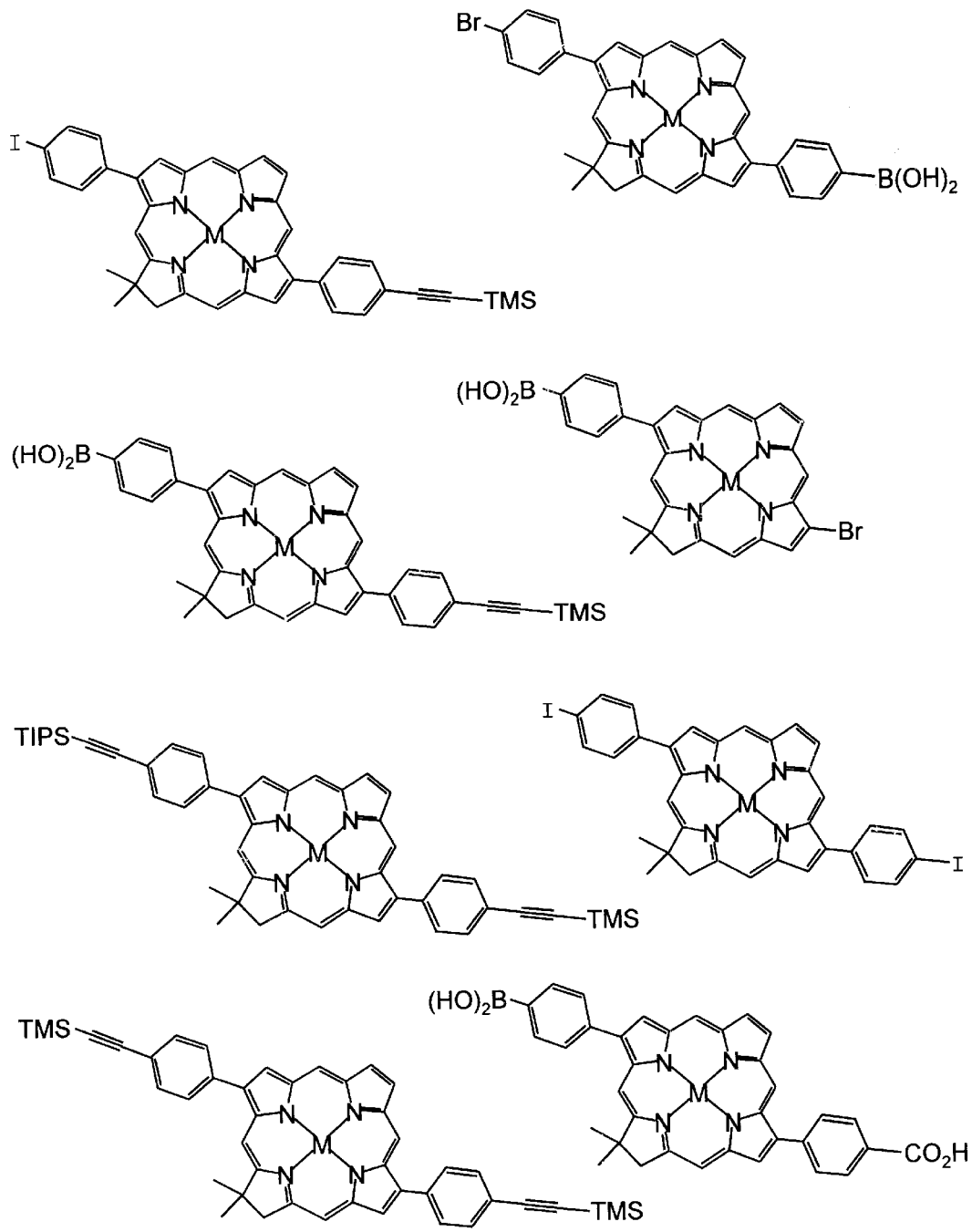
FIG. 36. Other chlorin building blocks that are accessible via this same synthetic strategy shown above, and that have substantially the same physical properties.

The chlorin building block shown in FIG. 33 bears one 4-(TMS-ethynyl)phenyl group and one 4-iodophenyl group. This particular building block should enable the synthesis of diphenylethyne linked chlorin containing arrays in a linear architecture. Other chlorin building blocks that are accessible via this same synthetic strategy, and that have the same desirable physical properties, are shown in FIG. 36.

Figure 37:
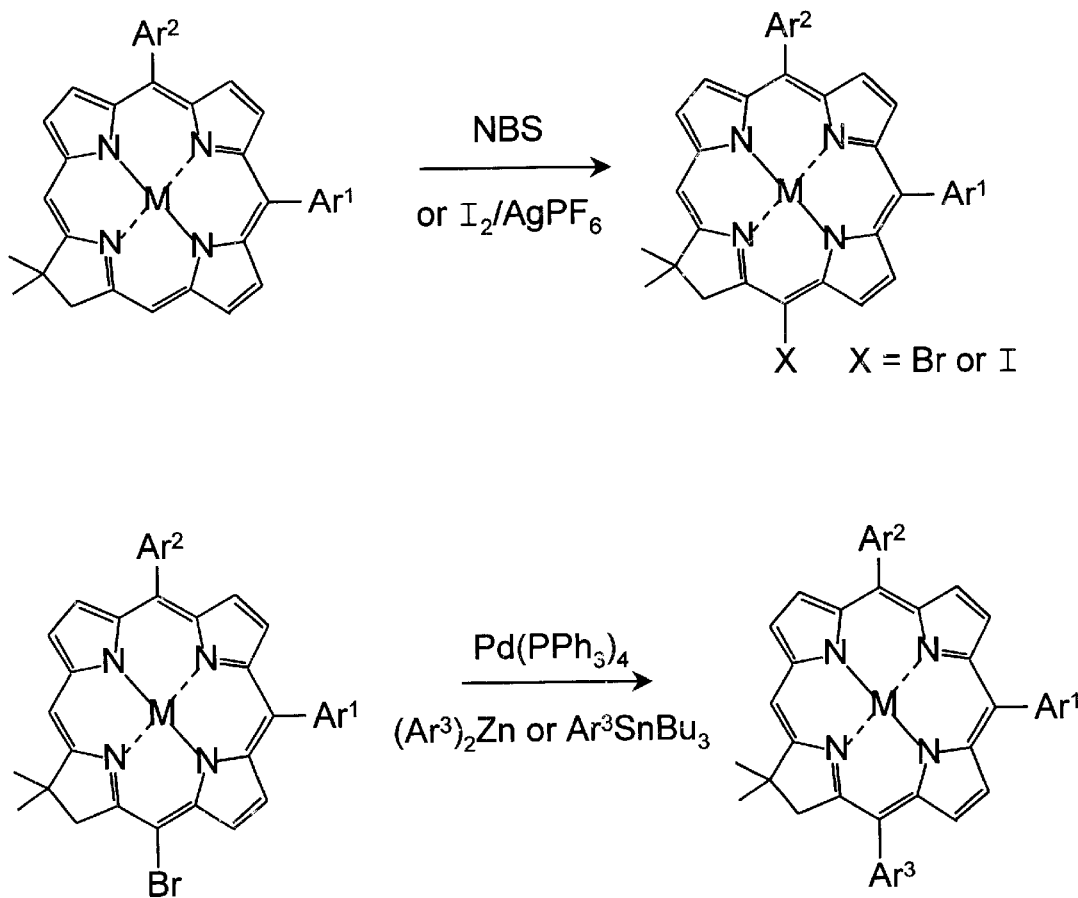
FIG. 37. The synthesis of the trans meso-substituted chlorin building blocks (type III) by an extension of the route for preparing chlorins bearing adjacent (cis) meso-substituted chlorins.

The synthesis of the trans meso-substituted chlorin building blocks (type III) is obtained in two ways. One route involves an extension of the route recently established for preparing chlorins bearing adjacent (cis) meso-substituted chlorins (FIG. 27) (Strachan, J. P. et al., *J. Org. Chem.* 2000, 118, 3160). Treatment of a cis meso-substituted chlorin with NBS (DiMagno, S. G. et al., *J. Org. Chem.* 1993, 58, 5983–5993) is anticipated to give selective bromination as shown in FIG. 37. Alternatively iodination can be performed using iodine and $AgPF_6$ (Nakano, A. et al., *Tetrahedron Lett.* 1998, 39, 9489–9492). Woodward demonstrated that the two methine positions flanking ring D are highly reactive toward electrophilic reagents (Woodward, R. B.; Skaric, V. *J. Am. Chem. Soc.* 1961, 83, 4676–4678). The position between rings A and D is sterically hindered by the geminal methyl substituents, which should be sufficient to give reaction selectively at the methine positionss between rings D and C. Subsequent Pd-mediated cross-coupling (DiMagno, S. G. et al., *J. Org. Chem.* 1993, 58, 5983–5993) then gives the desired trans substituted ($Ar^2$, $Ar^3$) chlorin building block.

Figure 38:
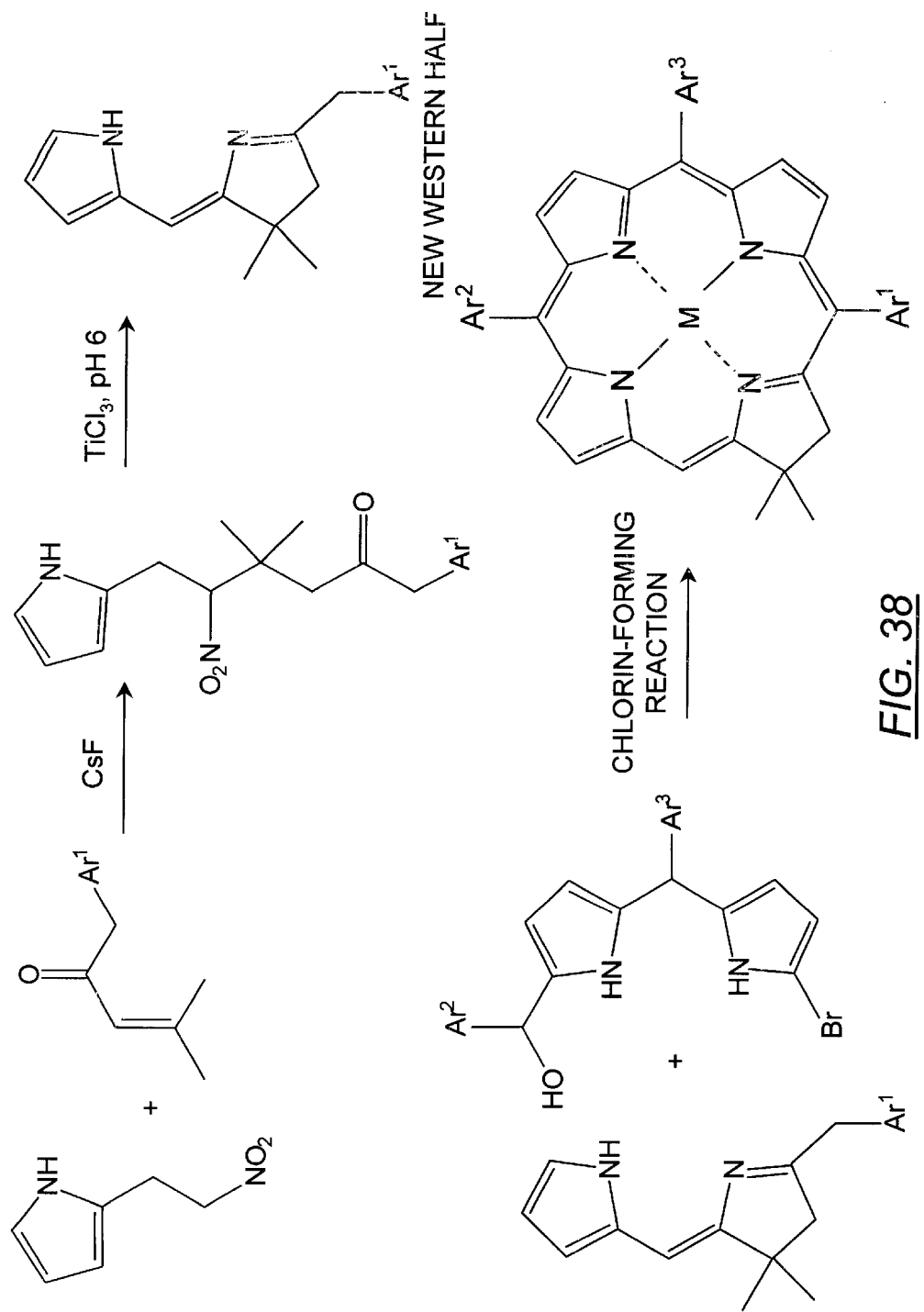
FIG. 38. A second route to trans meso-substituted chlorin building blocks (type III).

A second route to trans meso-substituted chlorin building blocks (type III) is shown in FIG. 38. A new Western half is prepared that bears, attached to the partially saturated ring, the substituent destined to be the corresponding meso substituent.

Figure 39:
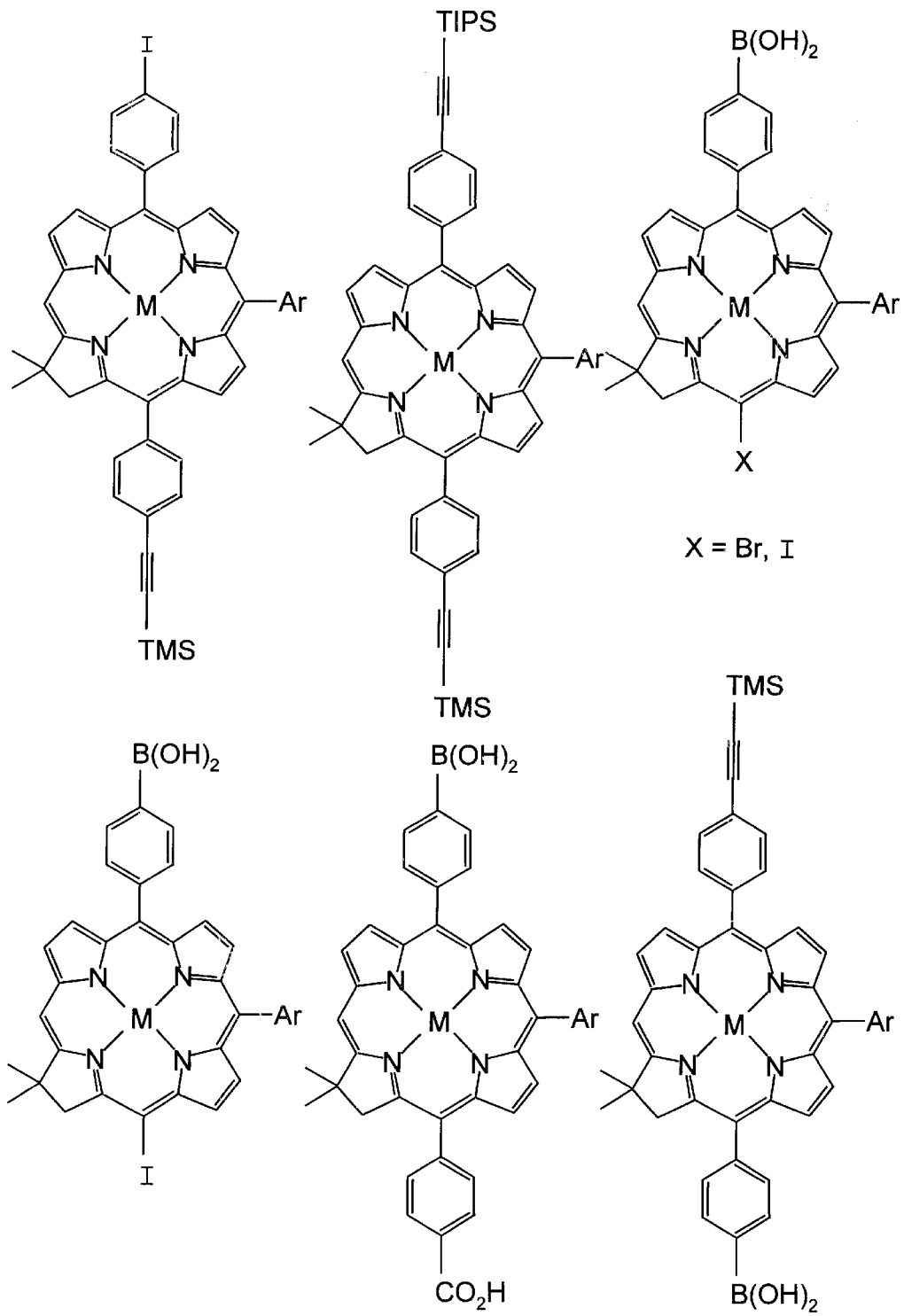
FIG. 39. Various meso-substituted chlorin building blocks that can be accessed in the synthetic manner described above.

Various meso-substituted chlorin building blocks that can be accessed in this manner, and that are useful for incorporation in synthetic light-harvesting arrays, are shown in FIG. 39. Note that substituents to be employed as the aryl unit (Ar) can be used to tune the electrochemical potential, for solubility purposes, or to control packing of the light-harvesting arrays in self-assembled structures.

For all of the chlorin building blocks, a wide variety of metals can be employed, given that the metals meet the requirement of affording a photochemically active excited state. Preferred embodiments of such metals are Zn, Mg, Pd, Sn, and Al. The free base chlorin (M=H, H) can also be employed. In the syntheses employed, the chlorin-forming reaction yields the zinc chlorin, which is easily demetalated with mild acid to give the free base chlorin. The desired metallochlorin can then be prepared via well known metalation reactions.

IV. The Flow of Excited-state Energy and Ground-state Holes in Opposite Directions in Light Harvesting Arrays A. Introduction.

Figure 40:
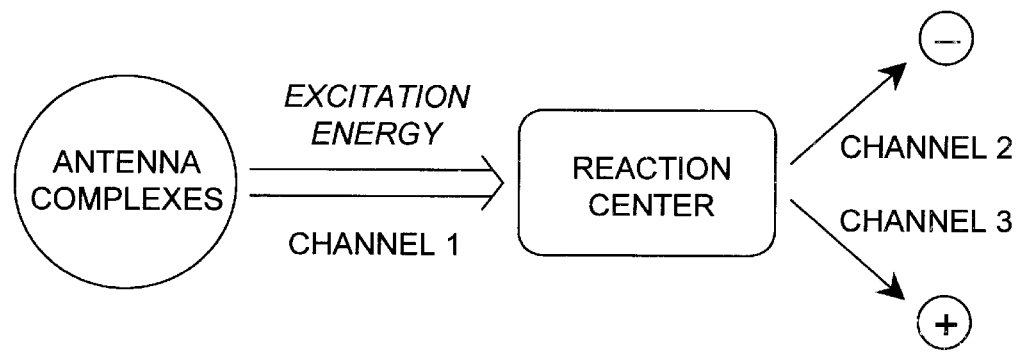
FIG. 40. The relationship of antenna complexes and reaction center for the production of holes and electrons from excitation energy flowing from the antenna.

Sunlight is dilute and therein lies one of the major challenges in developing efficient means of utilizing sunlight as a source of energy. The strategy employed by photosynthetic organisms is to absorb sunlight with multipigment antenna complexes and then funnel the resulting excited-state energy among the pigments such that the excitation reaches a reaction center (i.e., a charge separation unit). In the reaction center a charge separation reaction occurs, giving a reducing equivalent (electron) and an oxidizing equivalent (hole). In plants, the reducing and oxidizing equivalents are ultimately used to reduce carbon dioxide (forming carbohydrates) and oxidize water (liberating oxygen), respectively. Thus, electrons flow both from the reaction center and to the reaction center (filling the hole created by charge separation). The reaction center therefore must have three channels; a channel for the flow of excitation energy from the antenna, a channel for the emanation of electrons following charge separation, and a channel for the input of electrons to regenerate the reaction center following charge separation (FIG. 40). Note that the inward flow of electrons and the outward migration of holes are equivalent processes and these terms are used synonymously.

In terms of size, the antenna complexes dwarf the reaction centers. While chlorophyll molecules are contained both in the antenna complexes and in the reaction center, the bulk of the chlorophyll is located in the antenna complexes. For example, about six chlorophylls (or chlorophyll derivatives) typically reside in a bacterial photosynthetic reaction center, whereas up to several hundred chlorophylls can be present in the antenna complexes. The antenna complexes serve to collect dilute sunlight, and the reaction centers initiate the transduction of excited-state energy into chemical fuel via the intermnediacy of a stabilized charge-separated state.

The generation of stable separated charges in the reaction center involves a series of electron transfer steps among a series of electron acceptors. With each step the overall reverse (i.e., recombination) rate of electron transfer becomes slower. After three steps the rate differential of the initial forward step (kf) and the rate of recombination (krecomb) is given by $k_f/k_{recomb} \sim 10^6$. The series of fast forward transfers and slow reverse transfers affords rapid and efficient separation of the electron and hole over a long distance.

A large effort has been devoted to the development of synthetic antenna molecules and synthetic charge-separation units (i.e., the equivalent of the reaction center). In general the antennas prepared to date are comprised of 10 or fewer pigments (Li, J.; Lindsey, J. S. *J. Org. Chem.* 1999, 64, 9101–9108). Other molecules have been constructed that provide small antennas attached to a charge-separation unit (CSU) (Kuciauskas, D. et al., *J. Am. Chem. Soc.* 1999, 121, 8604–8614). These molecules have demonstrated efficient light harvesting (i.e., light absorption and energy migration) and efficient charge separation. For the most part, the synthetic antennas, CSU, and integrated antenna-CSU systems have been studied in solution. Such studies can provide deep insight into mechanisms and properties but rarely address issues for organizing a collection of light-harvesting antennas and CSUs, as must be done for constructing any practical system for utilizing sunlight.

Figure 41:
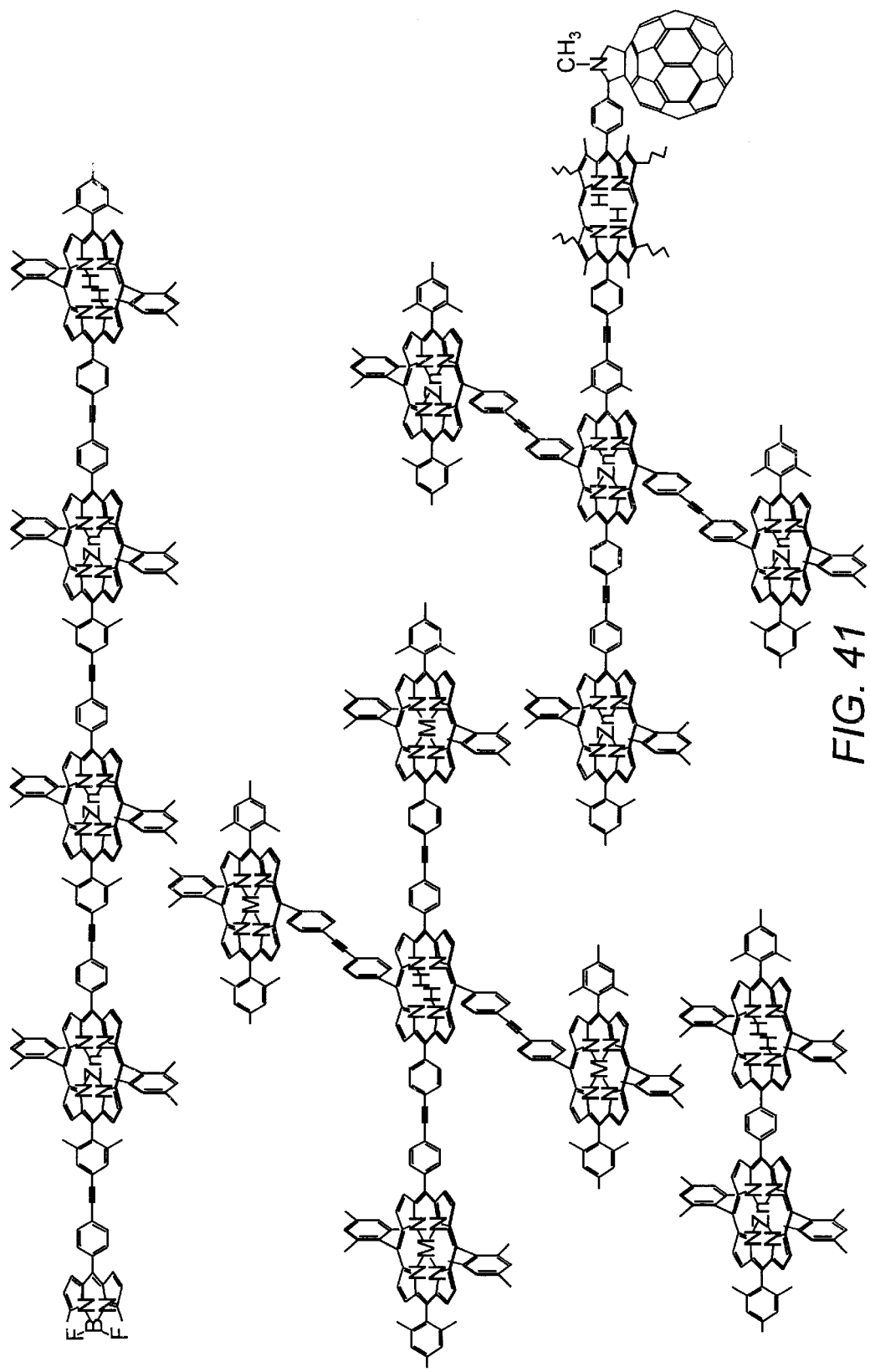
FIG. 41. Light-harvesting arrays that absorb light and undergo efficient intramolecular energy transfer.

Light-harvesting arrays that absorb light and undergo efficient intramolecular energy transfer have been designed and synthesized. Examples of such molecules are shown in FIG. 41. With a diphenylethyne linker, the rate of energy transfer from zinc porphyrin to free base porphyrin is $(24\ ps)^{-1}$. With a p-phenylene linker, the rate of energy transfer from zinc porphyrin to free base porphyrin is $(2\ ps)^{-1}$. In order to probe the role of the linker in mediating excited-state energy transfer among the porphyrins, examined the electrochemical properties of these multiporphyrin arrays was examined. The electrochemical potentials of the individual pigments are maintained upon incorporation into the arrays. However, the hole created in the multiporphyrin array is delocalized as determined by EPR analysis. The rate of hole-hopping among porphyrins in the array in fluid solution is faster than can be resolved by the EPR technique, implying a rate $>10^7\ s^{-1}$ (Seth, J. et al., *J. Am. Chem. Soc.* 1994, 116, 10578–10592; Seth, J. et al., *J. Am. Chem. Soc.* 1996, 118, 11194–11207). These studies revealed that there exist significant ground-state electronic interactions in the multiporphyrin arrays and that the interaction must be mediated by the linker that joins the porphyrins. In summary, the multiporphyrin arrays have the desired features of light absorption and excited-state energy migration that are essential for efficient light-harvesting, and in addition, have the unexpected feature of facile ground-state hole-hopping processes upon formation of the oxidized complexes.

B. Design of Linear Arrays.

Figure 43:
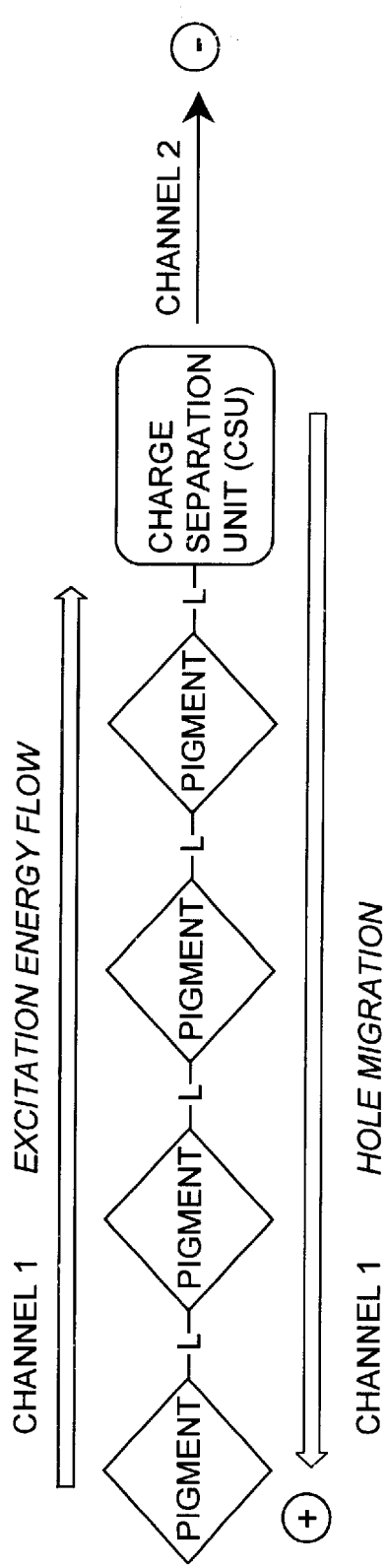
FIG. 43. The design of FIG. 42 has two significant ramifications. (1) Only two access channels are required at the CSU: one for emanation of the electrons, and one where excitation energy flows in and oxidizing equivalents (holes) flow out.

One of the challenges in designing a solar cell involves integrating the various components, which include an antenna, CSU, and pathways for electron flow from and to the CSU. Here a novel means of moving the oxidizing equivalent away from the charge-separation unit is proposed. In essence, the antenna is designed such that energy flows along the light-harvesting array to the charge-separation unit, while the oxidizing equivalent (hole) flows in the reverse direction from the CSU to a site in the antenna where subsequent electron-transfer reactions can take place (FIG. 42). This design has two significant ramifications. (1) Only two access channels are required at the CSU: one for emanation of the electrons, and one where excitation energy flows in and oxidizing equivalents (holes) flow out (FIG. 43). The existence of two channels rather than three eases the 3-dimensional packing constraints for organizing light-harvesting antennas around a CSU. (2) The migration of the hole away from the charge-separation unit results in stabilization of the charge-separated state. The vast majority of approaches explored for stabilizing the charge-separated state in synthetic systems has focused on the use of a series of electron acceptors for moving the electron away from the hole. The converse approach (described herein) employs a series of hole acceptors to move the hole far from the electron and thereby give a stable charge-separated state.

Porphyrinic molecules are central to this design. Porphyrins strongly absorb light, and give stable radical cations upon oxidation. A characteristic feature of porphyrins is that changes in the nature of electron-withdrawing or electron-releasing substituents attached to a porphyrin cause commensurate changes in the electrochemical potentials of the porphyrin, but do not significantly alter the absorption spectrum of the porphyrin (Seth, J.; Palaniappan, V.; Wagner, R. W.; Johnson, T. E.; Lindsey, J. S.; Bocian, D. F. *J. Am. Chem. Soc.* 1996, 118, 11194–11207). Hence, the electrochemical potentials of porphyrins can be tuned without changing the energy levels that play a role in energy migration. Said differently, the substituents shift the energy levels of both the HOMO and LUMO, causing changes in the oxidation and reduction potentials, respectively. The absorption spectrum depends on the difference between the energy of the HOMO and LUMO; if both HOMO and LUMO are shifted identically, no difference in the HOMO-LUMO gap is observed, and therefore the absorption spectrum remains unchanged. The ability to tune the oxidation potential without affecting the absorption spectrum makes possible the design of hole-transfer cascades while maintaining the energy-transfer properties of the arrays. The judicious choice of pigments with different absorption spectra, in conjunction with structural modifications for electrochemical tuning, allows energy and holes to flow downhill in opposite directions.

The following examples illustrate the opposite flow of excitation energy and ground-state holes. In FIGS. 44–49, the energy level diagrams are illustrative.

Figure 44:
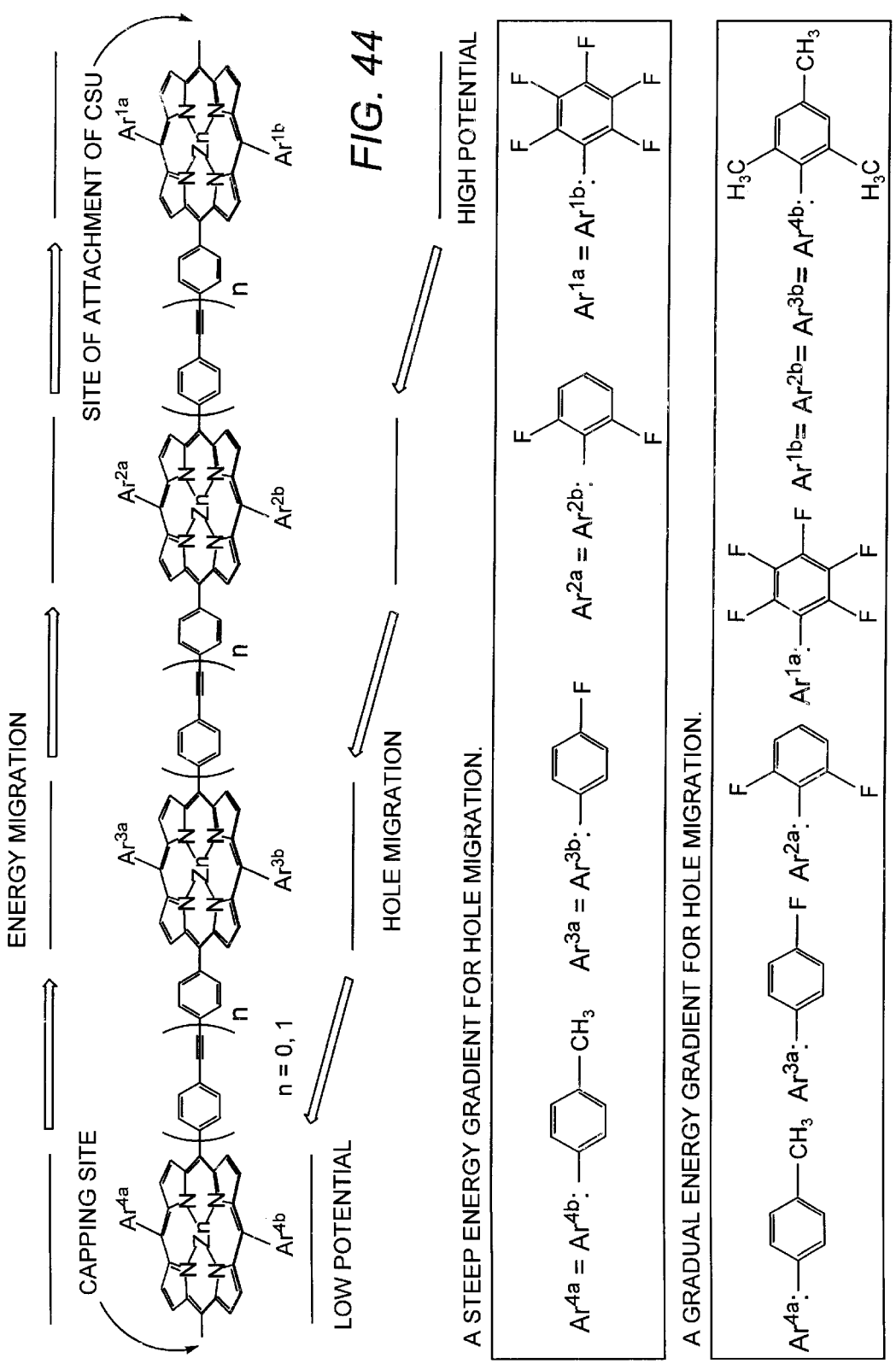
FIG. 44 illustrates a linear array of zinc porphyrins bearing different meso substituents.

(1) A linear array of zinc porphyrins bearing different meso substituents (FIG. 44). The four porphyrins have essentially identical absorption spectra, hence energy migration occurs among four isoenergetic porphyrins. The transfer of energy occurs reversibly among the four porphyrins. The electrochemical potentials are arranged in a cascade, with the highest potential proximal to the CSU and the lowest potential distal to the CSU. Hence hole migration occurs irreversibly in moving from high to low potential.

Figure 45:
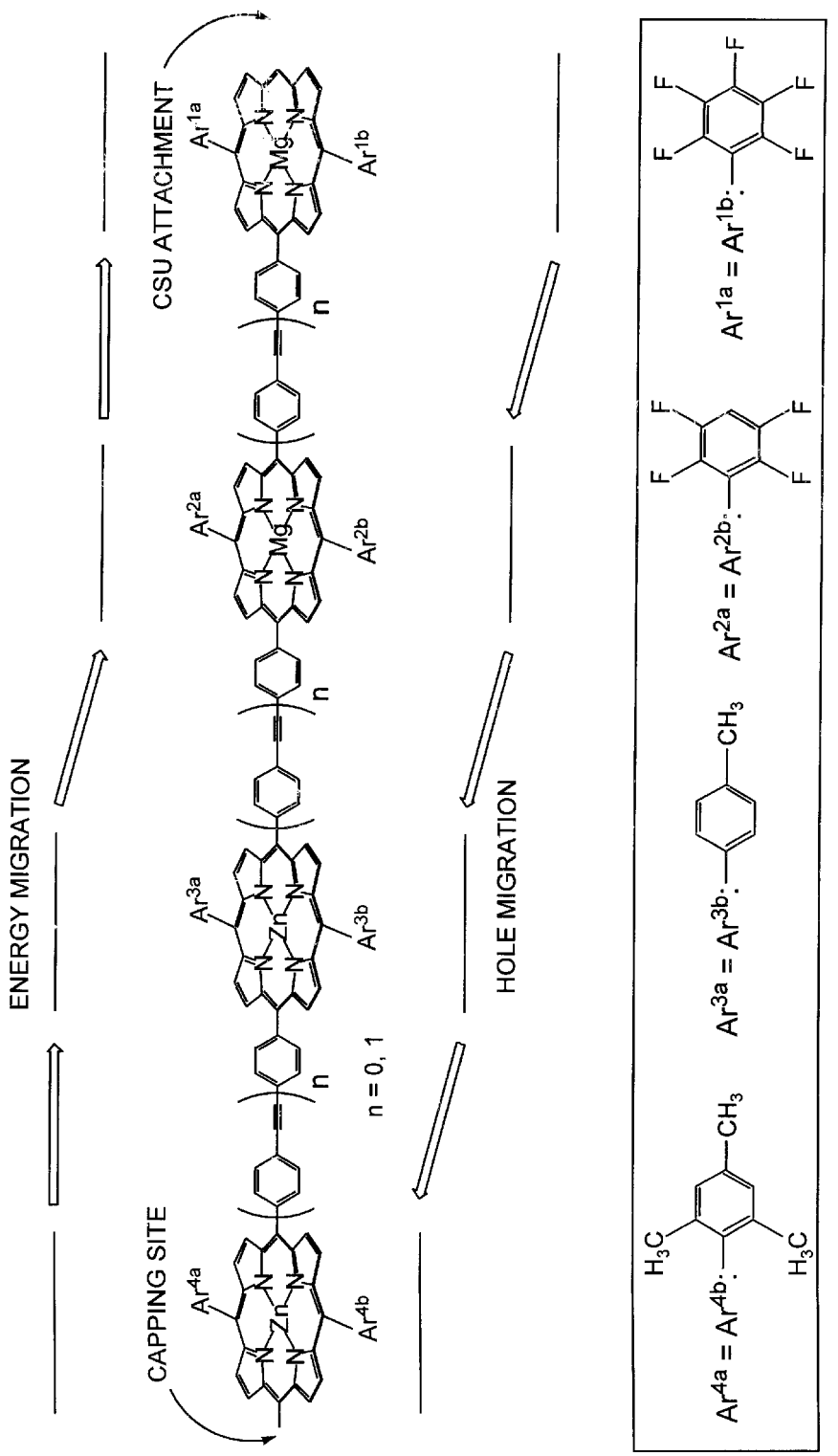
FIG. 45 illustrates a linear array of Mg and Zn porphyrins bearing different meso substituents.

(2) A linear array of Mg and Zn porphyrins bearing different meso substituents (FIG. 45). Mg porphyrins absorb at slightly longer wavelength (~5–10 nm) than Zn porphyrins and are more easily oxidized (i.e., lower potential) than Zn porphyrins (Li, F. et al., *J. Mater. Chem.* 1997, 7, 1245–1262; Hascoat, P. et al., *Inorg. Chem.* 1999, 38, 4849–4853). The sequence of Zn, Zn, Mg, Mg in going toward the CSU results in reversible energy transfer among the two isoenergetic Zn porphyrins, irreversible energy migration from Zn to Mg porphyrins, and reversible energy transfer among the two isoenergetic Mg porphyrins. Though Mg porphyrins are more easily oxidized than Zn porphyrins (with identical substituents), the placement of strongly electron-withdrawing substituents on Mg porphyrins and electron-releasing substituents on Zn porphyrins causes reversal of the ordering of the oxidation potentials (Yang, S. I. et al., *J. Porphyrins Phthalocyanines* 1999, 3, 117–147). For the linear array of porphyrins shown in FIG. 45, the arrangement of such substituents causes a cascade from high potential proximal to the CSU to low potential distal to the CSU. Thus, this system affords a partial cascade for energy migration and a stepwise cascade for hole migration in the opposite direction.

Figure 46:
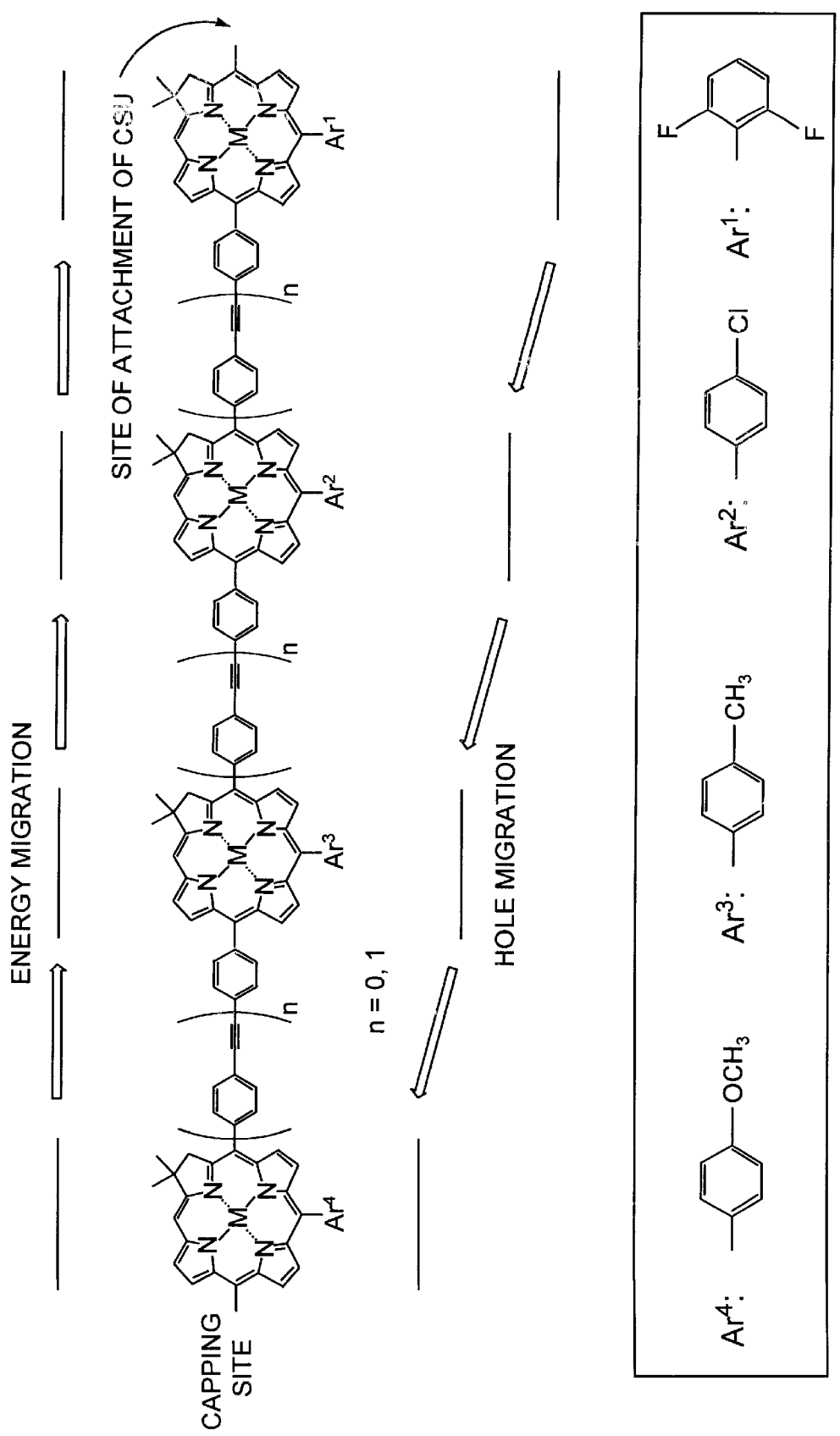
FIG. 46 illustrates a linear array of metallochlorins bearing different meso substituents.

(3) A linear array of metallochlorins bearing different meso substituents (FIG. 46). Chlorins absorb strongly both in the blue and in the red regions, effectively covering much of the solar spectrum. Chlorins are members of the porphyrinic (i.e., cyclic tetrapyrrole) family. As with porphyrins, the electrochemical potentials of chlorins are altered in a rational and predictable manner by the presence of electron-withdrawing or electron-releasing substituents. However, the absorption spectra are essentially unaffected by the inductive effects of substituents. Thus, the arrangement of chlorins in the linear array results in reversible energy migration among isoenergetic pigments but irreversible hole transfer in moving away from the CSU.

Figure 47:
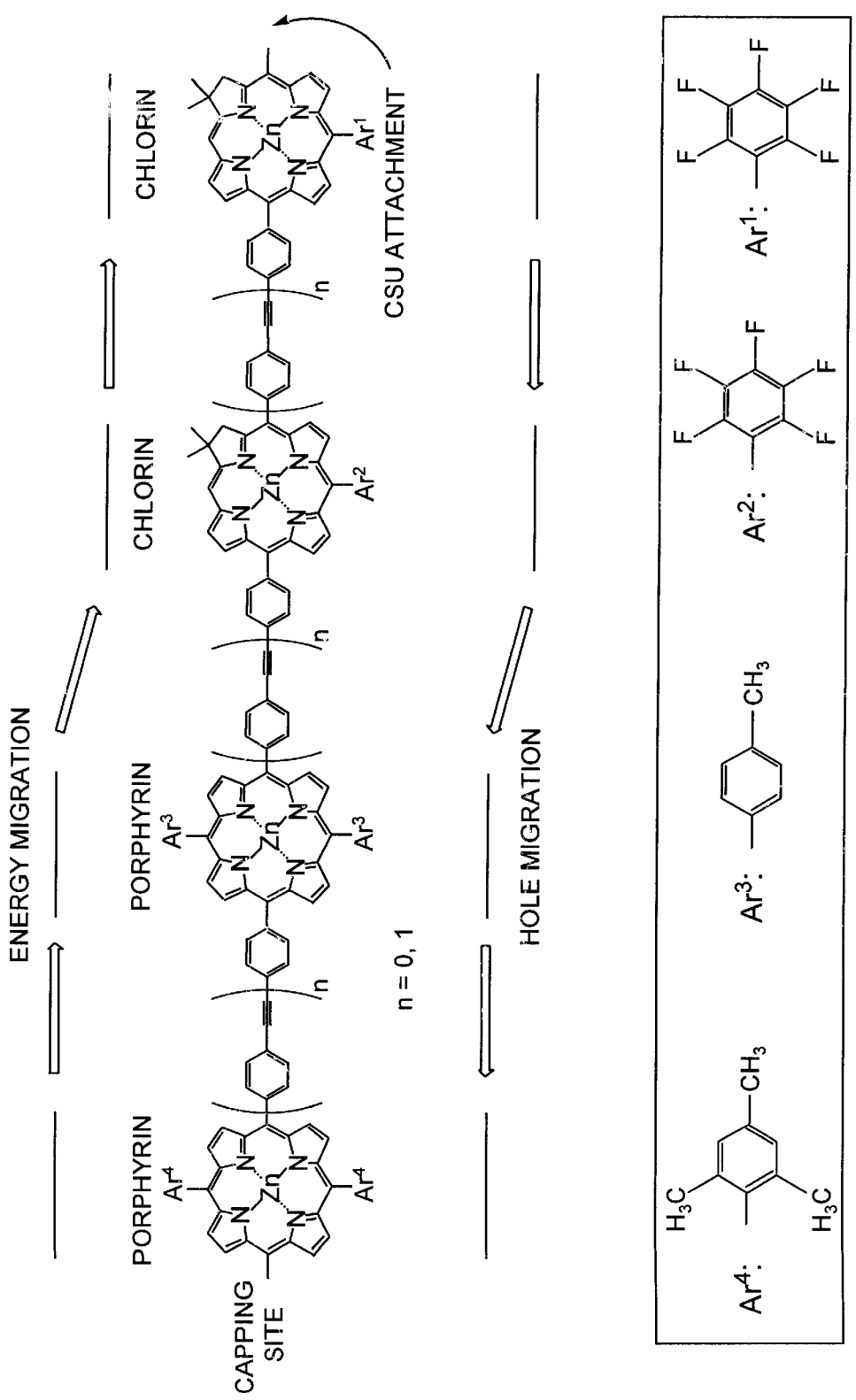
FIG. 47 illustrates a linear array of porphyrins and chlorins bearing different meso substituents.

(4) A linear array of porphyrins and chlorins bearing different meso substituents (FIG. 47). The long-wavelength absorption band (and therefore the energy of the excited singlet state) of a metalloporphyrin falls at shorter wavelength (higher energy) than that of the corresponding metallochlorin. On the other hand, a chlorin is more readily oxidized (lower potential) than the corresponding metalloporphyrin. An energy cascade and a hole cascade can be created as shown in FIG. 47. Strongly electron-withdrawing substituents are employed with chlorins and electron-releasing substituents are employed with the porphyrins, shifting the chlorins to higher potential than the porphyrins. Reversible energy transfer occurs among the pair of porphyrins, irreversible transfer occurs from porphyrin to chlorin, and reversible transfer occurs among the pair of chlorins. Reversible hole transfer occurs among the pair of chlorins, followed by irreversible hole transfer from chlorin to porphyrin and again from porphyrin to porphyrin.

Figure 48:
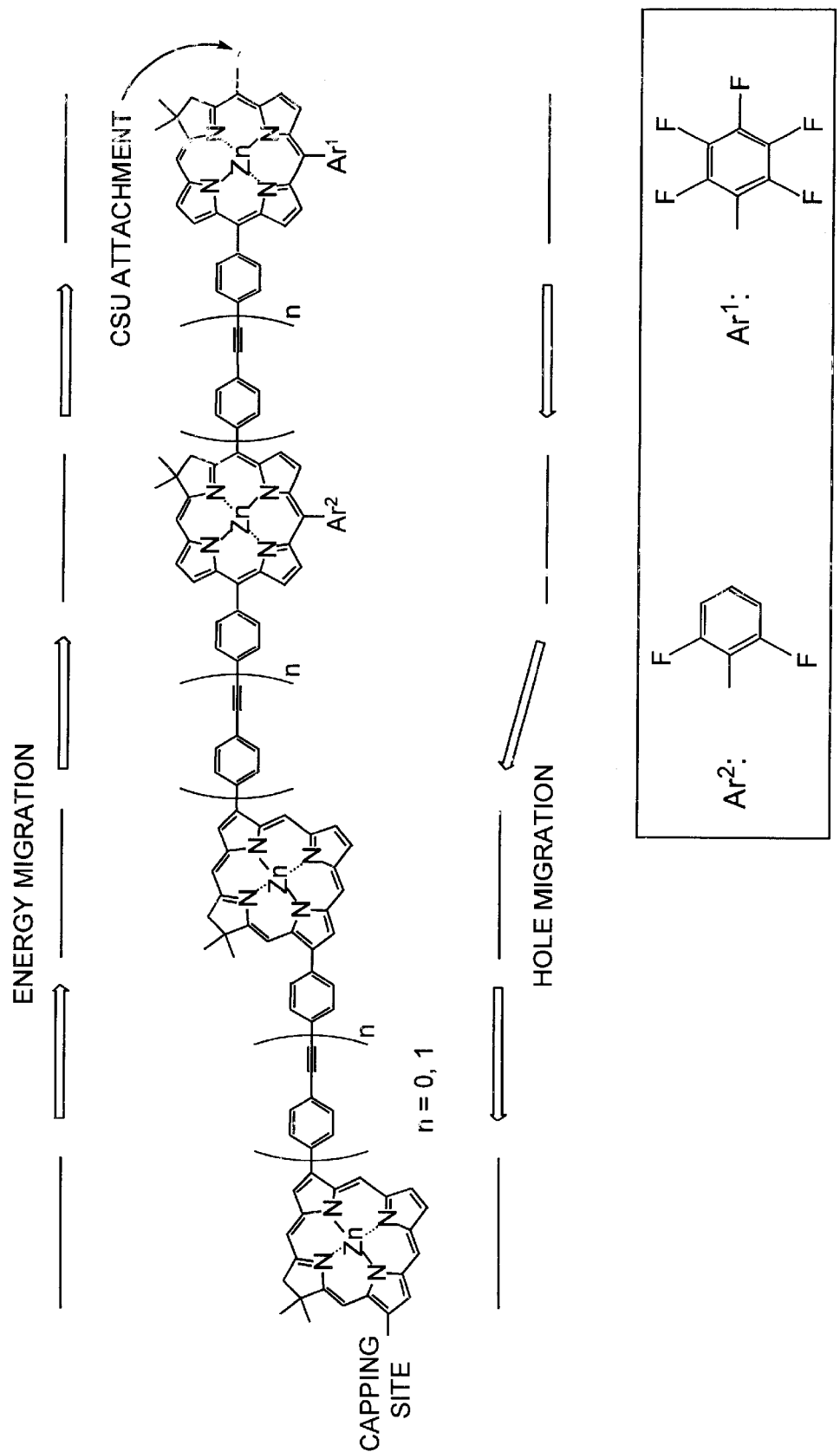
FIG. 48 illustrates a linear array of β-substituted chlorins and meso-substituted chlorins.

(5) A linear array of β-substituted chlorins and meso-substituted chlorins (FIG. 48). The β-substituted chlorins that are currently available do not bear a third substituent for tuning the electrochemical potential, as do the meso-substituted chlorins. Still, the β-substituted chlorins can be incorporated fruitfully as shown in FIG. 48. This arrangement affords reversible energy migration and a cascade of hole transfer processes. Note that the chlorins can be arranged with the partially saturated ring pointed toward or away from the CSU; no differences in performance are implied by the different orientations displayed in FIG. 48.

Figure 49:
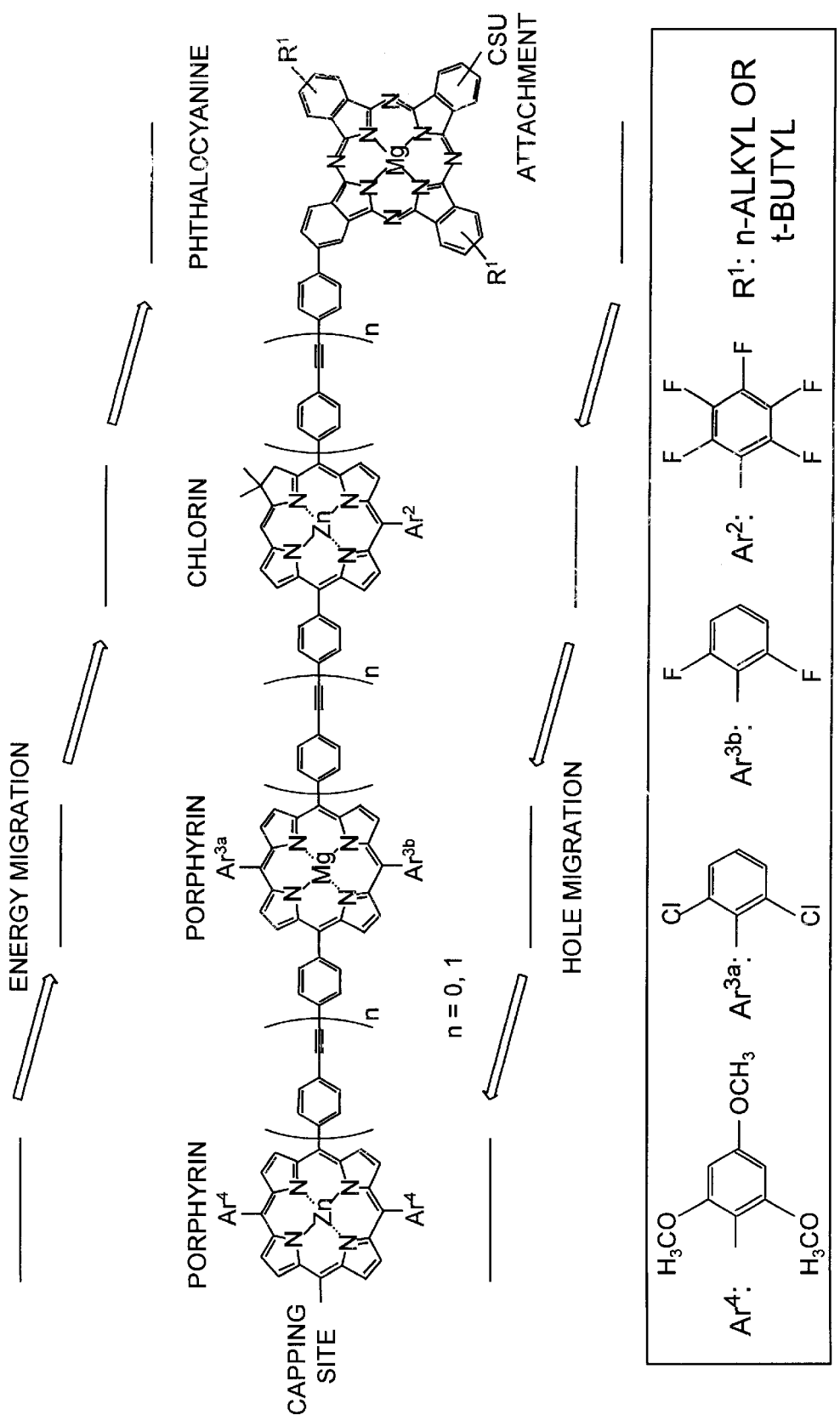
FIG. 49 illustrates a linear array of porphyrin, chlorin, and phthalocyanine components.

(6) A linear array of porphyrin, chlorin, and phthalocyanine components (FIG. 49). Phthalocyanines are characterized by very strong absorption in the red ($\epsilon$~250,000 $M^{-1}cm^{-1}$) and high oxidation potentials (Li, J. et al., *J. Org. Chem.* 1999, 64, 9090–9100; Yang, S. I. et al., *J. Mater. Chem.* 2000, 10, 283). The array shown in FIG. 49 exhibits a progressive energy cascade from Zn porphyrin to Mg porphyrin to chlorin to phthalocyanine. The hole migration process occurs in the opposite direction, with tuning of the Mg chlorin and Zn porphyrin using meso substituents.

C. Other Compositions.

The porphyrinic family includes diverse pigments, many of which can be employed in linear architectures for energy and hole migration in opposite directions. Noteworthy members include tetraazaporphyrins, heteroatom-modified porphyrins (e.g., $N_3O$— or $N_3S$— instead of the standard $N_4$-porphyrins) (Cho, W.-S. et al., *J. Org. Chem.* 1999, 64, 7890–7901), corrole, and various expanded and contracted porphyrins (Van Patten, P. G. et al., *J. Phys. Chem. B* 1998, 102, 4209–4216).

In general, a wide variety of substituents are available for tuning electrochemical potentials, including diverse aryl and alkyl groups. Halogenated aryl groups are particularly attractive for fine tuning the electrochemical potentials.

The arrays displayed in FIGS. 44–49 all employ diphenylethyne or p-phenylene linkers. The energy-transfer rate in going from a diphenylethyne linker to a p-phenylene linker increases by about 10-times for porphyrins ($\sim$(2 ps)$^{-1}$)$^5$ and 100-times for chlorins (sub-picoseconds). While these linkers are quite attractive, other linkers also can be used.

D. Other Designs.

The availability of rapid energy-transfer processes (i.e., with p-phenylene linked chlorins or porphyrins) has important consequences for the design of light-harvesting arrays. Simulations of the effects of energy-transfer rates on the quantum yield for energy transfer to the trap positioned at the end of a linear array showed the following (Van Patten, P. G. et al., *J. Phys. Chem. B* 1998, 102, 4209–4216): With reversible transfer among isoenergetic pigments, the quantum yield falls off very steeply with number of pigments. However, the quantum yield is also very sensitive to the rate of transfer. An increased rate, even for reversible transfer among isoenergetic pigments, mitigates the falloff in quantum yield with increasing numbers of pigments. With rates in the few ps to sub-ps regime, linear arrays of a reasonable number of isoenergetic pigments (e.g., up to 20) should afford acceptable quantum yields for excitation reaching the trap (i.e, the CSU). Conversely, with slow transfer rates (tens of psec), a high quantum yield in a modestly sized linear array can be obtained only by using an energy cascade (i.e., irreversible energy transfer steps). In summary, a linear array comprised of several identical (iosoenergetic) pigments will afford efficient energy transfer if the rate of transfer is very rapid.

Figure 50:
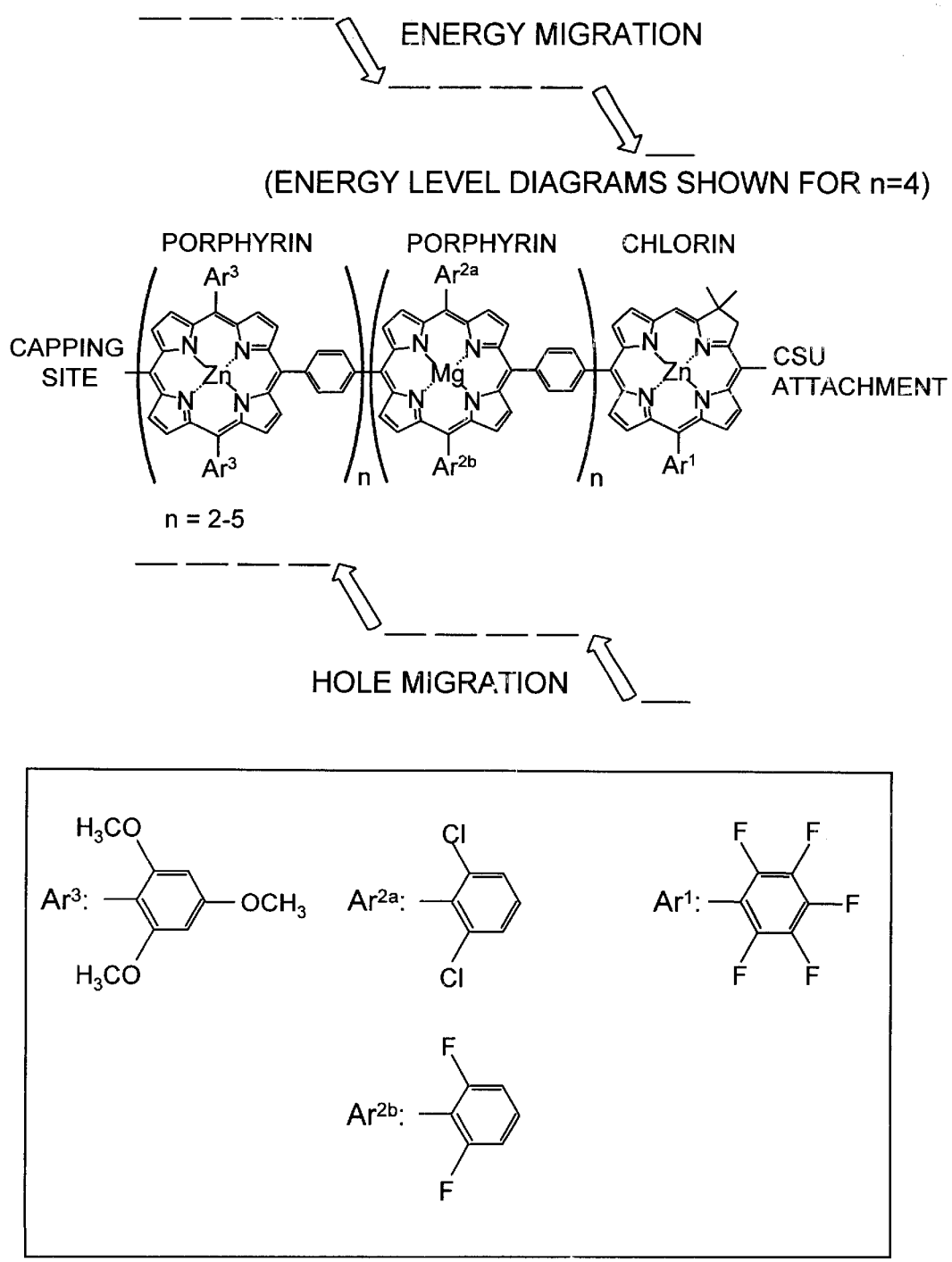
FIG. 50 illustrates a cataract linear array employing domains comprised of multiple isoenergetic pigments.

An example of an array employing multiple isoenergetic pigments is illustrated in FIG. 50. This array incorporates the same Zn porphyrin, Mg porphyrin, and Zn chlorin pigments as employed in FIG. 49. The linkers are exclusively p-phenylene groups. The architecture employs a set of n Zn porphyrins, then a set of n Mg porphyrins, and then one Zn chlorin. Energy and hole transfer occur reversibly among members of a given set, but transfer occurs irreversibly (downhill) between sets. This arrangement of pigments resembles a type of cataract architecture. This design illustrates the concept that it is not necessary to have a downhill energy transfer step occur at each pigment in order to achieve efficient energy transfer from the site of light absorption to the CSU.

For rapid energy transfer, ideal choices are to use p-phenylene linkers with porphyrins (having $a_2$, HOMOs and linkers at the meso positions) (Yang, S. I. et al., *J. Am. Chem. Soc.* 1999, 121, 4008–4018) and/or chlorins (having linkers at the meso or β positions). For rapid hole-hopping, the linker should be connected at a site on the pigment having significant electron density in the HOMO. While energy transfer can proceed via TS and/or TB mechanisms, ground-state hole-hopping proceeds exclusively via a TB mechanism (at least for the rapid rates observed). The factors that affect TB energy migration are similar to those that affect ground-state hole-hopping. Thus, those arrays with fast TB energy migration should also give rapid rates of hole-hopping. For efficient hole-hopping, it also is not essential to have a downhill hole-hopping step occur at each pigment in order to achieve efficient transfer from the CSU to a site far removed in the light-harvesting antenna.

Although in these designs excited-state energy and ground-state holes are formed in the same array, given the rapid dynamics of energy migration and the low flux of ambient sunlight, the probability is quite low for the simultaneous presence of an excited state and a hole. Accordingly, excited-state quenching by ground-state holes is anticipated to be an infrequent occurrence.

V. IN Situ Synthesis of Light-Harvesting Polymers on Electroactive Surfaces

The synthesis of oligomers of pigment building blocks (BB), or light-harvesting rods, can proceed via several different types of reactions. A general issue is that the reaction used to join the pigment building blocks into a dyad architecture also creates the linker that provides electronic communication between the two pigments. Accordingly, a more limited set of reactions is generally envisaged than that in the entire corpus of organic chemistry. The methods for synthesis of polymeric arrays of pigment building blocks include but are not restricted to use of the following types of reactions (FIG. 51):

- Glaser (or Eglinton) coupling of a monomeric pigment building blocks (generating a butadiyne linker)
- Cadiot-Chodkiewicz coupling of two different pigment building blocks (generating a butadiyne linker joining a block copolymer)
- Sonogashira coupling of two different pigment building blocks (generating an ethyne linker joining a block copolymer)
- Heck or Witting reactions of two different pigment building blocks (generating an alkene linker joining a block copolymer)
- Suzuki coupling of two different pigment building blocks (generating a phenylene or biphenyl linker joining a block copolymer)
- Polymerization of pigment building blocks bearing substituents such as two or more thiophene groups (generating an oligothiophene linker) or two or more pyrrole groups (generating a polypyrrole linker).

The synthesis of the oligomers can be performed using stepwise methods or using polymerization methods. Both methods generally require two reactive groups attached to the pigment building block in order to prepare a polymer where the pigment building blocks are integral components of the polymer backbone. (An alternative, less attractive design yields pendant polymers where the pigment building blocks are attached via one linkage to the polymer backbone.) The stepwise synthetic method generally requires the use of protecting groups to mask one reactive site, and one cycle of reactions then involves coupling followed by deprotection. In the polymerization method no protecting groups are employed and the polymer is prepared in a one-flask process.

The polymerizations can take place in solution or can be performed with the polymer growing from a surface. The polymerization can be performed beginning with a solid support as in solid-phase peptide or DNA synthesis, then removed, purified, and elaborated further for specific applications. The polymerization with the nascent polymer attached to an electroactive surface generates the desired light-harvesting material in situ. This latter approach is exceptionally attractive in eliminating the need for handling of the polymers. The ability to avoid handling of the polymers makes possible the synthesis of compounds that do not exhibit sufficient solubility in most solvents for convenient handling (dissolution, purification, processing, solution characterization).

Polymers can be created that are composed of identical units, or dissimilar units as in block copolymers or random copolymers. Alternatively, the polymerization can be performed to create a linear array where the composition of different pigment building blocks is organized in a gradient. This latter approach affords the possibility of creating an energy cascade for the flow of excited-state energy and/or the reverse flow of ground-state holes in a systematic manner along the length of the array as described elsewhere in this application.

The following describes the in situ synthesis of the cascade polymers on an electroactive surface such as gold or $TiO_2$: A polymerizable unit (pigment building block or linker) is attached to the surface (for Au, a thiol attachment group is used for $Y^1$; for $TiO_2$, a carboxylic acid attachment group is used for $Y^2$). The first pigment building block ($BB^1$) is added and the coupling reagents are added in order to perform the polymerization (e.g., a Glaser coupling). Then the surface is washed to remove the coupling reagents (copper reagents in the case of the Glaser coupling) and any unreacted $BB^1$. Then the second pigment building block ($BB^2$) is added followed by coupling reagents and the polymerization is allowed to continue. The same wash procedure is performed again and then the third pigment building block ($BB^3$) is added followed by coupling reagents and the polymerization is allowed to continue. Repetition of this process enables the systematic construction of a linear array of pigment building blocks with graded energy levels for the flow of excited-state energy and ground-state holes. The last monomer attached bears a single reactive site (J—L—(BB)—L—Y) and the attachment group Y is used for subsequent coupling to an opposing surface. Characterization of the surface-immobilized polymer is achieved by absorption spectroscopy, IR spectroscopy, reflectance spectroscopy and laser desorption time of flight mass spectrometry.

Figure 52:
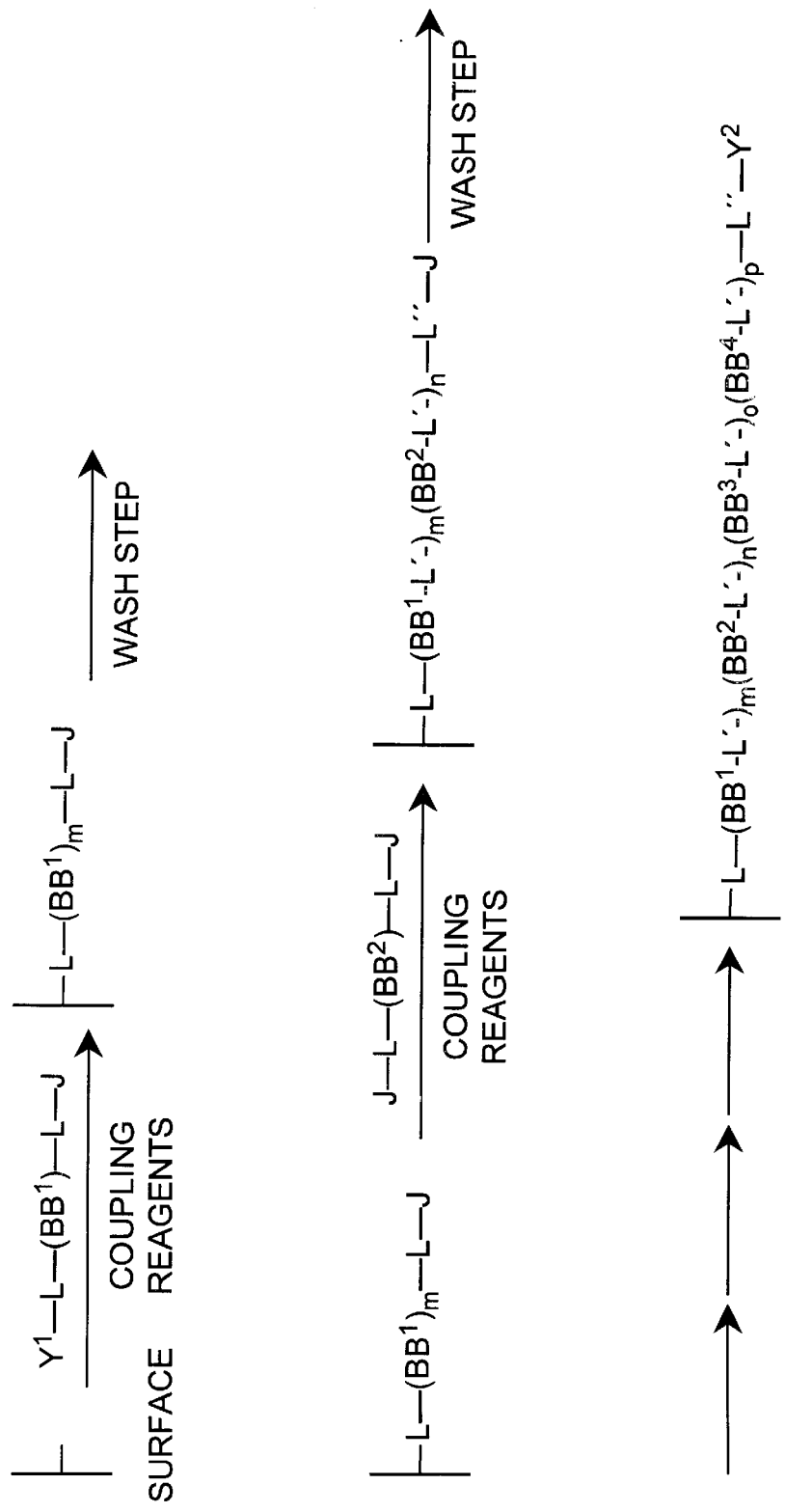
FIG. 52. In situ polymerization yielding a light-harvesting rod on a surface (e.g., Au or $TiO_2$) that will serve as one of the solar cell electrodes.

In the example shown (see FIG. 52), for a surface of Au, a thiol attachment group (X) is used, creating the self-assembled monolayer on gold. Such self-assembled monolayers are known for thiol-derivatized porphyrins (Gryko, D. T. et al., *J. Org. Chem.* 1999, 64, 8635–8647). For the other surface composed of $TiO_2$, a carboxylic acid attachment group is used for the attachment (Y). The polymerizable groups can be any of the type described above using the various name reactions (Glaser, Sonogashira, Cadiot-Chodkiewicz, Heck, Wittig, Suzuki, etc.). The final polymeric product is comprised of domains of the various pigment building blocks $[(BB^i)_n]$ in a linear array.

VI. Applications of Solar Cells of the Invention

Solar cells of the present invention can be used in a variety of different electrical devices. Such devices typically comprise a solar cell as described above, and a circuit (e.g., a resistive load) electrically coupled to said solar cell (e.g., by providing a first electrical coupling of the circuit to one electrode of the solar cell, and a second electrical coupling of the circuit to the other electrode of the solar cell). The solar cell may provide the sole source of power to the circuit, may be a supplemental source, may be incorporated to charge a battery, etc. Any of a variety of different electrical devices may incorporate a solar cell of the invention, including but not limited to radios, televisions, computers (such as personal computers), processors, calculators, telephones, wireless communication devices such as pagers, watches, emergency location devices, electric vehicles, emergency power supplies, power generators, lights or lamps, and other illuminating devices, monitoring devices, inspection devices, radiation detectors, imaging devices, optical coupling devices.

The following examples are provided to illustrate certain aspects of the invention, and are not to be construed as limiting thereof.

EXAMPLES

Rational Synthesis of β-Substituted Chlorin Building Blocks

Figure 53:
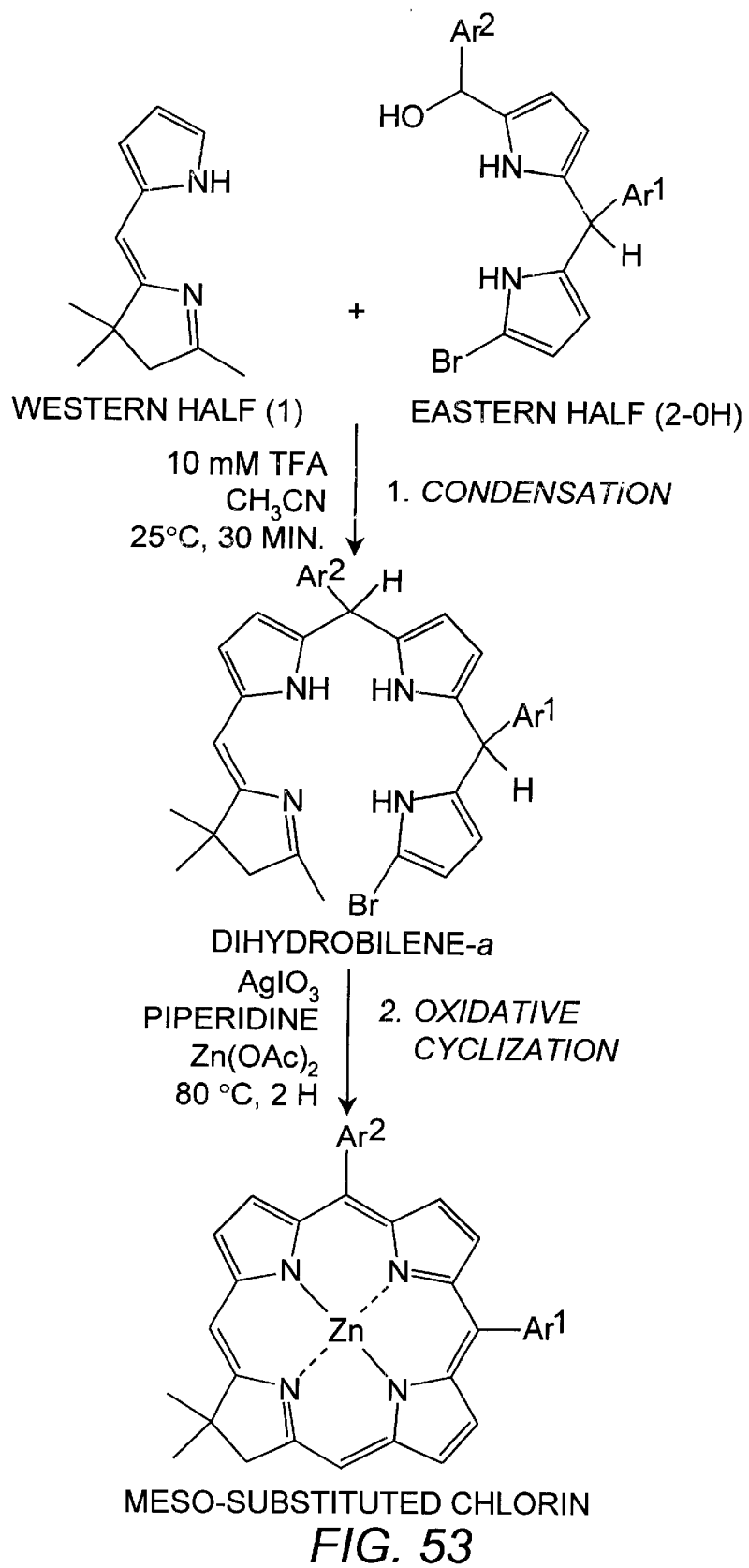
FIG. 53 illustrates the synthesis of meso-substituted chlorins by previously disclosed techniques.

In these examples the synthesis of β-substituted chlorin building blocks is presented. Two new Eastern halves have been constructed in which each bears one β substituent and one (non-flanking) meso substituent, and one new Western half has been prepared that bears one β substituent. These new precursors have been used in conjunction with the prior Western half (1) to yield three new chlorins each bearing one β and one meso substituent. A chlorin bearing one meso substituent and substituents at the 2 and 12 positions also has been prepared. Such building blocks have heretofore not been available and in conjunction with the meso-substituted chlorins previously disclosed (synthesis summarized in FIG. 53), should enable a variety of fundamental studies, including investigation of the effects of site of linker connection on electronic communication in various chlorin-based architectures.

Results and Discussion

Figure 54:
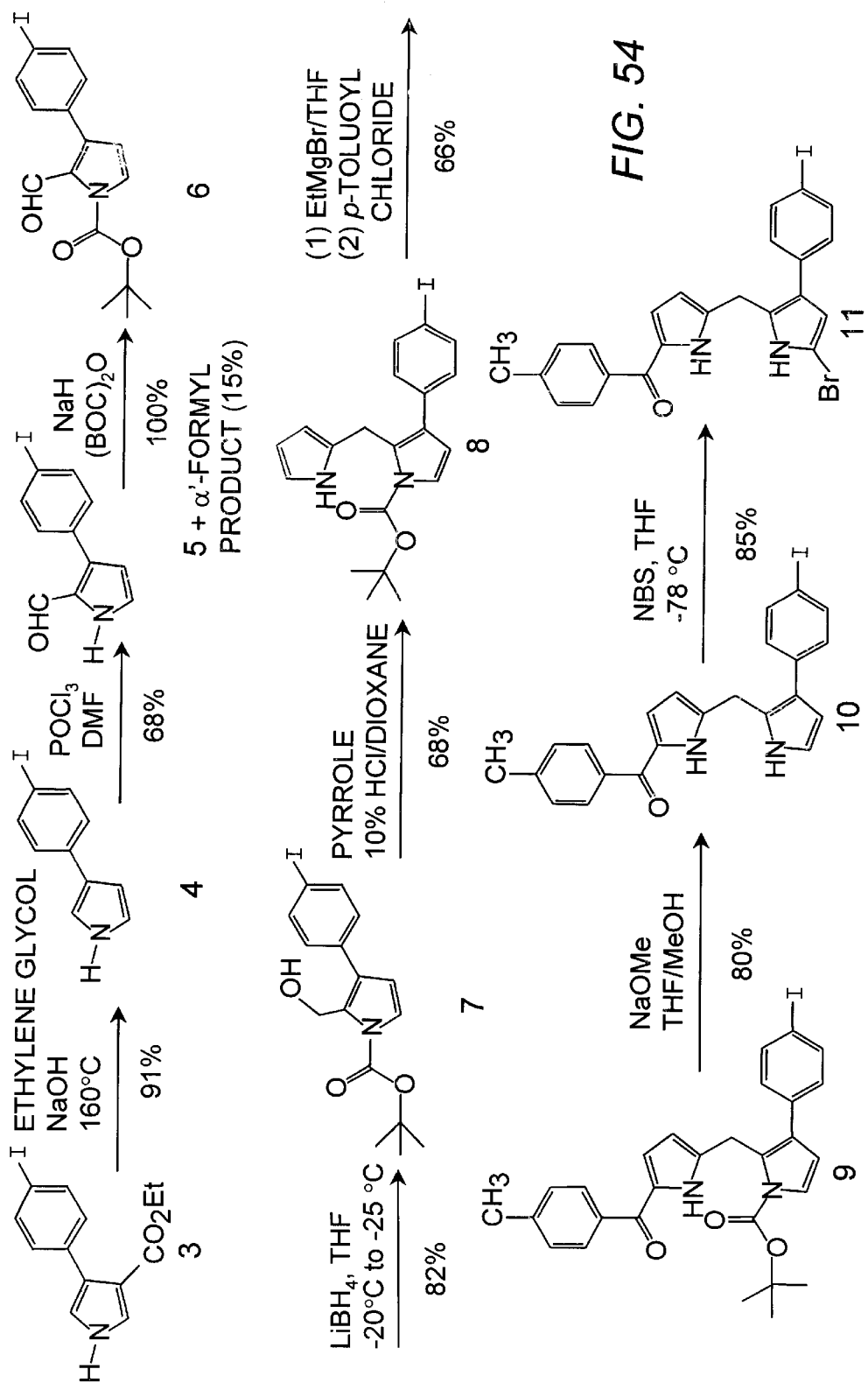
FIG. 54 illustrates the synthesis of β-substituted chlorin eastern half (EH) precursors.

Synthesis of the Eastern Half (EH): The synthesis of the β-substituted EH begins in the same manner as the prior synthesis of β-substituted dipyrromethanes (Balasubramanian, T.; Lindsey, *J. S. Tetrahedron* 1999, 55, 6771–6784) but employs a number of significant improvements (FIG. 54). The iodophenyl substituted pyrrole (3) is readily prepared from 4-iodobenzaldehyde, monoethyl malonate, and tosylmethylisocyanide. The ethoxycarbonyl group was removed by treatment with NaOH in ethylene glycol at 160° C. to give the 3-(4-iodophenyl)pyrrole (4) in 91% yield as pale brown crystals. It is noteworthy that this single-step decarboxylation is superior to the two-step transformation on similar pyrrole compounds (Pavri, N. R.; Trudell, M. L. *J. Org. Chem.* 1997, 62, 2649–2651). Vilsmeier-Haack formylation of 4 yielded a mixture of two regioisomers (~6:1 ratio) which were readily distinguished by $^1$H NMR spectroscopy (See Experimental Section). The major isomer was the desired compound (5) and was obtained in pure form by recrystallization in 62% yield. Protection of the pyrrolic nitrogen with the BOC group (Tietze, L. F.; Kettschau, G.; Heitmann, K. *Synthesis* 1996, 851–857) gave pyrrole 6 in quantitative yield. Reduction to alcohol 7 was achieved by treatment with $LiBH_4$ at low temperature (longer reaction time or higher temperature led to the over-reduced and deprotected compound 2-methyl-3-(4-iodophenyl)pyrrole). Treatment of 7 with excess pyrrole under acidic conditions furnished the β-substituted, monoprotected dipyrromethane 8 in 68% yield. Excess pyrrole is necessary to minimize the formation of the tripyrromethane, while protection of the pyrrolic nitrogen is necessary to facilitate the reaction, avoid self condensation and allow the subsequent selective monoacylation. This methodology afforded the β-substituted dipyrromethane as a single regioisomer, in contrast to earlier methodology which gave a mixture of two regioisomers (Balasubramanian, T.; Lindsey, J. S. *Tetrahedron* 1999, 55, 6771–6784).

Methods for acylation of β-substituted dipyrromethanes have been developed that involve formation of the pyrrolic Grignard reagent followed by treatment with an acid chloride (Lee, C.-H.; Li, F.; Iwamoto, K.; Dadok, J.; Bothner-By, A. A.; Lindsey, J. S. *Tetrahedron* 1995, 51, 11645–11672). In this case, the N-protected dipyrromethane was retained for selective monoacylation of the α-position in the unprotected pyrrole unit. Treatment of 8 with 2.5 equivalents of EtMgBr in THF followed by p-toluoyl chloride afforded the monoacylated dipyrromethane 9 in 66% yield (FIG. 54). However, similar reaction in toluene led to a mixture of the mono-acylated product, deprotected compound and some unidentified impurities. A control experiment involving treatment of 8 with a slight excess of EtMgBr at 0° C. in THF for 1 h and the usual workup afforded the starting material in quantitative yield, thus revealing that the BOC group is stable to the acylation conditions. Removal of the BOC group under standard conditions (Hasan, I. et al., *J. Org. Chem.* 1981, 46, 157–164) gave 10. Electrophilic bromination of 10 with NBS (1 equiv) in THF at ~78° C. following earlier methods (excess NBS led to a considerable amount of a dibromo compound) afforded 11.

A second β-substituted dipyrromethane was prepared by Sonogashira coupling (Sonogashira, K. et al., *Tetrahedron Lett.* 1975, 4467–4470) of iodophenyl-substituted 10 with trimethylsilylacetylene. In this manner the trimethylsilylethynyl dipyrromethane 12 was obtained in quantitative yield (FIG. 55). Reaction of 12 with NBS at ~78° C. furnished the corresponding bromodipyrromethane 13 in 91% yield.

The preparation of a dipyrromethane bearing a substituent at a different β site using the same BOC protected dipyrromethane 8 was also sought reversing the order of acylation and deprotection that led to 10. Thus, deprotection of 8 with NaOMe/MeOH afforded the β-substituted dipyrromethane 14 (FIG. 55). A procedure was recently devised for the selective mono-acylation of meso-substituted dipyrromethanes using EtMgBr and an S-pyridyl substituted benzothioate (Rao, P. D.; Dhanalekshmi, S.; Littler, B. J.; Lindsey, J. S. *J. Org. Chem.* submitted). Application of this monoacylation method to 14 resulted in a mixture of two regioisomers (10, 16). Attempts to obtain 16 as the major product by varying the experimental conditions were unsuccessful. Separation of the two regioisomers was difficult and required extensive flash column chromatography. The minor isomer 16 was obtained in 25% yield. Treatment of 16 with 1 equivalent of NBS in THF at ~78° C. yielded 17 in 87% yield as a yellow solid. All β-substituted 1-bromodipyrromethanes (11, 13, 17) are somewhat unstable but remain intact for a few weeks upon storage at 0° C. under argon.

Figure 56:
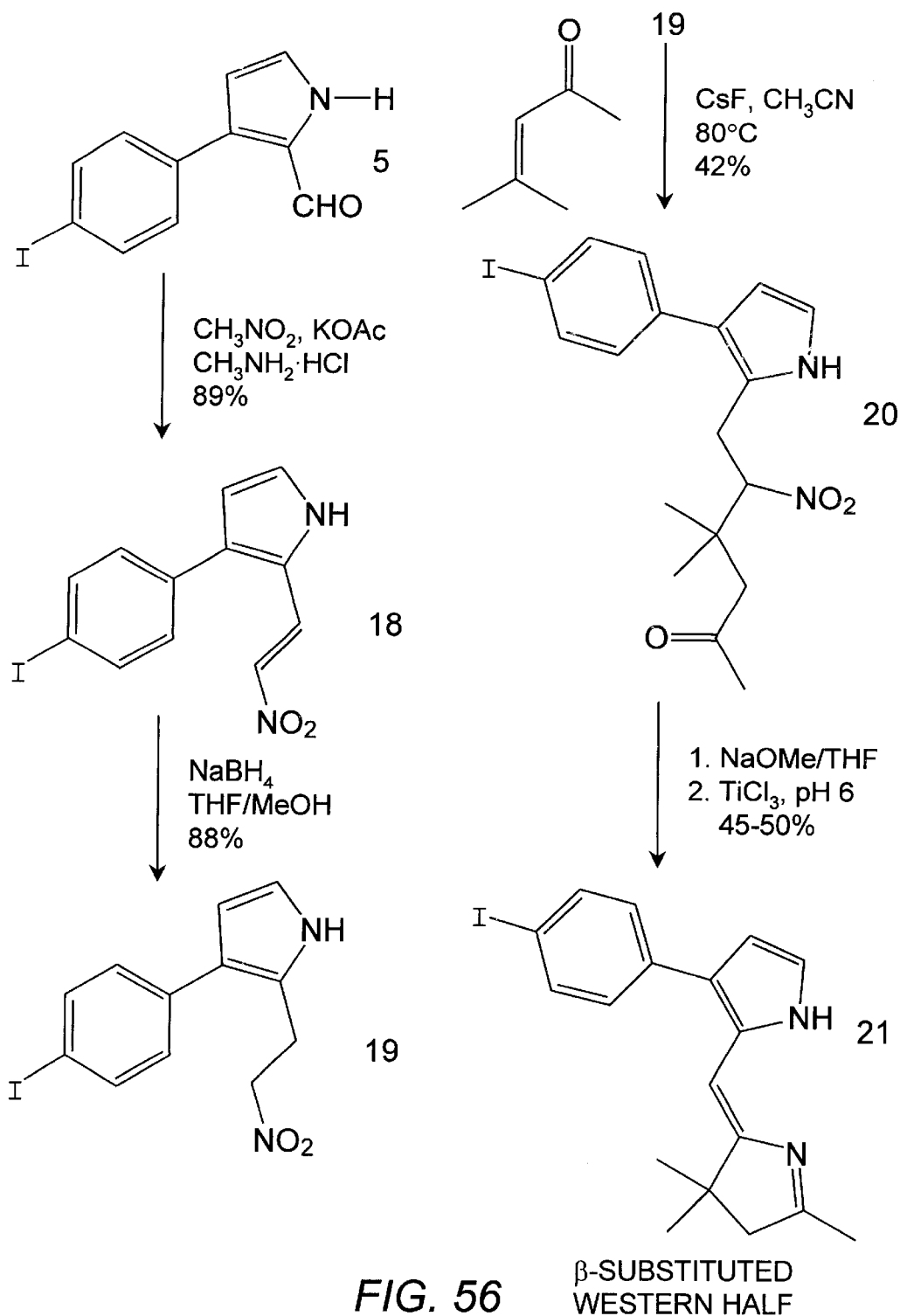
FIG. 56 illustrates the synthesis of a β-substituted chlorin western half (WH).

Synthesis of a β-substituted Western Half. The synthesis of a Western half lacking any β-substituents except for the geminal dimethyl group (1) was previously developed (Strachan, J. P. et al., *J. Org. Chem.* 2000, 65, 3160–3172). Pyrrole-carboxaldehyde 5, available in multi-gram quantities, provided a convenient starting point for the synthesis of a new Western half bearing a synthetic handle at a β position. A β-substituted Western half in conjunction with the β-substituted Eastern half would enable the synthesis of chlorin building blocks bearing two β substituents positioned at opposite sides of the macrocycle. Application of the reaction conditions used to obtain 2-(2-nitrovinyl) pyrrole from 2-formylpyrrole (Strachan, J. P.; O'Shea, D. F.; Balasubramanian, T.; Lindsey, J. S. *J. Org. Chem.* 2000, 65, 3160–3172) to the reaction of 5 resulted largely in recovery of starting material. After a limited study, it was found that treatment of 5 with KOAc and a slight excess of methylamine-hydrochloride in nitromethane (instead of methanol) as solvent at room temperature for 2 h (instead of 16 h) yielded the desired aldol-condensation product 18 in 89% yield (FIG. 56). It is noteworthy that a longer reaction time led to the formation of the Michael addition product of nitromethane at the nitrovinyl group in 18, forming 2-(1,3-dinitro-2-propyl)-3-(4-iodophenyl)pyrrole in ~30% yield. NaBH$_4$ reduction of 18 gave 19, which underwent Michael addition with mesityl oxide in the presence of CsF at 80° C. to give the nitro-hexanone product 20, the precursor to the β-substituted Western half. Although the Michael addition was fast compared to that forming the β-unsubstituted counterpart (precursor to 1), the yield was slightly lower (42% vs. 65%). Treatment of 20 with NaOMe followed by a buffered TiCl$_3$ solution yielded the β-substituted Western half 21 in 45–50% yield as a light green solid. The yield and stability of the β-substituted WH is greater than that of the unsubstituted analog (21 has mp=141–142° C.; 1 is an oil).

Figure 57:
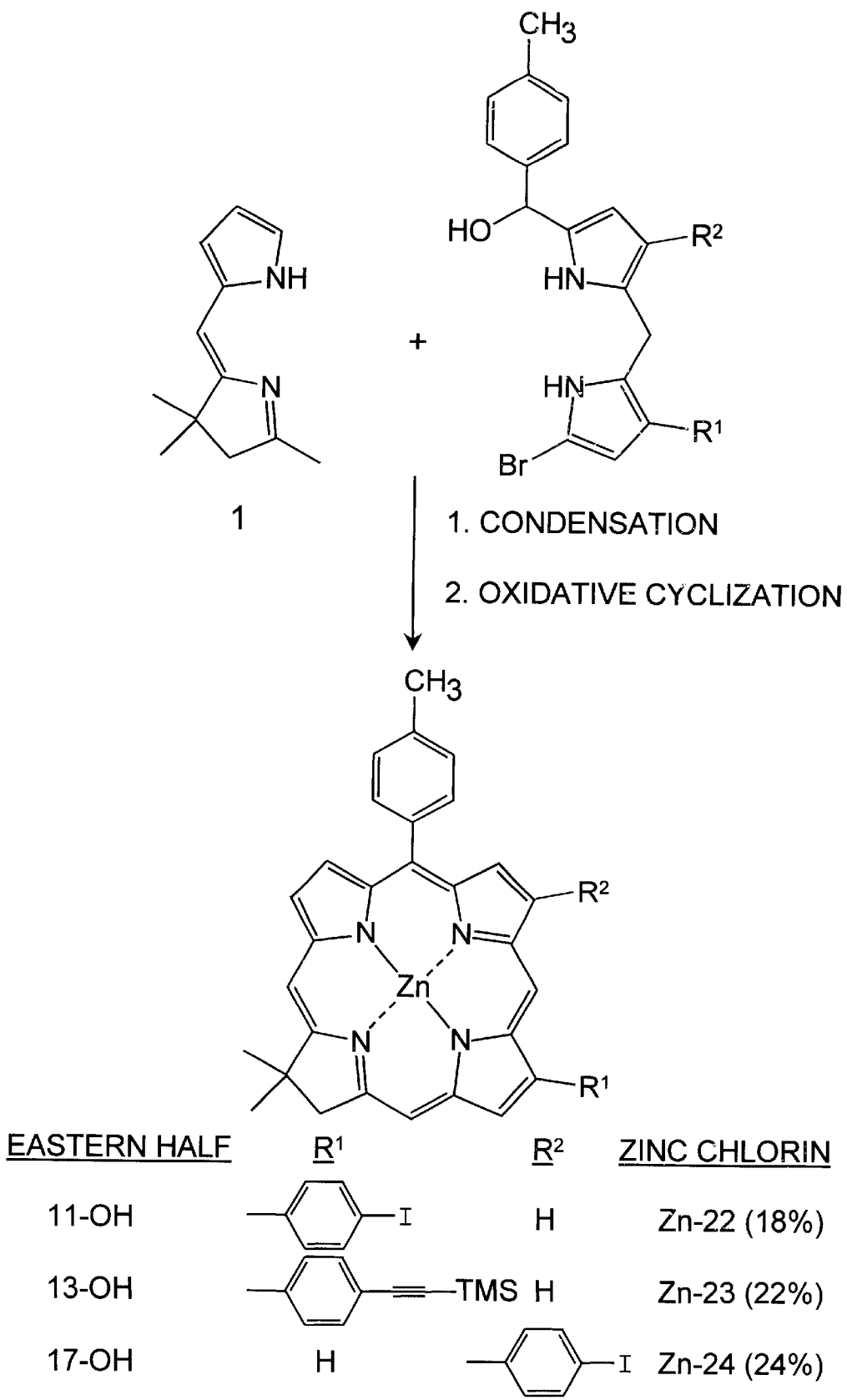
FIG. 57 illustrates the synthesis of a β-substituted chlorin.

Chlorin Formation. Prior synthesis of chlorins involved (1) formation of the bromodipyrromethane-monocarbinol (2-OH, EH) by reduction of the carbonyl group in the EH precursor, (2) acid-catalyzed condensation of the EH and WH (1) to obtain the dihydrobilene-α, and (3) oxidative metal-mediated cyclization to give the chlorin (Strachan, J. P.; O'Shea, D. F.; Balasubramanian, T.; Lindsey, J. S. *J. Org. Chem.* 2000, 65, 3160–3172). All the three steps are done in succession on the same day. This same procedure was employed herein except that the workup conditions are different due to the labile nature of the β-substituted EH precursors (11, 13, 17) and corresponding β-substituted Eastern halves. In a typical reaction, 11 was treated with NaBH$_4$ in THF/MeOH (4:1) at room temperature under argon. Upon the disappearance of starting material (TLC analysis), the reaction mixture was worked up and the carbinol 11-OH was treated with 1.2 equivalents of WH 1 at room temperature in CH$_3$CN containing TFA. After 25–30 minutes the resulting dihydrobilene-α was obtained by quenching the reaction mixture with aqueous NaHCO$_3$ and workup in CH$_2$Cl$_2$. Anhydrous toluene and 15 molar equivalents each of AgIO$_3$, Zn(OAc)$_2$ and piperidine were added, and the mixture was heated at 80° C. for ~2.5 h. The reaction mixture slowly changed from red to green, indicating the formation of chlorin. Filtration of the reaction mixture through a pad of silica followed by column chromatography afforded the chlorin Zn-22 in >90% purity. Precipitation with CH$_2$Cl$_2$/hexanes furnished pure chlorin (Zn-22) in 18% yield (FIG. 57). Similar treatment of Eastern half 13-OH and 1 gave the zinc chlorin Zn-23 in 22% yield. The Eastern half (17) bearing a β substituent at position 8 reacted similarly with 1 affording zinc chlorin Zn-24.

Figure 58:
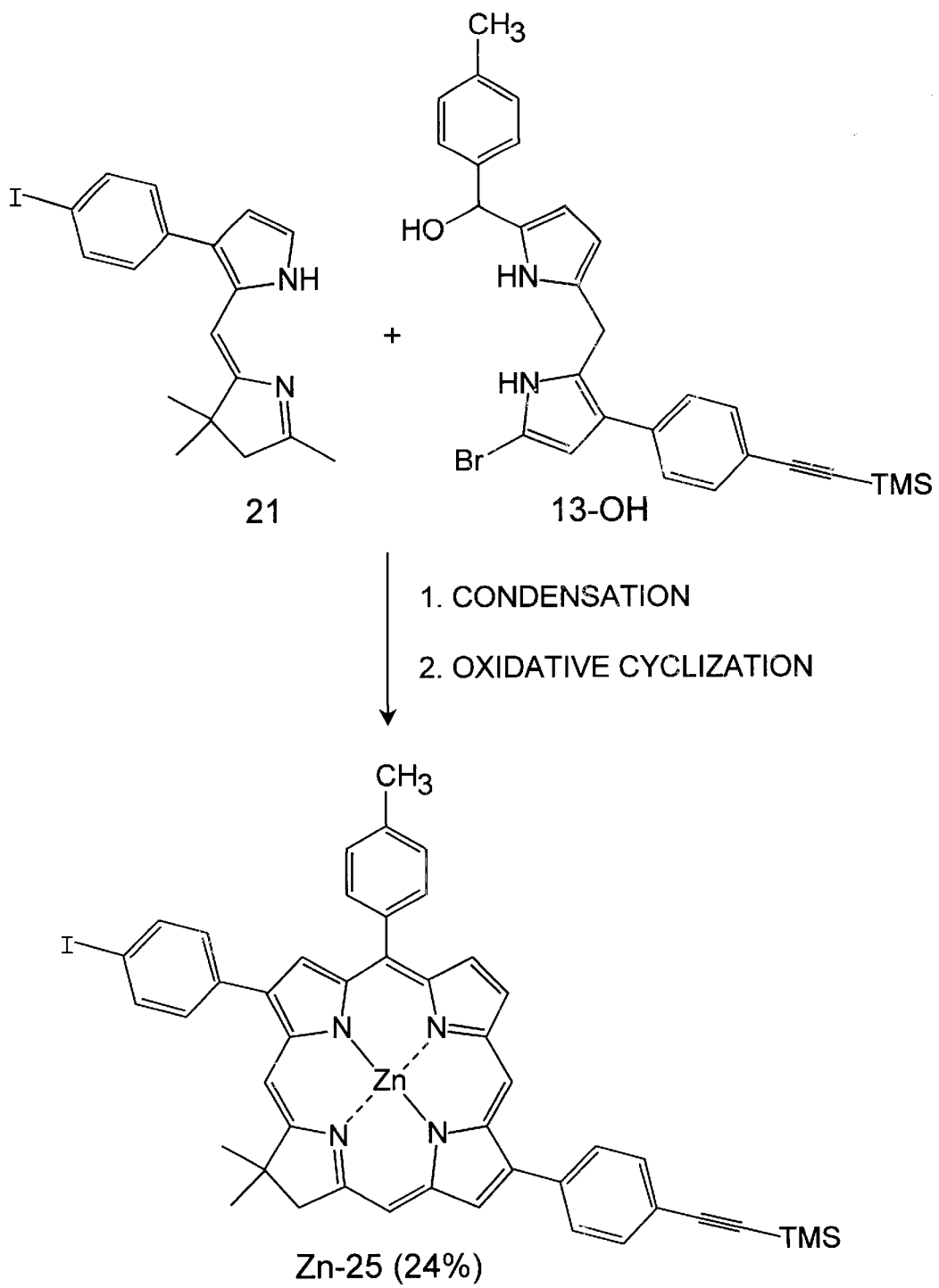
FIG. 58 illustrates the synthesis of a trans β-substituted chlorin.

The chlorins Zn22–24 each bear one D substituent. In order to prepare a chlorin bearing two β substituents, 13-OH and Western half 21 were reacted to give zinc chlorin Zn-25 in 24% yield (FIG. 58). This chlorin has an iodophenyl group and an ethynylphenyl group at β positions on opposite sides of the macrocycle. Porphyrins bearing iodophenyl and ethynylphenyl groups in a trans orientation have been employed in the stepwise synthesis of linear multi-porphyrin arrays (Wagner, R. W.; Lindsey, J. S. *J. Am. Chem. Soc.* 1994, 116, 9759–9760; Wagner, R. W.; Ciringh, Y.; Clausen, P. C.; Lindsey, J. S. *Chem. Mater.* 1999, 11, 2974–2983; Lindsey, J. S. et al., *Tetrahedron* 1994, 50, 8941–8968). Analogous linear multi-chlorin arrays should be attainable with Zn-25.

In each of these chlorin-forming reactions only one chlorin product was obtained, indicating the absence of scrambling during the course of the reaction. This methodology is quite general and the yields of 18–24% obtained with the three β-substituted Eastern halves (11-OH, 13-OH, 17-OH) and the β-substituted Western half (21) are noticeably superior to the ~10% obtained with the meso-substituted Eastern halves (2-OH) and Western half (1).

The Zn-chlorins were demetalated to give the corresponding free base chlorins by treatment with TFA in $CH_2Cl_2$. In most cases the crude product was pure enough for analysis while in other cases the free base chlorin was further purified by a short silica column.

Spectral Properties of the Chlorins. $^1H$ NMR Spectra. The NMR spectral information available for chlorins has been obtained largely from naturally occurring chlorins, which bear alkyl groups at most of the β positions. The $^1H$ NMR spectra of β-substituted free base chlorins (22–25) and Zn chlorins (Zn-22–Zn-25) are readily assignable and confirm the expected substitution patterns. In 22, the two NH protons appear as broad peaks at δ −2.15 and −1.85 ppm, and a downfield signal appears for one of the meso substituted protons (assigned to C-10) at δ 9.84 ppm. The reduced ring exhibits a singlet at δ 2.07 ppm (geminal dimethyl groups) and another singlet at δ 4.64 ppm (ring $CH_2$), as also observed in the meso-substituted chlorins. Other characteristic features include an AB quartet at δ 8.85 ppm (β-pyrrole protons of ring A), two doublets at δ 8.64 and 8.90 ppm (β-pyrrole protons of ring B), and singlets at δ 8.91 (for 2H) and 8.99 ppm (two meso protons at C-15 and C-20, and one β-pyrrole proton of ring C). The significant changes for the β-substituted Zn-22 are the absence of signals corresponding to NH protons, and slight upfield shifts of the geminal dimethyl group (δ 2.01 ppm), ring methylene protons (δ 4.48 ppm) and all of the meso and β-pyrrole protons. Similar trends were observed for free base chlorin 23 and zinc chlorin Zn-23.

The $^1H$ NMR spectrum of chlorin 24 is slightly different due to the difference in the substitution pattern at the perimeter of the molecule. Characteristic features in addition to the different chemical shifts of the two NH protons include the singlet at δ 8.64 ppm β-pyrrole proton of ring B) and the downfield signal at δ 9.17 ppm as a doublet (one of the β-pyrrole protons of ring C). The $^1H$ NMR spectrum of chlorin 25 is more simple. The β-pyrrole protons of ring B appear as two doublets at δ 8.62 and 8.88, and the AB quartet corresponding to the β-pyrrole protons of ring A in chlorins 22–24 is absent. The remaining meso protons and β-pyrrole protons resonate as five singlets. Zn-25 showed a similar pattern except for the slight upfield shift of the peaks due to the meso and β protons.

A distinctive feature of this set of chlorins is that the β-pyrrole protons of ring B appear slightly upfield compared to the other pyrrole protons. This indicates that the β-pyrrole double bond of ring B does not participate as fully in the 18π electron ring current of the chlorin macrocycle.

Absorption Spectra. Each of the free base chlorins (22–25) exhibits an intense Soret band and a characteristic strong $Q_y$ band. The Soret band in each case exhibited a short-wavelength shoulder of significant intensity, resulting in a fwhm ranging from 32–35 nm for 22–25. A similar spectral feature was observed for the previous set of meso-substituted free base chlorins that were examined. The Soret band red-shifted slightly as the substituent was moved from position 8(24) to 12 (22, 23) to 2 and 12 (25). Significant differences in $Q_y$ absorption maximum and absorption intensity occurred depending on the site of substitution of the chlorin. The $Q_y$ absorption maximum ranged from 637 to 655 nm, and paralleled the redshift of the Soret band. In addition, a hyperchromic effect of the $Q_y$ band was observed accompanying the bathochromic shift. Although the accurate determination of molar absorption coefficients can be difficult especially with handling small samples, the ratio of the $Q_y$ and Soret bands provides a relative measure of the changing band intensities. The Soret/$Q_y$ band ratio decreases from 4.3 (24) to 2.5 (25). These data are listed in Table 1. It is noteworthy that the chlorins with an iodophenyl or ethynylphenyl group at the 12 position exhibited nearly identical absorption spectra. For comparison, the meso-substituted free base chlorins exhibited absorption maxima at 411–414 nm and 640–644 nm.

Each of the zinc chlorins (Zn-22–Zn25) exhibits an intense Soret band and a characteristic strong $Q_y$ band. The Soret band in each case was sharp (fwhm 18–21 nm) with only a very weak short-wavelength shoulder. The $Q_y$ band underwent a redshift from 606 nm to 628 nm as the substituent location was changed from 8(Zn-24) to 12 (Zn-22, Zn-23) to 2 and 12 (Zn-25). A concomitant increase in intensity of the $Q_y$ band also was observed. These results are listed in Table 1. In all of the chlorins examined, a redshift in the Soret band was accompanied by a more pronounced redshift in the $Q_y$ band. The only discrepancy in this trend occurred in comparing Zn-24 and Zn-22 (or Zn-23). The former has the shortest wavelength Qy band (606 nm) but a Soret band at 415 nm, compared with 615 nm and 411 nm for that of the latter. For comparison, the meso-substituted zinc chlorins exhibited absorption maxima at 412 nm and 608 nm.

Fluorescence Spectra and Yields. Similar to the meso-substituted chlorins, the free base chlorins 22–24 exhibit a characteristic sharp fluorescence band at 640 nm and a weaker emission in the region 660–720 nm. The latter exhibited two discernible maxima at approximately 680 and 710 nm. The emission spectrum of free base chlorin 25 was shifted to 660 nm and 726 nm. The Zn chlorins Zn-22 and Zn-23 each exhibit a sharp fluorescence band at around 620 nm and a weak band at 676 nm, whereas the emission of Zn-24 appears at 609 and 661 nm. The emission spectrum of Zn-25 is more red shifted as observed in free base 25 (635 and 691 nm). The fluorescence quantum yields were determined for those chlorins lacking iodophenyl substituents (which exhibit decreased yields due to the heavy atom effect). The fluorescence quantum yield of free base chlorin 23 was 0.25, while that of Zn-23 was 0.11. These values are in line with those of other naturally occurring or synthetic chlorins.

Conclusions. The synthesis of chlorins described herein provides the following features: (1) control over the location of the reduced ring, (2) locking in of the chlorin hydrogenation level through use of a geminal dimethyl group, (3) location of synthetic handles at designated sites at the perimeter of the macrocycle, and (4) a single chlorin product thereby facilitating purification. The ability to incorporate substituents at distinct locations (2, 5, 8, 10, or 12) about the chlorin perimeter opens a number of opportunities. With different substitution patterns, the $Q_y$ absorption band can be tuned over the range 637–655 nm for free base chlorins and 606–628 mn for zinc chlorins, enabling greater spectral coverage. The chlorin bearing synthetic handles at the 2 and 12 positions (25) should enable the incorporation of chlorin building blocks into linear architectures. The availability of a family of synthetic chlorins bearing diverse substituents at defined locations should facilitate the systematic study of substituent effects and broaden the scope of chlorin containing model systems.

Experimental Section

General. $^1H$ and $^{13}C$ NMR spectra (300 MHz) were obtained in $CDCl_3$ unless noted otherwise. Absorption spectra (Cary 3, 0.25 nm data intervals) and fluorescence spectra (Spex FluoroMax, 1 nm data intervals) were collected routinely. Chlorins were analyzed in neat form by laser desorption mass spectrometry (LD-MS) in the absence of a matrix (Fenyo, D. et al., *J. Porphyrins Phthalocyanines* 1997, 1, 93–99; Srinivasan, N. et al., *J. Porphyrins Phthalocyanines* 1999, 3, 283–291). Pyrrole was distilled at atmospheric pressure from $CaH_2$. Melting points are uncorrected. p-Iodobenzaldehyde was obtained from Karl Industries. All other reagents and starting materials were obtained from Aldrich. Spectral parameters including molar absorption coefficients and fluorescence quantum yields ($\Phi_f$) were determined as previously described (Strachan, J. P. et al., *J. Org. Chem.* 2000, 65, 3160–3172).

Chromatography. Preparative chromatography was performed using silica (Baker) or alumina (Fisher A540, 80–200 mesh) and eluting solvents based on hexanes admixed with ethyl acetate or $CH_2Cl_2$.

Solvents. THF was distilled from sodium benzophenone ketyl as required. $CH_3CN$ (Fisher certified A.C.S.) was distilled from $CaH_2$ and stored over powdered molecular sieves. Nitromethane was stored over $CaCl_2$. $CH_2Cl_2$ was distilled from $CaH_2$. Dry methanol was prepared as follows. Magnesium turnings (5 g) and iodine (0.5 g) with 75 mL of methanol were warmed until the iodine disappeared and all the magnesium was converted to the methoxide. Up to 1 L of methanol was added and heated at reflux for a minimum of 2 h before collecting. Other solvents were used as received.

Compounds 1 (Strachan, J. P. et al., *J. Org. Chem.* 2000, 65, 3160–3172) and 3 (Balasubramanian, T.; Lindsey, J. S. *Tetrahedron* 1999, 55, 6771–6784) were prepared according to literature procedures.

3-(4-Iodophenyl)pyrrole (4). Following earlier procedures (Balasubramanian, T.; Lindsey, J. S. *Tetrahedron* 1999, 55, 6771–6784), a mixture of 3-ethoxycarbonyl-4-(4-iodophenyl)pyrrole (7.20 g, 21.1 mmol) and ethylene glycol (55 mL) in a 100-mL Claisen flask was flushed with argon for 10 min and powdered NaOH (2.2 g, 55 mmol) was then added. The flask was placed in an oil bath at 120° C. and the oil bath temperature was raised to 160° C. After 2.5 h, the flask was cooled to room temperature and treated with 10% aq NaCl (100 mL). The aqueous layer was extracted with $CH_2Cl_2$, the organic layers were collected, washed with 10% aq NaCl, dried ($Na_2SO_4$), concentrated, and recrystallized in ethanol affording light brown crystals (5.18 g, 91%). mp 164–165° C.; $^1H$ NMR $\delta$ 6.51 (m, 1H), 6.83 (m, 1H), 7.08 (s, 1H), 7.27 (d, J=8.7 Hz, 2H), 7.63 (d, J=8.7 Hz, 2H); $^{13}C$ NMR $\delta$ 89.9, 106.3, 114.7, 119.1, 123.8, 127.0, 135.2, 137.5; EI-MS obsd 268.9702, calcd 268.9702. Anal. Calcd for $C_{10}H_8IN$: C, 44.6; H, 3.0; N, 5.2. Found: C, 44.7; H, 3.0; N, 5.1. The synthesis starting from 4-iodobenzaldehyde (35 g), monoethyl malonate, and TosMIC has been performed with linear scale up of the established procedures, affording 21.5 g of 4.

2-Formyl-3-(4-iodophenyl)pyrrole (5). A solution of 4 (5.15 g, 19.1 mmol) in DMF (6.1 mL) and $CH_2Cl_2$ (140 mL) under argon was cooled to 0° C. and then $POCl_3$ (2.11 mL, 22.6 mmol) was added dropwise. After 1 h, the flask was warmed to room temperature and stirred overnight. The reaction was quenched at 0° C. with 2.5 M NaOH (100 mL). The mixture was poured into water (500 mL), extracted with $CH_2Cl_2$, and the combined organic layers were washed with water, brine, dried ($Na_2SO_4$), and the solvent was removed in vacuo. $^1H$ NMR spectroscopy showed two regioisomers in a 6:1 ratio. The minor isomer exhibited signals at $\delta$ 7.21 and 7.39 ppm, compared with signals at $\delta$ 6.42 and 7.14 for the major isomer. The most downfield signal (7.39 ppm) is assigned to the proton adjacent to a formyl group, which occurs in the 2-formyl-4-aryl substituted pyrrole. Recrystallization from ethyl acetate afforded an orange solid corresponding to the major aldehyde (2.25 g). The mother liquor was concentrated and purified by flash column chromatography [silica, hexanes/ethyl acetate (3:1)]. The first fraction corresponded to the major aldehyde (1.25 g). The total yield of the title compound was 3.50 g (62%): mp 153–154° C.; $^1H$ NMR $\delta$ 6.42 (m, 1H), 7.14 (m, 1H), 7.22 (m, 2H), 7.76 (m 2H), 9.59 (s, 1H), 10.72 (br, 1H); $^{13}C$ NMR $\delta$ 93.5, 104.3, 111.4, 125.8, 128.6, 130.8, 133.1, 137.8, 179.4; FAB-MS obsd 296.9663, calcd 296.9651; Anal. Calcd for $C_{10}H_8INO$: C, 44.5; H, 2.7; N, 4.7. Found: C, 44.4; H, 2.7; N, 4.6.

N-tert-Butoxycarbonyl-2-formyl-3-(4-iodophenyl) pyrrole (6). Following a standard procedure (Tietze, L. F.; Kettschau, G.; Heitmann, K. *Synthesis* 1996, 851–857), sample of NaH (70 mg, 1.75 mmol, 60% dispersion in mineral oil) in a round-bottomed flask under argon was washed twice with anhydrous pentane (~5 mL). Anhydrous THF (14 mL) was added followed by 5 (400 mg, 1.35 mmol). After stirring for 30 min at room temperature, $(BOC)_2O$ (325 mg, 1.5 mmol) was added and stirring was continued for another 2 h. The reaction was quenched with 50% satd. aq $NH_4Cl$ (50 mL). The mixture was extracted with ether, and the combined organic layers were washed with brine, dried ($Na_2SO_4$), and filtered [silica, hexanes/ethyl acetate (4:1)] to yield a viscous oil (535 mg, quantitative). $^1H$ NMR $\delta$ 1.64 (s, 9H), 6.33 (d, J=3.0 Hz, 1H), 7.30 (d, J=8.1 Hz, 2H), 7.46 (d, J=3.0 Hz, 1H), 7.72 (d, J=8.1 Hz, 2H), 10.22 (s, 1H); $^{13}C$ NMR $\delta$ 27.7, 85.8, 94.2, 113.2, 126.7, 128.5, 131.3, 132.8, 137.0, 137.4, 148.3, 181.6; FAB-MS obsd 397.0176, calcd 397.0175 ($C_{16}H_{16}INO_3$).

N-tert-Butoxycarbonyl-2-hydroxymethyl-3-(4-iodophenyl)pyrrole (7). A solution of 6(400 mg, 1.0 mmol) in anhydrous THF (12 mL) under argon was cooled to –20 to –25° C. and $LiBH_4$ (55 mg, 2.5 mmol) was added in portions. The reaction was monitored by TLC (silica, hexanes/ethyl acetate (4:1)), and when no starting material was detected (20–25 min), the reaction was quenched with cold water (30 mL). The aqueous layer was extracted with $CH_2Cl_2$ and the organic layer was dried ($Na_2SO_4$), concentrated, and purified by flash column chromatography [silica, hexanes/ethyl acetate containing 1% $Et_3N$ (3:1)] yielding a gum (330 mg, 82%). $^1H$ NMR $\delta$ 1.62 (s, 9H), 3.61 (br, 1H), 4.66 (d, J=7.2 Hz, 2H), 6.25 (d, J=3.6 Hz, 1H), 7.18 (d, J=8.1 Hz, 2H), 7.22 (d, J=3.6 Hz, 1H), 7.71 (d, J=8.1 Hz, 2H); $^{13}C$ NMR $\delta$ 27.8, 55.3, 84.7, 92.4, 111.2, 121.3, 127.9, 130.0, 130.4, 134.1, 137.5, 149.8; FAB-MS obsd 399.0336, calcd 399.0331 ($C_{16}H_{18}INO_3$).

3-(4-Iodophenyl)-10-N-(tert-butoxycarbonyl) dipyrromethane (8). A solution of 7 (1.2 g, 3.0 mmol) and pyrrole (3.36 mL, 48 mmol) in 1,4-dioxane (36 mL) at room temperature was treated with 10% aq HCl (6.0 mL). The reaction was monitored by TLC [silica, hexanes/ethyl acetate (4:1)]. After 4 h, satd aq $NaHCO_3$ (50 mL) and water (50 mL) were added and the mixture was extracted with $CH_2Cl_2$. The combined organic layers were washed with water, brine, dried ($Na_2SO_4$), concentrated, and purified by flash chromatography [silica, hexanes/ethyl acetate (4:1)]. A non-polar product was isolated in minor amount (uncharacterized). The desired product was obtained as a pale brown solid (920 mg, 68% yield): mp 128–129° C.; $^1H$ NMR $\delta$ 1.57 (s, 9H), 4.18 (s, 2H), 5.87 (br, 1H), 6.10 (m, 1H), 6.22 (d, J=3.0 Hz, 1H), 6.64 (m, 1H), 7.16 (d, J=8.0 Hz, 2H), 7.24 (d, J=3.6 Hz, 1H), 7.71 (d, J=8.0 Hz, 2H), 8.78 (br, 1H); $^{13}C$ NMR $\delta$ 24.6, 27.8, 84.3, 92.1, 105.8, 107.9, 111.6, 116.3, 121.0, 126.8, 128.5, 130.4, 130.8, 135.0, 137.4, 150.0; FAB-MS obsd 448.0659, calcd 448.0648; Anal.

Calcd for $C_{20}H_{21}IN_2O_2$: C, 53.6; H, 4.7; N, 6.3. Found: C, 54.1; H, 4.9; N, 5.9.

3-(4-Iodophenyl)-9-(4-methylbenzoyl)-10-N-(tert-butoxycarbonyl)dipyrromethane (9). A solution of 8(448 mg, 1.0 mmol) in anhydrous THF (15 mL) under argon at 0° C. was treated slowly with EtMgBr (1 M in THF, 2.5 mL, 2.5 mmol). The mixture was stirred for 30 minutes at 0° C., then, p-toluoyl chloride (200 µL, 1.5 mmol) was added slowly and stirring was continued for 1 h at 0° C. The reaction was quenched with satd. aq $NH_4Cl$ and extracted with $CH_2Cl_2$. The combined organic layers were washed with water, brine, dried ($Na_2SO_4$), concentrated, and the product was purified by flash column chromatography [silica, hexanes/ethyl acetate (4:1)]. The product was obtained as a pale white solid (375 mg, 66%): mp 120–121° C.; (due to possible rotamers the $^1H$ NMR and $^{13}C$ NMR are not very clean) $^1H$ NMR δ 1.56 (s, 9H), 2.42 (s, 3H), 4.29 (s, 2H), 5.95 (m, 1H), 6.26 (m, 1H), 6.76 (m, 1H), 7.09 (m, 2H), 7.16 (m, 1H), 7.25 (m, 2H), 7.31 (m, 1H), 7.71 (d, 8.7 Hz, 2H), 7.77 (d, J=8.1 Hz, 2H), 9.95 (br, 1H); $^{13}C$ NMR δ 25.2, 27.8, 31.7, 84.8, 92.3, 109.3, 111.5, 119.6, 121.5, 125.8, 126.3, 128.9, 129.0, 130.2, 130.6, 134.7, 135.8, 137.5, 138.6, 142.0, 149.7, 183.8; Anal. Calcd for $C_{28}H_{27}IN_2O_3$: C, 59.4; H, 4.8; N, 5.0. Found: C, 59.4; H, 4.6; N, 5.1.

3-(4-Iodophenyl)-9-(4-methylbenzoyl)dipyrromethane (10). Following a standard method for the deprotection of BOC-protected pyrroles (Hasan, I. et al., *J. Org. Chem.* 1981, 46, 157–164), a solution of 9 (328 mg, 0.58 mmol) in anhydrous THF (4 mL) under argon at room temperature was treated with methanolic NaOMe (0.7 mL, prepared by dissolving 200 mg of NaOMe in 1.0 mL of MeOH). After 20–25 min, the reaction was quenched with a mixture of hexanes and water (20 mL, 1:1) and extracted with ethyl acetate. The combined organic layers were washed with water, brine, dried (Na2SO4), and purified by flash column chromatography [silica, hexanes/ethyl acetate (3:1)] to yield a pale brown solid (216 mg, 80%): mp 185–186° C.; $^1H$ NMR δ 2.43 (s, 3H), 4.17 (s, 2H), 6.15 (m, 1H), 6.56 (m, 1H), 6.85 (m, 1H), 7.17 (m, 2H), 7.28 (m, 2H), 7.69 (m, 2H), 7.77 (d, J=7.8 Hz, 2H), 9.43 (br, 1H), 10.88 (br, 1H); $^{13}C$ NMR δ 21.6, 25.2, 90.6, 108.6, 110.3, 117.4, 121.1, 122.3, 123.9, 129.0, 129.1, 130.0, 130.7, 135.5, 136.2, 137.4, 139.4, 142.6, 185.2; FAB-MS obsd 466.0561, calcd 466.0542; Anal. Calcd for $C_{23}H_{19}IN_2O$: C, 59.2; H, 4.1; N, 6.0. Found: C, 59.3; H, 4.2; N, 5.9.

1-Bromo-3-(4-iodophenyl)-9-(4-methylbenzoyl)dipyrromethane (11). Following earlier procedures (Strachan, J. P. et al., *J. Org. Chem.* 2000, 65, 3160–3172), 10 (120 mg, 0.26 mmol) was dissolved in anhydrous THF (6 mL) and cooled to −78° C. under argon. Recrystallized NBS (46 mg, 0.26 mmol) was added and the reaction mixture was stirred for 1 h (−78° C.) and then quenched with a mixture of hexanes and water (20 mL, 1:1) and allowed to warm to 0° C. The aqueous portion was extracted with reagent-grade ether and the combined organic layers were dried over $K_2CO_3$. The solvent was evaporated under vacuum at room temperature. Purification by flash column chromatography [silica, hexanes/ether (2:1)] afforded a yellow solid (120 mg, 85%). The bromodipyrromethane is unstable but can be stored for several weeks at 0° C. mp 160° C. (decomp); $^1H$ NMR δ 2.44 (s, 3H), 4.09 (s, 2H), 6.12 (d, J=3.0 Hz, 1H), 6.16 (m, 1H), 6.89 (m, 1H), 7.14 (d, J=7.8 Hz, 2H), 7.30 (d, J=7.8 Hz, 2H), 7.71 (d, J=8.1 Hz, 2H), 7.80 (d, J=8.1 Hz, 2H), 10.33 (br, 1H), 11.59 (br, 1H); 13C NMR δ 21.6, 24.9, 91.1, 97.9, 110.2, 110.5, 122.8, 123.5, 125.4, 129.2, 130.2, 130.0, 130.8, 135.2, 135.4, 137.5, 139.9, 142.8, 186.1; FAB-MS obsd 543.9642, calcd 543.9647; Anal. Calcd for $C_{23}H_{18}BrIN_2O$: C, 50.7; H, 3.3; N, 5.1. Found: C, 51.3; H, 3.5; N, 5.2.

3-[4-(Trimethylsilylethynyl)phenyl]-9-(4-methylbenzoyl)dipyrromethane (12). Samples of 10 (279 mg, 0.599 mmol), $Pd_2(dba)_3$ (42 mg, 0.046 mmol), $Ph_3As$ (113 mg, 0.369 mmol), and CuI (9 mg, 0.047 mmol) were added to a 25-mL Schlenk flask. The flask was evacuated and purged with argon for three times. Then deaerated anhydrous $THF/Et_3N$ (6 mL, 1:1) was added and followed by trimethylsilylacetylene (127 µL, 0.90 mmol). The flask was sealed, immersed in an oil bath (37° C.), and the mixture was stirred overnight. Then $CH_2Cl_2$ (20 mL) was added and the mixture was filtered through a pad of Celite, washed several times with $CH_2Cl_2$, concentrated, and the residue was purified by flash column chromatography [silica, hexanes/ethyl acetate (3:1)] to afford a yellow solid (262 mg, quantitative): mp 126–127° C.; $^1H$ NMR δ 0.26 (s, 9H), 2.43 (s, 3H), 4.19 (s, 2H), 6.16 (m, 1H), 6.28 (m, 1H), 6.55 (m, 1H), 6.85 (m, 1H), 7.28 (d, J=8.7 Hz, 2H), 7.38 (d, J=8.1 Hz, 2H), 7.49 (d, J=8.7 Hz, 2H), 7.77 (d, J=8.1 Hz, 2H), 9.51 (br, 1H), 10.96 (br, 1H); $^{13}C$ NMR δ 0.0, 21.5, 25.3, 105.4, 108.6, 110.3, 117.4, 119.9, 121.5, 122.3, 124.1, 127.6, 129.0, 129.1, 130.7, 132.0, 135.5, 137.0, 139.5, 142.6, 185.2; FAB-MS obsd 436.1972, calcd 436.1971; Anal. Calcd for $C_{28}H_{28}N_2OSi$: C, 77.0; H, 6.5; N, 6.4. Found: C, 76.3; H, 6.3; N, 6.3.

1-Bromo-3-[4-(trimethylsilylethynyl)phenyl]-9-(4-methylbenzoyl)dipyrromethane (13). Following the procedure for the synthesis of 11, treatment of 12 (150 mg, 0.34 mmol) with NBS (60 mg, 0.34 mmol) afforded a pale yellow solid (160 mg, 91%): mp 140° C. (decomp); $^1H$ NMR δ 0.26 (s, 9H), 2.44 (s, 3H), 4.12 (s, 2H), 6.17 (m, 2H), 6.89 (m, 1H), 7.31 (m, 4H), 7.50 (d, J=9.0 Hz, 2H), 7.80 (d, J=8.1 Hz, 2H), 10.16 (br, 1H), 11.42 (br, 1H); $^{13}C$ NMR δ 0.0, 21.5, 25.0, 94.1, 97.9, 105.2, 110.3, 110.5, 120.4, 123.3, 125.5, 127.7, 129.2, 130.7, 132.1, 135.4, 135.9, 139.7, 142.8, 185.9; FAB-MS obsd 514.1079, calcd 514.1076; Anal. Calcd for $C_{28}H_{27}BrN_2OSi$: C, 65.2; H, 5.3; N, 5.4. Found: C, 65.1; H, 5.2; N, 5.3.

3-(4-Iodophenyl)dipyrromethane (14). Following the deprotection procedure used to prepare 10, a sample of 8(225 mg, 0.50 mmol) in anhydrous THF (4 mL) under argon at room temperature was treated with methanolic NaOMe (0.6 mL, prepared by dissolving 200 mg of NaOMe in 1.0 mL of MeOH). After 15 min, the reaction was quenched with mixture of hexanes and water (14 mL, 1:1), extracted with ethyl acetate, and the combined organic layers were washed with water, brine, then dried over $Na_2SO_4$. The residue was passed through a filtration column to yield a light brown solid (160 mg, 92%). Analytical data are in accord with the literature (Balasubramanian, T.; Lindsey, J. S. *Tetrahedron* 1999, 55, 6771–6784).

3-(4-Iodophenyl)-1-(4-methylbenzoyl)dipyrromethane (16). Following a general monoacylation procedure for unprotected dipyrromethanes (Rao, P. D. et al., *J. Org. Chem.* 2000, 65, 1084–1092. ), EtMgBr (1 M solution in THF, 2.2 mL, 2.2 mmol) was added to a solution of 14 (385 mg, 1.1 mmol) in anhydrous THF (14 mL). After stirring for 10 min, the flask was cooled to −78° C. and a solution of pyridyl thioester 15 (255 mg, 1.1 mmol) in anhydrous THF (3 mL) was added slowly. After a few min the cooling bath was removed, stirring was continued for 1 h, then the mixture was quenched with satd aq $NH_4Cl$, water, and then extracted with $CH_2Cl_2$. The combined organic layers were washed with water, brine, dried ($Na_2SO_4$), and concentrated. The two regioisomers formed were purified by two successive flash columns [silica, hexanes/ethyl acetate (3:1)], affording the minor isomer 16 (130 mg, 25%) and the major isomer 10 (270 mg, 53%). Data for 16: mp 190° C. (decomp); $^1$H NMR δ 2.43 (s, 3H), 4.15 (s, 2H), 6.05 (m, 1H), 6.13 (m, 1H), 6.58 (m, 1H), 6.94 (m, 1H), 7.19 (d, J=8.7 Hz, 2H), 7.28 (d, J=8.1 Hz, 2H), 7.73 (d, J=8.7 Hz, 2H,) 7.78 (d, J=8.1 Hz, 2H), 9.17 (br, 1H), 10.83 (br, 1H); $^{13}$C NMR δ21.6, 25.2, 91.8, 106.8, 108.3, 117.8, 121.1, 124.3, 127.2, 129.1, 129.2, 129.7, 130.2, 134.6, 135.4, 136.3, 137.6, 142.9, 185.4; FAB-MS obsd 466.0573, calcd 466.0542; Anal. Calcd for $C_{23}H_{19}IN_2O$: C, 59.2; H, 4.1; N, 6.0. Found: C, 59. 1; H, 4.2; N, 5.8.

9-Bromo-3-(4-iodophenyl)-1-(4-methylbenzoyl) dipyrromethane (17). Following the procedure for the synthesis of 11, treatment of 16 (186 mg, 0.400 mmol) with NBS (72 mg, 0.405 mmol) gave a pale yellow solid (189 mg, 87%): mp 140° C. (decomp); $^1$H NMR δ 2.43 (s, 3H), 4.08 (s, 2H), 5.94 (m, 1H), 6.00 (m, 1H), 6.96 (d, J=2.1 Hz, 1H), 7.18 (d, J=8.7 Hz, 2H), 7.29 (d, J=8.1 Hz, 2H), 7.74 (d, J=8.7 Hz, 2H), 7.80 (d, J=8.1 Hz, 2H), 9.80 (br, 1H), 11.53 (br, 1H); $^{13}$C NMR was attempted in CDCl$_3$ but the compound decomposed upon lengthy data acquisition. FAB-MS obsd 543.9628, calcd 543.9647; Anal. Calcd for $C_{23}H_{19}IN_2O$: C, 50.7; H, 3.3; N, 5.1. Found: C, 51.2; H, 3.4; N, 5.0.

2-(2-trans-Nitrovinyl)-3-(4-iodophenyl)pyrrole (18). A mixture of 5 (1.485 g, 5.00 mmol), KOAc (492 mg, 5.01 mmol), methylamine-hydrochloride (402 mg, 5.95 mmol), and nitromethane (45 mL) under argon was stirred at room temperature. The mixture slowly became orange and yielded an orange-red precipitate. The reaction was monitored by TLC and after stirring for 2 h, the TLC showed the appearance of a new component and the disappearance of 5. (A longer reaction time (10 h) led to formation of the Michael addition product, 2-(1,3-dinitro-2-propyl)-3-(4-iodophenyl) pyrrole, in ~30% yield.) The reaction was quenched with brine, extracted with ethyl acetate, and the organic layers were dried (Na$_2$SO$_4$) and concentrated. The residue was treated with hot ethyl acetate and filtered, then concentrated and dissolved in hot CH$_2$Cl$_2$, followed by precipitation upon adding cold hexanes, affording an orange solid (1.52 g, 89%): mp 217–218° C. (decomp); $^1$H NMR (acetone-d$_6$) δ 6.56 (d, J=2.1 Hz, 1H), 7.32 (d, J=8.2 Hz, 2H), 7.35 (m, 1H), 7.81 (d, J=13.5 Hz, 1H), 7.90 (d, J=8.3 Hz, 2H), 7.99 (d, J=13.4 Hz, 1H); $^{13}$C NMR (acetone-d$_6$) δ 93.4, 112.5, 121.3, 127.1, 127.2, 128.4, 131.8, 132.8, 135.4, 138.9; FAB-MS obsd 339.9720, calcd 339.9709. Anal. Calcd for $C_{12}H_9IN_2O_2$: C, 42.4; H, 2.7; N, 8.2. Found: C, 41.8; H, 2.6; N, 7.9; $λ_{abs}$ (toluene) 395 nm.

2-(2-Nitroethyl)-3-(4-iodophenyl)pyrrole (19). Following the procedure for a β-unsubstituted pyrrole (Strachan, J. P. et al., J. Org. Chem. 2000, 65, 3160–3172), a sample of 18 (1.36 g, 4.00 mmol) was dissolved in anhydrous THF/MeOH (40 mL, 9:1) under argon at 0° C. NaBH$_4$ (605 mg, 16.00 mmol) was added in portions and stirring was continued for 1 h at 0° C. Then the mixture was stirred for 2 h at room temperature. The reaction mixture was neutralized with acetic acid (pH=7), then water (50 mL) was added and the mixture was extracted with ethyl acetate. The combined organic layers were washed with water, brine, dried (Na$_2$SO$_4$), concentrated, and purified by passage through a short column [silica, hexanes/ethyl acetate (3:1)] to give a pale white solid (1.2 g, 88%): mp 88–89° C.; $^1$H NMR δ 3.41 (t, J=6.6 Hz, 2H), 4.52 (t, J=6.6 Hz, 2H), 6.26 (s, 1H), 6.74 (s, 1H), 7.07 (d, J=8.1 Hz, 2H), 7.69 (d, J=8.1 Hz, 2H), 8.33 (br, 1H); $^{13}$C NMR δ 24.0, 75.0, 91.1, 109.3, 117.8, 122.1, 122.2, 129.8, 135.7, 137.7; FAB-MS obsd 341.9877, calcd 341.9865; Anal. Calcd for $C_{12}H_{11}IN_2O_2$: C, 42.1; H, 3.2; N, 8.2. Found: C, 42.3; H, 3.3; N, 8.1.

1-[3-(4-Iodophenyl)pyrro-2-yl]-2-nitro-3,3-dimethyl-5-hexanone (20). Following the procedure for a β-unsubstituted pyrrole (Strachan, J. P. et al., J. Org. Chem. 2000, 65, 3160–3172), a mixture of 19 (1.03 g, 3.0 mmol), CsF (2.28 g, 15.0 mmol), and mesityl oxide (1.72 mL, 15.0 mmol) in anhydrous acetonitrile (22.5 mL) was heated at 80° C. for 2.5 h to 3 h, during which the mixture turned from colorless to brown and then dark red. TLC analysis confirmed the absence of starting material. The solvent was evaporated under vacuum, the residue was taken up in ethyl acetate and filtered through a pad of silica using ethyl acetate as eluant. The solvent was evaporated under vacuum and the product was purified by a gravity column [alumina, hexanes/ethyl acetate (2:1)] followed by recrystallization from CH$_2$Cl$_2$/hexanes to afford brown crystals (550 mg, 42%): mp 124–125° C.; $^1$H NMR δ 1.08 (s, 3H), 1.19 (s, 3H), 2.11 (s, 3H), 2.37 (d, J=17.4 Hz, 1H), 2.56 (d, J=17.4 Hz, 1H), 3.15 (m, 1H), 3.39 (m, 1H), 5.20 (m, 1H), 6.21 (m, 1H), 6.68 (m, 1H), 7.10 (m, 2H), 7.70 (m, 2H), 8.22 (br, 1H); $^{13}$C NMR δ 23.9, 24.2, 24.8, 31.6, 36.8, 51.2, 91.1, 94.2, 109.1, 117.8, 122.2, 122.4, 130.1, 135.9, 137.5, 206.7; FAB-MS obsd 440.0605, calcd 440.0597; Anal. Calcd for $C_{18}H_{21}IN_2O_3$: C, 49.1; H, 4.8; N, 6.4. Found: C, 49.1; H, 4.7; N, 6.3.

1,3,3-Trimethyl-7-(4-iodophenyl)-2,3-dihydrodipyrrin (21). Following the procedure for a β-unsubstituted pyrrole (Strachan, J. P. et al., J. Org. Chem. 2000, 65, 3160–3172), a solution of 20 (220 mg, 0.50 mmol) in anhydrous THF (5.0 mL) under argon was treated with NaOMe (135 mg, 2.5 mmol) and the mixture was stirred for 1 h at room temperature (first flask). In a second flask, TiCl$_3$ (8.6 wt % TiCl$_3$ in 28 wt % HCl, 3.8 mL, 2.5 mmol, 5.0 mol equivalent) and H$_2$O (20 mL) were combined, NH$_4$OAc (~15 g) was added to buffer the solution to pH 6.0, and then THF (5 mL) was added. The nitronate anion of 20 formed in the first flask was transferred via a cannula to the buffered TiCl$_3$ solution in the second flask. Additional THF (3 mL) was added to the nitronate anion flask and the supernatant was also transferred to the buffered TiCl$_3$ solution. The resulting mixture was stirred at room temperature for 8 h under argon. Then the mixture was extracted with ethyl acetate and the combined organic layers were washed with satd aq NaHCO$_3$, water, brine, and then dried (MgSO$_4$). The solvent was removed under reduced pressure at room temperature. The crude product was passed through a short column [alumina, hexanes/ethyl acetate (2:1)] to afford a light green solid (80–92 mg, 45–50%): mp 140–142° C.; $^1$H NMR 6 1.18 (s, 6H), 2.22 (s, 3H), 2.52 (s, 2H), 5.89 (s, 1H), 6.26 (m, 1H), 6.85 (m, (m, 2H), 7.69 (m, 2H), 11.09 (br, 1H); $^{13}$C NMR δ 20.7, 29.1, 29.7, 41.2, 53.7, 90.3, 102.3, 108.6, 118.5, 122.2, 127.5, 130.4, 136.8, 137.4, 161.9, 177.2; FAB-MS obsd 390.0595, calcd 390.0593 ($C_{18}H_{18}IN_2$); $λ_{abs}$ (toluene) 352 nm.

General procedure for chlorin formation: Zn(II)-17,18-DiHydro-18,18-dimethyl-5-(4-methylphenyl)-12-(4-iodophenyl)porphyrin (Zn-22). Following a general procedure (Strachan, J. P. et al., J. Org. Chem. 2000, 65, 3160–3172), to a solution of 11 (110 mg, 0.20 mmol) in 7.5 mL of anhydrous THF/MeOH (4:1) at room temperature was added excess of NaBH$_4$ (100 mg, 2.6 mmol) in small portions. The reaction was monitored by TLC [alumina, hexanes/ethyl acetate (3:1)] and upon completion the mixture was quenched with cold water (~10 mL), then extracted with distilled CH$_2$Cl$_2$ (3×25 mL). The combined organic layers were washed with brine (50 mL), dried (K$_2$CO$_3$) for 2–3 min, and concentrated in vacuo at room temperature to leave the resulting carbinol 11-OH in ~1–2 mL of CH$_2$Cl$_2$.

The WH 1 (45 mg, 0.24 mmol) was dissolved in a few mL of anhydrous $CH_3CN$ and combined with 11-OH, then additional anhydrous $CH_3CN$ was added to give a total of 22 mL $CH_3CN$. The solution was stirred at room temperature under argon and TFA (20 µL, 0.26 mmol) was added. The reaction was monitored by TLC [alumina, hexanes/ethyl acetate (3:1)], which after 25–30 min showed the disappearance of the EH and the appearance of a bright spot just below the WH. The reaction mixture was quenched with 10% aq $NaHCO_3$ and extracted with distilled $CH_2Cl_2$ (3×25 mL). The combined organic layers were washed with water, brine, dried ($Na_2SO_4$) and the solvent was removed in vacuo at room temperature. The residue was dissolved in 14 mL of anhydrous toluene under argon, then $AgIO_3$ (848 mg, 3.0 mmol), piperidine (300 µL, 3.0 mmol) and $Zn(OAc)_2$ (550 mg, 3.0 mmol) were added. The resulting mixture was heated at 80° C. for 2.5 h. The reaction was monitored by TLC [silica, hexanes/$CH_2Cl_2$, (1:1); showing a single green spot)] and absorption spectroscopy (bands at ~410 nm and ~610 nm). The color change of the reaction mixture from red to green indicates the formation of chlorin. The reaction mixture was cooled to room temperature then passed through a short column (silica, $CH_2Cl_2$). The major fraction was concentrated and again chromatographed [silica, hexanes/$CH_2Cl_2$ (2:1 then 1:1)]. The greenish blue solid obtained was dissolved in a minimum of $CH_2Cl_2$ and precipitated by adding hexanes, affording a greenish blue solid (25 mg, 18%). $^1H$ NMR δ 2.01 (s, 6H), 2.67 (s, 3H), 4.48 (s, 2H), 7.50 (d, J=7.2 Hz, 2H), 7.91 (d, J=7.2 Hz, 2H), 7.95 (d, J=8.1 Hz, 2H), 8.09 (d, J=8.1 Hz, 2H), 8.51 (d, J=4.2 Hz, 1H), 8.67 (m, 5H), 8.78 (d, J=4.2 Hz, 1H), 9.56 (s, 1H); LD-MS obsd 693.78; FAB-MS obsd 694.0580, calcd 694.0572 ($C_{35}H_{27}IN_4Zn$); $\lambda_{abs}$ (toluene)/nm 411 (log ε=5.33, fwhm=18 nm), 616 (4.76), $\lambda_{em}$ 619, 674 nm.

Notes about chlorin formation: (1) The complete reduction of the carbonyl in the EH precursor to the corresponding carbinol sometimes requires additional $NaBH_4$. The reduction must be complete prior to performing the chlorin forming reaction. (2) Upon workup of the EH the organic layers were dried in $K_2CO_3$ (the carbinol decomposes quickly upon drying over $Na_2SO_4$ or $MgSO_4$). It is important to not take the EH solution to dryness, as the EH in dried form is quite labile. (3) The EH upon workup, and the condensation solution giving the diHydrobilene-α, generally were either yellow or light red; these solutions led to chlorins in good yield. In some instances, further darkening was observed, in which case low yields of chlorins were obtained.

General conditions for demetalation. 17,18-DiHydro-18,18-dimethyl-5-(4-methylphenyl)-12-(4-iodophenyl)porphyrin (22). To a solution of Zn-22 (10 mg, 14.4 µmol) in anhydrous $CH_2Cl_2$ (5 mL) was added TFA (58 JL, 0.75 mmol). After stirring for 30 min at room temperature (monitoring by TLC and UV-Visible spectroscopy), the reaction was quenched with 10% aq $NaHCO_3$ (20 mL) and extracted with $CH_2Cl_2$. The combined organic layers were washed with water, dried ($Na_2SO_4$), and concentrated. Further purification (if necessary) was achieved by chromatography on a short column [silica, hexanes/$CH_2Cl_2$ (1:1 then 1:2)] affording a green solid (8.0 mg, 88%). $^1H$ NMR δ −2.15 (br, 1H), −1.85 (br, 1H), 2.07 (s, 6H), 2.69 (s, 3H), 4.64 (s, 2H), 7.54 (d, J=7.5 Hz, 2H), 8.04 (m, 4H), 8.16 (d, J=8.1 Hz, 2H), 8.64 (d, J=4.5 Hz, 11H), 8.85 (AB quartet, J=4.5 Hz, 2H), 8.90 (m, 3H), 8.99 (s, 1H), 9.84 (s, 1H); LD-MS obsd 633.88; FAB-MS obsd 632.1434, calcd 632.1437 ($C_{35}H_{29}IN_4$); $\lambda_{abs}$ (toluene)/nm 414 (log ε=5.13, fwhm=34 nm), 505 (4.12), 643 (4.65); $\lambda_{em}$ 646, 682 nm.

Zn(II)-17,18-DiHydro-18,18-dimethyl-5-(4-methylphenyl)-12-{4-[2-(trimethylsilyl)ethynyl]phenyl}porphyrin (Zn-23). Following the general procedure for chlorin formation, the reaction of 13-OH [prepared from 13 (130 mg, 0.25 mmol)] and 1 (57 mg, 0.30 mmol) yielded a blue solid (36 mg, 22%). $^1H$ NMR δ 0.35 (s, 9H), 2.03 (s, 6H), 2.67 (s, 3H), 4.54 (s, 2H), 7.50 (d, J=8.1 Hz, 2H), 7.86 (d, J=8.1 Hz, 2H), 7.96 (d, J=7.5 Hz, 2H), 8.16 (d, J=8.1 Hz, 2H), 8.53 (d, J=4.5 Hz, 1H), 8.60 (s, 1H), 8.68 (m, 2H), 8.73 (d, J=4.5 Hz, 1H), 8.75 (s, 1H), 8.80 (d, J=4.5 Hz, 1H), 9.63 (s, 1H); LD-MS obsd 665.74; FAB-MS obsd 664.2007, calcd 664.2001; ($C_{40}H_{36}IN_4SiZn$); $\lambda_{abs}$ (toluene)/nm 413 (log ε=5.31, fwhm=21 nm), 618 (4.77), $\lambda_{em}$ 622, 676 nm (($\Phi_f$=0.11).

17,18-DiHydro-18,18-dimethyl-5-(4-methylphenyl)-12-{4-[2-(trimethylsilyl)ethynyl]phenyl}porphyrin (23). Following the general demetalation procedure, a sample of Zn-23 (10 mg, 15 pmol) gave a green solid (8.0 mg, 89%). $^1H$ NMR δ −2.15 (br, 1H), −1.85 (br, 1H), 0.35 (s, 9H), 2.07 (s, 6H), 2.69 (s, 3H), 4.64 (s, 2H), 7.53 (d, J=7.5 Hz, 2H), 7.91 (d, J=8.1 Hz, 2H), 8.03 (d, J=8.1 Hz, 2H), 8.27 (d, J=8.1 Hz, 2H), 8.64 (d, J=4.5 Hz, 11H), 8.84 (AB quartet, J=4.5 Hz, 2H), 8.89 (m, 2H), 8.93 (s, 1H), 8.99 (s, 1H), 9.86 (s, 1H); LD-MS obsd 604.31; FAB-MS obsd 602.2880, calcd 602.2866 ($C_{40}H_{38}IN_4Si$); $\lambda_{abs}$ (toluene)/nm 415 (log ε=4.97, fwhm=36 nm), 506 (3.96), 647 (4.49); $\lambda_{em}$ 648, 685, 715 nm ($\Phi_f$=0.25).

Zn(II)-17,18-DiHydro-18,18-dimethyl-5-(4-methylphenyl)-8-(4-iodophenyl)porphyrin (Zn-24). Following the general procedure for chlorin formation, the reaction of 17-OH (prepared from 17 (110 mg, 0.20 mmol)] and 1 (45 mg, 0.24 mmol) yielded a blue solid (30 mg, 24%). $^1H$ NMR δ 2.03 (s, 6H), 2.67 (s, 3H), 4.51 (s, 2H), 7.50 (d, J=8.1 Hz, 2H), 7.86 (d, J=8.1 Hz, 2H), 7.97 (d, J=8.1 Hz, 2H), 8.02 (d, J=8.1 Hz, 2H), 8.54 (s, 11H), 8.60 (s, 11H), 8.69 (m, 4H), 8.97 (d, J=4.2 Hz, 1H), 9.61 (s, 1H); LD-MS obsd 696.39; FAB-MS obsd 694.0607, calcd 694.0572 ($C_{35}H_{27}IN_4Zn$); $\lambda_{abs}$ (toluene)/nm 416 (log ε=5.13, fwhm=18 nm), 607 (4.49); $\lambda_{em}$ 609, 661 nm.

17,18-DiHydro-18,18-dimethyl-5-(4-methylphenyl)-8-(4-iodophenyl)porphyrin (24). Following the general demetalation procedure, a sample of Zn-24 (10 mg, 14.4 µmol) gave a green solid (7.5 mg, 83%). $^1H$ NMR δ −2.20 (br, 1H), −1.96 (br, 1H), 2.07 (s, 6H), 2.68 (s, 3H), 4.63 (s, 2H), 7.53 (d, J=8.1 Hz, 2H), 7.86 (d, J=8.7 Hz, 2H), 8.03 (m, 4H), 8.64 (s, 1H), 8.85 (m, 3H), 8.91 (s, 1H), 8.99 (s, 1H), 9.17 (d, J=4.5 Hz, 1H), 9.83 (s, 1H); LD-MS obsd 631.58; FAB-MS obsd 632.1454, calcd 632.1437 ($C_{35}H_{29}IN_4$); $\lambda_{abs}$ (toluene)/nm 410 (log ε=5.11, fwhm=32 nm), 504 (4.01), 638 (4.48); $\lambda_{em}$ 639, 679, 702 nm.

Zn(II)-17,18-DiHydro-18,18-dimethyl-2-(4-iodophenyl)-5-(4-methylphenyl)-12-{4-[2-(trimethylsilyl)ethynyl]phenyl}porphyrin (Zn-25). Following the general procedure for chlorin formation, the reaction of 13-OH [prepared from 13 (103 mg, 0.20 mmol)] and 21 (86 mg, 0.22 mmol) yielded a blue solid (42 mg, 24%). $^1H$ NMR δ 0.36 (s, 9H), 1.96 (s, 6H), 2.67 (s, 3H), 4.48 (s, 1H), 7.50 (d, J=7.5 Hz, 2H), 7.82 (d, J=8.7 Hz, 2H), 7.86 (d, J=8.1 Hz, 2H), 7.97 (d, J=8.1 Hz, 2H), 8.02 (d, J=8.1 Hz, 2H), 8.13 (d, J=7.8 Hz, 2H), 8.51 (d, J=4.2 Hz, 1H), 8.63 (s, 1H), 8.67 (s, 1H), 8.70 (s, 2H), 8.78 (d, J=4.2 Hz, 1H), 9.58 (s, 1H); LD-MS 866.34; FAB-MS obsd 866.1257, calcd 866.1280 ($C_{46}H_{39}IN_4SiZn$); $\lambda_{abs}$ (toluene)/nm 417 (log ε=5.32, fwhm=21 nm), 629 (4.90); $\lambda_{em}$ 635, 691 nm.

17,18-DiHydro-18,18-dimethyl-2-(4-iodophenyl)-5-(4-methylphenyl)-12-{4-[2-(trimethylsilyl)ethynyl]phenyl}porphyrin (25). Following the general demetalation procedure, a sample of Zn-25 (11.0 mg, 13.7 μmol) gave a green solid (8.0 mg, 78%). $^1$H NMR δ −1.95 (br, 1H), −1.70 (br, 1H), 0.36 (s, 9H), 2.0 (s, 6H), 2.68 (s, 3H), 4.60 (s, 2H), 7.53 (d, J=8.1 Hz, 2H), 7.91 (d, J=8.1 Hz, 2H), 8.03 (d, J=8.1 Hz, 2H), 8.07 (d, J=8.1 Hz, 2H), 8.26 (d, J=8.1 Hz, 2H), 8.62 (d, J=4.2 Hz, 1H), 8.81 (s, 1H), 8.88 (d, J=4.2 Hz, 1H), 8.91 (s, 1H), 8.95 (s, 1H), 8.96 (s, 1H), 9.84 (s, 1H); LD-MS 804.02; FAB-MS obsd 804.2157, calcd 804.2145 ($C_{46}H_{41}IN_4Si$); $\lambda_{abs}$ (toluene)/nm 422 (log ε=5.09, fwhm= 34 nm), 509 (4.08), 655 (4.68); $\lambda_{em}$ 660, 726 mn.

TABLE 1

Absorption spectral properties of chlorins.[a]

| Chlorins | $\lambda_{max}$ (nm), Soret | $\lambda_{max}$ (nm), Q | Soret/Q intensity ratio |
|---|---|---|---|
| 24 | 409 | 637 | 4.3 |
| 22 | 414 | 643 | 3.0 |
| 23 | 416 | 645 | 3.1 |
| 25 | 422 | 655 | 2.5 |
| Pheophytin a[b] | 408 | 667 | 2.1 |
| Pheophytin b[b] | 434 | 655 | 5.1 |
| Zn-24 | 415 | 606 | 4.3 |
| Zn-22 | 411 | 615 | 3.6 |
| Zn-23 | 412 | 617 | 3.5 |
| Zn-25 | 417 | 628 | 2.6 |
| Chlorophyll a[b] | 430 | 662 | 1.3 |
| Chlorophyll b[b] | 455 | 644 | 2.8 |

[a]Intoluene at room temperature.
[b]In diethyl ether (Smith, J.H.C.; Benitez, A. In Modern Methods of Plant Analysis, Paech, K.; Tracey, M.V., Eds.; Springer-Verlag: Berlin 1955, Vol. IV, pp. 142–196).

An alternative approach to chlorins that bear a geminal dimethyl lock, avoid flanking meso and β substituents, and can be used in model systems has involved reaction of a tripyrrole complex with a pyrrole functionalized for subsequent elaboration (Montforts, F.-P.; Kutzki, O. *Angew. Chem. Int. Ed.* 2000, 39, 599–601; Abel, and Montforts, F.-P. *Tetrahedron Lett.* 1997, 38, 1745–1748: Schmidt, W.; Montforts, F.-P. *Synlett* 1997, 903–904).

The foregoing is illustrative of the present invention, and is not to be construed as limiting thereof. The invention is defined by the following claims, with equivalents of the claims to be included therein.

What is claimed is:

1. A light harvesting array, comprising:
   (a) a first substrate comprising a first electrode; and
   (b) a layer of light harvesting rods electrically coupled to said first electrode, each of said light harvesting rods comprising a polymer of Formula I:

$$X^1\text{-}(X^{m+1})_m \quad (I)$$

wherein:
   m is at least 1;
   $X^1$ is a charge separation group having an excited-state of energy equal to or lower than that of $X^2$;
   $X^2$ through $X^{m+1}$ are chromophores; and
   at least one of $X^1$ through $X^{m+1}$ is selected from the group consisting of chlorins, bacteriochlorins, and isobacteriochlorins.

2. A light harvesting array according to claim 1, wherein $X^1$ comprises a porphyrinic macrocycle.

3. A light-harvesting array according to claim 1, wherein $X^1$ comprises a double-decker sandwich coordination compound.

4. A light harvesting array according to claim 1, wherein $X^2$ through $X^{m+1}$ comprise porphyrinic macrocycles.

5. A light-harvesting array according to claim 1, wherein $X^1$ through $X^{m+1}$ comprise porphyrinic macrocycles.

6. A light harvesting array according to claim 1, wherein m is from 2 to 20.

7. A light harvesting array according to claim 1, wherein at least one of $X^2$ through $X^{m+1}$ comprises a meso-linked porphyrinic macrocycle.

8. A light harvesting array according to claim 1, wherein at least one of $X^2$ through $X^{m+1}$ comprises a trans meso-linked porphyrinic macrocycle.

9. A light harvesting array according to claim 1, wherein $X^2$ through $X^{m+1}$ consist of meso-linked porphyrinic macrocycles.

10. A light harvesting array according to claim 1, wherein $X^2$ through $X^{m+1}$ consist of trans meso-linked porphyrinic macrocycles.

11. A light harvesting array according to claim 1, wherein at least one of $X^2$ through $X^{m+1}$ comprises a β-linked porphyrinic macrocycle.

12. A light harvesting array according to claim 1, wherein at least one of $X^2$ through $X^{m+1}$ comprises a trans β-linked porphyrinic macrocycle.

13. A light harvesting array according to claim 1, wherein $X^2$ through $X^{m+1}$ consist of β-linked porphyrinic macrocycles.

14. A light harvesting array according to claim 1, wherein $X^2$ through $X^{m+1}$ consist of trans β-linked porphyrinic macrocycles.

15. A light harvesting array according to claim 1, wherein $X^1$ through $X^{m+1}$ each independently comprise a porphyrinic macrocycle selected from the group consisting of Formula X, Formula XI, Formula XII, Formula XIII, Formula XIV, Formula XV, Formula XVI, and Formula XVII:

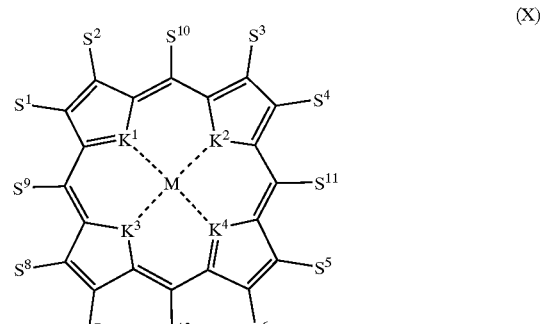

(X)

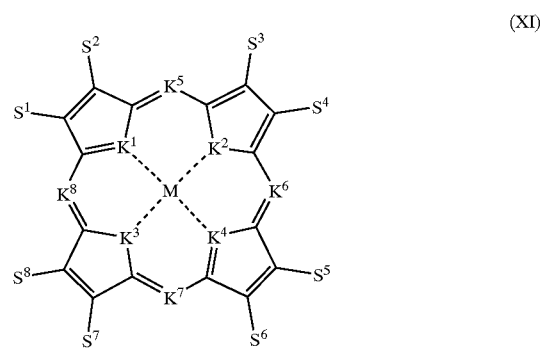

(XI)

-continued (XII) 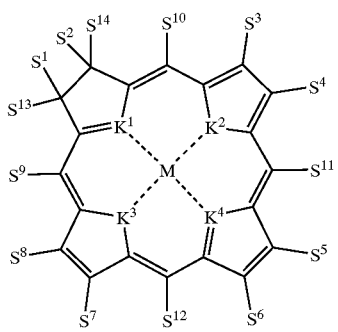

(XIII) 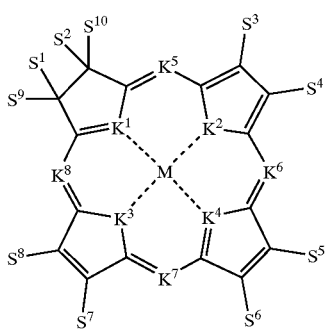

(XIV) 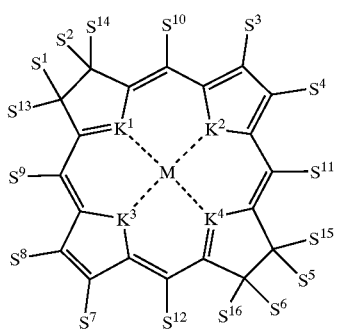

(XV) 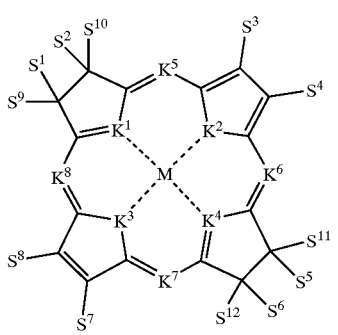

(XVI) 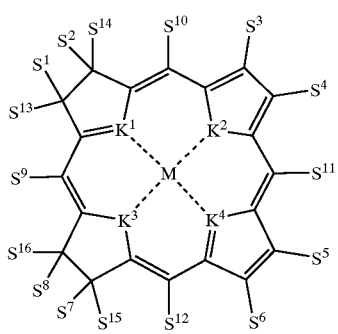

-continued (XVII) 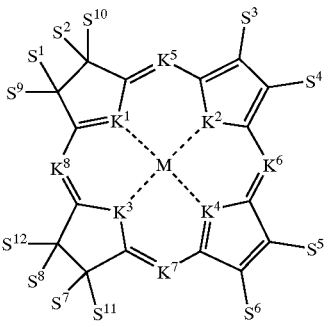

wherein:
M is selected from the group consisting of Zn, Mg, Pt, Pd, Sn and Al, or M is absent;
$K^1$, $K^2$, $K^3$, $K^4$, $K^5$, $K^6$, $K^7$, and $K^8$ are independently selected from the group consisting of N, O, S, Se, Te, and CH;
$S^1, S^2, S^3, S^4, S^5, S^6, S^7, S^8, S^9, S^{10}, S^{11}, S^{12}, S^{13}, S^{14}, S^{15}$ and $S^{16}$ are each independently selected from the group consisting of H, aryl, phenyl, cycloalkyl, alkyl, halogen, alkoxy, alkylthio, perfluoroalkyl, perfluoroaryl, pyridyl, cyano, thiocyanato, nitro, amino, alkylamino, acyl, sulfoxyl, sulfonyl, imido, amido, and carbamoyl;
and wherein each pair of $S^1$ and $S^2$, $S^3$ and $S^4$, $S^5$ and $S^6$, and $S^7$ and $S^8$, optionally independently form an annulated arene, which annulated arene optionally is unsubstituted or substituted one or more times with a substituent selected from the group consisting of H, aryl, phenyl, cycloalkyl, alkyl, halogen, alkoxy, alkylthio, perfluoroalkyl, perfluoroaryl, pyridyl, cyano, thiocyanato, nitro, amino, alkylamino, acyl, sulfoxyl, sulfonyl, imido, arnido, and carbamoyl;
and wherein $S^1$ through $S^{16}$ optionally comprise a linking group covalently linked to an adjacent porphyrinic macrocycle of $X^1$ through $X^{m+1}$ or a linking group covalently linked to said first electrode.

16. A light harvesting array according to claim 15, wherein at least one of $X^2$ through $X^{m+1}$ comprises a meso-linked porphyrinic macrocycle.

17. A light harvesting array according to claim 15, wherein at least one of $X^2$ through $X^{m+1}$ comprises a trans meso-linked porphyrinic macrocycle.

18. A light harvesting array according to claim 15, wherein $X^2$ through $X^{m+1}$ consist of meso-linked porphyrinic macrocycles.

19. A light harvesting array according to claim 15, wherein $X^2$ through $X^{m+1}$ consist of trans meso-linked porphyrinic macrocycles.

20. A light harvesting array according to claim 15, wherein at least one of $X^2$ through $X^{m+1}$ comprises a β-linked porphyrinic macrocycle.

21. A light harvesting array according to claim 15, wherein at least one of $X^2$ through $X^{m+1}$ comprises a trans β-linked porphyrinic macrocycle.

22. A light harvesting array according to claim 15, wherein $X^2$ through $X^{m+1}$ consist of β-linked porphyrinic macrocycles.

23. A light harvesting array according to claim 15, wherein $X^2$ through $X^{m+1}$ consist of trans β-linked porphyrinic macrocycles.

24. A light harvesting array according to claim 1, wherein said light harvesting rods are oriented substantially perpendicularly to said first electrode.

25. A light harvesting array according to claim 1, wherein said substrate is rigid.

26. A light harvesting array according to claim 1, wherein said substrate is flexible.

27. A light harvesting array according to claim 1, wherein said substrate is transparent.

28. A light harvesting array according to claim 1, wherein said substrate is opaque.

29. A light harvesting array according to claim 1, wherein said substrate is reflective.

30. A light harvesting array according to claim 1, wherein said substrate is substantially planar in shape.

31. A light harvesting array according to claim 1, wherein said electrode comprises a metallic conductor.

32. A light harvesting array according to claim 1, wherein said electrode comprises a nonmetallic conductor.

33. A light harvesting array according to claim 1, wherein said light-harvesting rods are intrinsic rectifiers of excited-state energy.

34. A light harvesting array according to claim 1, wherein said light harvesting rods are intrinsic rectifiers of holes.

35. A light harvesting array according to claim 1, wherein said light harvesting rods are not greater than 500 nanometers in length.

36. A light harvesting array, comprising:
    (a) a first substrate comprising a first electrode; and
    (b) a layer of light harvesting rods electrically coupled to said first electrode, each of said light harvesting rods comprising a polymer of Formula I:

$$X^1\text{-}(X^{m+1})_m \qquad (I)$$

wherein:
    m is at least 2;
    $X^1$ is a charge separation group having an excited-state of energy equal to or lower than that of $X^2$;
    $X^2$ through $X^{m+1}$ are chromophores;
    wherein at least one of $X^2$ through $X^{m+1}$ comprises a meso-linked porphyrinic macrocycle;
    $X^1$ through $X^{m+1}$ are selected so that, upon injection of either an electron or hole from $X^1$ into said first electrode, the corresponding hole or electron from $X^1$ is transferred to at least $X^2$; and
    said light-harvesting rods are intrinsic rectifiers of excited-state energy.

37. A light harvesting array according to claim 36, wherein $X^1$ through $X^{m+1}$ are selected so that, upon injection of an electron from $X^1$ into said first electrode, the corresponding hole from $X^1$ is transferred to at least $X^2$.

38. A light harvesting array according to claim 36, wherein at least one of $X^1$ through $X^{m+1}$ is selected from the group consisting of chlorins, bacteriochlorins, and isobacteriochlorins.

39. A light harvesting array according to claim 36, wherein $X^1$ comprises a porphyrinic macrocycle.

40. A light-harvesting array according to claim 36, wherein $X^1$ comprises a double-decker sandwich coordination compound.

41. A light harvesting array according to claim 36, wherein $X^2$ through $X^{m+1}$ comprise porphyrinic macrocycles.

42. A light-harvesting array according to claim 36, wherein $X^1$ through $X^{m+1}$ comprise porphyrinic macrocycles.

43. A light harvesting array according to claim 36, wherein m is from 2 to 20.

44. A light harvesting array according to claim 36, wherein at least one of $X^2$ through $X^{m+1}$ comprises a trans meso-linked porphyrinic macrocycle.

45. A light harvesting array according to claim 36, wherein $X^2$ through $X^{m+1}$ consist of meso-linked porphyrinic macrocycles.

46. A light harvesting array according to claim 36, wherein $X^2$ through $X^{m+1}$ consist of trans meso-linked porphyrinic macrocycles.

47. A light harvesting array according to claim 36, wherein at least one of $X^2$ through $X^{m+1}$ comprises a β-linked porphyrinic macrocycle.

48. A light harvesting array according to claim 36, wherein at least one of $X^2$ through $X^{m+1}$ comprises a trans β-linked porphyrinic macrocycle.

49. A light harvesting array according to claim 36, wherein $X^1$ through $X^{m+1}$ each independently comprise a porphyrinic macrocycle selected from the group consisting of Formula X, Formula XI, Formula XII, Formula XIII, Formula XIV, Formula XV, Formula XVI, and Formula XVII:

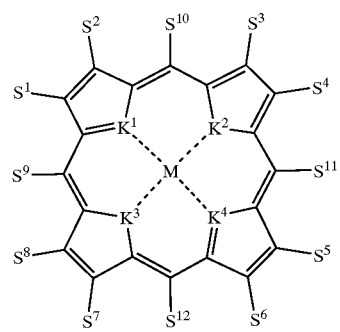

(X)

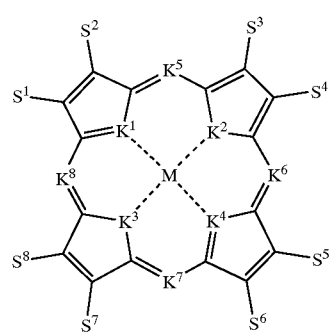

(XI)

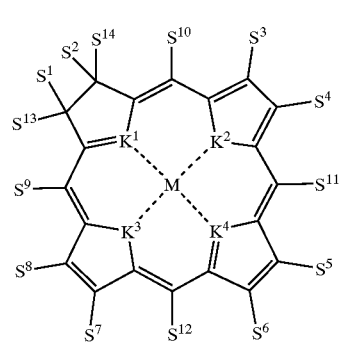

(XII)

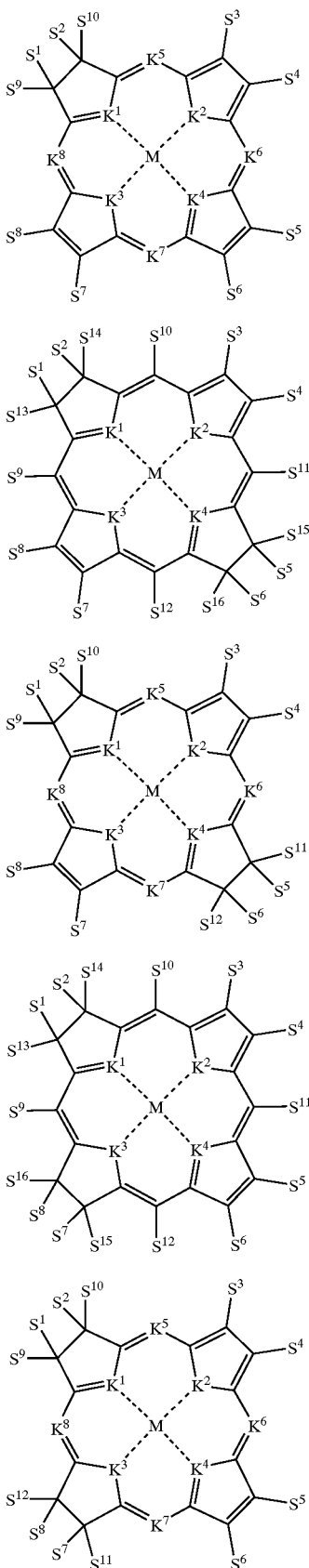

(XIII)

(XIV)

(XV)

(XVI)

(XVII)

wherein:
M is selected from the group consisting of Zn, Mg, Pt, Pd, Sn and Al, or M is absent;
$K^1, K^2, K^3, K^4, K^5, K^6, K^7$, and $K^8$ are independently selected from the group consisting of N, O, S, Se, Te, and CH;
$S^1, S^2, S^3, S^4, S^5, S^6, S^7, S^8, S^9, S^{10}, S^{11}, S^{12}, S^{13}, S^{14}, S^{15}$ and $S^{16}$ are each independently selected from the group consisting of H, aryl, phenyl, cycloalkyl, alkyl, halogen, alkoxy, alkylthio, perfluoroalkyl, perfluoroaryl, pyridyl, cyano, thiocyanato, nitro, amino, alkylarnino, acyl, sulfoxyl, sulfonyl, imido, amido, and carbamoyl;
and wherein each pair of $S^1$ and $S^2$, $S^3$ and $S^4$, $S^5$ and $S^6$, and $S^7$ and $S^8$, optionally independently form an annulated arene, which annulated arene optionally is unsubstituted or substituted one or more times with a substituent selected from the group consisting of H, aryl, phenyl, cycloalkyl, alkyl, halogen, alkoxy, alkylthio, perfluoroalkyl, perfluoroaryl, pyridyl, cyano, thiocyanato, nitro, amino, alkylamino, acyl, sulfoxyl, sulfonyl, imido, amido, and carbamoyl;
and wherein $S^1$ through $S^{16}$ optionally comprise a linking group covalently linked to an adjacent porphyrinic macrocycle of $X^1$ through $X^{m+1}$ or a linking group covalently linked to said first electrode.

50. A light harvesting array according to claim 49, wherein at least one of $X^2$ through $X^{m+1}$ comprises a trans meso-linked porphyrinic macrocycle.

51. A light harvesting array according to claim 49, wherein $X^2$ through $X^{m+1}$ consist of meso-linked porphyrinic macrocycles.

52. A light harvesting array according to claim 49, wherein $X^2$ through $X^{m+1}$ consist of trans meso-linked porphyrinic macrocycles.

53. A light harvesting array according to claim 49, wherein at least one of $X^2$ through $X^{m+1}$ comprises a β-linked porphyrinic macrocycle.

54. A light harvesting array according to claim 49, wherein at least one of $X^2$ through $X^{m+1}$ comprises a trans β-linked porphyrinic macrocycle.

55. A light harvesting array according to claim 36, wherein said substrate is rigid.

56. A light harvesting array according to claim 36, wherein said substrate is flexible.

57. A light harvesting array according to claim 36, wherein said substrate is transparent.

58. A light harvesting array according to claim 36, wherein said substrate is opaque.

59. A light harvesting array according to claim 36, wherein said substrate is reflective.

60. A light harvesting array according to claim 36, wherein said substrate is substantially planar in shape.

61. A light harvesting array according to claim 36, wherein said electrode comprises a metallic conductor.

62. A light harvesting array according to claim 36, wherein said electrode comprises a nonmetallic conductor.

63. A light harvesting array according to claim 36, wherein said light-harvesting rods are intrinsic rectifers of holes.

64. A light harvesting array according to claim 36, wherein said light harvesting rods are not greater than 500 nanometers in length.

65. A light harvesting array, comprising:
(a) a first substrate comprising a first electrode; and
(b) a layer of light harvesting rods electrically coupled to said first electrode, each of said light harvesting rods comprising a polymer of Formula I:

$$X^1 \text{---}(X^{m+1})_m \quad (I)$$

wherein:

m is at least 1;

$X^1$ is a charge separation group having an excited-state of energy equal to or lower than that of $X^2$;

$X^2$ through $X^{m+1}$ are chromophores;

wherein at least one of $X^2$ through $X^{m+1}$ comprises a meso-linked porphyrinic macrocycle;

$X^1$ through $X^{m+1}$ are selected so that. upon injection of either an electron or hole from $X^1$ into said first electrode, the corresponding hole or electron from $X^1$ is transferred to at least $X^2$ ; and said light-harvesting rod is chemically bonded to said electrode.

66. A light harvesting array according to claim 65, wherein $X^1$ through $X^{m+1}$ are selected so that, upon injection of an electron from $X^1$ into said first electrode, the corresponding hole from $X^1$ is transferred to at least $X^2$.

67. A light harvesting array according to claim 65, wherein at least one of $X^1$ through $X^{m+1}$ is selected from the group consisting of chlorins, bacteriochlorins, and isobacteriochlorins.

68. A light harvesting array according to claim 65, wherein $X^1$ comprises a porphyrinic macrocycle.

69. A light harvesting array according to claim 65, wherein $X^1$ comprises a double-decker sandwich coordination compound.

70. A light harvesting array according to claim 65, wherein $X^2$ through $X^{m+1}$ comprise porphyrinic macrocycles.

71. A light-harvesting array according to claim 65, wherein $X^1$ through $X^{m+1}$ comprise porphyrinic macrocycles.

72. A light harvesting array according to claim 65, wherein m is from 2 to 20.

73. A light harvesting array according to claim 65, wherein at least one of $X^2$ through $X^{m+1}$ comprises a trans meso-linked porphyrinic macrocycle.

74. A light harvesting array according to claim 65, wherein $X^2$ through $X^{m+1}$ consist of meso-linked porphyrinic macrocycles.

75. A light harvesting array according to claim 65, wherein $X^2$ through $X^{m+1}$ consist of trans meso-linked porphyrinic macrocycles.

76. A light harvesting array according to claim 65, wherein at least one of $X^2$ through $X^{m+1}$ comprises a β-linked porphyrinic macrocycle.

77. A light harvesting array according to claim 65, wherein at least one of $X^2$ through $X^{m+1}$ comprises a trans β-linked porphyrinic macrocycle.

78. A light harvesting array according to claim 65, wherein $X^1$ through $X^{m+1}$ each independently comprise a porphyrinic macrocycle selected from the group consisting of Formula X, Formula XI, Formula XII, Formula XIII, Formula XIV, Formula XV, Formula XVI, and Formula XVII:

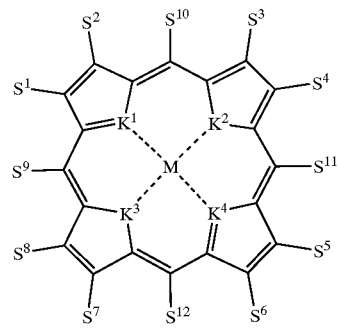

(X)

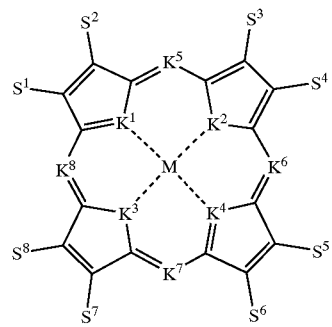

(XI)

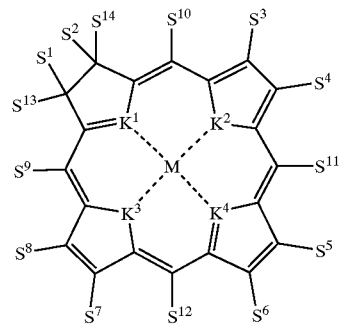

(XII)

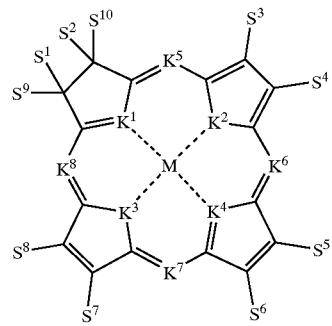

(XIII)

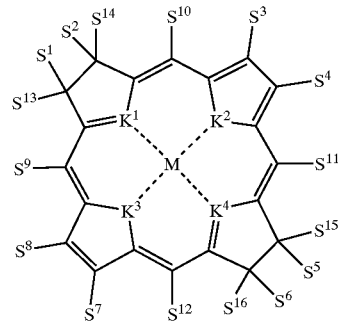

(XIV)

-continued

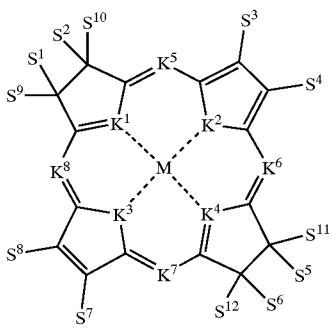

(XV)

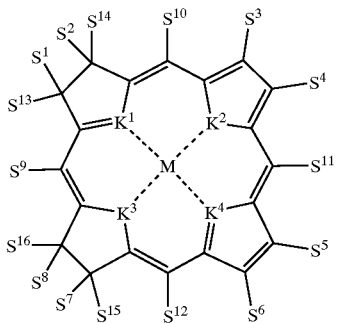

(XVI)

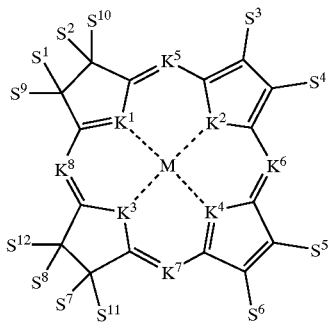

(XVII)

wherein:
M is selected from the group consisting of Zn, Mg, Pt, Pd, Sn and Al, or M is absent;
$K^1$, $K^2$, $K^3$, $K^4$, $K^5$, $K^6$, $K^7$, and $K^8$ are independently selected from the group consisting of N, O, S, Se, Te, and CH;
$S^1, S^2, S^3, S^4, S^5, S^6, S^7, S^8, S^9, S^{10}, S^{11}, S^{12}, S^{13}, S^{14}, S^{15}$ and $S^{16}$ are each independently selected from the group consisting of H, aryl, phenyl, cycloalkyl, alkyl, halogen, alkoxy, alkylthio, perfluoroalkyl, perfluoroaryl, pyridyl, cyano, thiocyanato, nitro, amino, alkylamino, acyl, sulfoxyl, sulfonyl, imido, amido, and carbamoyl;
and wherein each pair of $S^1$ and $S^2$, $S^3$ and $S^4$, $S^5$ and $S^6$, and $S^7$ and $S^8$, optionally independently form an annulated arene, which annulated arene optionally is unsubstituted or substituted one or more times with a substituent selected from the group consisting of H, aryl, phenyl, cycloalkyl, alkyl, halogen, alkoxy, alkylthio, perfluoroalkyl, perfluoroaryl, pyridyl, cyano, thiocyanato, nitro, amino, alkylamino, acyl, sulfoxyl, sulfonyl, imido, amido, and carbamoyl;
and wherein $S^1$ through $S^{16}$ optionally comprise a linking group covalently linked to an adjacent porphyrinic macrocycle of $X^1$ through $X^{m+1}$ or a linking group covalently linked to said first electrode.

79. A light harvesting array according to claim 78, wherein at least one of $X^2$ through $X^{m+1}$ comprises a trans meso-linked porphyrinic macrocycle.

80. A light harvesting array according to claim 78, wherein $X^2$ through $X^{m+1}$ consist of meso-linked porphyrinic macrocycles.

81. A light harvesting array according to claim 78, wherein $X^2$ through $X^{m+1}$ consist of trans meso-linked porphyrinic macrocycles.

82. A light harvesting array according to claim 78, wherein at least one of $X^2$ through $X^{m+1}$ comprises a β-linked porphyrinic macrocycle.

83. A light harvesting array according to claim 78, wherein at least one of $X^2$ through $X^{m+1}$ comprises a trans β-linked porphyrinic macrocycle.

84. A light harvesting array according to claim 65, wherein said light harvesting rods are oriented substantially perpendicularly to said first electrode.

85. A light harvesting array according to claim 65, wherein said substrate is rigid.

86. A light harvesting array according to claim 65, wherein said substrate is flexible.

87. A light harvesting array according to claim 65, wherein said substrate is transparent.

88. A light harvesting array according to claim 65, wherein said substrate is opaque.

89. A light harvesting array according to claim 65, wherein said substrate is reflective.

90. A light harvesting array according to claim 65, wherein said substrate is substantially planar in shape.

91. A light harvesting array according to claim 65, wherein said electrode comprises a metallic conductor.

92. A light harvesting array according to claim 65, wherein said electrode comprises a nonmetallic conductor.

93. A light harvesting array according to claim 65, wherein said light-harvesting rods are intrinsic rectifiers of excited-state energy.

94. A light harvesting array according to claim 65, wherein said light-harvesting rods are intrinsic rectifers of holes.

95. A light harvesting array according to claim 36, wherein said light harvesting rods are not greater than 500 nanometers in length.

96. A light harvesting array, comprising:
(a) a first substrate comprising a first electrode; and
(b) a layer of light harvesting rods electrically coupled to said first electrode, each of said light harvesting rods comprising a polymer of Formula I:

$$X^1\text{-}(X^{m+1})_m \qquad (I)$$

wherein:
m is at least 1;
$X^1$ is a charge separation group having an excited-state of energy equal to or lower than that of $X^2$;
$X^2$ through $X^{m+1}$ are chromophores;
wherein at least one of $X^1$ through $X^{m+1}$ comprises a meso-linked porphyrinic macrocycle;
$X^1$ through $X^{m+1}$ are selected so that, upon injection of either an electron or hole from $X^1$ into said first electrode, the corresponding hole or electron from $X^1$ is transferred to at least $X^2$; and
said light harvesting rods are oriented substantially perpendicularly to said first electrode.

97. A light harvesting array according to claim 96, wherein $X^1$ through $X^{m+1}$ are selected so that, upon injection of an electron from $X^1$ into said first electrode, the corresponding hole from $X^1$ is transferred to at least $X^2$.

98. A light harvesting array according to claim 96, wherein at least one of $X^1$ through $X^{m+1}$ is selected from the group consisting of chlorins, bacteriochlorins, and isobacteriochlorins.

99. A light harvesting array according to claim 96, wherein $X^1$ comprises a porphyrinic macrocycle.

100. A light harvesting array according to claim 96, wherein $X^1$ comprises a double-decker sandwich coordination compound.

101. A light harvesting array according to claim 96, wherein $X^2$ through $X^{m+1}$ comprise porphyrinic macrocycles.

102. A light-harvesting array according to claim 96, wherein $X^1$ through $X^{m+1}$ comprise porphyrinic macrocycles.

103. A light harvesting array according to claim 96, wherein m is from 2 to 20.

104. A light harvesting array according to claim 96, wherein at least one of $X^2$ through $X^{m+1}$ comprises a trans meso-linked porphyrinic macrocycle.

105. A light harvesting array according to claim 96, wherein $X^2$ through $X^{m+1}$ consist of meso-linked porphyrinic macrocycles.

106. A light harvesting array according to claim 96, wherein $X^2$ through $X^{m+1}$ consist of trans meso-linked porphyrinic macrocycles.

107. A light harvesting array according to claim 96, wherein at least one of $X^2$ through $X^{m+1}$ comprises a β-linked porphyrinic macrocycle.

108. A light harvesting array according to claim 96, wherein at least one of $X^2$ through $X^{m+1}$ comprises a trans β-linked porphyrinic macrocycle.

109. A light harvesting array according to claim 96, wherein $X^1$ through $X^{m+1}$ each independently comprise a porphyrinic macrocycle selected from the group consisting of Formula X, Formula XI, Formula XII, Formula XIII, Formula XIV, Formula XV, Formula XVI, and Formula XVII:

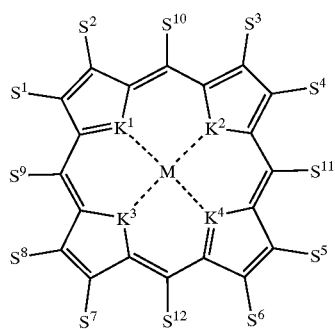

(X)

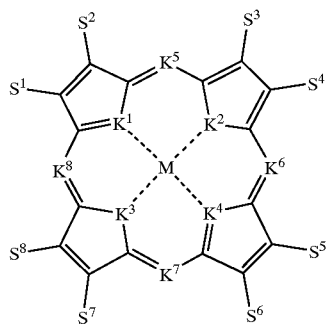

(XI)

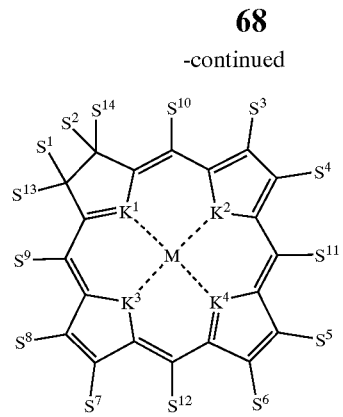

(XII)

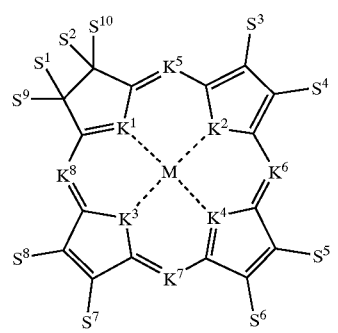

(XIII)

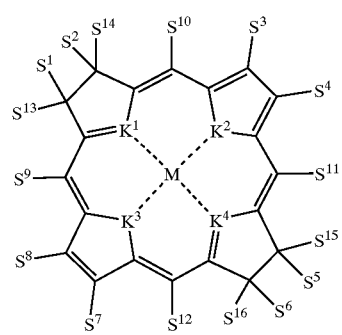

(XIV)

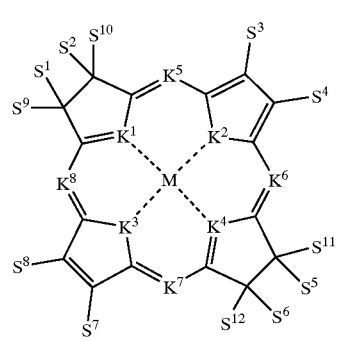

(XV)

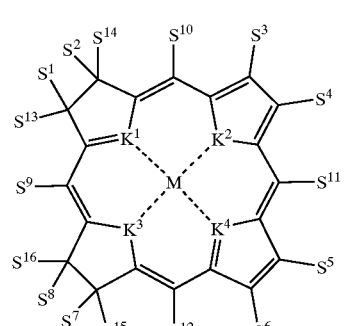

(XVI)

-continued

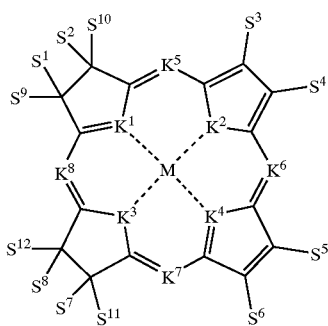

(XVII)

wherein:
M is selected from the group consisting of Zn, Mg, Pt, Pd, Sn and Al, or M is absent;
$K^1$, $K^2$, $K^3$, $K^4$, $K^5$, $K^6$, $K^7$, and $K^8$ are independently selected from the group consisting of N, O, S, Se, Te, and CH;
$S^1, S^2, S^3, S^4, S^5, S^6, S^7, S^8, S^9, S^{10}, S^{11}, S^{12}, S^{13}, S^{14}, S^{15}$ and $S^{16}$ are each independently selected from the group consisting of H, aryl, phenyl, cycloalkyl, alkyl, halogen, alkoxy, alkylthio, perfluoroalkyl, perfluoroaryl, pyridyl, cyano, thiocyanato, nitro, amino, alkylamino, acyl, sulfoxyl, sulfonyl, imido, amido, and carbamoyl;
and wherein each pair of $S^1$ and $S^2$, $S^3$ and $S^4$, $S^5$ and $S^6$, and $S^7$ and $S^8$, optionally independently form an annulated arene, which annulated arene optionally is unsubstituted or substituted one or more times with a substituent selected from the group consisting of H, aryl, phenyl, cycloalkyl, alkyl, halogen, alkoxy, alkylthio, perfluoroalkyl, perfluoroaryl, pyridyl, cyano, thiocyanato, nitro, amino, alkylamino, acyl, sulfoxyl, sulfonyl, imido, amido, and carbamoyl;
and wherein $S^1$ through $S^{16}$ optionally comprise a linking group covalently linked to an adjacent porphyrinic macrocycle of $X^1$ through $X^{m+1}$ or a linking group covalently linked to said first electrode.

110. A light harvesting array according to claim 109, wherein at least one of $X^2$ through $X^{m+1}$ comprises a trans meso-linked porphyrinic macrocycle.

111. A light harvesting array according to claim 109, wherein $X^2$ through $X^{m+1}$ consist of meso-linked porphyrinic macrocycles.

112. A light harvesting array according to claim 109, wherein $X^2$ through $X^{m+1}$ consist of trans meso-linked porphyrinic macrocycles.

113. A light harvesting array according to claim 109, wherein at least one of $X^2$ through $X^{m+1}$ comprises a β-linked porphyrinic macrocycle.

114. A light harvesting array according to claim 109, wherein at least one of $X^2$ through $X^{m+1}$ comprises a trans β-linked porphyrinic macrocycle.

115. A light harvesting array according to claim 96, wherein said substrate is rigid.

116. A light harvesting array according to claim 96, wherein said substrate is flexible.

117. A light harvesting array according to claim 96, wherein said substrate is transparent.

118. A light harvesting array according to claim 96, wherein said substrate is opaque.

119. A light harvesting array according to claim 96, wherein said substrate is reflective.

120. A light harvesting array according to claim 96, wherein said substrate is substantially planar in shape.

121. A light harvesting array according to claim 96, wherein said electrode comprises a metallic conductor.

122. A light harvesting array according to claim 96, wherein said electrode comprises a nonmetallic conductor.

123. A light harvesting array according to claim 96, wherein said light-harvesting rods are intrinsic rectifiers of excited-state energy.

124. A light harvesting array according to claim 96, wherein said light-harvesting rods are intrinsic rectifers of holes.

125. A light harvesting array according to claim 96, wherein said light harvesting rods are not greater than 500 nanometers in length.

* * * * *

UNITED STATES PATENT AND TRADEMARK OFFICE
CERTIFICATE OF CORRECTION

PATENT NO. : 6,420,648 B1
DATED : July 16, 2002
INVENTOR(S) : Jonathan S. Lindsey It is certified that error appears in the above-identified patent and that said Letters Patent is hereby corrected as shown below:

<u>Title page,</u>
Please insert the following:
-- (*) Notice: This patent is subject to a terminal disclaimer. --

<u>Column 62,</u>
Line 12, should read as follows:
-- amino, alkylamino, acyl, sulfoxyl, sulfonyl, imido, --

<u>Column 66,</u>
Line 56, should read as follows:
-- wherein at least one of $X^2$ through $X^{m+1}$ comprises a --

Signed and Sealed this

Eighteenth Day of March, 2003

JAMES E. ROGAN
*Director of the United States Patent and Trademark Office*